(12) United States Patent
Castro Palomino Laria et al.

(10) Patent No.: US 8,536,165 B2
(45) Date of Patent: Sep. 17, 2013

(54) AZABIPHENYLAMINOBENZOIC ACID DERIVATIVES AS DHODH INHIBITORS

(75) Inventors: Julio Cesar Castro Palomino Laria, Barcelona (ES); Emma Terricabras Belart, Barcelona (ES); Montserrat Erra Sola, Barcelona (ES); Eloisa Navarro Romero, Barcelona (ES); Silvia Fonquerna Pou, Barcelona (ES); Aranzazu Cardus Figueras, Barcelona (ES); Maria Estrella Lozoya Toribio, Barcelona (ES)

(73) Assignee: Almirall, S.A., Barcelona (ES)

( * ) Notice: Subject to any disclaimer, the term of this patent is extended or adjusted under 35 U.S.C. 154(b) by 425 days.

(21) Appl. No.: 12/672,725

(22) PCT Filed: Aug. 8, 2008

(86) PCT No.: PCT/EP2008/006573
§ 371 (c)(1),
(2), (4) Date: Mar. 16, 2010

(87) PCT Pub. No.: WO2009/021696
PCT Pub. Date: Feb. 19, 2009

(65) Prior Publication Data
US 2011/0212945 A1   Sep. 1, 2011

(30) Foreign Application Priority Data

Aug. 10, 2007  (ES) .................................. 200702261
Mar. 13, 2008  (EP) .................................... 08382011

(51) Int. Cl.
| | |
|---|---|
| A61K 31/4439 | (2006.01) |
| A61K 31/505 | (2006.01) |
| A61K 31/444 | (2006.01) |
| A61K 31/4545 | (2006.01) |

(52) U.S. Cl.
USPC ...... 514/217.04; 514/352; 514/256; 514/340; 514/330; 514/314; 514/318; 514/236.5

(58) Field of Classification Search
USPC .................... 514/217.04, 352, 256, 340, 334, 514/314, 318, 235.5
See application file for complete search history.

(56) References Cited

U.S. PATENT DOCUMENTS

| | | | |
|---|---|---|---|
| 5,780,592 | A | 7/1998 | Müllner et al. |
| 7,071,222 | B2 | 7/2006 | Bartlett et al. |
| 7,258,118 | B2 | 8/2007 | Goede et al. |
| 8,258,308 | B2 | 9/2012 | Castro Palomino Laria et al. |
| 2003/0004171 | A1 | 1/2003 | Humphrey et al. |
| 2006/0081246 | A1 | 4/2006 | Goede et al. |
| 2010/0074898 | A1 | 3/2010 | Castro Palomino Laria et al. |
| 2011/0129445 | A1 | 6/2011 | Godessart Marina et al. |
| 2011/0280831 | A1 | 11/2011 | Godessart Marina et al. |
| 2012/0003183 | A1 | 1/2012 | Garcia Gonzales et al. |
| 2012/0003184 | A1 | 1/2012 | Garcia Gonzales et al. |
| 2012/0014918 | A1 | 1/2012 | Perez Garcia et al. |
| 2012/0245359 | A1 | 9/2012 | Boix Bernardini |

FOREIGN PATENT DOCUMENTS

| | | |
|---|---|---|
| EP | 0 780 128 | 6/1997 |
| WO | WO 97/34600 | 1/1997 |
| WO | WO 97/00703 | 9/1997 |
| WO | WO 99/45926 | 9/1999 |
| WO | WO 00/76489 | 12/2000 |
| WO | WO 02/080897 | 10/2002 |
| WO | WO 03/000325 | 1/2003 |
| WO | WO 03/006425 | 1/2003 |
| WO | WO 03/061742 | 7/2003 |
| WO | WO 2004/048314 | 6/2004 |
| WO | WO 2004/056746 | 7/2004 |
| WO | WO 2004/056747 | 7/2004 |
| WO | WO 2005/075410 | 8/2005 |
| WO | WO 2006/001961 | 1/2006 |
| WO | WO 2006/022442 | 3/2006 |
| WO | WO 2006/044741 | 4/2006 |
| WO | WO 2006/122788 | 11/2006 |
| WO | WO 2008/077639 | 7/2008 |
| WO | WO 2008/097180 | 8/2008 |
| WO | WO 2009/153043 | 12/2009 |
| WO | WO 2010/083975 | 7/2010 |
| WO | WO 2010/102824 | 9/2010 |
| WO | WO 2010/102825 | 9/2010 |
| WO | WO 2010/102826 | 9/2010 |
| WO | WO 2011/045059 | 4/2011 |

OTHER PUBLICATIONS

Kermack, "Some anilinopyridine derivatives", Journal of the Chemical Society, 1942, 726-727.*
Grigor'eva, "Catalytic activity of complexes of copper(II) with carboxyphenylaminopyrimidines (antiinflammatory drugs) in model reactions of oxidase and catalase type", Khimiko-Farmatsevticheskii Zhurnal (1978), 12(4), pp. 7-18.*
U.S. Appl. No. 12/520,237, filed Sep. 9, 2009, Castro Palomino Laria et al.
U.S. Appl. No. 12/999,698, filed Dec. 17, 2010, Godessart Marina et al.
U.S. Appl. No. 13/145,628, filed Jul. 21, 2011, Godessart Marina et al.
U.S. Appl. No. 13/256,104, filed Sep. 19, 2011, Garcia Gonzales et al.
U.S. Appl. No. 13/256,127, filed Sep. 19, 2011, Garcia Gonzales et al.
U.S. Appl. No. 13/256,349, filed Sep. 28, 2011, Perez Garcia et al.
U.S. Appl. No. 13/501,847, filed Jun. 12, 2012, Boix Bernardini et al.
Batt, DG, "Inhibitors of dihydroorotate dehydrogenase," *Expert Opinion on Therapeutic Patents*, 9(1): 41-54 (1999).
Baughman, RP et al., "Leflunomide for chronic sarcoidosis," *Clinical Research*, 21: 43-48 (2004).

(Continued)

*Primary Examiner* — Sreeni Padmanabhan
*Assistant Examiner* — Sahar Javanmard
(74) *Attorney, Agent, or Firm* — Finnegan, Henderson, Farabow, Garrett & Dunner LLP

(57) ABSTRACT

The present disclosure relates to new azabiphenylaminobenzoic acid derivatives of formula (I); as well as processes for their preparation, pharmaceutical compositions comprising them, and their use in therapy as inhibitors of the dehydroorotate dihydrogenase (DHODH).

24 Claims, No Drawings

(56) References Cited

OTHER PUBLICATIONS

Berge, S.M. et al., "Pharmaceutical salts," *Journal of Pharmaceutical Science*, American Pharmaceutical Association, Washington, DC, 66(1):1-19, XP00562636, ISSN: 0022-3549 (1977).
Breedveld, FC et al., "Leflunomide: mode of action in the treatment of rheumatoid arthritis," *Annals of the Rheumatic Diseases*, 59: 841-849 (2000).
ClinialTrials.gov Identifier: NCT00637819, Sanofi-Aventis, Double blind, randomized, placebo controlled pilot study of leflunomide in systemic lupus erythematosus (SLE) (2008).
Dexter, DL et al., "Activity of a novel 4-quinolinecarboxylic acid, NSC 368390 [6-fluoro-2-(2'-fluoro-1,1'-biphenyl-4-yl)-3-methyl-4-quinolinecarboxylic acid sodium salt], against experimental tumors," *Cancer Research*, 45:5563-5568 (1985).
Dimitrova, P. et al., "Restriction of de novo primidine biosynthesis inhibits Th1 cell activation and promotes Th2 cell differentiation," *The Journal of Immunology*, 169:3392-3399 (2002).
English-language Derwent Abstract for WO 06/022442.
Fox, RI, "Mechanism of action of leflunomide in rheumatoid arthritis," *The Journal of Rheumatology*, 25(53):20-26 (1998).
Gu, L. et al., "Preformulation salt selection. Physical property comparisons of the tris (hydroxymethyl) aminomethane (THAM) salts of four analgesic/anti-inflammatory agents with the sodium salts and the free acids," *Pharmaceutical Research*, Kluwer Academic Publishers, 4(3):255-257, XP002099348, ISSN: 0724-8741. (1987).
Haibel, J. et al., "Six month open label trial of leflunomide in active ankylosing spondylitis," *Annals of the Rheumatic Diseases*, 64: 124-126 (2005).
International Search Report mailed May 8, 2008, for International Application No. PCT/EP2007/011401 (WO 2008/077639 A1).
International Search Report mailed Jul. 31, 2009, for International Application No. PCT/EP2009/004404 (WO 2009/153043).
International Search Report mailed Apr. 16, 2010, for International Application No. PCT/EP2010/000270 (WO 2010/083975).
International Search Report for International Application No. PCT/EP2010/001549 dated May 31, 2010.
International Search Report for International Application No. PCT/EP2010/001548 dated Nov. 18, 2010.
International Search Report for International Application No. PCT/EP2010/001550 mailed Apr. 23, 2010.
International Search Report for International Application No. PCT/EP2010/006283.
John, GT et al., "Leflunomide therapy for cytomegalovirus disease in renal allograft recipients," *Transplantation*, 77(9):1460-1461 (2003).
Kremer, JM, "Concomitant leflunomide therapy in patients with active rheumatoid arthritis despite stable doses of methotrexate," *Annals of Internal Medicine*, 137(9):726-733 (2002).
Kremer, JM, "Methotrexate and leflunomide: biochemical basis for combination therapy in the treatment of rheumatoid arthritis," *Seminars in Arthritis and Rheumatism*, 29(1):14-26 (1999).
Kulkarni, OP et al., "4SC-101, a novel small molecule dihydroorotate dehydrogenase inhibitor, suppresses systemic lupus erythematosus in MRL-(Fas)lpr mice," *The American Journal of Pathology*, 176(6):2840-2847 (2010).
Leban, J. et al., "Biphenyl-4-ylcarbamoyl thiophene carboxylic acids as potent DHODH inhibitors," *Bioorganic & Medicinal Chemistry Letters*, 16(2):267-270 (2006).
Liu, S. et al., "Structures of human dihydroorotate dehydrogenase in complex with antiproliferative agents," *Structure*, 8(1):25-33 (2000).
Löffler, M. et al., "Dihydroorotat-ubiquinone oxidoreductase links mitochondria in the biosynthesis of pyrimidine nucleotides," *Molecular and Cellular Biochemistry*, 174:125-129 (1997).
Majithia, V. et al., "Successful treatment of sarcoidosis with leflunomide," *Rheumatology*, 42:700-702 (2003).
Manna, SK et al., "Leflunomide suppresses TNF-induced cellular responses: effects on NF-{kappa}B, activator protein-1, c-Jun N-terminal protein kinase, and apoptosis," *Journal of Immunology*, 165:5962-5969 (2000).
McRobert, L. et al., "RNA interference (RNAi) inhibits growth of *Plasmodium falciparum*," *Molecular & Biochemical Parasitology*, 19:273-278 (2002).
Mehta, V. et al., "Leflunomide," *Indian J. Dermatol. Venereol. Leprol.*, 75(4): 422-425 (2009).
Metzler, C. et al., "Maintenance of remission with leflunomide in wegener's granulomatosis," *Rheumatology*, 43:315-320 (2004).
Miyaura, N. et al., "Palladium-catalyzed cross-coupling reactions of organoboron compounds," *Chemical Reviews*, 35:2457-2483 (1995).
Notice of Allowance dated May 2, 2012, in U.S. Appl. No. 12/520,237.
O'Connor, PW et al., "A phase II study of the safety and efficacy of teriflunomide in multiple sclerosis with relapses," *Neurology*, 66:894-900 (2006).
Office Action dated Feb. 28, 2011, in U.S. Appl. No. 12/520,237.
Office Action dated Jun. 2, 2011, in U.S. Appl. No. 12/520,237.
Office Action dated Nov. 4, 2011, in U.S. Appl. No. 12/520,237.
Office Action dated Jun. 4, 2012, in U.S. Appl. No. 12/999,698.
Phillips, Margaret A. et al., "Triazolopyrimidine-based dihydroorotate dehydrogenase inhibitors with potent and selective activity against the malaria parasite *Plasmodium falciparum*," *J. Med. Chem.*, 51:3649-3653 (2008).
Sanders, S. et al., "Leflunomide for the treatment of rheumatoid arthritis and autoimmunity," *American Journal of the Medical Sciences*, 323(4):190-193 (2002).
Schläpfer, E. et al., "Anti-HIV-1 activity of leflunomide: a comparison with mycophenolic acid and hydroxyurea," 6*AIDS*, 17(11):1613-1620 (2003).
Silverman, E. et al., "Long-term open-label preliminary study of the safety and efficacy of leflunomide in patients with polyarticular-course juvenile rheumatoid arthritis," *Arthritis & Rheumatism*, 52(2):554-562 (2005).
Silverman, RB, "The organic chemistry of drug design and drug action," Chapter 2, Section 2.2, pp. 29-32, Elsevier Academic Press (2004).
Spano, R. et al., "Preparation and pharmacology of some derivatives of 2-aminonicotinic," *Farmaco, Edizione Scientifica, Societe Chimica Italiana*, Pavia, IT, 26(9): 844-849 (1971).
English Language Caplus Abstract for SPANO, R. et al. "Preparation and pharmacology of some derivatives of 2-aminonicotinic," *Farmaco, Edizione Scientifica*, Societa Chimica Italiana, Pavia, IT, 26(9): 844-849 (1971).
Stahl, P.H. et al., "Tromethamine," *Handbook of Pharmaceutical Salts Properties, Selection and Use*, pp. 324-325, XP002214621 (2002).
Tlacuilo Parra, JA et al., "Leflunomide in the treatment of psoriasis: results of a phase II open trial," *British Journal of Dermatology*, 150: 970-976 (2004).
Urushibara, M. et al., "The antirheumatic drug leflunomide inhibits osteoclastogenesis by interfering with receptor activator of NF-κB ligand-stimulated induction of nuclear factor of activated T cells c1," *Arthritis & Rheumatism*, 50(3):794-804 (2004).
Vyas, V.K. et al., "Recent developments in the medicinal chemistry and therapeutic potential of dihydroorotate dehydrogenase (DHODH) inhibitors", *Mini-Reviews in Medicinal Chemistry*, 11:1039-1055 (2011).
Weinblatt, ME et al., "Pharmacokinetics, safety, and efficacy of combination treatment with methotrexate and leflunomide in patients with active rheumatoid arthritis," *Arthritis & Rheumatism*, 42(7):1322-1328 (1999).
International Search Report from International Application No. PCT/EP2008/006573, dated Oct. 20, 2008.
Ando et al., in Remington: The Science and Practice of Pharmacy. 20th Edition. Alfonso R. Gennaro (Ed.), Philadelphia, PA: Lippincott Willliams & Wilkins, 2000; pp. 704-712.
Bastin, R.J. et al., "Salt Selection and Optimisation Procedures for Pharmaceutical New Chemical Entities" Organic Process Research & Development (2000) 4:427-435.
Cutolo, M. et al. "Anti-inflammatory mechanisms of methotrexate in rheumatoid arthritis," Ann. Rheum. Dis., 60:729-735 (2001).
English translation of Grigoreva, "Catalytic Activity," Khimiko-Farmatsevticheskii Zhurnal (1978) 12(4):7-18.

Morissette, S.L. et al. "High-throughput crystallization: polymorphs, salts, co-crystals and solvates of pharmaceutical solids," Advanced Drug Delivery Reviews, 56:275-300 (2004).

Mroczkowski, P.J. et al., "Methotrexate and leflunomide combination therapy for patients with active rheumatoid arthritis", Clin. Exp. Rheumatol, 1999, 17(Suppl. 18): S66-S68.In.

Notice of Allowability (Corrected) dated Jun. 26, 2012, in U.S. Appl. No. 12/520,237.

Notice of Allowance dated May 1, 2013, in U.S. Appl. No. 13/256,127.

Office Action (Restriction Requirement) dated Sep. 13, 2012, in U.S. Appl. No. 13/145,628.

Office Action dated Sep. 28, 2012, in U.S. Appl. No. 12/999,698.

Office Action (Restriction Requirement) dated Jun. 14, 2012, in U.S. Appl. No. 13/256,127.

Office Action dated Sep. 21, 2012, in U.S. Appl. No. 13/256,127.

Office Action (Restricted Requirement) dated Apr. 2, 2013, in U.S. Appl. No. 13/567,437.

Office Action (Restriction Requirement) dated Apr. 12, 2013, in U.S. Appl. No. 12/256,349.

Patani et al., "Bioisosterism: A Rational Approach in Drug Design," Chem. Rev. 1996, 3147-3176, Saag, K. et al. "American College of Rheumatology 2008 Recommendations for the Use of Nonbiologic and Biologic Disease-Modifying Antirheumatic Drugs in Rheumatoid Arthritis" *Arthritis & Rheumatism* 59 (6), 762-784 (2008).

Silverman, RB "The Organic Chemistry of Drug Design and Drug Action," Section 2.1, pp. 9, Elsevier Academic Press (2004).

Swierkot, Jerzy et al., Methotrexate in rheumatoid arthritis, Pharmacological Reports, Institute of Pharmacological Polish Academy of Sciences, 2006, 58,473-492.

Vippagunta, S.R. et al. "Crystalline Solids," Advanced Drug Delivery Reviews, 48:3-26 (2001).

Wahl, C. et al. "Sulfasalazine: a Potent and Specific inhibitor of Nuclear Factor Kappa B," J. Clin. Invest., 101(5): 1163-1174 (1998).

\* cited by examiner

AZABIPHENYLAMINOBENZOIC ACID DERIVATIVES AS DHODH INHIBITORS

This application is a national stage filing under 35 U.S.C. §371 of International Application No. PCT/EP2008/006573 filed on 8 Aug. 2008, which claims priority of Spanish Patent Application No. P200702261, filed on 10 Aug. 2007, and also claims priority of European Patent Application No. 08382011.8, filed on 13 Mar. 2008. The contents of all three applications are incorporated herein by reference.

The present invention relates to new inhibitors of the dihydroorotate dehydrogenase (DHODH). These compounds are useful in the treatment, prevention or suppression of diseases and disorders known to be susceptible to improvement by inhibition of dihydroorotate dehydrogenase, such as autoimmune diseases, immune and inflammatory diseases, destructive bone disorders, malignant neoplastic diseases, angiogenic-related disorders, viral diseases, and infectious diseases.

The enzyme dihydroorotate dehydrogenase (DHODH) is the enzyme that catalyzes the fourth step in the pyrimidine biosynthetic pathway namely the conversion of dihydroorotate to orotate concomitantly with a electron transfer to ubiquinone (cofactor Q) via a flavin mononucleotide intermediate (Loffler et al Mol Cell Biochem, 1997). In contrast to parasites (*Plasmodium falciparum*) (McRobert et al Mol Biochem Parasitol 2002) and bacteria (*E. coli*) which exclusively have this de novo pathway as the source of pyrimidines, mammal cells have an additional salvage pathway.

During homeostatic proliferation, the salvage pathway which is independent of DHODH seems sufficient for the cellular supply with pyrimidine bases. Only, cells with a high turnover and particularly T and B lymphocytes need the de novo pathway to proliferate. In these cells, DHODH inhibition stops the cell cycle progression suppressing DNA synthesis and consequently cell proliferation (Breedveld F C et al Ann Rheum Dis 2000).

Therefore, inhibitors of DHODH show beneficial immunosuppressant and antiproliferative effects in human diseases characterized by abnormal and uncontrollable cell proliferation causing chronic inflammation and tissue destruction.

In addition to abolish lymphocyte proliferation inhibitors of DHODH (i.e. teriflunomide, Maritimus (FK778) and brequinar) have an anti-inflammatory action by inhibition of cytokine production and nuclear factor (NF)-kB-signalling, monocyte migration and increased production of transforming growth factor beta-1 and induces a shift from T helper cell type 1 (Th1) to type 2 (Th2) subpopulation differentiation (Manna et al. J Immunol 2000) (Dimitrova et al J. Immunol. 2002). Furthermore, the osteoclast differentiation mediated by RANKL decreased by DHODH inhibition (Urushibara et al. Arthritis Rheum 2004).

In co-crystallisation experiments with two inhibitors of DHODH that reached clinical trials, Brequinar (Dexter D. L. et al.; Cancer Res. 1985) and Teriflunomide (A77-1726), were both found to bind in a common site, that is also believed to be the binding site of the cofactor ubiquinone (Liu et al; Struc. Fold. Des. 2000).

Leflunomide sold under the trade name Arava (EP 0 780 128, WO 97/34600), was the first DHODH inhibitor that reached the market place. Leflunomide is the prodrug of teriflunomide, which is the active metabolite inhibiting human DHODH with a moderate potency (Fox et al, J. Rheumatol. Suppl. 1998).

Leflunomide is a DMARD (disease modifying anti-rheumatic drug) from Aventis, which was approved by the FDA for the treatment of rheumatoid arthritis in 1998 and by the EMEA for the treatment of psoriatic arthritis in 2004. Currently Leflunomide is under active development for the treatment of systemic lupus erythematosus, Wegener's granulomatosis (Metzler et al; Rheumatology 2004; 43(3), 315-320) and HIV infection. Moreover, teriflunomide, its active metabolite is efficacious in multiple sclerosis and right now is in Phase III clinical trials (O'Connor et al Neurology 2006).

Other data are emerging in other closely related diseases such as ankylosing spondilitis (Haibel et al.; Ann. Rheum. Dis. 2005), polyarticular juvenile idiopathic arthritis (Silverman et al.; Arthritis Rheum. 2005) and Sarcoidosis (Baughman et al.; Sarcoidosis Vasc. Diffuse Lung Dis. 2004). Furthermore, leflunomide and FK778 have shown and excellent antiviral activity against cytomegalovirus. Leflunomide is currently indicated as second-line therapy for cytomegalovirus disease after organ transplantation (John et al Transplantation 2004). In addition Leflunomide reduces HIV replication by about 75% at concentration that can be obtained with conventional dosing (Schlapfer E et al. AIDS 2003).

In view of the physiological effects mediated by inhibition of dehydroorotate dehydrogenase, several DHODH inhibitors have been recently disclosed for the treatment or prevention of autoimmune diseases, immune and inflammatory diseases, destructive bone disorders, malignant neoplastic diseases, angiogenic-related disorders, viral diseases, and infectious diseases. See for example WO 06/044741; WO 06/022442; WO 06/001961, WO 04/056747, WO 04/056746, WO 03/006425, WO 02/080897 and WO 99/45926.

Diseases or disorders in which DHODH inhibition plays a role include without limitation autoimmune diseases, immune and inflammatory diseases, destructive bone disorders, malignant neoplastic diseases, angiogenic-related disorders, viral diseases, and infectious diseases.

Autoimmune diseases which may be prevented or treated include but are not limited to rheumatoid arthritis, psoriatic arthritis, systemic lupus erythematosus, multiple sclerosis, psoriasis, ankylosing spondilytis, Wegener's granulomatosis, polyarticular juvenile idiopathic arthritis, inflammatory bowel disease such as ulcerative colitis and Crohn's disease, Reiter's syndrome, fibromyalgia and type-1 diabetes.

Immune and inflammatory diseases which may be prevented or treated include but are not limited to asthma, COPD, respiratory distress syndrome, acute or chronic pancreatitis, graft versus-host disease, chronic sarcoidosis, transplant rejection, contact dermatitis, atopic dermatitis, allergic rhinitis; allergic conjunctivitis, Behcet syndrome, inflammatory eye conditions such as conjunctivitis and uveitis.

Destructive bone disorders which may be prevented or treated include but are not limited to osteoporosis, osteoarthritis and multiple myeloma-related bone disorder. Malignant neoplastic diseases that may be prevented or treated include but are not limited to prostate, ovarian and brain cancer.

Agiogenesis-related disorders that may be prevented or treated include but are not limited to hemangiomas, ocular neovascularization, macular degeneration or diabetic retinopathy. Viral diseases which may be prevented or treated include but are not limited to HIV infection, hepatitis and cytomegalovirus infection.

Infectious diseases which may be prevented or treated include but are not limited to sepsis, septic shock, endotoxic shock, Gram negative sepsis, toxic shock syndrome, Shigellosis and other protozoal infestations such as malaria.

It has now been found that certain azabiphenylaminobenzoic acid derivatives are novel potent inhibitors of DHODH and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible to improvement by inhibition of DHODH wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis and methods of treatment of pathological conditions or diseases susceptible to amelioration by inhibition of DHODH wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis comprising the administration of the compounds of the invention to a subject in need of treatment.

Thus, the present invention is directed to compounds of formula (I) for use in the treatment or prevention of a pathological condition or disease susceptible to amelioration by inhibition of dehydroorate dehydrogenase

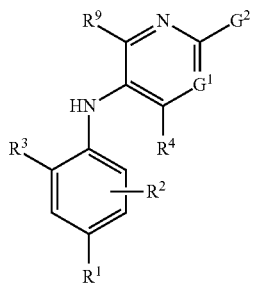

wherein:
$R^1$ is selected from the group consisting of hydrogen atoms, halogen atoms, $C_{1-4}$ alkyl, $C_{3-4}$ cycloalkyl, —$CF_3$ and —$OCF_3$,
$R^2$ is selected from the group consisting of hydrogen atoms, halogen atoms and $C_{1-4}$ alkyl group,
$R^3$ is selected from the group consisting of —$COOR^5$, —$CONHR^5$, tetrazolyl, —$SO_2NHR^5$ and —$CONHSO_2R^5$ groups, wherein $R^5$ is selected from the group consisting of a hydrogen atom and linear or branched $C_{1-4}$ alkyl groups,
$R^4$ is selected from the group consisting of a hydrogen atom, and a $C_{1-4}$ alkyl group,
$R^9$ is selected from the group consisting of a hydrogen atom and a phenyl group,
$G^1$ represents a group selected from N and $CR^6$ wherein $R^6$ is selected from the group consisting of hydrogen atoms, halogen atoms, $C_{1-4}$ alkyl, $C_{3-4}$ cycloalkyl, $C_{1-4}$ alkoxy, —$CF_3$, —$OCF_3$, monocyclic N-containing $C_{5-7}$ heteroaryl, monocyclic N-containing $C_{3-7}$ heterocyclyl groups and a $C_{6-10}$ aryl group which is optionally substituted with one or more substituents selected from halogen atoms and a $C_{1-4}$ alkyl group,
$G^2$ represents a group selected from:
    a hydrogen atom, a hydroxy group, a halogen atom, a $C_{3-4}$ cycloalkyl group, a $C_{1-4}$ alkoxy group and —$NR^aR^b$, wherein
    $R^a$ represents a $C_{1-4}$ alkyl group and $R^b$ is selected from a group consisting of $C_{1-4}$ alkyl group and $C_{1-4}$ alkoxy-$C_{1-4}$ alkyl group, or
    $R^a$ and $R^b$ together with the nitrogen atom to which they are attached form a saturated 6 to 8 membered heterocyclic ring optionally containing one oxygen atom as an additional heteroatom.

a monocyclic or bicyclic 5 to 10 membered heteroaromatic ring containing one or more nitrogen atoms which is optionally substituted by one or more substituents selected from halogen atoms, $C_{1-4}$ alkyl, $C_{1-4}$ alkoxy, $C_{3-4}$ cycloalkyl, $C_{3-4}$ cycloalkoxy, —$CF_3$, —$OCF_3$, and —$CONR^7R^8$, wherein $R^7$ and $R^8$ are independently selected from hydrogen atom, linear or branched $C_{1-4}$ alkyl group, $C_{3-7}$ cycloalkyl group, or $R^7$ and $R^8$ together with the nitrogen atom to which they are attached form a group of formula

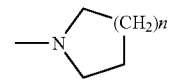

wherein n is an integer from 0 to 3,
and
    a phenyl group which is optionally substituted by one or more substituents selected from halogen atoms, $C_{1-4}$ alkyl, hydroxy, $C_{1-4}$ alkoxy, $C_{3-4}$ cycloalkyl, $C_{3-4}$ cycloalkoxy, cyano, —$CF_3$, —$OCF_3$, —$CONR^7R^8$, oxadiazolyl, triazolyl, pyrazolyl and imidazolyl groups, wherein the oxadiazolyl, triazolyl, pyrazolyl and imidazolyl groups are optionally substituted by $C_{1-4}$ alkyl or $C_{3-7}$ cycloalkyl group and wherein $R^7$ and $R^8$ are independently selected from hydrogen atom, linear or branched $C_{1-4}$ alkyl group, a $C_{3-7}$ cycloalkyl group, or $R^7$ and $R^8$ together with the nitrogen atom to which they are attached form a group of formula

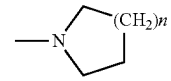

wherein n is an integer from 0 to 3
or, $G^2$ together with $R^6$ form a non-aromatic $C_{5-10}$ carbocyclic group or a $C_{6-10}$ aryl group,
and the pharmaceutically acceptable salts and N-oxides thereof.

As used herein the term alkyl embraces optionally substituted, linear or branched hydrocarbon radicals having 1 to 4 carbon atoms. Preferred substituents on the alkyl groups are halogen atoms and hydroxy groups.

Examples include methyl, ethyl, n-propyl, i-propyl, n-butyl, sec-butyl and tert-butyl radicals.

As used herein the term alkoxy embraces optionally substituted, linear or branched oxygen containing radicals each having 1 to 4 carbon atoms. Preferred substituents on the alkoxy groups are halogen atoms and hydroxy groups.

Examples include methoxy, ethoxy, n-propoxy, i-propoxy, n-butoxy, sec-butoxy and tert-butoxy radicals.

As used herein, the term cycloalkyl embraces optionally substituted saturated carbocyclic radicals and, unless otherwise specified, a cycloalkyl radical typically has from 3 to 7 carbon atoms, preferably from 3 to 4 carbon atoms.

Examples include cyclopropyl, cyclobutyl, cyclopentyl, cyclohexyl and cycloheptyl. When a cycloalkyl radical carries 2 or more substituents, the substituents may be the same or different. Preferred substituents on the cycloalkyl groups are halogen atoms and hydroxy groups.

As used herein, the term cycloalkoxy embraces saturated oxy-containing carbocyclic radicals and, unless otherwise specified, a cycloalkoxy radical typically has from 3 to 8 carbon atoms, preferably from 3 to 4 carbon atoms.

Examples include cyclopropyloxy, cyclobutyloxy, cyclopentyloxy, cyclohexyloxy and cycloheptyloxy. When a cycloalkoxy radical carries 2 or more substituents, the substituents may be the same or different. Preferred substituents on the cycloalkoxy groups are halogen atoms and hydroxy groups.

As used herein, the term aryl radical embraces typically optionally substituent $C_6$-$C_{10}$ monocyclic or polycyclic aryl radical such as phenyl, naphthyl, anthranyl and phenanthryl. Phenyl is preferred.

A said optionally substituted aryl radical is typically unsubstituted or substituted with 1, 2 or 3 substituents which may be the same or different. The substituents are preferably selected from halogen atoms, preferably fluorine atoms, hydroxy groups, alkoxycarbonyl groups in which the alkyl moiety has from 1 to 4 carbon atoms, hydroxycarbonyl groups, carbamoyl groups, nitro groups, cyano groups, $C_1$-$C_4$ alkyl groups, $C_1$-$C_4$ alkoxy groups and $C_1$-$C_4$ hydroxyalkyl groups. When an aryl radical carries 2 or more substituents, the substituents may be the same or different. Unless otherwise specified, the substituents on an aryl group are typically themselves unsubstituted.

As used herein, the terms heteroaryl and heteroaromatic ring are used interchangeably and typically embrace a 5- to 14-membered ring system, preferably a 5- to 10-membered ring system, comprising at least one heteroaromatic ring and containing at least one heteroatom selected from O, S and N. A heteroaryl radical may be a single ring (monocyclic) or two or more fused rings (polycyclic) wherein at least one ring contains a heteroatom.

As used herein, the term heterocyclyl radical embraces typically a non-aromatic, saturated or unsaturated $C_3$-$C_{10}$ carbocyclic ring system, such as a 5, 6 or 7 membered radical, in which one or more, for example 1, 2, 3 or 4 of the carbon atoms preferably 1 or 2 of the carbon atoms are replaced by a heteroatom selected from N, O and S. Saturated heterocyclyl radicals are preferred.

As used herein, the term halogen atom embraces chlorine, fluorine, bromine or iodine atoms typically a fluorine, chlorine or bromine atom. The term halo when used as a prefix has the same meaning.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic, cyclohexylsulfamic (cyclamic) or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X) is associated with the positive charge of the N atom. $X^-$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

In the particular case where $R^3$ is a COOH group, it is advantageous to have salts derived from the corresponding carboxylic acid by replacement of the hydrogen atom of the carboxylic group with a cation derived from a pharmaceutically acceptable base as described above.

As used herein, an N-oxide is formed from the tertiary basic amines or imines present in the molecule, using a convenient oxidising agent.

Preferably, the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis.

Typically, $R^1$ is selected from the group consisting of hydrogen atoms, fluorine atoms, chlorine atoms, bromine atoms, $C_{1-4}$ alkyl, $C_{3-4}$ cycloalkyl and —$CF_3$ groups.

Typically $R^2$ is selected from the group consisting of a hydrogen, halogen atom and a methyl group.

Typically, $G^1$ is selected from the group consisting of nitrogen atoms, CCl, CF, CH, C(CH$_3$), C(cyclopropyl), C(phenyl) and C(CF$_3$) groups.

Typically $G^2$ represents a group selected from:
a hydrogen atom, a halogen atom, a $C_{3-4}$ cycloalkyl group, a $C_{1-2}$ alkoxy group and —$NR^aR^b$, wherein
$R^a$ represents a $C_{1-2}$ alkyl group and $R^b$ is selected from the group consisting of $C_{1-2}$ alkyl groups and $C_{1-2}$ alkoxy-$C_{1-2}$ alkyl groups, or
$R^a$ and $R^b$ together with the nitrogen atom to which they are attached form a saturated 6 or 7 membered heterocyclic ring optionally containing one oxygen atom as an additional heteroatom,
a monocyclic or bicyclic 5 to 10 membered heteroaromatic ring containing one or two nitrogen atoms which is optionally substituted by one or more substituents selected from halogen atoms and $C_{1-4}$ alkyl groups, and
a phenyl group which is optionally substituted by one, two or three substituents selected from halogen atoms, $C_{1-4}$ alkyl, hydroxyl, $C_{1-4}$ alkoxy, $C_{3-4}$ cycloalkyl, $C_{3-4}$ cycloalkoxy, cyano, —$CF_3$, —$OCF_3$, —$CONR^7R^8$ and oxadiazolyl groups, wherein the oxadiazolyl group is optionally substituted by a $C_{1-4}$ alkyl or a $C_{3-7}$ cycloalkyl group and wherein $R^7$ and $R^8$ are independently selected from hydrogen atoms, linear or branched $C_{1-4}$ alkyl groups, $C_{3-4}$ cycloalkyl groups or $R^7$ and $R^8$ together with the nitrogen atom to which they are attached form a group of formula

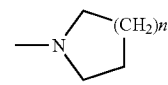

wherein n is 1 or 2,
or, $G^2$ together with $R^8$ form a non-aromatic $C_6$ carbocyclic group or a phenyl group.

More typically G² represents a group selected from:
a hydrogen atom, a fluorine atom, a cyclopropyl group, a methoxy group, —NMeEt, —NEt₂, —N(Me)-(CH₂)₂—O—CH₃, 6-morpholinyl, azepan-1-yl and piperidin-1-yl,
a pyridinyl, pyrimidinyl, quinolinyl or pyrazinyl ring optionally substituted with one or two substituents selected from Me and F
and
a phenyl group which is optionally substituted by one, two or three substituents selected from fluorine, chlorine, methyl, hydroxy, methoxy, ethoxy, isopropyloxy, cyclopropyl, cyclopropyloxy, cyano, —CF₃, —OCF₃, —CONR⁷R⁸ and oxadiazolyl groups, wherein the oxadiazolyl group is optionally substituted by a methyl group and wherein R⁷ and R⁸ are independently selected from hydrogen atom, methyl group, isopropyl group, cyclopropyl group, or R⁷ and R⁸ together with the nitrogen atom to which they are attached form a group of formula

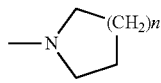

wherein n is 1,
or, G² together with R⁶ forms non-aromatic C₆ carbocyclic group or a phenyl group.

In one embodiment of the present invention, R¹ is selected from the group consisting of hydrogen atoms, halogen atoms, C₁₋₄ alkyl, C₃₋₄ cycloalkyl, —CF₃ and —OCF₃,
R² is selected from the group consisting of hydrogen atoms, halogen atoms and C₁₋₄ alkyl group,
R³ is selected from the group consisting of —COOR⁵, —CONHR⁶, tetrazolyl, —SO₂NHR⁵ and —CONHSO₂R⁵ groups, wherein R⁵ is selected from the group consisting of a hydrogen atom and lineal or branched C₁₋₄ alkyl groups,
R⁴ is selected from the group consisting of a hydrogen atom and a C₁₋₄ alkyl group
R⁹ represents a hydrogen atom,
G¹ represents a group selected from N and CR⁶ wherein R⁶ is selected from the group consisting of hydrogen atoms, halogen atoms, C₁₋₄ alkyl, C₃₋₄ cycloalkyl, C₁₋₄ alkoxy, —CF₃, —OCF₃, monocyclic N-containing C₅₋₇ heteroaryl, monocyclic N-containing C₃₋₇ heterocyclyl groups and a C₆₋₁₀ aryl group which is optionally substituted with one or more substituents selected from halogen atoms and a C₁₋₄ alkyl group,
G² represents a group selected from:
a monocyclic or bicyclic 5 to 10 membered heteroaromatic ring containing a nitrogen atom which is optionally substituted by one or more substituents selected from halogen atoms, C₁₋₄ alkyl, C₁₋₄ alkoxy, C₃₋₄ cycloalkyl, C₃₋₄ cycloalkoxy, —CF₃, —OCF₃, and —CONR⁷R⁶, wherein R⁷ and R⁸ are independently selected from hydrogen atom, lineal or branched C₁₋₄ alkyl group, C₃₋₇ cycloalkyl group, or R⁷ and R⁸ together with the nitrogen atom to which they are attached form a group of formula

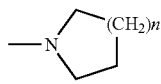

wherein n is an integer from 0 to 3,
and
a phenyl group which is optionally substituted by one or more substituents selected from halogen atoms, C₁₋₄ alkyl, C₁ alkoxy, C₃₋₄ cycloalkyl, C₃₋₄ cycloalkoxy, —CF₃, —OCF₃, —CONR⁷R⁸, oxadiazolyl, triazolyl, pyrazolyl and imidazolyl groups, wherein the oxadiazolyl, triazolyl, pyrazolyl and imidazolyl groups are optionally substituted by C₁₋₄ alkyl or C₃₋₇ cycloalkyl group and wherein R⁷ and R⁸ are independently selected from hydrogen atom, lineal or branched C₁₋₄ alkyl group, a C₃₋₇ cycloalkyl group, or R⁷ and R⁸ together with the nitrogen atom to which they are attached form a group of formula

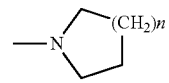

wherein n is an integer from 0 to 3
and the pharmaceutically acceptable salts and N-oxides thereof.

Typically, R¹ is selected from the group consisting of C₁₋₄ alkyl, C₃₋₄ cycloalkyl and —CF₃, preferably methyl and cyclopropyl group, more preferably a cyclopropyl group.
Typically, R² is selected from a hydrogen or halogen atom, preferably a hydrogen atom.
Typically, R³ is selected from COOR^S, —CONHR⁵ and tetrazolyl group; preferably R³ is a COOH group.
Typically, R⁴ represents a hydrogen atom or a methyl group, preferably a hydrogen atom.
Typically, R⁹ represents a hydrogen atom.
Typically, G¹ represents a group selected from N, CH, C(CH₃), C(cyclopropyl), C(phenyl) or C(CF₃) group.
Typically, G² is selected from the group consisting of a methoxy group, a cyclopropyl group and optionally substituted phenyl, pyridyl, quinolynyl, pyrimidinyl and pyrazinyl groups, more preferably, G² is selected from the group consisting of optionally substituted phenyl, pyridyl, quinolynyl, pyrimidinyl and pyrazinyl groups, being most preferably an optionally substituted phenyl, 4-pyridyl, 5-quinolynyl and 2-pyrazinyl groups.

In yet another embodiment of the present invention, R¹ is selected from a methyl or cyclopropyl group, R² represents a hydrogen atom, R³ is a COOH group, R⁴ represents a hydrogen atom or a methyl group, G¹ is selected from N, CH, C(CH₃), C(cyclopropyl), C(phenyl) and C(CF₃) groups, and G² represents a group selected from the group consisting of an optionally substituted phenyl, 4-pyridyl, 5-quinolynyl y 2-pyrazinyl groups, more preferably R⁹ represent a hydrogen group.

In yet another embodiment of the present invention, R¹ is selected from a methyl or cyclopropyl group, R² represents a hydrogen atom, R³ is a COOH group, R⁴ represents a hydrogen atom, G¹ is selected from nitrogen atoms and CH, C(CH₃) and C(CF₃) groups and G² represents a phenyl group optionally substituted with one or two substituents selected from chloro, fluoro, methoxy, ethoxy, isopropoxy, trifluoromethoxy and —CONR⁷R⁸, wherein R⁷ is hydrogen and R⁸ is cyclopropyl or R⁷ and R⁸ together with the nitrogen atom to which they are attached form a group of formula

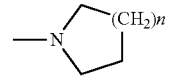

wherein n is 1.
Particular individual compounds of the invention include:
5-cyclopropyl-2-(2-phenylpyrimidin-5-ylamino)benzoic acid
2-(6-Cyclopropyl-5-methylpyridin-3-ylamino)-5-methylbenzoic acid
5-(2-Carboxy-4-cyclopropylphenylamino)-3-methyl-2-phenylpyridine 1-oxide 5-Methyl-2-(6-(3-(trifluoromethyl)phenyl)pyridin-3-ylamino)benzoic acid
5-cyclopropyl-2-(6-hydroxy-5-phenylpyridin-3-ylamino)benzoic acid
5-cyclopropyl-2-(2-(2,6-difluoro-4-hydroxyphenyl)pyrimidin-5-ylamino)benzoic acid
5-Cyclopropyl-2-(6-methoxy-5-phenylpyridin-3-ylamino)benzoic acid
2-(5-Fluoro-6-phenylpyridin-3-ylamino)-5-methylbenzoic acid
2-(6-(Ethyl(methyl)amino)-5-methylpyridin-3-ylamino)-5-methylbenzoic acid
5-Cyclopropyl-2-(3'-fluoro-2,4'-bipyridin-5-ylamino)benzoic acid
2-(6-(Diethylamino)-5-methylpyridin-3-ylamino)-5-methylbenzoic acid
2-(6-((2-Methoxyethyl)(methyl)amino)-5-methylpyridin-3-ylamino)-5-methylbenzoic acid
2-(5-Chloro-6-phenylpyridin-3-ylamino)-5-methylbenzoic acid
5-Cyclopropyl-2-(2-(2-cyclopropylphenyl)pyrimidin-5-ylamino)benzoic acid
5-cyclopropyl-2-(5-phenylpyridin-3-ylamino) benzoic acid
5-methyl-2-(quinolin-3-ylamino)benzoic acid
5-methyl-2-(5,6,7,8-tetrahydroquinolin-3-ylamino)benzoic acid
2-(5-Chloro-2-phenylpyridin-3-ylamino)-5-methylbenzoic acid
5-Cyclopropyl-2-(5,6-diphenylpyridin-3-ylamino)benzoic acid
5-cyclopropyl-2-(2-(2,6-difluorophenyl)pyrimidin-5-ylamino)benzoic acid
5-Cyclopropyl-2-(5-methylpyridin-3-ylamino)benzoic acid
2-(2-(3-Cyclopropoxyphenyl)pyrimidin-5-ylamino)-5-cyclopropylbenzoic acid
5-Methyl-2-(6-morpholinopyridin-3-ylamino)benzoic acid
5-Methyl-2-(5-methyl-6-morpholinopyridin-3-ylamino)benzoic acid
5-cyclopropyl-2-(6-cyclopropyl-5-phenylpyridin-3-ylamino)benzoic acid
2-(6-(2-Cyclopropylphenyl)-5-methylpyridin-3-ylamino)-5-methylbenzoic acid
2-(6-(2-Cyanophenyl)-5-methylpyridin-3-ylamino)-5-methylbenzoic acid
2-(2-(3-Chlorophenyl)pyrimidin-5-ylamino)-5-cyclopropylbenzoic acid
5-Methyl-2-(6-phenyl-5-(trifluoromethyl)pyridin-3-ylamino)benzoic acid
5-Methyl-2-(5-methyl-6-(piperidin-1-yl)pyridin-3-ylamino)benzoic acid
2-(6-(Azepan-1-yl)-5-methylpyridin-3-ylamino)-5-methylbenzoic acid
2-(6-(3-Methoxyphenyl)-5-phenylpyridin-3-ylamino)-5-methylbenzoic acid
2-(2,3'-bipyridin-5-ylamino)-5-cyclopropylbenzoic acid
2-(3'-chloro-2,4'-bipyridin-5-ylamino)-5-methylbenzoic acid
5-Methyl-2-(3-methyl-2,2'-bipyridin-5-ylamino)benzoic acid
2-(5,6-Difluoropyridin-3-ylamino)-5-methylbenzoic acid
2-(6-(3-Methoxyphenyl)pyridin-3-ylamino)benzoic acid
2-(6-(3-Ethoxyphenyl)pyridin-3-ylamino)benzoic acid
2-(6-(3-Ethoxyphenyl)pyridin-3-ylamino)-5-fluorobenzoic acid
2-(6-(3-Ethoxyphenyl)-5-methylpyridin-3-ylamino)benzoic acid
2-(6-(3-Ethoxyphenyl)pyridin-3-ylamino)-5-methylbenzoic acid
2-(6-(3-Ethoxyphenyl)-5-methylpyridin-3-ylamino)-5-methylbenzoic acid
2-(6-(3-Ethoxy-2-fluorophenyl)pyridin-3-ylamino)benzoic acid
2-(6-(3-Ethoxyphenyl)-4-methylpyridin-3-ylamino)-5-methylbenzoic acid
2-(6-(3-Ethoxyphenyl)-4-methylpyridin-3-ylamino)benzoic acid
5-Bromo-2-(6-(3-ethoxyphenyl)pyridin-3-ylamino)benzoic acid
5-Chloro-2-(6-(3-ethoxyphenyl)pyridin-3-ylamino)benzoic acid
2-(6-(5-Ethoxy-2-fluorophenyl)pyridin-3-ylamino)benzoic acid
2-(6-(3-Ethoxyphenyl)-5-methylpyridin-3-ylamino)-5-(trifluoromethyl)benzoic acid
2-(6-(3-Methoxyphenyl)-5-methylpyridin-3-ylamino)-5-(trifluoromethyl)benzoic acid
2-(6-(3-Methoxyphenyl)-5-methylpyridin-3-ylamino)-5-methylbenzoic acid
2-(6-(3-Methoxyphenyl)-5-methylpyridin-3-ylamino)-6-methylbenzoic acid
5-Fluoro-2-(6-(3-methoxyphenyl)-5-methylpyridin-3-ylamino)benzoic acid
2-(6-(5-Ethoxy-2-fluorophenyl)pyridin-3-ylamino)-5-methylbenzoic acid
2-(6-(2-Fluoro-5-methoxyphenyl)-5-methylpyridin-3-ylamino)-5-methylbenzoic acid
Ethyl 2-(6-(2-fluoro-5-methoxyphenyl)-5-methylpyridin-3-ylamino)-5-methylbenzoate
2-(6-(2-Fluorophenyl)pyridin-3-ylamino)-5-methylbenzoic acid
2-(6-(3-Methoxyphenyl)-5-phenylpyridin-3-ylamino)-5-methylbenzoic acid
Ethyl 2-(6-(3-methoxyphenyl)-5-phenylpyridin-3-ylamino)-5-methylbenzoate
5-Methyl-2-(5-methyl-6-phenylpyridin-3-ylamino)benzoic acid
Ethyl 5-methyl-2-(5-methyl-6-phenylpyridin-3-ylamino)benzoate
5-Methyl-2-(5-methyl-6-(3-(trifluoromethoxy)phenyl)pyridin-3-ylamino)benzoic acid
Ethyl 5-methyl-2-(5-methyl-6-(3-(trifluoromethoxy)phenyl)pyridin-3-ylamino)benzoate
2-(5-Cyclopropyl-6-(3-methoxyphenyl)pyridin-3-ylamino)-5-methylbenzoic acid
Ethyl 2-(5-cyclopropyl-6-(3-methoxyphenyl)pyridin-3-ylamino)-5-methylbenzoate
2-(6-(2-Fluoro-5-isopropoxyphenyl)pyridin-3-ylamino)-5-methylbenzoic acid
2-(6-(3-Isopropoxyphenyl)-5-methylpyridin-3-ylamino)-5-methylbenzoic acid
Ethyl 2-(6-(3-isopropoxyphenyl)-5-methylpyridin-3-ylamino)-5-methylbenzoate
2-(6-(3-Cyclopropoxyphenyl)-5-methylpyridin-3-ylamino)-5-methylbenzoic acid tert-Butyl 2-(6-(3-cyclopropoxyphenyl)-5-methylpyridin-3-ylamino)-5-methylbenzoate
2-(6-(2-Chlorophenyl)-5-methylpyridin-3-ylamino)-5-methylbenzoic acid
tert-Butyl 2-(6-(2-chlorophenyl)-5-methylpyridin-3-ylamino)-5-methylbenzoate
2-(6-(3-Carbamoylphenyl)-5-methylpyridin-3-ylamino)-5-methylbenzoic acid Ethyl 2-(6-(3-carbamoylphenyl)-5-methylpyridin-3-ylamino)-5-methylbenzoate
2-(6-(2-Fluoro-5-methoxyphenyl)-4-methylpyridin-3-ylamino)-5-methylbenzoic acid
Ethyl 2-(6-(2-fluoro-5-methoxyphenyl)-4-methylpyridin-3-ylamino)-5-methylbenzoate
2-(6-(3-Methoxyphenyl)-5-(trifluoromethyl)pyridin-3-ylamino)-5-methylbenzoic acid
Ethyl 2-(6-(3-methoxyphenyl)-5-(trifluoromethyl)pyridin-3-ylamino)-5-methylbenzoate
2-(6-(3-(Dimethylcarbamoyl)phenyl)-5-methylpyridin-3-ylamino)-5-methylbenzoic acid
Ethyl 2-(6-(3-(dimethylcarbamoyl)phenyl)-5-methylpyridin-3-ylamino)-5-methylbenzoate
2-(6-(3-Isopropoxyphenyl)-5-methylpyridin-3-ylamino)-3-methylbenzoic acid
tert-Butyl 2-(6-(3-isopropoxyphenyl)-5-methylpyridin-3-ylamino)-3-methylbenzoate
3-Methyl-2-(5-methyl-6-phenylpyridin-3-ylamino)benzoic acid tert-Butyl 3-methyl-2-(5-methyl-6-phenylpyridin-3-ylamino)benzoate
2-(6-(2-Chlorophenyl)pyridin-3-ylamino)-5-methylbenzoic acid tert-Butyl 2-(6-(2-chlorophenyl)pyridin-3-ylamino)-5-methylbenzoate
3-Fluoro-2-(6-(3-methoxyphenyl)-5-methylpyridin-3-ylamino)benzoic acid tert-Butyl 3-fluoro-2-(6-(3-methoxyphenyl)-5-methylpyridin-3-ylamino)benzoate
5-Cyclopropyl-2-(5-methyl-6-(3-(trifluoromethoxy)phenyl)pyridin-3-ylamino)benzoic acid
Ethyl 5-cyclopropyl-2-(5-methyl-6-(3-(trifluoromethoxy)phenyl)pyridin-3-ylamino)benzoate
5-Cyclopropyl-2-(5-methyl-6-phenylpyridin-3-ylamino)benzoic acid
Ethyl 5-cyclopropyl-2-(5-methyl-6-phenylpyridin-3-ylamino)benzoate
5-Methyl-2-(5-methyl-6-(2-(trifluoromethyl)phenyl)pyridin-3-ylamino)benzoic acid tert-Butyl 5-methyl-2-(5-methyl-6-(2-(trifluoromethyl)phenyl)pyridin-3-ylamino)benzoate
2-(6-(3-Chlorophenyl)-5-methylpyridin-3-ylamino)-5-methylbenzoic acid tert-Butyl 2-(6-(3-chlorophenyl)-5-methylpyridin-3-ylamino)-5-methylbenzoate
2-(6-(2-Fluorophenyl)-5-methylpyridin-3-ylamino)-5-methylbenzoic acid
tert-Butyl 2-(6-(2-fluorophenyl)-5-methylpyridin-3-ylamino)-5-methylbenzoate
5-Methyl-2-(5-methyl-6-(quinolin-5-yl)pyridin-3-ylamino)benzoic acid tert-Butyl 5-methyl-2-(5-methyl-6-(quinolin-5-yl)pyridin-3-ylamino)benzoate
2-(3'-Fluoro-3-methyl-2,4'-bipyridin-5-ylamino)-5-methylbenzoic acid tert-Butyl 2-(3'-fluoro-3-methyl-2,4'-bipyridin-5-ylamino)-5-methylbenzoate
5-Methyl-2-(5-methyl-6-(pyrazin-2-yl)pyridin-3-ylamino)benzoic acid tert-Butyl 5-methyl-2-(5-methyl-6-(pyrazin-2-yl)pyridin-3-ylamino)benzoate
5-Cyclopropyl-2-(6-phenyl-5-(trifluoromethyl)pyridin-3-ylamino)benzoic acid
Ethyl 5-cyclopropyl-2-(6-phenyl-5-(trifluoromethyl)pyridin-3-ylamino)benzoate
5-Cyclopropyl-2-(6-(3-methoxyphenyl)-5-(trifluoromethyl)pyridin-3-ylamino)benzoic acid
Ethyl 5-cyclopropyl-2-(6-(3-methoxyphenyl)-5-(trifluoromethyl)pyridin-3-ylamino)benzoate
5-Chloro-2-(6-(2-fluorophenyl)pyridin-3-ylamino)benzoic acid
5-Chloro-2-(6-(2-chlorophenyl)pyridin-3-ylamino)benzoic acid
5-Chloro-2-(6-(quinolin-5-yl)pyridin-3-ylamino)benzoic acid
2-(6-(2-Chlorophenyl)pyridin-3-ylamino)-5-cyclopropylbenzoic acid
Ethyl 2-(6-(2-chlorophenyl)pyridin-3-ylamino)-5-cyclopropylbenzoate
5-Chloro-2-(6-(2-(trifluoromethyl)phenyl)pyridin-3-ylamino)benzoic acid
5-Fluoro-2-(6-(2-(trifluoromethyl)phenyl)pyridin-3-ylamino)benzoic acid
2-(3'-Fluoro-2,4'-bipyridin-5-ylamino)-5-methylbenzoic acid
2-(2-(2-Fluorophenyl)pyrimidin-5-ylamino)-5-methylbenzoic acid tert-Butyl 2-(2-(2-fluorophenyl)pyrimidin-5-ylamino)-5-methylbenzoate
2-(6-(2,6-Difluorophenyl)pyridin-3-ylamino)-5-methylbenzoic acid
Ethyl 2-(6-(2,6-difluorophenyl)pyridin-3-ylamino)-5-methylbenzoate
2-(2-(2-Chlorophenyl)pyrimidin-5-ylamino)-5-cyclopropylbenzoic acid
Methyl 2-(2-(2-chlorophenyl)pyrimidin-5-ylamino)-5-cyclopropylbenzoate
2-(2-(2-Chlorophenyl)pyrimidin-5-ylamino)-5-methylbenzoic acid
tert-Butyl 2-(2-(2-chlorophenyl)pyrimidin-5-ylamino)-5-methylbenzoate
5-Methyl-2-(5-methyl-6-(3-(pyrrolidine-1-carbonyl)phenyl)pyridin-3-ylamino)benzoic acid
2-(6-(3-(Cyclopropylcarbamoyl)phenyl)-5-methylpyridin-3-ylamino)-5-methylbenzoic acid
5-Cyclopropyl-2-(2-(2-fluorophenyl)pyrimidin-5-ylamino)benzoic acid
2-(2-(2-trifluoromethylphenyl)pyrimidin-5-ylamino)-5-cyclopropylbenzoic acid
2-(2-o-tolylpyrimidin-5-ylamino)-5-cyclopropylbenzoic acid
2-(2-(2-cyclopropoxyphenyl)pyrimidin-5-ylamino)-5-cyclopropylbenzoic acid
2-(2-(2,5-difluorophenyl)pyrimidin-5-ylamino)-5-cyclopropylbenzoic acid
2-(2-(2,3-difluorophenyl)pyrimidin-5-ylamino)-5-cyclopropylbenzoic acid
2-(2-(2-fluoro-5-chlorophenyl)pyrimidin-5-ylamino)-5-cyclopropylbenzoic acid
2-(2-(2-trifluoromethylphenyl)pyrimidin-5-ylamino)-5-methylbenzoic acid
2-(2-(2-fluoro-5-trifluoromethoxyphenyl)pyrimidin-5-ylamino)-5-cyclopropylbenzoic acid
2-(6-(2-trifluoromethylphenyl)pyridin-3-ylamino)-5-methylbenzoic acid
2-(6-phenylpyridin-3-ylamino)-5-cyclopropylbenzoic acid
2-(6-(2-fluorophenyl)pyridin-3-ylamino)-5-cyclopropylbenzoic acid 2-(6-(3,5-difluoropyridin-4-yl)pyridin-3-ylamino)-5-methylbenzoic acid
2-(6-(3-cyclopropylcarbamoylphenyl)pyridin-3-ylamino)-5-methylbenzoic acid
2-(6-(2,4-difluorophenyl)pyridin-3-ylamino)-5-methylbenzoic acid
2-(6-(2,5-difluorophenyl)pyridin-3-ylamino)-5-methylbenzoic acid
2-(6-(2-fluorophenyl)pyridin-3-ylamino)-5-cyclopropyl-3-fluorobenzoic acid
2-(6-(2,3,6-trifluorophenyl)pyridin-3-ylamino)-5-methylbenzoic acid
2-(6-(3-(5-methyl-1,3,4-oxadiazol-2-yl)phenyl)pyridin-3-ylamino)-5-methylbenzoic acid
2-(5-methyl-6-(pyrimidin-5-yl)pyridin-3-ylamino)-5-methylbenzoic acid
2-(6-(2,3-difluorophenyl)pyridin-3-ylamino)-5-methylbenzoic acid
2-(6-(5-fluoro-2-methoxyphenyl)-5-methylpyridin-3-ylamino)-5-methylbenzoic acid, and
2-(6-(4-carbamoylphenyl)-5-methylpyridin-3-ylamino)-5-methylbenzoic acid
and the pharmaceutically acceptable salts and N-oxides thereof.

Of outstanding interest are:
5-cyclopropyl-2-(2-phenylpyrimidin-5-ylamino)benzoic acid
5-(2-Carboxy-4-cyclopropylphenylamino)-3-methyl-2-phenylpyridine 1-oxide
5-Methyl-2-(6-(3-(trifluoromethyl)phenyl)pyridin-3-ylamino)benzoic acid
2-(5-Fluoro-6-phenylpyridin-3-ylamino)-5-methylbenzoic acid
5-Cyclopropyl-2-(3'-fluoro-2,4'-bipyridin-5-ylamino)benzoic acid
2-(5-Chloro-6-phenylpyridin-3-ylamino)-5-methylbenzoic acid
5-Cyclopropyl-2-(2-(2-cyclopropylphenyl)pyrimidin-5-ylamino)benzoic acid
5-cyclopropyl-2-(5-phenylpyridin-3-ylamino)benzoic acid
2-(5-Chloro-2-phenylpyridin-3-ylamino)-5-methylbenzoic acid
5-Cyclopropyl-2-(5,6-diphenylpyridin-3-ylamino)benzoic acid
5-cyclopropyl-2-(2-(2,6-difluorophenyl)pyrimidin-5-ylamino)benzoic acid
2-(2-(3-Cyclopropoxyphenyl)pyrimidin-5-ylamino)-5-cyclopropylbenzoic acid
5-Methyl-2-(6-morpholinopyridin-3-ylamino)benzoic acid
5-Methyl-2-(5-methyl-6-morpholinopyridin-3-ylamino)benzoic acid
5-cyclopropyl-2-(6-cyclopropyl-5-phenylpyridin-3-ylamino)benzoic acid
2-(6-(2-Cyclopropylphenyl)-5-methylpyridin-3-ylamino)-5-methylbenzoic acid
2-(6-(2-Cyanophenyl)-5-methylpyridin-3-ylamino)-5-methylbenzoic acid
2-(2-(3-Chlorophenyl)pyrimidin-5-ylamino)-5-cyclopropylbenzoic acid
5-Methyl-2-(6-phenyl-5-(trifluoromethyl)pyridin-3-ylamino)benzoic acid
5-Methyl-2-(5-methyl-6-(piperidin-1-yl)pyridin-3-ylamino)benzoic acid
2-(6-(Azepan-1-yl)-5-methylpyridin-3-ylamino)-5-methylbenzoic acid
2-(2,3'-bipyridin-5-ylamino)-5-cyclopropylbenzoic acid
2-(3'-chloro-2,4'-bipyridin-5-ylamino)-5-methylbenzoic acid
5-Methyl-2-(3-methyl-2,2'-bipyridin-5-ylamino)benzoic acid
2-(6-(3-Ethoxyphenyl)-5-methylpyridin-3-ylamino)-5-methylbenzoic acid
2-(6-(3-Methoxyphenyl)-5-methylpyridin-3-ylamino)-5-methylbenzoic acid
5-Methyl-2-(5-methyl-6-phenylpyridin-3-ylamino)benzoic acid
2-(6-(3-Isopropoxyphenyl)-5-methylpyridin-3-ylamino)-5-methylbenzoic acid
5-Cyclopropyl-2-(5-methyl-6-(3-(trifluoromethoxy)phenyl)pyridin-3-ylamino)benzoic acid
5-Cyclopropyl-2-(5-methyl-6-phenylpyridin-3-ylamino)benzoic acid
2-(6-(2-Fluorophenyl)-5-methylpyridin-3-ylamino)-5-methylbenzoic acid
5-Cyclopropyl-2-(6-phenyl-5-(trifluoromethyl)pyridin-3-ylamino)benzoic acid
5-Cyclopropyl-2-(6-(3-methoxyphenyl)-5-(trifluoromethyl)pyridin-3-ylamino)benzoic acid
2-(6-(2-Chlorophenyl)pyridin-3-ylamino)-5-cyclopropylbenzoic acid
2-(2-(2-Chlorophenyl)pyrimidin-5-ylamino)-5-cyclopropylbenzoic acid
2-(2-(2-Chlorophenyl)pyrimidin-5-ylamino)-5-methylbenzoic acid
2-(6-(2,6-Difluorophenyl)pyridin-3-ylamino)-5-methylbenzoic acid
5-Methyl-2-(5-methyl-6-(3-(pyrrolidine-1-carbonyl)phenyl)pyridin-3-ylamino)benzoic acid
2-(6-(3-(Cyclopropylcarbamoyl)phenyl)-5-methylpyridin-3-ylamino)-5-methylbenzoic acid,
5-Cyclopropyl-2-(2-(2-fluorophenyl)pyrimidin-5-ylamino)benzoic acid.
and the pharmaceutically acceptable salts and N-oxides thereof.

The compounds of formula (I) are new, provided that when G2 is a hydrogen or chlorine atom, a methoxy or butoxy group, or together with R6 forms a phenyl group, then R1 is not a hydrogen atom or a chlorine atom.

Thus, the present invention also relates to compounds of formula (I)

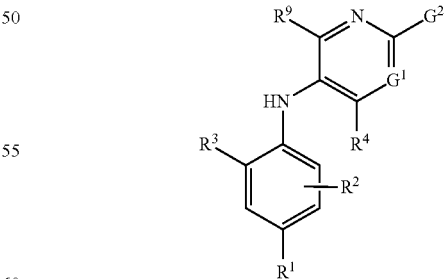

wherein R1, R², R³, R⁴, R⁹, G¹ and G² are as defined above, with the proviso that when G² is a hydrogen or chlorine atom, a methoxy or butoxy group or together with R⁶ forms a phenyl group, then R¹ is not a hydrogen atom or a chlorine atom.

Compounds of general formula (I) may be prepared following the synthetic scheme depicted in figure 1.

Figure 1

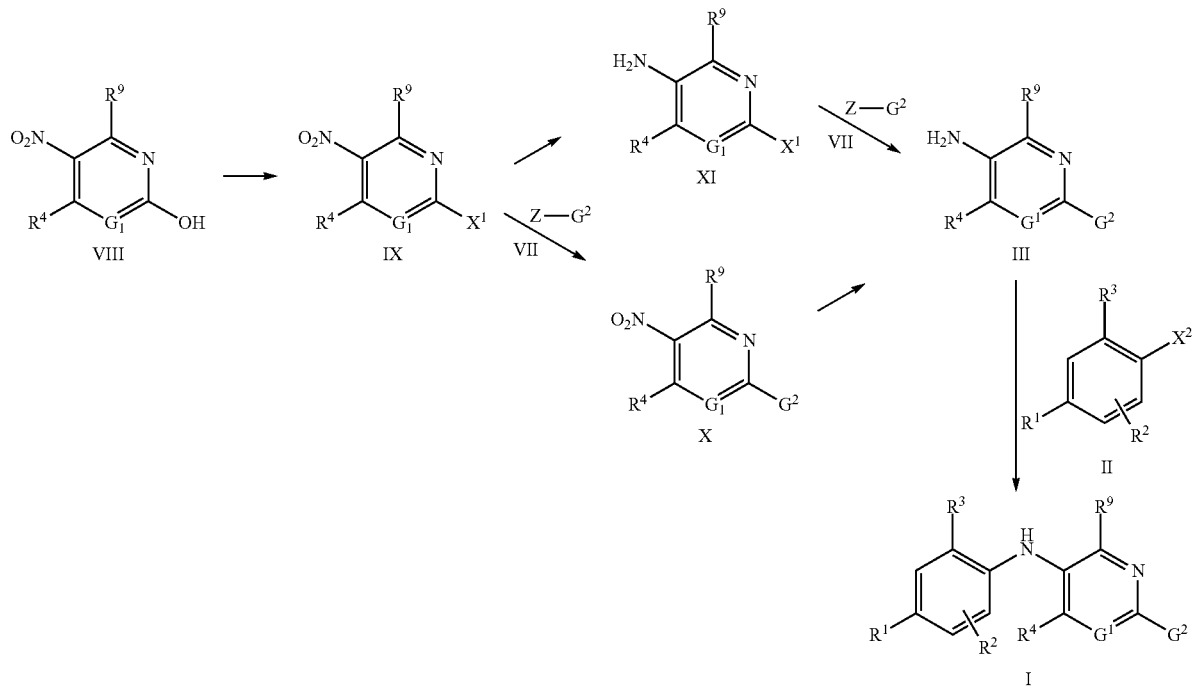

Compounds of general formula (I) may be prepared by reaction of intermediates (II) wherein $R^1$, $R^2$ and $R^3$ are as described above and $X^2$ is a chlorine or bromine atom, with intermediates (III) wherein $R^4$, $R^9$, $G^1$ and $G^2$ are as described above. The reaction may be carried out under inert atmosphere over a palladium catalyst such as $Pd(OAc)_2$ or Tris (dibenzylideneacetone)dipalladium(0) $(Pd_2(dba)_3)$, using a phosphine ligand such as rac-2,2'-bis(diphenylphosphino)-1,1'-binaphtyl (BINAP) or Xanthphos, in the presence of a base such as $Cs_2CO_3$, $K_2CO_3$ or $NaO^tBu$ in a high boiling point solvent such as toluene, xylene, DMF, water or dioxane at a range of temperatures from 80° C. to 160° C. for 0.5 to 24 hours. The reaction may also be performed in a microwave oven at a temperature ranging from 100° C. to 160° C. for 0.5 to 15 hours.

Alternatively, the reaction may be mediated by a copper catalyst such as a mixture of a Cu and $Cu_2O$, using a base such as $Cs_2CO_3$, $K_2CO_3$ or $Na_2CO_3$ in a high boiling point solvent such as toluene, xylene, DMF, water or dioxane at a range of temperatures from 80° C. to 160° C. for 0.5 to 24 hours. The reaction may also be performed in a microwave oven at a temperature ranging from 100° C. to 160° C. for 0.5 to 15 hours.

Intermediates of general formula (III) may be obtained from Intermediates (X) by reduction of the nitro group using hydrogen and a catalyst such as Pd/C, Pt/C, $PtO_2$, $Pd(OH)_2$ or Ni-Raney optionally in the presence of $ZnBr_2$, in a solvent such as EtOAc, MeOH, THF or EtOH, at room temperature for 1 to 24 hours.

Alternatively, intermediates of general formula (III) may also be obtained from the reaction of Intermediates (XI) wherein $X^1$ is a chlorine or bromine atom, with intermediates (VII) wherein Z is a boronic acid, a boronate, trialkylstannane or zincate derivative. The reaction may be mediated under inert atmosphere by a palladium catalyst such as $Pd(OAc)_2$, $Pd_2(dba)_3$, $Pd(PPh_3)_4$, $PdCl_2(PPh_3)_2$ or [1,1'-Bis(diphenylphosphino)-ferrocene]dichloropalladium(II) ($PdCl_2$(dppf)DCM), using a phosphine ligand such as BINAP, tricyclohexylphosphine ($P(Cy)_3$) or Xanthphos when needed, in the presence of a base such as $Cs_2CO_3$, $K_2CO_3$ or $NaO^tBu$ in a high boiling point solvent such as toluene, xylene, DMF, water, dioxane or THF at a range of temperatures from 40° C. to 160° C. for 0.5 to 24 hours. The reaction may also be performed in a microwave oven at a range of temperatures from 100° C. to 160° C. for 0.5 to 15 hours. In the particular case that Z is a trialkylstannane derivative, CuI is added as a co-catalyst.

Intermediates of general formula (X) may be obtained by the reaction of Intermediates (IX) wherein $X^1$ is a chlorine or bromine atom, with Intermediates (VII) wherein Z is a boronic acid, a boronate, trialkylstannane or zincate derivative. The reaction may be mediated under inert atmosphere by a palladium catalyst such as $Pd(OAc)_2$, $Pd_2(dba)_3$, $Pd(PPh_3)_4$, $PdCl_2(PPh_3)_2$ or $PdCl_2$(dppf), using a phosphine ligand such as BINAP, $P(Cy)_3$ or Xanthphos when needed, in the presence of a base such as $Cs_2CO_3$, $K_2CO_3$ or $NaO^tBu$ in a high boiling point solvent such as toluene, xylene, DMF, water, dioxane or THF at a range of temperatures from 40° C. to 160° C. for 0.5 to 24 hours. The reaction may also be performed in a microwave oven at a range of temperatures from 100° C. to 160° C. for 0.5 to 15 hours. In the particular case that Z is a trialkylstannane derivative, CuI is added as a co-catalyst.

Intermediates of formula (XI) are commercially available or may be prepared from intermediates of formula (IX) by reduction of the nitro group using hydrogen and a catalyst such as Pd/C, Pt/C, $PtO_2$, $Pd(OH)_2$ or Ni-Raney optionally in the presence of $ZnBr_2$, in a solvent such as EtOAc, MeOH, THF or EtOH at room temperature for 1 to 24 hours.

Intermediates of formula (IX) are commercially available or may be obtained from Intermediates of formula (VIII). The reaction may be carried out in the presence of $POCl_3$ or $POBr_3$ with the assistance of $PCl_5$ or $PBr_3$ at a range of temperatures between 70° C. to 140° C. for 15 minutes to 24 hours.

In the particular case that $R^6$ is a group selected from $C_{3-4}$ cycloalkyl, $C_{6-10}$ aryl, $C_{3-7}$ heterocyclyl or $C_{5-7}$ heteroaryl, Intermediates of general formula (IIIb) may be obtained following the synthetic scheme depicted in figure 2.

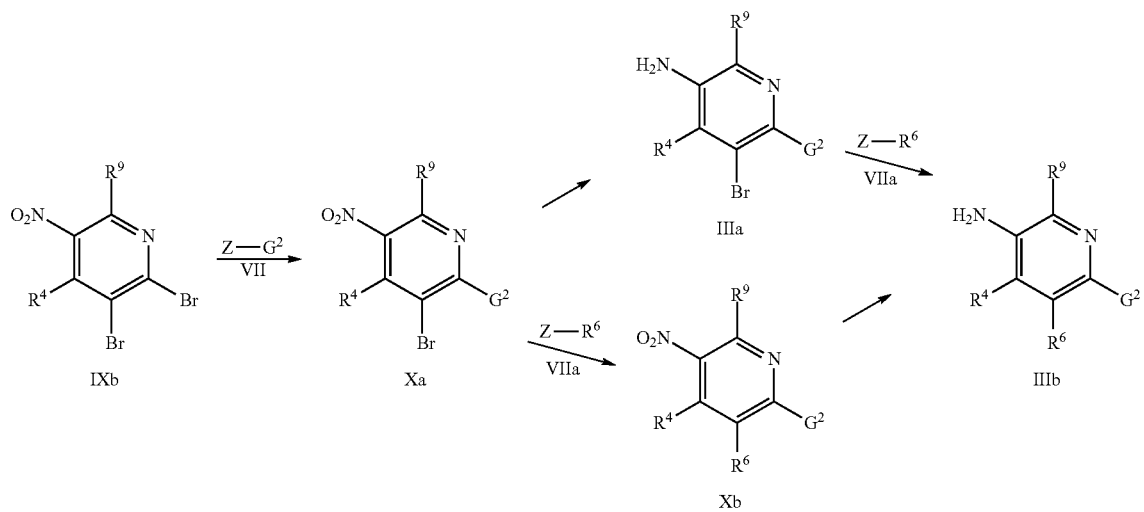

Figure 2

Intermediates (IIIb) wherein $R^4$, $R^9$ and $G^2$ are as described above, may be obtained by the reaction of Intermediates (IIIa) with Intermediates (VIIa) wherein Z is a boronic acid, a boronate ester, a trialkylstannane or zincate derivative. The reaction may be mediated under inert atmosphere by a palladium catalyst such as $Pd(OAc)_2$, $Pd_2(dba)_3$, $Pd(PPh_3)_4$, $PdCl_2(PPh_3)_2$ or $PdCl_2(dppf)DCM$, using a phosphine ligand such as BINAP, $P(Cy)_3$ or Xanthphos when needed, in the presence of a base such as $Cs_2CO_3$, $K_2CO_3$ or $NaO^tBu$ in a high boiling point solvent such as toluene, xylene, DMF, water, dioxane or THF at a range of temperatures from 40° C. to 160° C. for 0.5 to 24 hours. The reaction may also be performed in a microwave oven at a range of temperatures from 100° C. to 160° C. for 0.5 to 15 hours. In the particular case that Z is a trialkylstannane derivative, CuI is added as a co-catalyst.

Alternatively, Intermediates of general formula (IIIb) may be obtained from Intermediates of general formula (Xb) by reduction of the nitro group using hydrogen and a catalyst such as Pd/C, Pt/C, $PtO_2$, $Pd(OH)_2$ or Ni-Raney optionally in the presence of $ZnBr_2$, in a solvent such as EtOAc, MeOH, THF or EtOH at room temperature for 1 to 24 hours.

Intermediates of general formula (IIIa) wherein $R^4$ and $G^2$ are as described before may be obtained from Intermediates of general formula (Xa) by reduction of the nitro group using hydrogen and a catalyst such as Pd/C, Pt/C, $PtO_2$, $Pd(OH)_2$ or Ni-Raney optionally in the presence of $ZnBr_2$, in a solvent such as EtOAc, MeOH, THF or EtOH at room temperature for 1 to 24 hours.

Intermediates of general formula (Xb) may be obtained by the reaction of Intermediates of general formula (Xa) wherein $R^4$ and $G^2$ are as described above with Intermediates (VIIa) wherein Z is a boronic acid, a boronate ester, trialkylstannane or zincate derivative. The reaction may be mediated under inert atmosphere by a palladium catalyst such as $Pd(OAc)_2$, $Pd_2(dba)_3$, $Pd(PPh_3)_4$, $PdCl_2(PPh_3)_2$ or $PdCl_2(dppf)DCM$, using a phosphine ligand such as BINAP, $P(Cy)_3$ or Xanthphos when needed, in the presence of a base such as $Cs_2CO_3$, $K_2CO_3$ or $NaO^tBu$ in a high boiling point solvent such as toluene, xylene, DMF, water, dioxane or THF at a range of temperatures from 40° C. to 160° C. for 0.5 to 24 hours. The reaction may also be performed in a microwave oven at a range of temperatures from 100° C. to 160° C. for 0.5 to 15 hours. In the particular case that Z is a trialkylstannane, CuI is added as a co-catalyst.

Intermediates of general formula (Xa) may be obtained by the reaction of Intermediates (IXb) with intermediates (VII) wherein Z is a boronic acid, a boronate ester, trialkylstannane or zincate derivative. The reaction may be mediated under inert atmosphere by a palladium catalyst such as $Pd(OAc)_2$, $Pd_2(dba)_3$, $Pd(PPh_3)_4$, $PdCl_2(PPh_3)_2$ or $PdCl_2(dppf)DCM$, using a phosphine ligand such as BINAP, $P(Cy)_3$ or Xanthphos when needed, in the presence of a base such as $Cs_2CO_3$, $K_2CO_3$ or $NaO^tBu$ in a high boiling point solvent such as toluene, xylene, DMF, water or dioxane or THF at a range of temperatures from 40° C. to 160° C. for 0.5 to 24 hours. The reaction may also be performed in a microwave oven at a range of temperatures from 100° C. to 160° C. for 0.5 to 15 hours. In the particular case that Z is a trialkylstannane derivative, CuI is added as a co-catalyst.

Intermediates of general formula (IXb) are commercially available or may be prepared by an analogous process to that shown for intermediates of formula (IX) in figure 1.

In an alternative procedure, compounds of general formula (I) may be prepared following the synthetic scheme shown in figure 3.

Figure 3

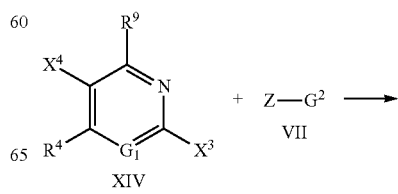

-continued

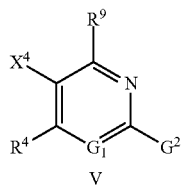

V

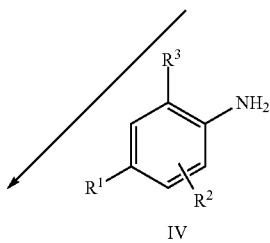

IV

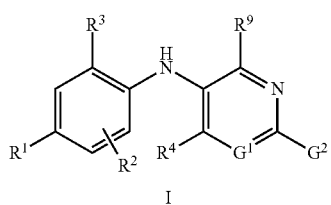

I

Compounds of general formula (I) may be prepared by reaction of intermediates (IV) wherein $R^1$, $R^2$ and $R^3$ are as described above with intermediates (V) wherein $R^4$, $R^9$, $G^1$ and $G^2$ are as described above and $X^4$ represents a bromine or iodine atom or a trialkylstannane derivative.

When $X^4$ is a bromine or iodine atom, the reaction may be mediated by a palladium catalyst such as $Pd(OAc)_2$ or $Pd_2$(dba)$_3$, using a phosphine ligand such as BINAP or Xanthphos, in the presence of a base such as $Cs_2CO_3$, $K_2CO_3$ or NaO$^t$Bu in a high boiling point solvent such as toluene, xylene, DMF, water or dioxane at a range of temperatures from 80° C. to 160° C. for 0.5 to 24 hours. The reaction may also be performed in a microwave oven at a range of temperatures from 100° C. to 160° C. for 0.5 to 15 hours.

When $X^4$ is a trialkylstannane derivative, a catalyst based on copper such as $Cu(OAc)_2$ is used in the presence of a base such as triethylamine, 1,2-lutidine, CsF or tetra-n-butylammonium fluoride (TBAF) in a solvent such as acetonitrile, toluene, dichloromethane or THF at a range of temperatures between 25° C. and 90° C.

Intermediates of general formula (V) may be prepared by the reaction of Intermediates (XIV) wherein $X^3$ is a bromine or chlorine atom, with intermediates (VII) wherein Z is a boronic acid, a boronate, trialkylstannane or zincate derivative. The reaction may be mediated under inert atmosphere by a palladium catalyst such as $Pd(OAc)_2$, $Pd_2$(dba)$_3$, $Pd(PPh_3)_4$, $PdCl_2(PPh_3)_2$ or $PdCl_2$(dppf)DCM, using a phosphine ligand such as BINAP, $P(Cy)_3$ or Xanthphos when needed, in the presence of a base such as $Cs_2CO_3$, $K_2CO_3$ or NaO$^t$Bu in a high boiling point solvent such as toluene, xylene, DMF, water, dioxane or THF at a range of temperatures from 40° C. to 160° C. for 0.5 to 24 hours. The reaction may also be performed in a microwave oven at a range of temperatures from 100° C. to 160° C. for 0.5 to 15 hours. When Z is a trialkylstannane, CuI is added as a co-catalyst.

In another alternative procedure, compounds of general formula (I) may be prepared following the synthetic scheme shown in figure 4.

Figure 4

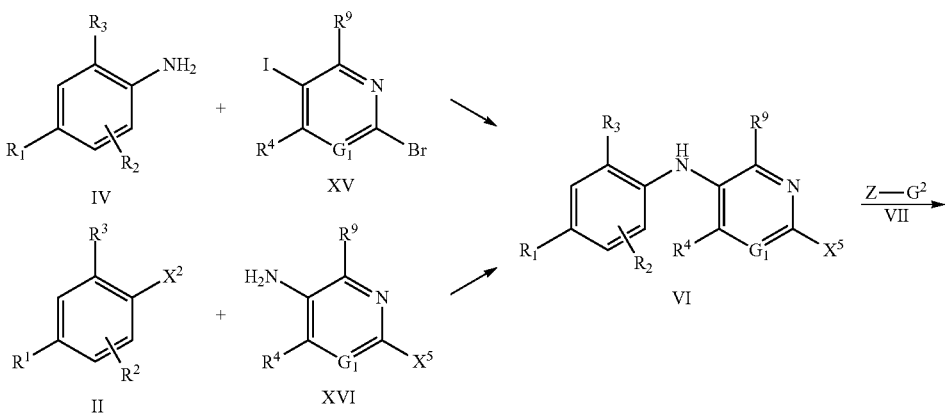

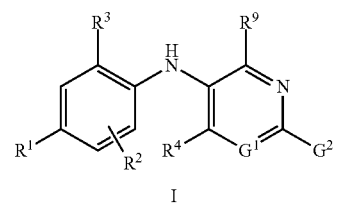

I

Compounds of general formula (I) may be prepared by reaction of intermediates (VI) wherein $R^1$, $R^2$, $R^3$, $R^4$, $R^9$ and $G^1$ are as described above and $X^5$ is a chlorine or bromine atom, with intermediates (VII) wherein $G^2$ is as described above and Z is selected from a boronic acid, a boronate, a trialkylstannane and a zincate derivative. The reaction may be mediated under inert atmosphere by a palladium catalyst such as $Pd(OAc)_2$, $Pd_2(dba)_3$, $Pd(PPh_3)_4$, $PdCl_2(PPh_3)_2$ or $PdCl_2$(dppf)DCM, using a phosphine ligand such as BINAP, $P(Cy)_3$ or Xanthphos when needed, a base such as $Cs_2CO_3$, $K_2CO_3$ or NaO$^t$Bu in a high boiling point solvent such as toluene, xylene, DMF, water or dioxane or THF at a range of temperatures from 40° C. to 160° C. for 0.5 to 24 hours. Alternatively the reaction may be performed in a microwave oven at a range of temperatures from 100° C. to 160° C. for 0.5 to 15 hours. When Z is a trialkylstannane derivative, CuI is added as a co-catalyst.

Intermediates of general formula (VI) may be obtained by the reaction of Intermediates (II) wherein $R^1$, $R^2$, $R^3$ and $X^2$ are as described above with intermediates (XVI) wherein $R^4$, $G^1$ and $X^5$ are as described above. The reaction may be mediated under inert atmosphere by a palladium catalyst such as $Pd(OAc)_2$ or $Pd_2(dba)_3$, using a phosphine ligand such as BINAP or Xanthphos, in the presence of a base such as $Cs_2CO_3$, $K_2CO_3$ or NaO$^t$Bu in a high boiling point solvent such as toluene, xylene, DMF, water or dioxane at a range of temperatures from 80° C. to 160° C. for 0.5 to 24 hours. The reaction may also be performed in a microwave oven at a range of temperatures from 100° C. to 160° C. for 0.5 to 15 hours. Alternatively, the reaction may be mediated by a copper catalyst such as Cu or $Cu_2O$, using a base such as $Cs_2CO_3$, $K_2CO_3$ or $Na_2CO_3$ in a high boiling point solvent such as toluene, xylene, DMF, water or dioxane at a range of temperatures from 80° C. to 160° C. for 0.5 to 24 hours. The reaction may also be performed in a microwave oven at a range of temperatures from 100° C. to 160° C. for 0.5 to 15 hours.

Intermediates of general formula (VI) may also be obtained from the reaction of Intermediates (IV) wherein $R^1$, $R^2$ and $R^3$ are as described above with intermediates (XV) wherein $R^4$, $R^9$ and $G^1$ are as described above. The reaction may be mediated under inert atmosphere by a palladium catalyst such as $Pd(OAc)_2$ or $Pd_2(dba)_3$ using a phosphine ligand such as BINAP or Xanthphos, in the presence of a base such as $Cs_2CO_3$, $K_2CO_3$ or NaO$^t$Bu in a high boiling point solvent such as toluene, xylene, DMF, water or dioxane at a range of temperatures from 80° C. to 160° C. for 0.5 to 24 hours. The reaction may also be performed in a microwave oven at a range of temperatures from 100° C. to 160° C. for 0.5 to 15 hours.

In the particular case wherein $G^2$ represents a hydrogen atom or an alkoxy group, Intermediates of formulae (IIIc) and (IIId) may be prepared following the synthetic scheme depicted in figure 5

Figure 5

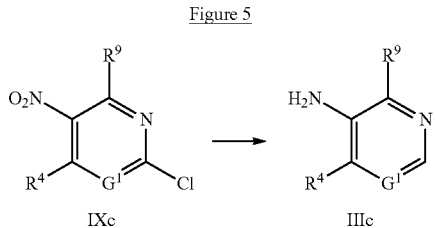

IXc → IIIc

-continued

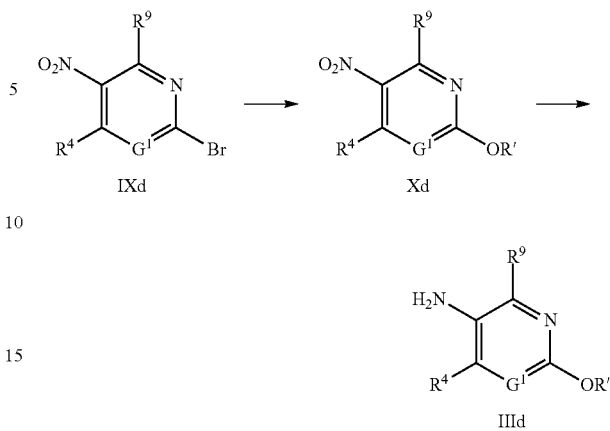

IXd → Xd → IIId

Intermediates of general formula (IIIc), may be obtained by reduction of intermediates of general formula (IXc) using hydrogen and a catalyst such as Pd/C, Pt/C, $PtO_2$, $Pd(OH)_2$ or Ni-Raney optionally in the presence of $ZnBr_2$ or $SnCl_2.H_2O$ or Fe—HCl in a solvent such as EtOAc, MeOH, THF or EtOH, at room temperature for 1 to 24 hours.

On the other hand, intermediates of general formula (IIId) wherein R' is a methyl group may be obtained by reduction of intermediates of general formula (Xd) using hydrogen and a catalyst such as Pd/C, Pt/C, $PtO_2$, $Pd(OH)_2$ or Ni-Raney optionally in the presence of $ZnBr_2$ or $SnCl_2.H_2O$ or Fe—HCl in a solvent such as EtOAc, Intermediates of general formula (Xd) may be obtained from intermediate of formula (IXd) by heating in the presence of methanol at 100° C.

Intermediates of general formula (IXc) and (IXd) are commercially available or may be prepared by an analogous process to that shown for intermediates of formula (IX) in figure 1.

In the particular case that $G_1$ is $CR^6$, wherein $R^6$ is —$CF_3$, intermediates of general formula (IXa) may be prepared following the synthetic scheme shown in figure 6.

Figure 6

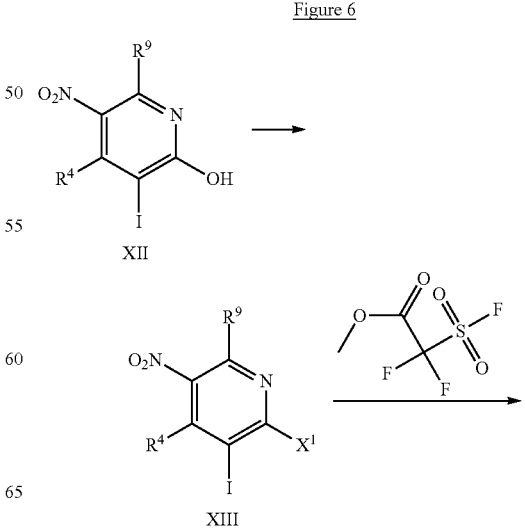

XII → XIII

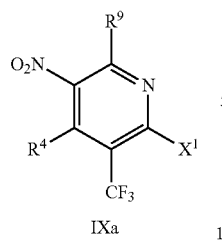

IXa

Intermediates of general formula (IXa) may be obtained from Intermediates of formula (XIII) in the presence of methyl 2,2-difluoro-2-(fluorosulfonyl)acetate in a solvent such as DMF or toluene at a range of temperatures from 40° C. to 130° C. for 1 to 48 hours.

Intermediates of formula (XIII) may be obtained from Intermediates of general formula (XII). The reaction may be carried out in the presence of POCl₃ or POBr₃ with the assistance of PCl₅ or PBr₃ at a range of temperatures between 70° C. to 140° C. for 15 minutes to 24 hours.

In general, intermediates of formula (II) and (IV) are commercially available. However in the particular case wherein R¹ is a cyclopropyl group, said intermediate may be obtained following the synthetic scheme shown in figure 7.

Figure 7

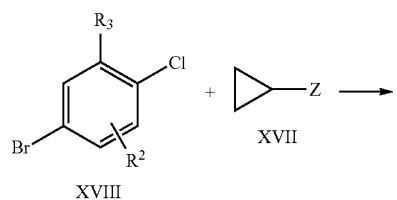

XVIII          XVII

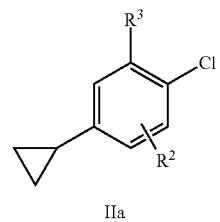

IIa

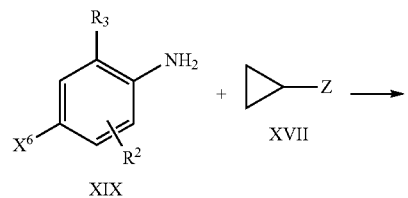

XIX          XVII

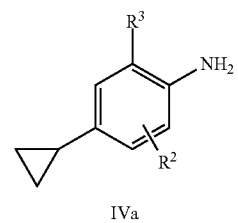

IVa

Intermediates of formula (IIa) and (IVa) may be prepared by the reaction of Intermediates (XVIII) and (XIX) respectively, wherein X⁶ is a bromine or chlorine atom, with Intermediate (XVII) wherein Z is a boronic acid or a boronate derivative. The reaction may be mediated under inert atmosphere by a palladium catalyst such as Pd(OAc)₂, Pd₂(dba)₃, Pd(PPh₃)₄, PdCl₂(PPh₃)₂ or PdCl₂(dppf)DCM, using a phosphine ligand such as BINAP, P(Cy)₃ or Xanthphos when needed, a base such as Cs₂CO₃, K₂CO₃ or NaO$^t$Bu in a high boiling point solvent such as toluene, xylene, DMF, water, dioxane or THF at a range of temperatures from 40° C. to 160° C. for 0.5 to 24 hours. The reaction may also be performed in a microwave oven at a range of temperatures from 100° C. to 160° C. for 0.5 to 15 hours.

In the particular case wherein G² represents a hydroxy group, Compounds of formula (Id) may be prepared following the scheme depicted in figure 8

Figure 8

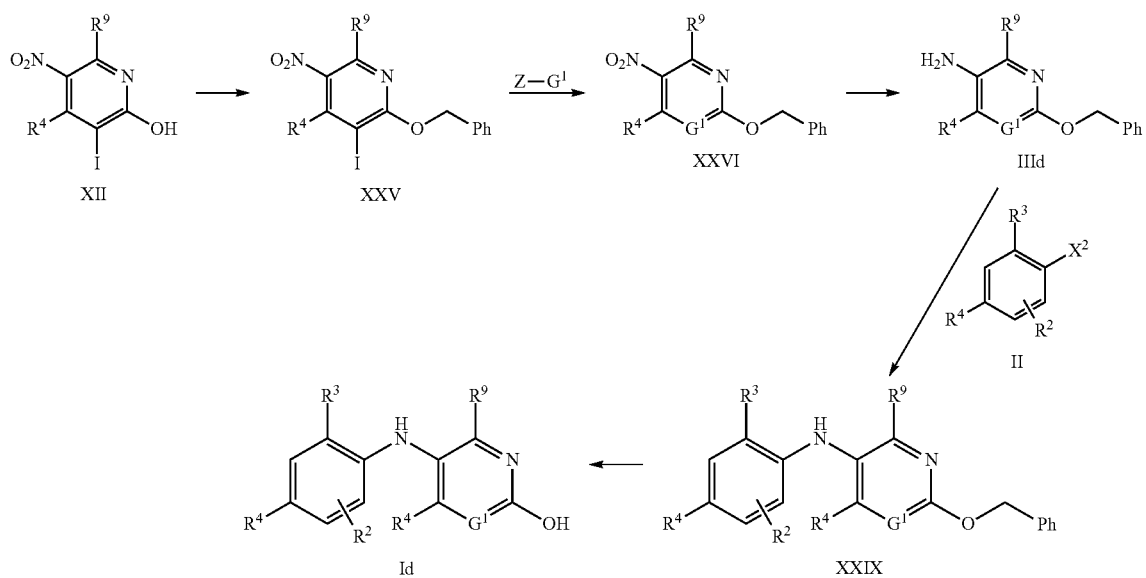

Compounds of general formula (Id) may be obtained from Intermediates of general formula (XXIX) by treatment with triflouroacetic acid a temperature between 25° C. and 60° C. for 30 minutes to 24 hours.

Intermediates of general formula (XXIX) may be obtained from the reaction of Intermediates of general formula (IIId) with Intermediates of general formula (II). The reaction may be mediated under inert atmosphere by a palladium catalyst such as $Pd(OAc)_2$, $Pd_2(dba)_3$, $Pd(PPh_3)_4$, $PdCl_2(PPh_3)_2$ or [1,1'-Bis(diphenylphosphino)-ferrocene]dichloropalladium (II) ($PdCl_2(dppf)DCM$), using a phosphine ligand such as BINAP, tricyclohexylphosphine ($P(Cy)_3$) or Xanthphos when needed, in the presence of a base such as $Cs_2CO_3$, $K_2CO_3$ or $NaO^tBu$ in a high boiling point solvent such as toluene, xylene, DMF, water or dioxane or THF at a range of temperatures from 40° C. to 160° C. for 0.5 to 24 hours. The reaction may also be performed in a microwave oven at a range of temperatures from 100° C. to 160° C. for 0.5 to 15 hours.

Intermediates of general formula (IIId) may be obtained by reduction of Intermediates of general formula (XXVI) using hydrogen and a catalyst such as Pd/C, Pt/C, $PtO_2$, $Pd(OH)_2$ Ni-Raney optionally in the presence of $ZnBr_2$ or $SnCl_2.H_2O$ or Fe—HCl in a solvent such as EtOAc, MeOH, THF or EtOH, at room temperature for 1 to 24 hours.

Intermediates of general formula (XXVI) may be obtained from the reaction of Intermediates of general formula (XXV) with $Z-G^1$, wherein Z is a boronic acid, a boronate, trialkylstannane or zincate derivative. The reaction may be mediated under inert atmosphere by a palladium catalyst such as $Pd(OAc)_2$, $Pd_2(dba)_3$, $Pd(PPh_3)_4$, $PdCl_2(PPh_3)_2$ or [1,1'-Bis (diphenylphosphino)-ferrocene]dichloropalladium(II) ($PdCl_2(dppf)DCM$), using a phosphine ligand such as BINAP, tricyclohexylphosphine ($P(Cy)_3$) or xanthphos when needed, in the presence of a base such as $Cs_2CO_3$, $K_2CO_3$ or $NaO^tBu$ in a high boiling point solvent such as toluene, xylene, DMF, water or dioxane or THF at a range of temperatures from 40° C. to 160° C. for 0.5 to 24 hours. The reaction may also be performed in a microwave oven at a range of temperatures from 100° C. to 160° C. for 0.5 to 15 hours. In the particular case that Z is a trialkylstannane derivative, CuI is added as a co-catalyst. In the particular case that Z is a zincate derivative, this is preformed in situ from the corresponding aryl derivative.

Intermediates of general formula (XXV) may be obtained from the reaction of Intermediates of general formula (XII) with benzyl bromide in the presence of a base such as $Cs_2CO_3$, $K_2CO_3$ or $Ag_2CO_3$ in a solvent such as toluene, benzene or DMF at temperature between 60° C. and 120° C. for 5 to 24 hours.

In an alternative procedure, compounds of the present invention of formula (Ib) wherein $R^3$ is a carboxylic acid, may also be obtained following the synthetic scheme shown in figure 9.

Figure 9

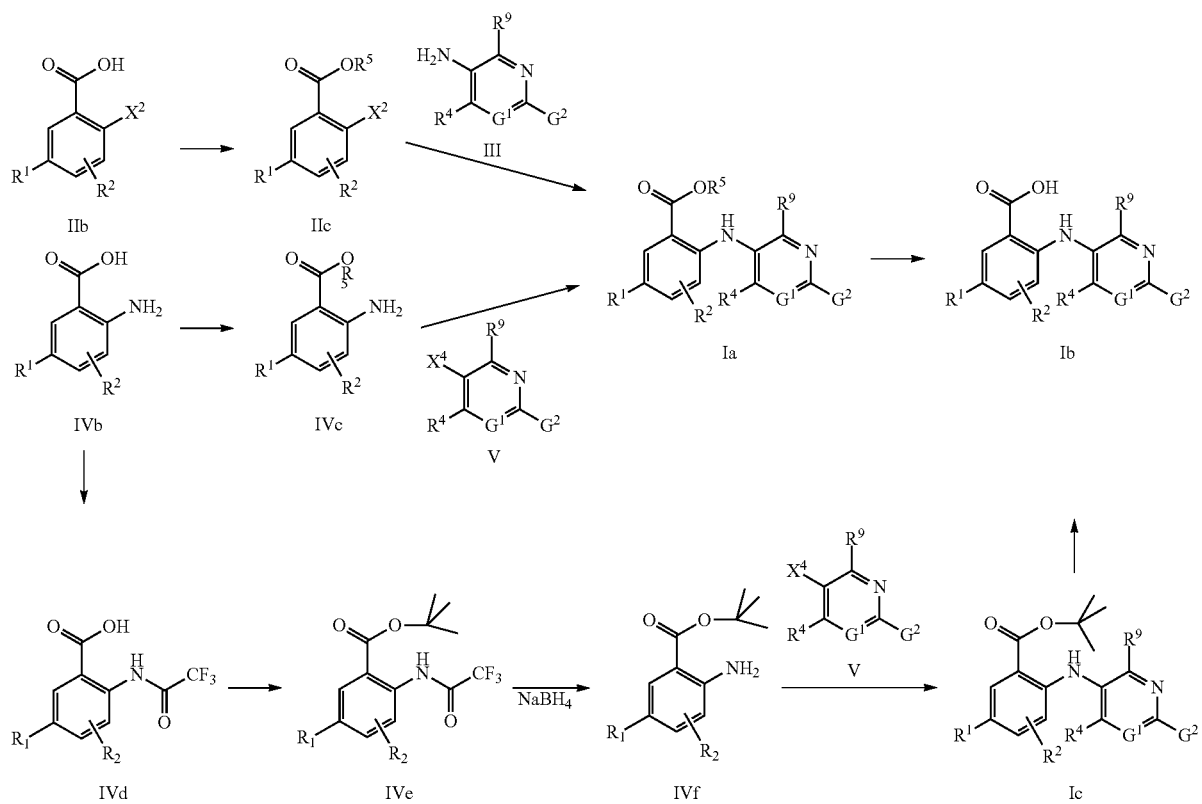

Compounds of general formula (Ib) may be prepared by hydrolysis of compounds of formula (Ia) or (Ic), wherein $R^1$, $R^2$, $R^4$, $R^9$, $G^1$ and $G^2$ are as described above and $R^5$ is a $C_{1-4}$ alkyl group. When $R^5$ is a methyl or ethyl group, an aqueous solution of sodium or lithium hydroxide is used in a solvent such as ethanol or THF at a range of temperatures between 20° C. and 70° C. for 1 to 16 hours. When $R^5$ is a tert-butyl group, the hydrolysis of compound of formula (Ic) may be run under acidic conditions using trifluoroacetic acid or hydrogen chloride in a solvent such as dichloromethane, THF or dioxane at a range of temperatures between 20° C. and 80° C. for 30 minutes to 16 hours.

Compounds of general formula (Ia) may be obtained by the reaction of intermediate (IIc) wherein $X^2$ is a described above, with intermediate (III) following the same procedure depicted in figure 1 for obtaining compounds of formula (I) from intermediates (II) and (III).

Alternatively, compounds of general formula (Ia) may also be obtained by the reaction of intermediate (IVc) with intermediate (V) following the same procedure depicted in figure 3 for obtaining compounds of formula (I) from intermediates (IV) and (V).

Intermediates of formula (IIc) and (IVc) may be obtained from Intermediate (IIb) and (IVb), respectively in the presence of an acid such as HCl or $H_2SO_4$ in a solvent such as methanol, ethanol or dioxane at a range of temperatures from 25° C. to 110° C. for 1 to 48 hours.

Compounds of general formula (Ic) may be obtained by the reaction of intermediate (IVf) with intermediate (V), following the same procedure depicted in figure 3 for obtaining compounds of formula (I) from intermediates (IV) and (V).

Intermediates of general formula (IVf) may be obtained from Intermediates (IVe) in the presence of $NaBH_4$ in a solvent such as methanol or ethanol at a range of temperatures between 0° C. and room temperature.

Intermediates of general formula (IVe) may be obtained from intermediate (IVd) in the presence of di-tert-butylcarbonate or 1,1-ditert-butoxy-N,N-dimethylmethanamine in a solvent such as ethanol, toluene, dichloromethane or DMF in a range of temperatures between 25° C. and 100° C. for 2 to 24 hours.

Intermediates of general formula (IVd) may be obtained from Intermediates of general formula (IVb) in the presence of trifluoroacetic acid or trifluoroacetic anhydride at a range of temperatures between 25° C. and 70° C. for 1 to 24 hours.

In the particular case that $R^1$ is —$CF_3$, Intermediates of general formula (IVc) may be obtained following the synthetic scheme shown in figure 10.

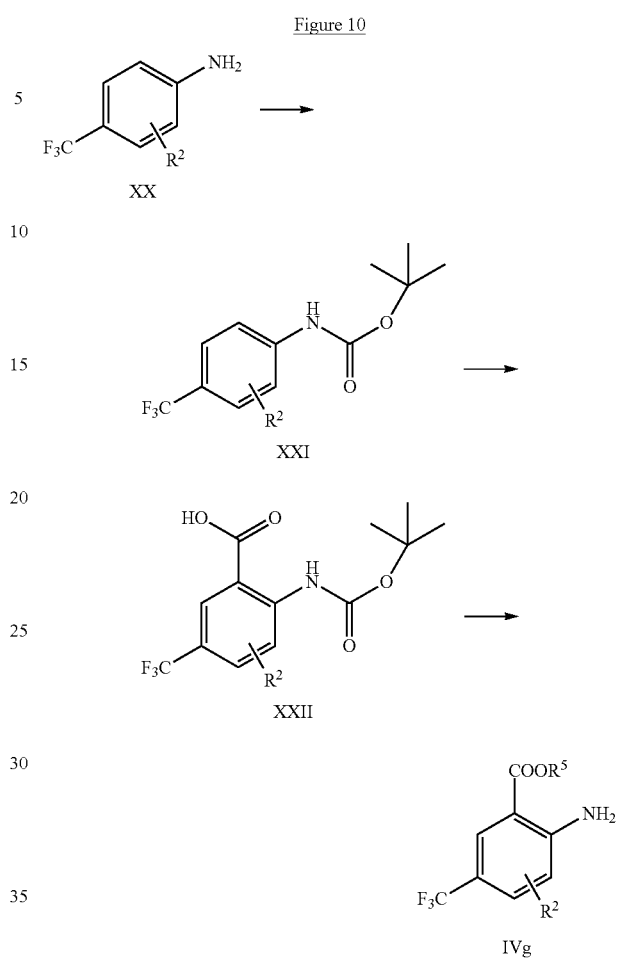

Figure 10

Intermediates of general formula (IVg) may be obtained from Intermediates of formula (XXII) in the presence of an inorganic acid such as HCl or $H_2SO_4$ in a alcoholic solvent such as ethanol or methanol at a range of temperatures between 70° C. to 120° C. for 8 to 24 hours.

Intermediates of general formula (XXII) may be obtained from Intermediates of general formula (XXI). The reaction may be carried out in the presence of n-butyl lithium and trimethylethylenediamine and bubbling $CO_2$ for 0.5 to 3 hours, in a solvent such as ethyl ether or THF at a range of temperatures between −78° C. to −40°.

Intermediates of general formula (XXI) may be obtained from Intermediates of general formula (XX). The reaction may be carried out in the presence of di-tert-butylcarbonate and aqueous solution of NaOH at room temperature for 6 to 48 hours.

In the particular case that $R^3$ is a tetrazolyl group, compounds of formula (Ie) may be obtained following the synthetic scheme shown in figure 11.

Figure 11

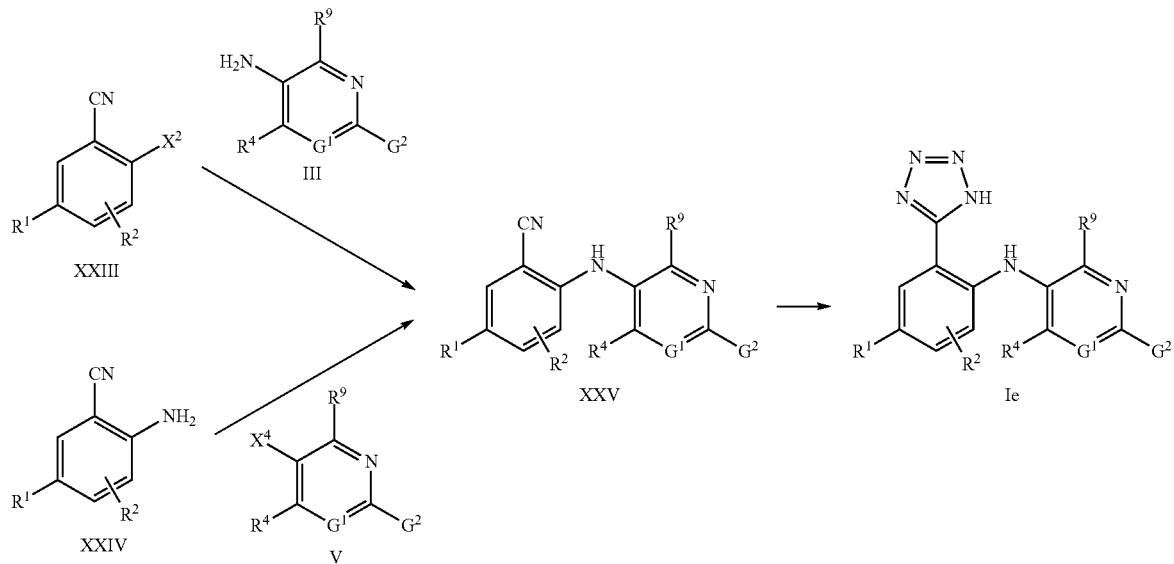

Compounds of general formula (Ie) may be obtained from Intermediates of general formula (XXV). The reaction may be carried out in the presence of $N_3SnMe_3$ or sodium azide with $NH_4Cl$ or $Bu_3SnCl$ in high boiling point solvent such as DMF or xylene at a range of temperatures between 100° C. to 150° C. for 20 to 120 hours.

Intermediates of general formula (XXXV) may be obtained from the reaction of Intermediates of general formula (XXIII), wherein $R^1$, $R^2$ and $X^2$ are as described above, with intermediates (III) following the procedure depicted in figure 1 for obtaining compounds of general formula (I) from intermediates (II) and (III). Alternatively Intermediates of general formula (XXXV) may be obtained from the reaction of Intermediates of general formula (XXIV), wherein $R^1$ and $R^2$ are as described above, with intermediates (V) following the procedure depicted in figure 3 for obtaining compounds of general formula (I) from Intermediates (V) and (IV).

Intermediates of general formula (VII) wherein Z and $G^2$ are as described above are commercially available. However in the particular case when $G^2$ is a cyclopropoxyphenyl group, said intermediate may be obtained following the synthetic scheme depicted in figure 12.

Figure 12

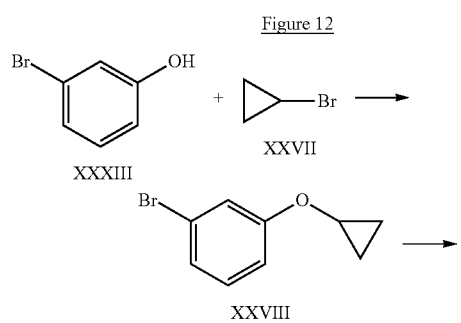

-continued

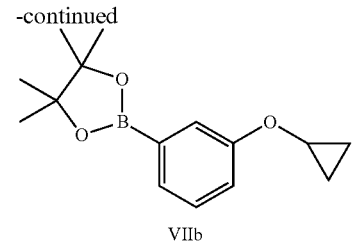

VIIb

Intermediate (VIIb) may be obtained from 1-bromo-3-cyclopropoxybenzene (XXVIII) in the presence of 4,4,4',4',5,5,5',5'-octamethyl-2,2'-bi(1,3,2-dioxaborolane), $PdCl_2dppf.DCM$ and a base such as KAcO in a high boiling point solvent such as DMF or DMSO at a range of temperatures between 130° C. and 180° C. for 45 minutes to 24 hours. Alternatively the reaction may be carried out in a microwave oven.

1-bromo-3-cyclopropoxybenzene (XXVIII) may be obtained from 3-bromophenol (XXXIII) and bromocyclopropane (XXVII) in the presence of a base such as $Cs_2CO_3$ or $K_2CO_3$ in a high boiling point solvent such as DMF or DMSO at a range of temperatures between 130° C. and 180° C. for 6 to 24 hours. Alternatively the reaction may be carried out in a microwave oven.

In the particular case that $G^2$ is a —$NR^aR^b$ group, compounds of formula (If) may be obtained following the synthetic scheme shown in figure 13 from the reaction of intermediates of general formula (VI), wherein $X^5$ is a bromine atom and intermediates of general formula (XXX).

Figure 13

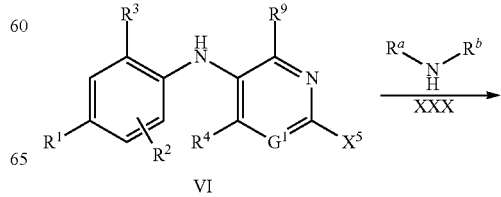

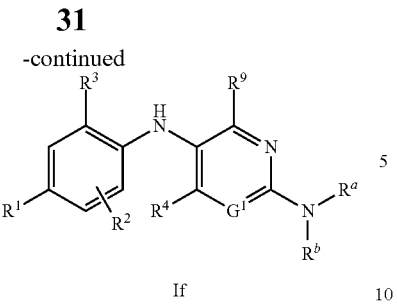

If

The reaction may be mediated under inert atmosphere by a palladium catalyst such as Pd(OAc)$_2$, Pd$_2$(dba)$_3$, Pd(PPh$_3$)$_4$, PdCl$_2$(PPh$_3$)$_2$ or [1,1'-Bis(diphenylphosphino)-ferrocene]dichloropalladium(II) (PdCl$_2$(dppf)DCM), using 1,3-bis(2,6-diisopropylphenyl)imidazolium chloride, in the presence of a base such as Cs$_2$CO$_3$, K$_2$CO$_3$ or NaO$^t$Bu in a high boiling point solvent such as toluene, xylene, DMF, water or dioxane or THF at a range of temperatures from 40° C. to 160° C. for 0.5 to 24 hours. The reaction may also be performed in a microwave oven at a range of temperatures from 100° C. to 160° C. for 0.5 to 15 hours.

In the particular case that G$^1$-G$^2$ is a tetrahydroquinolinylamino group compounds of formula (Ik) may be prepared by reduction of compounds of general formula (I) wherein G$^1$-G$^2$ is a quinolinylamino group (Ij) using hydrogen and a catalyst such as Pd/C, Pt/C, PtO$_2$, Pd(OH)$_2$ or Ni-Raney optionally in the presence of ZnBr$_2$ or SnCl$_2$.H$_2$O or Fe—HCl in a solvent such as trifluoroacetic acid, acetic acid, EtOAc, MeOH, THF or EtOH, at room temperature for 1 to 24 hours as shown in figure 14.

FIG. 14

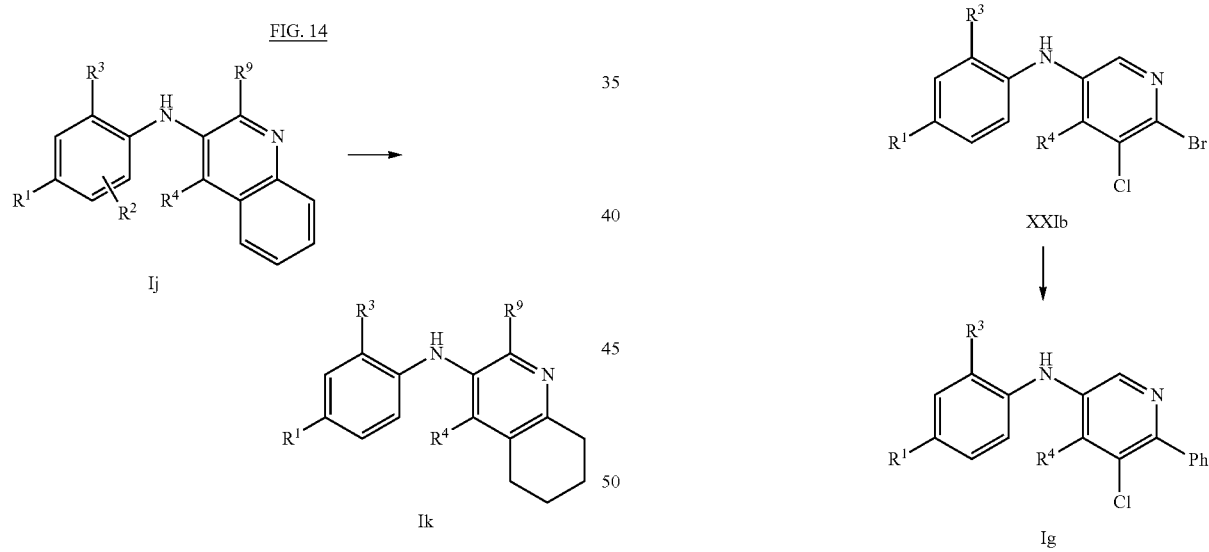

In the particular case of compounds of general formula (Ih) and (Ig), they may be obtained from Intermediates of general formula (XXIa) and (XXIb), respectively as shown in figure 15.

Figure 15

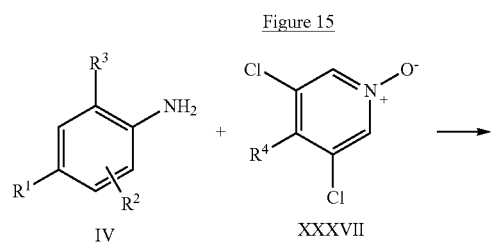

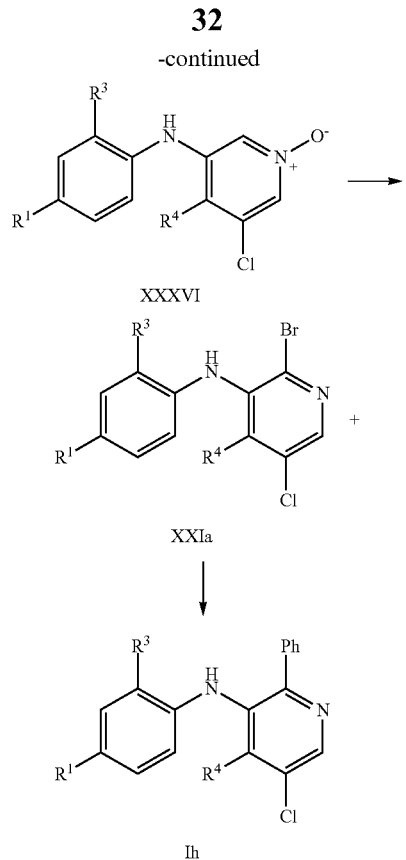

The reaction of compounds of formula (Ih) and (Ig) may be carried out by reaction of a phenyl boronic acid under inert atmosphere by a palladium catalyst such as Pd(OAc)$_2$, Pd$_2$(dba)$_3$, Pd(PPh$_3$)$_4$, PdCl$_2$(PPh$_3$)$_2$ or [1,1'-Bis(diphenylphosphino)-ferrocene]dichloropalladium(II) (PdCl$_2$(dppf)DCM), using a phosphine ligand such as BINAP, tricyclohexylphosphine (P(Cy)$_3$) or Xanthphos when needed, in the presence of a base such as Cs$_2$CO$_3$, K$_2$CO$_3$ or NaO$^t$Bu in a high boiling point solvent such as toluene, xylene, DMF, water or dioxane or THF at a range of temperatures from 40° C. to 160° C. for 0.5 to 24 hours. The reaction may also be performed in a microwave oven at a range of temperatures from 100° C. to 160° C. for 0.5 to 15 hours.

Intermediates of general formula (XXIa) and (XXIb) may be obtained from Intermediate of general formula (XXXVI) by treatment with POBr$_3$ in dichloromethane at reflux for 2 to 3 hours. Intermediates of general formula (XXIV) may be obtained from the reaction of Intermediates of general formula (IV) and Intermediates of general formula (XXXVII). The reaction may be mediated by a palladium catalyst such as Pd(OAc)$_2$ or Pd$_2$(dba)$_3$, using a phosphine ligand such as BINAP or xanthphos, in the presence of a base such as Cs$_2$CO$_3$, K$_2$CO$_3$ or NaO$^t$Bu in a high boiling point solvent such as toluene, xylene, DMF, water or dioxane at a range of temperatures from 80° C. to 160° C. for 0.5 to 24 hours. The reaction may also be performed in a microwave oven at a range of temperatures from 100° C. to 160° C. for 0.5 to 15 hours.

Compounds of general formula (II), (IV), (VII), (VIIa), (VIII), (XII), (IXb), (XIV), (XV), (XVI), (XVII), (XVIII), (XIX), (XX), (IIb), (IVb), (XXIII), (XXIV), (XXV), (XXVI), (XXVII), (XXXIII), and (XXXVII) are commercially available or may be obtained following conventional synthetic methods already known in the art.

The syntheses of the compounds of the invention and of the intermediates for use therein are illustrated by the following Examples (1 to 118) including Preparation Examples (Intermediates 1 to 74) which do not limit the scope of the invention in any way.

$^1$H Nuclear Magnetic Resonance Spectra were recorded on a Varian Mercury 200 spectrometer. Low Resolution Mass Spectra (m/z) were recorded on a Micromass ZMD mass spectrometer using ESI ionization. The chromatographic separations were obtained using a Waters 2690 system equipped with a Symmetry C18 (2.1×10 mm, 3.5 mM) column. The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially 0.5 min with 0% of B, then from 0% to 95% of B in 6.5 min, and then 1 min. with 95% of B. The reequilibration time between two injections was 1 min. The flow rate was 0.4 mL/min. The injection volume was 5 microliter. Diode array chromatograms were collected at 210 nM.

PREPARATION EXAMPLES

Synthesis of Intermediates

Intermediate 1

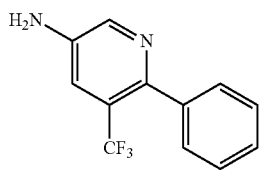 [SMILES: Nc1cnc(-c2ccccc2)c(C(F)(F)F)c1]

6-Phenyl-5-(trifluoromethyl)pyridin-3-amine

A. 2-Chloro-3-iodo-5-nitropyridine

A mixture of 3-iodo-5-nitropyridin-2-ol (37.60 mmol, 10 g), POCl$_3$ (86.47 mmol, 7.94 ml) and PCl$_5$ (48.87 mmol, 10.2 g) was heated at 140° C. for 45 minutes under argon atmosphere. The mixture was cooled at room temperature, poured slowly over iced-water and extracted with dichloromethane. The organic phase was washed with water, NaHCO$_3$ aqueous solution and brine. The solvent was evaporated and the crude mixture was purified by chromatography over SiO$_2$ eluting hexane/DCM mixtures affording 7.32 g (yield 69%) of the expected product.

$^1$H NMR (300 MHz, CDCl$_3$) δ ppm: 8.90 (s, 1H), 9.19 (s, 1H).

B. 2-Chloro-5-nitro-3-(trifluoromethyl)pyridine

In a schlenck tube, a mixture of 2-chloro-3-iodo-5-nitropyridine (17.58 mmol, 5.00 g), methyl 2,2-difluoro-2-(fluorosulfonyl)acetate (8.79 mmol, 1.12 ml) and CuI (2.64 mmol, 0.5 g) in DMF (30 ml) was heated at 70° C. for 3 hours under argon atmosphere. Methyl 2,2-difluoro-2-(fluorosulfonyl)acetate (4.40 mmol, 0.6 ml) was added and the mixture was heated at 70° C. for 16 hours. The solvent was evaporated and the crude mixture was extracted between ethyl acetate and water. The crude mixture was purified by chromatography over SiO$_2$ eluting with hexane/DCM mixtures affording 1.19 g (yield 30%) of the expected product.

$^1$H NMR (300 MHz, CDCl$_3$) δ ppm: 8.82 (s, 1H), 9.41 (s, 1H).

C. 6-Chloro-5-(trifluoromethyl)pyridin-3-amine

A mixture of 2-chloro-5-nitro-3-(trifluoromethyl)pyridine (5.25 mmol, 1.19 g), ZnBr$_2$ (1.05 mmol, 0.200 g) and 5% Pt (C) (1.58 mmol, 0.31 g) in ethyl acetate (50 ml) was stirred for 20 hours under hydrogen atmosphere. The catalyst was filtered off and the solid was washed with warmed ethanol. The solvent was evaporated affording the expected product (0.95 g, yield 92%).

$^1$H NMR (300 MHz, DMSO-d$_6$) δ ppm: 5.59 (bs, 1H), 7.37 (s, 1H), 7.92 (s, 1H).

D. N-(5-bromo-3-(trifluoromethyl)pyridin-2-yl)acetamide

A mixture of 6-chloro-5-(trifluoromethyl)pyridin-3-amine (2.95 mmol, 0.58 g) and 30% HBr in acetic acid (6 ml) in a sealed tube was heated at 100° C. overnight. The crude mixture was poured into ice water, the pH was set to 10 with 2N aqueous NaOH and extracted with CHCl$_3$.

The solvent was removed under reduced pressure to afford 0.680 g (82% of yield) of the expected product.

ESI/MS (m/e, %): 281.96 (100.0%), 283.96 (97.3%).

E. N-(6-phenyl-5-(trifluoromethyl)pyridin-3-yl)acetamide

In a schlenck tube, a mixture of N-(5-bromo-3-(trifluoromethyl)pyridin-2-yl)acetamide (2.40 mmol, 0.680 g), phenylboronic acid (3.22 mmol, 0.392 g), cessium carbonate (6.87 mmol, 2.238 g) and PdCl$_2$dppf.CH$_2$Cl$_2$ (0.24 mmol, 0.196 g) in dioxane/water 3:1 (20 ml) was heated at 110° C. overnight, under argon atmosphere. The solvent was evaporated and the crude mixture was purified over SiO$_2$ eluting with CH$_2$Cl$_2$/MeOH mixtures affording 0.478 g (71% of yield) of the expected compound.

ESI/MS (m/e, %): 280 (100.0%).

F. 6-Phenyl-5-(trifluoromethyl)pyridin-3-amine

To a solution of N-(6-phenyl-5-(trifluoromethyl)pyridin-3-yl)acetamide (1.68 mmol, 0.280 g) in ethanol (6 ml), 2N aqueous NaOH (5 ml) was added. The mixture was heated at 110° C. for 3 hours. The solvent was removed, the pH was set at 8 and extracted with CHCl₃. The solvent was removed to afford 0.394 g (98% of yield) of the expected product.

ESI/MS (m/e, %): 238 (100.0%).

Intermediate 2

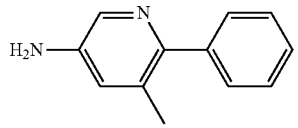

A. 3-Methyl-5-nitro-2-phenylpyridine

In a schlenck tube, a mixture of 2-bromo-3-methyl-5-nitropyridine (4.6 mmol, 1.0 g), phenylboronic acid (4.6 mmol, 0.560 g), PdCl₂dppf.DCM (0.47 mmol, 0.4 g), Cs₂CO₃ (13.8 mmol, 4.5 g) in a dioxane/water 4:1 mixture (18 ml) was heated at 100° C. for 14 hours, under argon atmosphere. The solvent was evaporated and the crude mixture was extracted between water and ethyl acetate. The solid residue was purified by chromatography over SiO₂ eluting with hexane/ethyl acetate mixtures affording 3-methyl-5-nitro-2-phenylpyridine (0.95 g, yield 97%) as major product.

ESI/MS (m/e, %): 215 [(M+1)⁺, 100].

B. 5-Methyl-6-phenylpyridin-3-amine

A mixture of 3-methyl-5-nitro-2-phenylpyridine (4.43 mmol, 0.95 g) and Pd/C 10% (0.1 g) in ethanol (40 ml) was stirred for 16 hours under hydrogen atmosphere. The catalyst was filtered off and the solid thoughtfully washed with warm ethanol. The filtrate was evaporated and the crude was purified by chromatography over SiO₂ eluting with DCM/methanol mixtures and affording 0.65 g (yield 80%) of the expected product.

¹H NMR (300 MHz, CDCl₃) δ ppm: 2.29 (s, 3H), 6.90 (m, 1H), 7.30-7.50 (m, 5H), 8.04 (m, 1H).

ESI/MS (m/e, %): 185 [(M+1)⁺, 100].

Intermediate 3

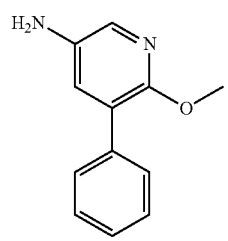

6-Methoxy-5-phenylpyridin-3-amine

A. 5-Nitro-3-phenylpyridin-2-ol

In a schlenck tube, a mixture of 3-iodo-5-nitropyridin-2-ol (7.52 mmol, 2 g), phenylboronic acid (8.28 mmol, 1.01 g), PdCl₂dppf.DCM (0.75 mmol, 0.6 g), Cs₂CO₃ (22.56 mmol, 7.4 g) in a dioxane/water 4:1 mixture (26 ml) was heated at 100° C. for 4 hours, under argon atmosphere. The solvent was evaporated and the crude mixture was extracted between water and ethyl acetate. The organic phase was evaporated and the crude was suspended in methanol affording a solid that was filtered off and dried under vacuum overnight affording 1.2 g (74% of yield) of the expected product.

¹H NMR (300 MHz, CDCl₃) δ ppm: 7.31-7.54 (m, 3H), 7.61-7.76 (m, 2H), 8.26 (d, 1H), 8.44 (s, 1H).

ESI/MS (m/e, %): 215 [(M−1)⁻, 100].

B. 2-Bromo-5-nitro-3-phenylpyridine

A mixture of 5-nitro-3-phenylpyridin-2-ol (4.63 mmol, 1 g), POBr₃ (4.74 mmol, 0.45 ml) and PBr₃ (4.71 mmol, 1.4 g) was heated at 120° C. for 3.5 hours. The crude mixture was poured into a mixture of ice and water and extracted with DCM. The organic phase was dried and evaporated affording 0.8 g (yield 62%) of the expected product.

¹H NMR (300 MHz, CDCl₃) δ ppm: 7.38-7.61 (m, 5H), 8.39 (d, J=2.20 Hz, 1H), 9.19 (d, J=2.20 Hz, 1H).

C. 2-Methoxy-5-nitro-3-phenylpyridine

A mixture of 2-bromo-5-nitro-3-phenylpyridine (0.72 mmol, 0.2 g), 2-cyclopropyl-4,4,5,5-tetramethyl-1,3,2-dioxaborolane (0.86 mmol, 0.16 ml), Pd(PPh₃)₄ (0.04 mmol, 0.05 g), K₂CO₃ (2 mmol, 0.28 g) in a toluene/methanol 4:1 mixture (10 ml) was heated at 100° C. for 30 minutes in a microwave, under argon atmosphere. The solvent was evaporated and the crude mixture was extracted between water and ethyl acetate. The solid residue was purified by chromatography over SiO₂ eluting with hexane/ethyl acetate mixtures affording 2-methoxy-5-nitro-3-phenylpyridine (0.1 g, yield 55%) of an unexpected product.

¹H NMR (300 MHz, CDCl₃) δ ppm: 4.11 (s, 3H) 7.41-7.54 (m, 3H) 7.54-7.64 (m, 2H) 8.41 (d, J=2.75 Hz, 1H) 9.07 (d, J=2.75 Hz, 1H).

D. 6-Methoxy-5-phenylpyridin-3-amine

A mixture of 2-methoxy-5-nitro-3-phenylpyridine (0.43 mmol, 0.1 g) and Pd/C 10% (0.14 mmol, 0.015 g) in ethanol (2 ml) was stirred for 16 hours under hydrogen atmosphere. The catalyst was filtered off and the solid thoughtfully washed with warm ethanol. The filtrate was evaporated affording 0.085 g (98% of yield) of the expected product.

ESI/MS (m/e, %): 201 [(M+1)⁺, 100].

Intermediate 4

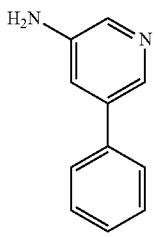 [SMILES: Nc1cncc(-c2ccccc2)c1]

A. 2-Chloro-3-iodo-5-nitropyridine

A mixture of 3-iodo-5-nitropyridin-2-ol (37.6 mmol, 10 g), POCl₃ (86.47 mmol, 7.94 ml) and PCl₅ (48.87 mmol, 10.2 g)

was heated at 140° C. for 1 h, under argon atmosphere. The crude mixture was poured into a mixture of ice and water and extracted with DCM. The solid residue was purified by chromatography over SiO$_2$ eluting with hexane/dichloromethane mixtures affording 2-chloro-3-iodo-5-nitropyridine (7.32 g, yield 69%) of the expected product.

$^1$H NMR (300 MHz, CDCl$_3$) δ ppm: 8.91 (d, J=2.47 Hz, 1H) 9.19 (d, J=2.47 Hz, 1H).

B. 2-Chloro-5-nitro-3-phenylpyridine

In a schlenck tube, a mixture of 2-chloro-3-iodo-5-nitropyridine (1.76 mmol, 0.5 g), phenylboronic acid (1.94 mmol, 0.24 g), PdCl$_2$dppf.DCM (0.18 mmol, 0.1 g), Cs$_2$CO$_3$ (5.28 mmol, 1.7 g) in a dioxane/water 4:1 mixture (6.5 ml) was heated at 120° C. for 4 hours, under argon atmosphere. The solvent was evaporated and the crude mixture was extracted between water and ethyl acetate. The solid residue was purified by chromatography over SiO$_2$ eluting with hexane/dichloromethane mixtures affording 2-chloro-5-nitro-3-phenylpyridine (0.23 g, yield 55%) of the expected product.

$^1$H NMR (300 MHz, CDCl$_3$) δ ppm: 7.36-7.67 (m, 5H) 8.47 (d, J=2.75 Hz, 1H) 9.23 (d, J=2.75 Hz, 1H).

C. 5-Phenylpyridin-3-amine

A mixture of 2-chloro-5-nitro-3-phenylpyridine (0.43 mmol, 0.1 g), KOAc (0.43 mmol, 0.042 g) and Pd/C 10% (0.03 g) in ethanol (4 ml) was stirred for 24 hours under hydrogen atmosphere. The catalyst was filtered off and the solid thoughtfully washed with warm ethanol. The solid residue was purified by chromatography over SiO$_2$ eluting with dichloromethane/methanol mixtures affording 5-phenylpyridin-3-amine (0.05 g, yield 69%) of the expected product.

$^1$H NMR (300 MHz, CDCl$_3$) δ ppm: 7.15-7.23 (m, 1H), 7.37-7.51 (m, 3H), 7.52-7.63 (m, 2H), 8.09 (d, 1H), 8.27 (d, 1H).

ESI/MS (m/e, %): 171 [(M+1)$^+$, 100].

Intermediate 5

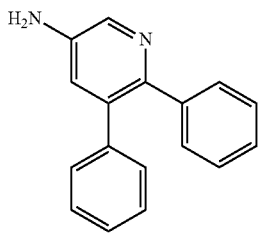 [SMILES: Nc1cnc(-c2ccccc2)c(-c2ccccc2)c1]

5,6-diphenylpyridin-3-amine

A. 3-Bromo-5-nitropyridin-2-ol

To a solution of 5-nitropyridin-2-ol (0.06 mol, 8.6 g) in 400 ml of water at 40°, 3.7 ml of Br$_2$ was added. The mixture was stirred at 40° C. for 2.5 h and then it was stirred at room temperature overnight. The solid formed was filtered off, washed with water and dried under vacuum overnight affording 12.5 g (93% of yield) of the expected product.

$^1$H NMR (300 MHz, DMSO-d$_6$) δ ppm: 8.57 (d, 1H) 8.74 (s, 2H).

B. 2,3-Dibromo-5-nitropyridine

Obtained (2.23 g, yield 87%) following the procedure described in Intermediate 2 (step B), starting with 3-bromo-5-nitropyridin-2-ol (9.13 mmol, 2 g).

$^1$H NMR (300 MHz, CDCl$_3$) δ ppm: 8.48-8.84 (m, 1H) 8.94-9.31 (m, 1H)

ESI/MS (m/e, %): 267 [(M−1)$^-$, 100].

C. 5-Nitro-2,3-diphenylpyridine

Obtained as a minor product (0.2 g) following the procedure described in Intermediate 2 (step A), starting with 2,3-dibromo-5-nitropyridine (3.55 mmol, 1 g).

$^1$H NMR (300 MHz, CDCl$_3$) δ ppm: 7.03-7.65 (m, 10H), 8.52 (d, J=2.47 Hz, 1H), 9.49 (d, J=2.47 Hz, 1H).

ESI/MS (m/e, %): 277 [(M+1)$^+$, 100].

D. 5,6-Diphenylpyridin-3-amine

A mixture of 5-nitro-2,3-diphenylpyridine (0.74 mmol, 0.21 g) and Pd/C 10% (0.02 g) in methanol (5 ml) was stirred for 16 hours under hydrogen atmosphere. The catalyst was filtered off and the solid thoughtfully washed with methanol. The solid residue was purified by chromatography over SiO$_2$ eluting with hexane/ethyl acetate mixtures affording 0.14 g (74% of yield) of the expected product.

$^1$H NMR (300 MHz, CDCl$_3$) δ ppm: 3.79 (s, 2H), 7.04 (d, J=2.75 Hz, 1H), 7.11-7.36 (m, 10H), 8.20 (d, J=2.75 Hz, 1H).

ESI/MS (m/e, %): 247 [(M+1)$^+$, 100].

Intermediate 6

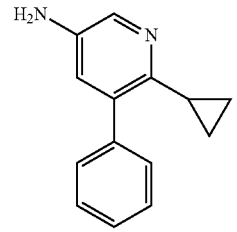 [SMILES: Nc1cnc(C2CC2)c(-c2ccccc2)c1]

6-cyclopropyl-5-phenylpyridin-3-amine

A. 2-Cyclopropyl-5-nitro-3-phenylpyridine

In a schlenck tube, a mixture of 2-chloro-5-nitro-3-phenylpyridine (described in Intermediate 3 (step B)) (1.43 mmol, 0.4 g), 2-cyclopropyl-4,4,5,5-tetramethyl-1,3,2-dioxaborolane (1.59 mmol, 0.29 ml), PdCl$_2$dppf.DCM (0.14 mmol, 0.12 g), Cs$_2$CO$_3$ (4.3 mmol, 1.4 g) in a dioxane/water 4:1 mixture (6.5 ml) was heated at 100° C. for 16 hours, under argon atmosphere. The solvent was evaporated and the crude mixture was extracted between water and ethyl acetate. The solid residue was purified by chromatography over SiO$_2$ eluting with hexane/ethyl acetate mixtures affording 2-cyclopropyl-5-nitro-3-phenylpyridine (0.06 g, 17% of yield) of the expected product.

$^1$H NMR (300 MHz, CDCl$_3$) δ ppm: 0.45-0.55 (m, 2H), 0.56-0.70 (m, 2H), 2.10-2.30 (m, 1H), 7.42-7.57 (m, 5H), 8.23-8.30 (m, 1H), 9.21-9.29 (m, 1H).

ESI/MS (m/e, %): 241 [(M+1)$^+$, 100].

B. 6-Cyclopropyl-5-phenylpyridin-3-amine

A mixture of 2-cyclopropyl-5-nitro-3-phenylpyridine (0.25 mmol, 0.06 g) and $SnCl_2.H_2O$ (0.89 mmol, 0.2 g) in ethanol (2 ml) was heated at 80° C. for 1 hour. The solvent was evaporated and the crude residue was dissolved in water. The solution neutralised with 6N NaOH aqueous solution and extracted with dichloromethane. The solid residue was purified by chromatography over $SiO_2$ eluting with dichloromethane/methanol mixtures affording 6-cyclopropyl-5-phenylpyridin-3-amine (0.03 g, 57% of yield) of the expected product.

$^1H$ NMR (300 MHz, $CDCl_3$) δ ppm: 0.61-0.92 (m, 2H), 0.89-1.10 (m, 2H), 1.78-2.12 (m, 1H), 3.56 (s, 2H), 6.87 (d, J=2.75 Hz, 1H), 7.31-7.57 (m, 5H), 7.78-8.15 (m, J=2.75 Hz, 1H).

ESI/MS (m/e, %): 211 [(M+1)$^+$, 100].

Intermediate 7

Process 1

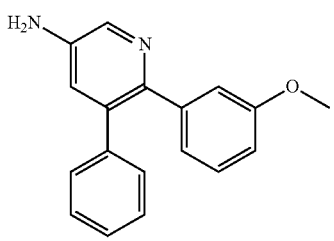 [SMILES: COc1cccc(-c2ncc(N)cc2-c2ccccc2)c1]

6-(3-Methoxyphenyl)-5-phenylpyridin-3-amine

A. 3-bromo-2-(3-methoxyphenyl)-5-nitropyridine

Obtained (1.15 g, 39% of yield) following the procedure described in Intermediate 2 (step A) starting with 2,3-dibromo-5-nitropyridine (described as Intermediate 5 (step B) (9.33 mmol, 2.630 g) and 3-methoxyphenylboronic acid (9.33 mmol, 1.42 g).

ESI/MS (m/e, %): 309 [(M+1)$^+$, 100], 311 [(M+1)$^+$, 80]

B. 2-(3-Methoxyphenyl)-5-nitro-3-phenylpyridine

Obtained (0.257 g, 87% of yield) following the procedure described in Intermediate 2 (step A) starting with 3-bromo-2-(3-methoxyphenyl)-5-nitropyridine (0.97 mmol, 0.300 g) and phenylboronic acid (1.07 mmol, 0.130 g).

ESI/MS (m/e, %): 307 [(M+1)$^+$, 100].

C. 6-(3-Methoxyphenyl)-5-phenylpyridin-3-amine

Obtained (0.160 g, 69% of yield) following the procedure described in Intermediate 5 (step D) starting with 2-(3-methoxyphenyl)-5-nitro-3-phenylpyridine (0.84 mmol, 0.257 g).

$^1H$ NMR (300 MHz, DMSO-$d_6$) δ ppm: 3.60 (s, 3H), 6.73-6.76 (m, 1H), 6.80-6.83 (m, 1H), 6.85-6.88 (m, 1H), 7.07-7.16 (m, 1H), 7.17-7.20 (m, 2H), 7.25-7.29 (m, 3H), 8.18-8.20 (m, 1H).

ESI/MS (m/e, %): 277 [(M+1)$^+$, 100].

Intermediate 7

Process 2

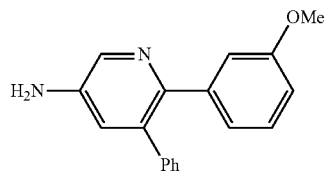 [SMILES: COc1cccc(-c2ncc(N)cc2-c2ccccc2)c1]

6-(3-Methoxyphenyl)-5-phenylpyridin-3-amine

A. 2,3-dibromo-5-nitropyridine

A mixture of 3-bromo-5-nitropyridin-2-ol, $POBr_3$ and $PBr_3$ was heated at 120° C. for 3.5 h. The crude mixture was poured into a mixture of ice and water and extracted with DCM. The crude mixture was purified by flash chromatography over $SiO_2$ eluting with hexane/ethyl acetate mixtures affording 2.63 g (yield 73%) of the expected product.

δ $^1$NMR (300 MHz, DMSO-$d_6$): 8.95 (s, 1H), 9.18 (s, 1H)

B. 3-Bromo-2-(3-methoxyphenyl)-5-nitropyridine

Obtained (1.15 g, yield 40%) following the procedure described in Intermediate 27, starting with 2,3-dibromo-5-nitropyridine (9.33 mmol, 2.63 g), 3-methoxyphenylboronic acid (9.33 mmol, 1.42 g).

δ $^1$H NMR (300 MHz, DMSO-$d_6$): 3.80 (s, 3H), 7.09-7.12 (d, 1H), 7.21-7.26 (m, 2H), 7.42-7.47 (t, 1H), 8.95 (s, 1H), 9.40 (s, 1H).

ESI/MS (m/e, %): 309 [(M+1)$^+$, 100], 311 [(M+1)$^+$, 98].

C. 2-(3-Methoxyphenyl)-5-nitro-3-phenylpyridine

Obtained (0.258 g, yield 87%) following the procedure described in Intermediate 27, starting with 3-bromo-2-(3-methoxyphenyl)-5-nitropyridine (0.97 mmol, 0.300 g), phenylboronic acid (1.07 mmol, 0.130 g).

δ $^1$H NMR (300 MHz, $CDCl_3$): 3.64 (s, 3H), 6.89-6.99 (m, 3H), 7.21-7.24 (m, 3H), 7.32-7.37 (m, 4H), 8.50 (s, 1H), 9.47 (s, 1H).

ESI/MS (m/e, %): 307 [(M+1)$^+$, 100].

D. 6-(3-Methoxyphenyl)-5-phenylpyridin-3-amine

A mixture of 2-(3-methoxyphenyl)-5-nitro-3-phenylpyridine (0.84 mmol, 0.257 g) and Pd/C 10% (0.08 mmol, 0.009 g) in ethanol (5 ml) was stirred for 16 hours under hydrogen atmosphere. The catalyst was filtered off and the solid thoughtfully washed with warm ethanol. The filtrate was evaporated and the crude was purified by chromatography over $SiO_2$ eluting with DCM/methanol mixtures and affording 0.160 g (yield 69%) of the expected product.

δ $^1$H NMR (300 MHz, $CDCl_3$): 3.60 (s, 3H), 3.91 (bs, 2H), 6.73-6.80 (m, 1H), 6.81-6.83 (t, 1H), 6.85-6.88 (m, 1H), 7.01 (s, 1H), 7.07-7.12 (t, 1H), 7.15-7.19 (m, 2H), 7.22-7.29 (m, 4H), 8.18 (s, 1H).

ESI/MS (m/e, %): 277 [(M+1)$^+$, 100].

Intermediate 8

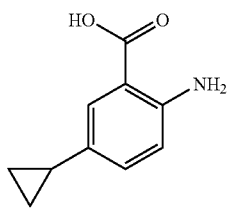 [SMILES: Nc1ccc(C2CC2)cc1C(=O)O]

2-Amino-5-cyclopropylbenzoic acid

A. Methyl 2-amino-5-cyclopropylbenzoate

In a schlenck tube, a mixture of methyl 2-amino-5-bromobenzoate (43.47 mmol, 10 g), cyclopropylboronic acid (112.92 mmol, 9.700 g), $K_3PO_4$ (144.16 mmol, 30.6 g), Pd(AcO)$_2$ (3.47 mmol, 0.780 g), P(Cy)$_3$ (7.85 mmol, 2.2 g) in toluene (170 ml) and water (10 ml) was heated for 2 hours at 100° C., under nitrogen atmosphere. The reaction mixture was filtered through celite and the organic phase was separated and evaporated affording 7.34 g (yield 77%) of the expected product.

$^1$H NMR (300 MHz, CDCl$_3$) δ ppm: 0.48-0.66 (m, 2H) 0.75-0.95 (m, 2H), 1.80 (s, 1H), 3.86 (s, 3H), 5.56 (s, 2H), 6.59 (d, J=8.50 Hz, 1H), 7.03 (dd, J=8.50, 2.15 Hz, 1H), 7.60 (s, 1H).

ESI/MS (m/e, %): 192 [(M+1)$^+$, 87].

B. 2-Amino-5-cyclopropylbenzoic acid

To a solution of Intermediate 36 (24.58 mmol, 4.70 g) in a MeOH/THF 8:1 mixture (225 ml) a solution (150 mmol, 75 ml) of 2N aqueous NaOH was added and the mixture was heated at 60° C. for 15 hours. The organic solvent was evaporated, the aqueous phase was acidified to pH 5 and extracted with ethyl acetate. The solvent was evaporated affording 3.93 g (yield 83%) of the expected product.

ESI/MS (m/e, %): 178 [(M+1)$^+$, 100].

Intermediate 9

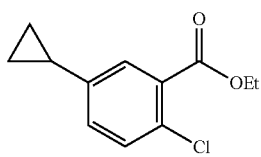 [SMILES: CCOC(=O)c1cc(C2CC2)ccc1Cl]

Ethyl 2-chloro-5-cyclopropylbenzoate

In a schlenck tube, a mixture of ethyl 5-bromo-2-chlorobenzoate (7.60 mmol, 2 g), 2-cyclopropyl-4,4,5,5-tetramethyl-1,3,2-dioxaborolane (7.59 mmol, 1.3 g), Cs$_2$CO$_3$ (18.97 mmol, 6.18 g), PdCl$_2$dppf.CH$_2$Cl$_2$ (0.76 mmol, 0.620 g) in dioxane (70 ml) and water (15 ml) was heated for 2 hours at 110° C., under argon atmosphere. The solvent was evaporated and the mixture was extracted between ethyl acetate and water. The crude mixture was purified by chromatography over SiO$_2$ eluting hexane/ethyl acetate mixtures and affording 1.5 g (yield 92%) of the expected product.

$^1$H NMR (300 MHz, CDCl$_3$) δ ppm: 0.67-0.71 (t, 3H), 0.97-1.01 (m, 2H), 1.38-1.43 (t, 3H), 1.85-1.91 (m, 1H), 4.36-4.43 (q, 2H), 7.07-7.10 (d, 1H), 7.26-7.32 (m, 1H), 7.49 (s, 1H).

ESI/MS (m/e, %): 225 [(M+1)$^+$, 100].

Intermediate 10

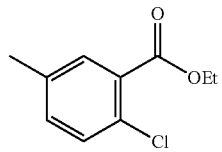

Ethyl 2-chloro-5-methylbenzoate

To a solution of 2-chloro-5-methylbenzoic acid (7.62 mmol, 1.30 g) in ethanol (16 ml), H$_2$SO$_4$ (35 mmol, 1.82 ml) was added and the mixture was refluxed for 20 hours. The solvent was evaporated and the crude residue was dissolved in water. The solution neutralised with 6N NaOH aqueous solution and extracted with CHCl$_3$. The organic phase was evaporated affording 1.46 g (yield 96%) of the expected product.

$^1$H NMR (300 MHz, CDCl$_3$) δ ppm: 1.41 (t, 3H), 2.35 (s, 3H), 4.40 (q, 2H), 7.21 (d, 1H), 7.32 (d, 1H), 7.61 (s, 1H).

ESI/MS (m/e, %): 199 [(M+1)$^+$, 100].

Intermediate 11

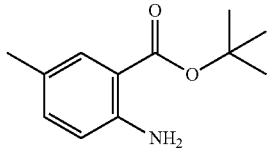

tert-Butyl 2-amino-5-methylbenzoate

A. 5-Methyl-2-(2,2,2-trifluoroacetamido)benzoic acid

In three bottle neck round flask, over trifluoroacetic anhydride (283.0 mmol, 40 ml), 2-amino-5-methylbenzoic acid (39.69 mmol, 6 g) was added in portions at a temperature between 20° C. and 30° C. The mixture was stirred at room temperature for 2 hours and water was slowly added at a temperature below 30° C. cooling the flask externally with ice. The solid formed was filtered off and dried under vacuum overnight affording 9.51 g (yield 91%).

$^1$H NMR (300 MHz, CDCl$_3$) δ ppm: 2.41 (s, 2H), 7.50-7.53 (d, 1H), 8.01 (s, 1H), 8.57-8.60 (d, 1H), 11.89 (bs, 1H).

B. tert-Butyl 5-methyl-2-(2,2,2-trifluoroacetamido)benzoate

To a solution of 5-methyl-2-(2,2,2-trifluoroacetamido) benzoic acid (20.23 mmol, 5.0 g) in toluene (40 ml), 1,1-di-tert-butoxy-N,N-dimethylmethanamine (80.92 mmol, 19.40 ml) was added drop wise. The mixture was stirred at 80° C. for 6 hours and the solvent was evaporated. The crude mixture was purified by chromatography over SiO₂ eluting with DCM/MeOH mixtures affording 6.01 g (yield 98%) of the expected product.

¹H NMR (300 MHz, CDCl₃) δ ppm: 1.63 (s, 9H), 2.37 (s, 3H), 7.38-7.41 (d, 1H), 7.81 (s, 1H), 8.51-8.54 (d, 1H), 12.36 (bs, 1H).

ESI/MS (m/e, %): 304 [(M+1)⁺, 100].

C. tert-Butyl 2-amino-5-methylbenzoate

To a suspension of tert-butyl 5-methyl-2-(2,2,2-trifluoroacetamido)benzoate (19.78 mmol, 6.0 g) in ethanol (19 ml) was cooled with a water-iced bath. NaBH₄ (39.57 mmol, 1.50 g) was added in portions and the mixture was stirred at room temperature for 3 hours. Water (40 ml) was added slowly and evaporated. The solid was dissolved with CHCl₃ and washed with water and brine. The organic phase was evaporated affording 3.73 g (yield 91%) of the expected product.

¹H NMR (300 MHz, CDCl₃) δ ppm: 1.59 (s, 9H), 2.23 (s, 3H), 5.52 (bs, 2H), 6.56-6.59 (d, 1H), 7.05-7.08 (d, 1H), 7.60 (s, 1H).

ESI/MS (m/e, %): 208 [(M+1)⁺, 100].

Intermediate 12

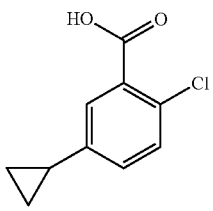 [SMILES: O=C(O)c1cc(C2CC2)ccc1Cl]

2-Chloro-5-cyclopropylbenzoic acid

Obtained (9.6 g, 91% of yield) following the procedure described in Intermediate 8 (step B) starting with Intermediate 9 (50 mmol, 16.4 g).

ESI/MS (m/e, %): 197 [(M+1)⁺, 100].

Intermediate 13

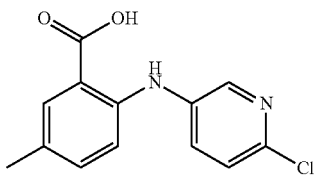 [SMILES: Cc1ccc(Nc2ccc(Cl)nc2)c(C(=O)O)c1]

2-(6-Chloropyridin-3-ylamino)-5-methylbenzoic acid

A mixture of 6-chloropyridin-3-amine (11.67 mmol, 1.5 g) and 2-bromo-5-methylbenzoic acid (23.34 mmol, 5.02 g), Cu (1.17 mmol, 0.1 g), Cu₂O (0.58 mmol, 0.1 g) and K₂CO₃ (23.34 mmol, 3.2 g) in 1,2-dimethoxyethane (15 ml) was heated at 130° C. for 16 hours, under argon atmosphere. Water was added and the mixture was filtered through celite. HCl 2N aqueous solution was added until pH 6 and the solid formed was filtered off. The crude was purified by chromatography eluting with DCM/MeOH mixtures affording 1.40 g (yield 46%).

¹H NMR (DMSO-d₆) δ ppm: 2.24 (s, 3H), 7.16-7.19 (d, 1H), 7.25-7.27 (d, 1H), 7.38-7.41 (d, 1H), 7.67-7.73 (m, 2H), 8.28 (s, 1H), 9.45 (bs, 1H).

ESI/MS (m/e, %): 263 [(M+1)⁺, 100].

Intermediate 14

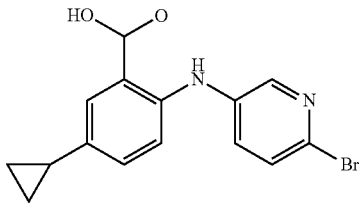 [SMILES: OC(O)c1cc(C2CC2)ccc1Nc1ccc(Br)nc1]

2-(6-Bromopyridin-3-ylamino)-5-cyclopropylbenzoic acid

Obtained (0.680 g, 6% of yield) following the procedure described in Intermediate 13 starting with 6-bromopyridin-3-amine (28.90 mmol, 5 g) and Intermediate 12 (34.68 mmol, 6.82 g).

ESI/MS (m/e, %): 333 [(M+1)⁺, 100], 335[(M+1)⁺, 97].

Intermediate 15

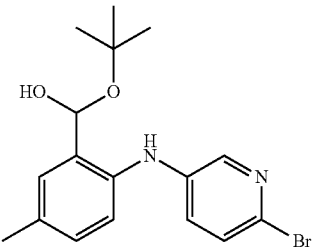 [SMILES: Cc1ccc(Nc2ccc(Br)nc2)c(C(O)OC(C)(C)C)c1]

tert-Butyl 2-(6-bromopyridin-3-ylamino)-5-methylbenzoate

In a schlenck tube, a mixture of tert-butyl 2-amino-5-methylbenzoate (2.89 mmol, 0.600 g), 2-bromo-5-iodopyridine (2.89 mmol, 0.822 g), BINAP (0.29 mmol, 0.096 g), Pd₂(dba)₃ (0.14 mmol, 0.132 g) and NaOʹBu (5.79 mmol, 0.556 g) in toluene (15 ml) was heated at 120° C. for 3 hours. Water and ethyl acetate were added to the reaction crude. The aqueous phase was extracted again with more ethyl acetate. The organic phase was washed with water and brine, dried, filtered and concentrated in vacuo. The crude mixture was purified by chromatography (Biotage 40S, SiO₂, Hexane:Ethyl acetate from 0% to 10%) affording 0.422 g (yield 40%) of the expected product.

¹H NMR (200 MHz, CDCl₃) δ ppm: 1.61 (s, 9H), 2.29 (s, 3H), 7.11-7.16 (m, 2H), 7.35-7.43 (m, 2H), 7.73 (s, 1H), 8.28 (s, 1H), 9.44 (s, 1H).

ESI/MS (m/e, %): 363 [(M+1)⁺, 100].

Intermediate 16

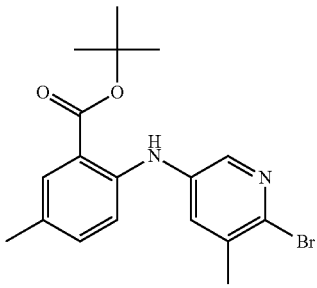 [SMILES: Cc1ccc(Nc2cnc(Br)c(C)c2)c(C(=O)OC(C)(C)C)c1]

tert-Butyl 2-(6-bromo-5-methylpyridin-3-ylamino)-5-methylbenzoate

Obtained following the procedure described in Intermediate 15 starting with Intermediate 11 (3.30 mmol, 0.683 g) and 2-bromo-5-iodo-3-methylpyridine (3.30 mmol, 0.982 g). After purification 0.552 g (yield 44%) of the expected product were obtained.

$^1$H NMR (200 MHz, CDCl$_3$) δ ppm: 2.29 (s, 3H), 2.35 (s, 3H), 7.11-7.21 (m, 2H), 7.39 (d, J=1.95 Hz, 1H), 7.73 (s, 1H), 8.14 (d, J=2.73 Hz, 1H), 9.39 (s, 1H).

ESI/MS (m/e, %): 377, 379 [(M+1)$^+$, 90].

Intermediate 17

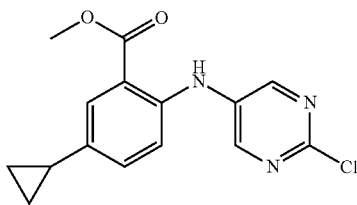 [SMILES: COC(=O)c1cc(C2CC2)ccc1Nc1cnc(Cl)nc1]

Methyl 2-(2-chloropyrimidin-5-ylamino)-5-cyclopropylbenzoate

In a schlenck tube, a mixture of methyl 2-amino-5-cyclopropylbenzoate (described in Intermediate 8 (step A) (26.15 mmol, 5 g), 5-bromo-2-chloropyrimidine (26.93 mmol, 5.21 g), Xantphos (1.07 mmol, 0.6 g), Pd$_2$(dba)$_3$ (1.07 mmol, 0.6 g) and Cs$_2$CO$_3$ (36.65 mmol, 11.9 g) in dioxane (210 ml) was heated at 100° C. overnight. Water and ethyl acetate were added to the reaction crude. The aqueous phase was extracted again with more ethyl acetate. The organic phase was washed with water and brine, dried, filtered and concentrated in vacuo. The crude mixture was purified by reverse chromatography (Water: MeOH/AcN 1:1 from 0% to 100%) affording 6 g (60% of yield) of the expected product.

ESI/MS (m/e, %): 304 [(M+1)$^+$, 90].

Intermediate 18

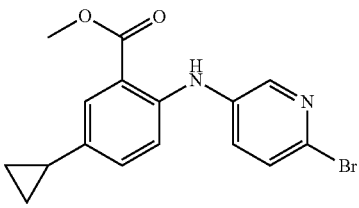 [SMILES: COC(=O)c1cc(C2CC2)ccc1Nc1ccc(Br)nc1]

Methyl 2-(6-bromopyridin-3-ylamino)-5-cyclopropylbenzoate

Obtained (0.155 g, 43% of yield) following the procedure described in Intermediate 15 starting with methyl 2-amino-5-cyclopropylbenzoate (described in Intermediate 8 (step A)) (1.05 mmol, 0.200 g), 2-bromo-5-iodopyridine (1.05 mmol, 0.297 g) and Cs$_2$CO$_3$ (2.09 mmol, 0.682 g) instead of NaO$^t$Bu.

ESI/MS (m/e, %): 347 [(M+1)$^+$, 100], 349 [(M+1)$^+$, 97]

Intermediate 19

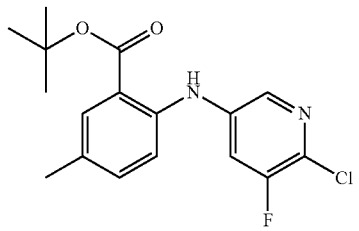 [SMILES: Cc1ccc(Nc2cnc(Cl)c(F)c2)c(C(=O)OC(C)(C)C)c1]

tert-Butyl 2-(6-chloro-5-fluoropyridin-3-ylamino)-5-methylbenzoate

Obtained (0.721 g, 51% of yield) following the procedure described in Intermediate 18 starting with Intermediate 11 (2.77 mmol, 0.573 g) and 5-bromo-2-chloro-3-fluoropyridine (2.77 mmol, 0.582 g).

ESI/MS (m/e, %): 337 [(M+1)$^+$, 100], 339 [(M+1)$^+$, 32]

Intermediate 20

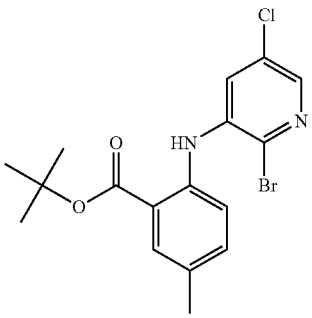 [SMILES: Cc1ccc(Nc2cc(Cl)cnc2Br)c(C(=O)OC(C)(C)C)c1]

tert-Butyl 2-(2-bromo-5-chloropyridin-3-ylamino)-5-methylbenzoate

A. tert-Butyl 2-(2-oxide-5-chloropyridin-3-ylamino)-5-methylbenzoate

Obtained (1.36 g, 44% of yield) following the procedure described in Intermediate 17 starting with intermediate 11 (8.54 mmol, 1.77 g) and 3,5-dichloropyridine 1-oxide (10.25 mmol, 1.68 g).

ESI/MS (m/e, %): 336 [(M+1)$^+$, 100]

B. tert-Butyl 2-(2-bromo-5-chloropyridin-3-ylamino)-5-methylbenzoate

To a solution of tert-Butyl 2-(2-oxide-5-chloropyridin-3-ylamino)-5-methylbenzoate (1.79 mmol, 0.6 g) in DCM (50 ml), POBr₃ (4.53 mmol, 1.300 g) was added in portions. The mixture was refluxed for 2.5 hours. The crude mixture was poured into a mixture of water, ice and NaHCO₃—K₂CO₃. The aqueous phase was extracted with ethyl acetate and the overall organic phase was dried over Na₂SO₄, filtered and the solvent was removed. The crude mixture was purified by flash chromatography over SiO₂ eluting with hexane/ethyl acetate mixtures affording 0.070 g (10% of yield) of tert-butyl 2-(2-bromo-5-chloropyridin-3-ylamino)-5-methylbenzoate (20A) and 0.060 g (9% of yield) of tert-butyl 2-(6-bromo-5-chloropyridin-3-ylamino)-5-methylbenzoate (20B).

Intermediate 21

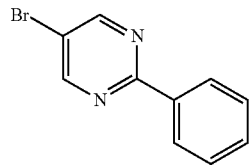 [SMILES: Brc1cnc(-c2ccccc2)nc1]

A mixture of 5-bromo-2-iodopyrimidine (1.76 mmol, 0.500 g), phenylboronic acid (1.93 mmol, 0.235 g), 2M aqueous solution of K₂CO₃ (4.40 mmol, 2.2 ml), Pd(PPh₃)₄ (0.18 mmol, 0.203 g) in dioxane (10 ml) was heated at 110° C. overnight in a microwave oven. The solvent was evaporated and the solid residue was extracted between water and ethyl acetate. The organic phase was evaporated and the crude residue was purified by chromatography over SiO₂ eluting with hexane/ethyl acetate mixtures affording 0.329 g (yield 65%) of the expected product.

ESI/MS (m/e, %): 235 [(M+1)⁺, 100], 237 [(M+1)⁺, 97].

Intermediate 22

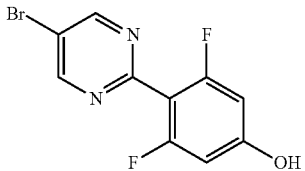 [SMILES: Oc1cc(F)c(-c2ncc(Br)cn2)c(F)c1]

4-(5-Bromopyrimidin-2-yl)-3,5-difluorophenol

A. 5-Bromo-2-(2,6-difluoro-4-methoxyphenyl)pyrimidine

In a three neck round bottle flask, to a mixture of 1,3-difluoro-5-methoxybenzene (8.39 mmol, 0.98 ml) in THF (40 ml) at –78° C. under argon atmosphere, a solution of n-BuLi (9.13 mmol, 3.65 ml) in THF (2.5M) was added. The mixture was stirred at –78° C. for 30 minutes and then it was heated to –50° C. A solution of ZnCl₂ (9.13 mmol, 18.3 ml) in THF (0.5M) was added dropwise and the mixture was stirred at this temperature for 20 minutes. A solution of 5-bromo-2-iodopyrimidine (7.02 mmol, 2.0 g) in THF (5 ml) and Pd(PPh₃)₄ (0.70 mmol, 0.81 g) were added respectively and the crude mixture was heated at 40° C. overnight. The solvent was evaporated and the crude mixture was purified over SiO₂ eluting with mixtures of hexane/ethyl acetate affording 0.89 g (39% of yield) of the expected product.

ESI/MS (m/e, %): 301 [(M+1)⁺, 100], 303 [(M+1)⁺, 97].

B. 4-(5-Bromopyrimidin-2-yl)-3,5-difluorophenol

To a solution of 5-bromo-2-(2,6-difluoro-4-methoxyphenyl)pyrimidine (0.887 g, 2.95 mmol) in DCM at 0° C., was added dropwise a solution of BBr₃ (1M in DCM) (22 ml, 22 mmol) and the reaction mixture was stirred overnight at room temperature. This mixture was then poured over cold MeOH and solid NaHCO₃ was added slowly until pH=4-5. The suspension obtained was filtered and the filtrate evaporated. The solid obtained was redissolved in ethyl acetate, washed with water and brine, dried and concentrated to give the desired compound as a white solid (0.817 g, 85% of yield).

ESI/MS (m/e, %): 287 [(M+1)⁺, 100], 289 [(M+1)⁺, 97].

Intermediate 23

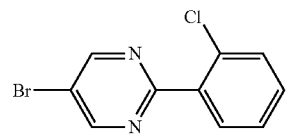 [SMILES: Clc1ccccc1-c1ncc(Br)cn1]

5-Bromo-2-(2-chlorophenyl)pyrimidine

Obtained (0.400 g, yield 69%) following the procedure described in Intermediate 21, starting with 5-bromo-2-iodopyrimidine (2.14 mmol, 0.61 g), 2-chlorophenylboronic acid (2.37 mmol, 0.37 g).

ESI/MS (m/e, %): 269 [(M+1)⁺, 48], 271 [(M+1)⁺, 100], 273 [(M+1)⁺, 23].

Intermediate 24

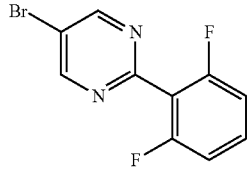 [SMILES: Fc1cccc(F)c1-c1ncc(Br)cn1]

In a three neck round bottle flask, to a mixture of 1,3-difluorobenzene (11.59 mmol, 2.14 ml) in THF (45 ml) at –78° C. under argon atmosphere, a solution of n-BuLi (7.3 ml) in THF (2.5M) was added. The mixture was stirred at –78° C. for 30 minutes and then it was heated to –50° C. A solution of ZnCl₂ (11.5 ml) in THF (1M) was added drop wise and the mixture was stirred at this temperature for 20 minutes. A solution of 5-bromo-2-iodopyrimidine (10.53 mmol, 3.0 g) in THF (5 ml) and Pd(PPh₃)₄ (0.74 mmol, 0.85 g) were added respectively and the crude mixture was heated at 40° C. overnight. The solvent was evaporated and the crude mixture was purified by reverse phase chromatography eluting with a water-MeOH/AcN system affording 1.376 g (yield 49%) of the expected product.

ESI/MS (m/e, %): 271 [(M+1)⁺, 100], 273 [(M+1)⁺, 98]

Intermediate 25

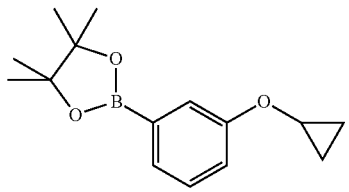 [SMILES: CC1(C)OB(c2cccc(OC3CC3)c2)OC1(C)C]

2-(3-Cyclopropoxyphenyl)-4,4,5,5-tetramethyl-1,3,2-dioxaborolane

A. 1-Bromo-3-cyclopropoxybenzene

A mixture of 3-bromophenol (4.80 mmol, 0.83 g), bromocyclopropane (27.71 mmol, 2.22 ml), $K_2CO_3$ (23.15 mmol, 3.2 g) in DMF (18 ml) was heated at 180° C. for 8 hours in a microwave oven. Water and diethyl ether were added and the organic phase was evaporated affording 0.85 g of the expected product.

B. 3-Cyclopropoxyphenylboronic acid

A mixture of 1-bromo-3-cyclopropoxybenzene (1.36 mmol, 0.289 g), 4,4,4',4',5,5,5',5'-octamethyl-2,2'-bi(1,3,2-dioxaborolane) (2.11 mmol, 0.321 mmol), $PdCl_2dppf.DCM$ (0.14 mmol, 0.112 g), KAcO (6.11 mmol, 0.600 g) in a DMSO (3 ml) was heated at 130° C. for 45 minutes, under argon atmosphere in a microwave oven. Ethyl acetate was added and filtered through celite. The organic phase was washed with water and evaporated. The crude mixture was purified by reverse phase using a water/AcN/MeOH system gradient affording 0.090 g (yield 23%) of the expected product.

$^1$H NMR (400 MHz, $CDCl_3$) δ ppm: 0.8 (m, 4H), 1.3 (s, 12H), 3.8 (m, 1H), 7.1 (dd, J=7.6, 2.2 Hz, 1H), 7.3 (m. 1H), 7.4 (d, J=7.0 Hz, 1H), 7.5 (d, J=2.0 Hz, 1H).

ESI/MS (m/e, %): 260 [(M+1)$^+$, 100]

Intermediate 26

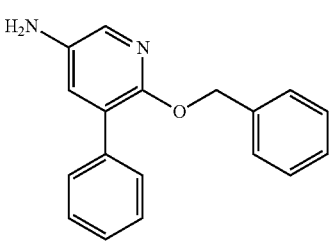 [SMILES: Nc1cnc(OCc2ccccc2)c(-c2ccccc2)c1]

6-(Benzyloxy)-5-phenylpyridin-3-amine

A. 2-(Benzyloxy)-3-iodo-5-nitropyridine

To a solution of 3-iodo-5-nitropyridin-2-ol (0.011 mol, 3 g) in 30 ml of toluene, 2.5 ml of (bromomethyl)benzene and 5.1 g of Ag2CO3 was added. The mixture was stirred at 70° C. for 6 h. The crude was filtered through Celite and washed with ethyl acetate. The solvent was evaporated affording 3.6 g (yield 90%) of the expected product.

$^1$H NMR (300 MHz, $CDCl_3$) δ ppm: 5.56 (s, 2H), 7.33-7.46 (m, 3H), 7.46-7.54 (m, 2H), 8.84 (d, 1H), 9.03 (d, 1H).

B. 2-(Benzyloxy)-5-nitro-3-phenylpyridine

Obtained (0.3 g, yield 70%) following the procedure described in Intermediate 2 (step A), starting with 2-(benzyloxy)-3-iodo-5-nitropyridine (1.4 mmol, 0.5 g).

$^1$H NMR (300 MHz, $CDCl_3$) δ ppm: 5.59 (s, 2H) 7.29-7.53 (m, 8H) 7.54-7.72 (m, 2H) 8.44 (s, 1H) 9.24 (m, 1H).

C. 6-(Benzyloxy)-5-phenylpyridin-3-amine

To a solution of 2-(benzyloxy)-5-nitro-3-phenylpyridine (0.98 mmol, 0.3 g) in 10 mL of ethanol, 0.1 mL of HCl 35% and 0.27 g of Fe was added. The mixture was heated at 90° C. for 4 hours. The crude was filtered through Celite and washed with ethanol. The solvent was evaporated, ethyl acetate was added and was washed with NaHCO3 4% aqueous solution, water and brine. The crude was purified by chromatography eluting with DCM/MeOH mixtures affording 0.22 g (yield 79%) of expected product.

ESI/MS (m/e, %): 277 [(M+1)$^+$, 100].

Intermediate 27

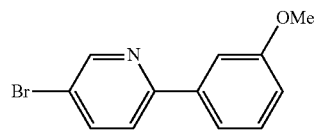 [SMILES: COc1cccc(-c2ccc(Br)cn2)c1]

5-Bromo-2-(3-methoxyphenyl)pyridine

In a schlenck tube, a mixture of 2,5-dibromopyridine (2.11 mmol, 0.500 g), 3-methoxyphenylboronic acid (2.11 mmol, 0.321 g), $PdCl_2dppf.DCM$ (0.21 mmol, 0.172 g), $Cs_2CO_3$ (6.33 mmol, 2.063 g) in a dioxane/water 4:1 mixture (14.5 ml) was heated at 100° C. for 14 hours, under argon atmosphere. The solvent was evaporated and the crude mixture was extracted between water and ethyl acetate. The solid residue was purified by chromatography over $SiO_2$ eluting with hexane/ethyl acetate mixtures affording 5-bromo-2-(3-methoxyphenyl)pyridine (0.242 g, yield 43%) as major product and 2-bromo-5-(3-methoxyphenyl)pyridine (0.039 g) as minor product.

δ $^1$H NMR (300 MHz, $CDCl_3$): 3.89 (s, 3H), 6.97-7.00 (m, 1H), 7.35-7.40 (t, 1H), 7.50-7.63 (m, 3H), 7.85-7.88 (m, 1H), 8.73 (s, 1H).

ESI/MS (m/e, %): 264 [(M+1)$^+$, 100], 266 [(M+1)$^+$, 97].

Intermediate 28

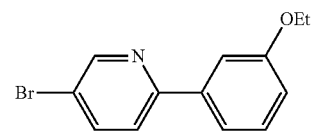 [SMILES: CCOc1cccc(-c2ccc(Br)cn2)c1]

5-Bromo-2-(3-ethoxyphenyl)pyridine

Obtained (0.977 g, yield 45%) following the procedure described in Intermediate 27, starting with 2,5-dibromopyridine (8.44 mmol, 2.0 g), 3-ethoxyphenylboronic acid (8.44 mmol, 1.40 g).

δ ¹H NMR (300 MHz, CDCl₃): 1.43-1.47 (t, 3H), 4.09-4.16 (q, 2H), 6.96-6.99 (m, 1H), 7.34-7.40 (t, 1H), 7.49-7.54 (m, 2H), 7.60-7.63 (d, 1H), 7.85-7.88 (m, 1H), 8.73 (s, 1H).
ESI/MS (m/e, %): 278 [(M+1)⁺, 100], 280 [(M+1)⁺, 97].

Intermediate 29

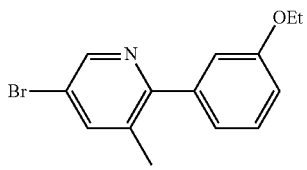 [SMILES: CCOc1cccc(-c2ncc(Br)cc2C)c1]

5-Bromo-2-(3-ethoxyphenyl)-3-methylpyridine

Obtained (1.30 g, yield 37%) following the procedure described in Intermediate 27, starting with 2,5-dibromo-3-methylpyridine (11.96 mmol, 3.0 g), 3-ethoxyphenylboronic acid (11.96 mmol, 1.98 g).
δ ¹H NMR (300 MHz, CDCl₃): 1.43-1.47 (t, 3H), 2.45 (s, 3H), 4.06-4.13 (q, 2H), 6.92-6.95 (dd, 1H), 7.05 (s, 1H), 7.09-7.12 (d, 1H), 7.34-7.40 (t, 1H), 7.68 (s, 1H), 8.41 (s, 1H).
ESI/MS (m/e, %): 292 [(M+1)⁺, 100], 294 [(M+1)⁺, 97].

Intermediate 30

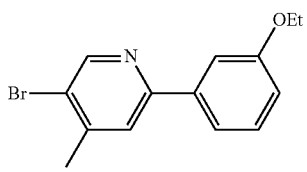 [SMILES: CCOc1cccc(-c2cc(C)c(Br)cn2)c1]

5-Bromo-2-(3-ethoxyphenyl)-4-methylpyridine

Obtained (1.14 g, yield 49%) following the procedure described in Intermediate 27, starting with 2,5-dibromo-4-methylpyridine (7.97 mmol, 2.0 g), 3-ethoxyphenylboronic acid (7.97 mmol, 1.32 gl).
δ ¹H NMR (300 MHz, CDCl₃): 1.42-1.46 (t, 3H), 2.45 (s, 3H), 4.08-4.15 (q, 2H), 6.94-6.97 (dd, 1H), 7.32-7.38 (t, 1H), 7.48-7.52 (m, 2H), 7.57 (s, 1H), 8.68 (s, 1H).
ESI/MS (m/e, %): 292 [(M+1)⁺, 100], 294 [(M+1)⁺, 97].

Intermediate 31

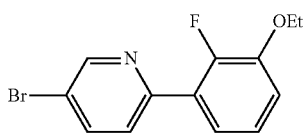 [SMILES: CCOc1cccc(-c2ccc(Br)cn2)c1F]

5-Bromo-2-(3-ethoxy-2-fluorophenyl)pyridine

Obtained (1.18 g, yield 47%) following the procedure described in Intermediate 27, starting with 2,5-dibromopyridine (8.44 mmol, 2.0 g), 3-ethoxy-2-fluorophenylboronic acid (8.43 mmol, 1.55 g).

δ ¹H NMR (300 MHz, CDCl₃): 1.48 (t, 3H), 4.15 (q, 2H), 7.03 (td, 1H), 7.16 (td, 1H), 7.49 (m, 1H), 7.70 (dd, 1H), 7.88 (dd, 1H), 8.77 (d, 1H).
ESI/MS (m/e, %): 296 [(M+1)⁺, 100].

Intermediate 32

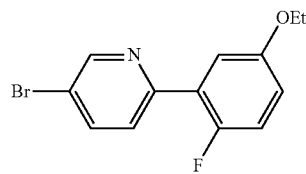 [SMILES: CCOc1ccc(F)c(-c2ccc(Br)cn2)c1]

5-Bromo-2-(5-ethoxy-2-fluorophenyl)pyridine

Obtained (1.18 g, yield 47%) following the procedure described in Intermediate 27, starting with 2,5-dibromopyridine (8.44 mmol, 2.0 g), 5-ethoxy-2-fluorophenylboronic acid (8.43 mmol, 1.55 g).
δ ¹H NMR (300 MHz, CDCl₃): 1.42 (t, 3H), 4.08 (q, 2H), 6090 (m, 1H), 7.07 (td, 1H), 7.51 (m, 1H), 7.72 (dd, 1H), 7.87 (dd, 1H), 8.76 (d, 1H).
ESI/MS (m/e, %): 296 [(M+1)⁺, 100].

Intermediate 33

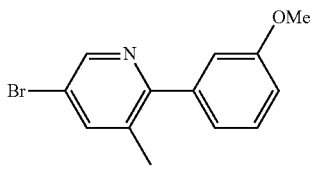

5-Bromo-2-(3-methoxyphenyl)-3-methylpyridine

Obtained (1.00 g, yield 23%) following the procedure described in Intermediate 27, starting with 2,5-dibromo-3-methylpyridine (15.94 mmol, 4.0 g), 3-methoxyphenylboronic acid (15.93 mmol, 2.42 g).
δ ¹H NMR (300 MHz, CDCl₃): 2.35 (s, 3H), 3.85 (s, 3H), 6.96 (m, 1H), 7.06 (m, 2H), 7.36 (t, 1H), 7.74 (s, 1H), 8.57 (s, 1H).
ESI/MS (m/e, %): 278 [(M+1)⁺, 100].

Intermediate 34

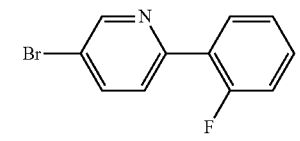 [SMILES: Fc1ccccc1-c1ccc(Br)cn1]

5-Bromo-2-(2-fluorophenyl)pyridine

Obtained (0.534 g, yield 50%) following the procedure described in Intermediate 27, starting with 2,5-dibromopyridine (4.22 mmol, 1.0 g), 2-fluorophenylboronic acid (4.22 mmol, 2.42 g).
ESI/MS (m/e, %): 252 [(M+1)⁺, 100].

Intermediate 35

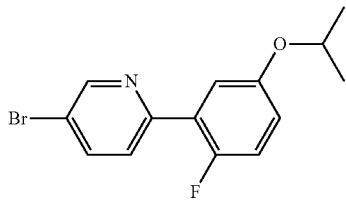 [SMILES: CC(C)Oc1ccc(F)c(-c2ccc(Br)cn2)c1]

5-Bromo-2-(2-fluoro-5-isopropoxyphenyl)pyridine

Obtained (0.600 g, yield 45%) following the procedure described in Intermediate 27, starting with 2,5-dibromopyridine (4.22 mmol, 1.0 g), 2-fluoro-5-isopropoxyphenylboronic acid (4.22 mmol, 0.836 g).
ESI/MS (m/e, %): 310 [(M+1)$^+$, 100].

Intermediate 36

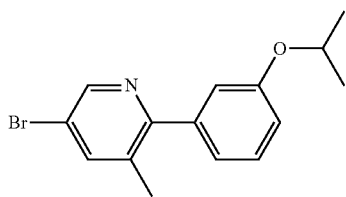 [SMILES: Cc1cc(Br)cnc1-c1cccc(OC(C)C)c1]

5-Bromo-2-(3-isopropoxyphenyl)-3-methylpyridine

Obtained (0.731 g, yield 45%) following the procedure described in Intermediate 27, starting with 2,5-dibromopyridine (4.22 mmol, 1.0 g), 2-fluoro-5-isopropoxyphenylboronic acid (4.22 mmol, 0.836 g).
ESI/MS (m/e, %): 306 [(M+1)$^+$, 100].

Intermediate 37

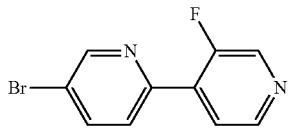 [SMILES: Fc1cnccc1-c1ccc(Br)cn1]

5-Bromo-3'-fluoro-2,4'-bipyridine

In a schlenck tube, a mixture of 2,5-dibromopyridine (2.11 mmol, 0.500 g), 3-fluoro-4-(tributylstannyl)pyridine (2.32 mmol, 0.896 g), PdCl$_2$(PPh$_3$)$_2$ (0.21 mmol, 0.148 g), CuI (0.43 mmol, 0.080 g) in DMF (5 ml) was heated at 130° C. for 12 hours, under argon atmosphere. The solvent was evaporated and the crude mixture was extracted between water and ethyl acetate. The solid residue was purified by chromatography over SiO$_2$ eluting with DCM/methanol mixtures affording 0.330 g (yield 62%) of the expected product.
δ $^1$H NMR (300 MHz, CDCl$_3$): 7.82-7.85 (d, 1H), 7.94-8.02 (m, 2H), 8.54-8.59 (m, 2H), 8.82 (s, 1H).
ESI/MS (m/e, %): 253 [(M+1)$^+$, 100].

Intermediate 38

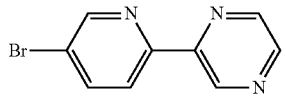 [SMILES: Brc1ccc(-c2cnccn2)nc1]

2-(5-Bromopyridin-2-yl)pyrazine

Obtained (0.310 g, yield 60%) following the procedure described in Intermediate 37, starting with 2,5-dibromopyridine (2.11 mmol, 0.5 g), 2-(tributylstannyl)pyrazine (2.32 mmol, 0.857 g).
ESI/MS (m/e, %): 236 [(M+1)$^+$, 100].

Intermediate 39

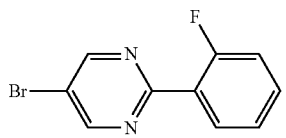

5-Bromo-2-(2-fluorophenyl)pyrimidine

A mixture of 5-bromo-2-iodopyrimidine (2.58 mmol, 0.500 g), 2-fluorophenylboronic acid (3.87 mmol, 0.542 g), 2M aqueous solution of K$_2$CO$_3$ (7.76 mmol, 3.9 ml), Pd(PPh$_3$)$_4$ in dioxane (12 ml) was heated at 110° C. overnight. The solvent was evaporated and the solid residue was extracted between water and ethyl acetate. The organic phase was evaporated and the crude residue was purified by chromatography over SiO$_2$ eluting with hexane/ethyl acetate mixtures affording 0.466 g (yield 56%) of the expected product.
ESI/MS (m/e, %): 253 [(M+1)$^+$, 100], 255 [(M+1)$^+$, 97].

Intermediate 40

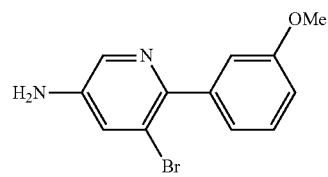

5-Bromo-6-(3-methoxyphenyl)pyridin-3-amine

A mixture of Intermediate 16B (0.84 mmol, 0.257 g), ZnBr$_2$ (0.17 mmol, 0.038 g) and Pt/C 10% (0.08 mmol, 0.016 g) in ethyl acetate (5 ml) was stirred for 20 hours under hydrogen atmosphere. The catalyst was filtered off and the solid thoughtfully washed with warm ethanol. The filtrate was evaporated and the crude was purified by chromatography over SiO$_2$ eluting with DCM/methanol mixtures and affording 0.170 g (yield 73%) of the expected product.
δ $^1$H NMR (300 MHz, CDCl$_3$): 3.86 (s, 3H), 6.91-6.95 (m, 1H), 7.17 (s, 1H), 7.20-7.23 (d, 1H), 7.31-7.37 (m, 2H), 8.11 (s, 1H).
ESI/MS (m/e, %): 279 [(M+1)$^+$, 100], 281 [(M+1)$^+$, 100].

Intermediate 41

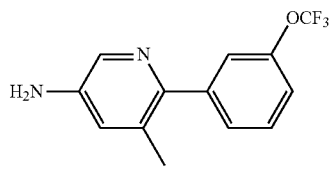 [SMILES: Cc1cc(N)cnc1-c1cccc(OC(F)(F)F)c1]

5-Methyl-6-(3-(trifluoromethoxy)phenyl)pyridin-3-amine

A. 3-Methyl-5-nitro-2-(3-(trifluoromethoxy)phenyl)pyridine

Obtained (1.25 g, yield 91%) following the procedure described in Intermediate 27, starting with 2-bromo-3-methyl-5-nitropyridine (4.61 mmol, 1.0 g), 3-(trifluoromethoxy)phenyl boronic acid (4.61 mmol, 0.95 g).

ESI/MS (m/e, %): 299 [(M+1)$^+$, 100].

B. 5-Methyl-6-(3-(trifluoromethoxy)phenyl)pyridin-3-amine

Obtained (0.890 g, yield 79%) following the procedure described in Intermediate 7 (process 2) (step D), starting with 3-methyl-5-nitro-2-(3-(trifluoromethoxy)phenyl)pyridine (4.19 mmol, 1.25 g).

δ $^1$H NMR (300 MHz, CDCl$_3$): 2.29 (s, 3H), 6.89 (s, 1H), 7.19 (s, 1H), 7.36 (m, 1H), 7.43 (d, 2H), 8.02 (s, 1H).

Intermediate 42

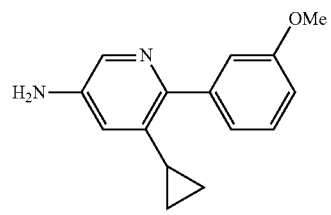 [SMILES: COc1cccc(-c2ncc(N)cc2C2CC2)c1]

5-Cyclopropyl-6-(3-methoxyphenyl)pyridin-3-amine

Obtained (0.1 g, yield 68%) following the procedure described in Intermediate 27, starting with 5-bromo-6-(3-methoxyphenyl)pyridin-3-amine (Intermediate 40) (0.61 mmol, 0.172 g), 2-cyclopropyl-4,4,5,5-tetramethyl-1,3,2-dioxaborolane (0.68 mmol, 0.123 ml).

δ $^1$H NMR (300 MHz, CDCl$_3$): 0.65-0.69 (m, 2H), 0.91-0.95 (m, 2H), 3.61-3.66 (m, 1H), 3.85 (s, 3H), 6.55 (s, 1H), 6.88-6.92 (dd, 1H), 7.15-7.21 (m, 2H), 7.30-7.35 (t, 1H), 7.98 (s, 1H).

ESI/MS (m/e, %): 241 [(M+1)$^+$, 100].

Intermediate 43

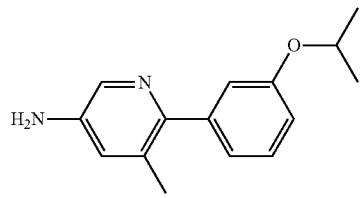 [SMILES: Cc1cc(N)cnc1-c1cccc(OC(C)C)c1]

6-(3-Isopropoxyphenyl)-5-methylpyridin-3-amine

A. 2-(3-isopropoxyphenyl)-3-methyl-5-nitropyridine

Obtained (1.03 g, yield 82%) following the procedure described in Intermediate 27, starting with 2-bromo-3-methyl-5-nitropyridine (4.61 mmol, 1.0 g), 3-isopropoxyphenylboronic acid (4.61 mmol, 0.83 g).

δ $^1$H NMR (300 MHz, CDCl$_3$): 1.39 (s, 6H), 2.53 (s, 3H), 4.61-4.65 (m, 1H), 7.00-7.03 (d, 1H), 7.08-7.12 (m, 2H), 7.38-7.43 (t, 1H), 8.40 (s, 1H), 9.34 (s, 1H).

ESI/MS (m/e, %): 273 [(M+1)$^+$, 100].

B. 6-(3-Isopropoxyphenyl)-5-methylpyridin-3-amine

Obtained (0.660 g, yield 72%) following the procedure described in Intermediate 7 (process 2) (step D), starting with 2-(3-isopropoxyphenyl)-3-methyl-5-nitropyridine (3.78 mmol, 1.03 g).

δ $^1$H NMR (300 MHz, CDCl$_3$): 1.34 (s, 6H), 2.29 (s, 3H), 3.66 (s, 2H), 4.57-4.63 (m, 1H), 6.86-6.90 (m, 2H), 7.01-7.04 (m, 2H), 7.26-7.32 (m, 1H), 8.02 (s, 1H).

ESI/MS (m/e, %): 243 [(M+12)$^+$, 100].

Intermediate 44

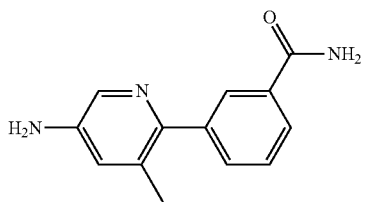 [SMILES: Cc1cc(N)cnc1-c1cccc(C(N)=O)c1]

3-(5-Amino-3-methylpyridin-2-yl)benzamide

A. 3-(3-Methyl-5-nitropyridin-2-yl)benzamide

Obtained (0.225 g, yield 95%) following the procedure described in Intermediate 27, starting with 2-bromo-3-methyl-5-nitropyridine (0.92 mmol, 0.200 g), 3-carbamoylphenyl boronic acid (0.92 mmol, 0.152 g).

ESI/MS (m/e, %): 258 [(M+1)$^+$, 100].

B. 3-(5-Amino-3-methylpyridin-2-yl)benzamide

Obtained (0.135 g, yield 65%) following the procedure described in Intermediate 7 (process 2) (step D), starting with 3-(3-methyl-5-nitropyridin-2-yl)benzamide (0.913 mmol, 0.235 g).

ESI/MS (m/e, %): 228 [(M+1)$^+$, 100].

Intermediate 45

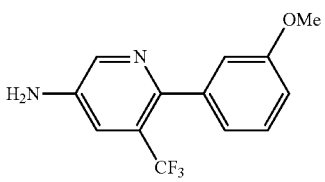 [SMILES: COc1cccc(-c2ncc(N)cc2C(F)(F)F)c1]

6-(3-Methoxyphenyl)-5-(trifluoromethyl)pyridin-3-amine

Obtained (0.077 g, yield 28%) following the procedure described in Intermediate 27, starting with Intermediate 60 (1.02 mmol, 0.200 g), 3-methoxyphenylboronic acid (1.22 mmol, 0.185 g) in the microwave oven for 60 minutes.
δ $^1$H NMR (300 MHz, CDCl$_3$): 3.85 (s, 3H), 6.94-7.06 (m, 2H), 7.27-7.36 (m, 2H), 8.25-8.29 (m, 2H).
ESI/MS (m/e, %): 269 [(M+1)$^+$, 100].

Intermediate 46

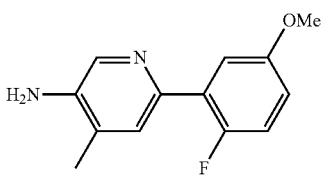 [SMILES: COc1ccc(F)c(-c2cc(C)c(N)cn2)c1]

6-(2-Fluoro-5-methoxyphenyl)-4-methylpyridin-3-amine

Obtained (1.225 g, yield 76%) following the procedure described in Intermediate 27, starting with 6-chloro-4-methylpyridin-3-amine (7.01 mmol, 1.000 g), 2-fluoro-5-methoxyphenylboronic acid (7.01 mmol, 1.191 g).
ESI/MS (m/e, %): 233 [(M+1)$^+$, 100].

Intermediate 47

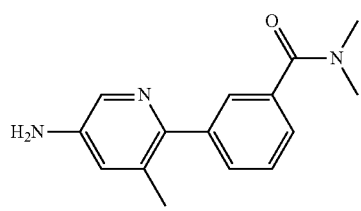 [SMILES: Cc1cc(N)cnc1-c1cccc(C(=O)N(C)C)c1]

3-(5-Amino-3-methylpyridin-2-yl)-N,N-dimethylbenzamide

A. N,N-Dimethyl-3-(3-methyl-5-nitropyridin-2-yl)benzamide

Obtained (0.620 g, yield 94%) following the procedure described in Intermediate 27, starting with 2-bromo-3-methyl-5-nitropyridine (2.30 mmol, 0.500 g), 3-(dimethylcarbamoyl)phenylboronic acid (2.33 mmol, 0.450 g).
ESI/MS (m/e, %): 286 [(M+1)$^+$, 100].

B. 3-(5-amino-3-methylpyridin-2-yl)-N,N-dimethylbenzamide

Obtained (0.440 g, yield 75%) following the procedure described in Intermediate 7 (process 2) (step D), starting with N,N-dimethyl-3-(3-methyl-5-nitropyridin-2-yl)benzamide (2.30 mmol, 0.657 g).
δ $^1$H NMR (CDCl$_3$): 2.28 (s, 3H), 3.01 (s, 3H), 3.11 (s, 3H), 3.70 (s, 2H), 6.90 (s, 1H), 7.37-7.53 (m, 4H), 8.02 (s, 1H).
ESI/MS (m/e, %): 256 [(M+1)$^+$, 100].

Intermediate 48

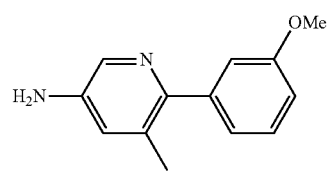 [SMILES: COc1cccc(-c2ncc(N)cc2C)c1]

6-(3-Methoxyphenyl)-5-methylpyridin-3-amine

A. 2-(3-Methoxyphenyl)-3-methyl-5-nitropyridine

Obtained (2.43 g, yield 72%) following the procedure described in Intermediate 27, starting with 2-bromo-3-methyl-5-nitropyridine (13.82 mmol, 3.0 g), 3-methoxyphenylboronic acid (13.82 mmol, 2.10 g).
δ $^1$H NMR (200 MHz, CDCl$_3$): 2.51 (s, 3H), 3.87 (s, 3H), 6.93-7.20 (m, 3H), 7.31-7.52 (m, 1H), 8.39 (d, J=1.95 Hz, 1H), 9.33 (d, J=3.12 Hz, 1H).
ESI/MS (m/e, %): 245 [(M+1)$^+$, 95].

B. 6-(3-Methoxyphenyl)-5-methylpyridin-3-amine

Obtained (2.12 g, yield 100%) following the procedure described in Intermediate 7 (process 2) (step D), starting with 2-(3-methoxyphenyl)-3-methyl-5-nitropyridine (9.83 mmol, 2.40 g).
δ $^1$H NMR (200 MHz, CDCl$_3$): 2.29 (s, 3H), 3.50-3.77 (m, 2H), 3.84 (s, 3H), 6.89 (d, J=2.73 Hz, 2H), 6.94-7.13 (m, 2H), 7.17-7.44 (m, 1H), 8.02 (d, J=2.34 Hz, 1H).
ESI/MS (m/e, %): 215 [(M+1)$^+$, 95].

Intermediate 49

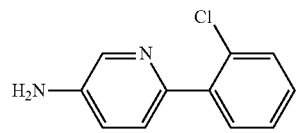 [SMILES: Nc1ccc(-c2ccccc2F)nc1]

6-(2-Chlorophenyl)pyridin-3-amine

Obtained (0.900 g, yield 76%) following the procedure described in Intermediate 27, starting with 5-bromopyridin-2-amine (5.78 mmol, 1.0 g), 2-chlorophenylboronic acid (6.94 mmol, 1.08 g).
δ $^1$H NMR (200 MHz, CDCl$_3$): 3.80 (s, 2H), 7.03-7.07 (d, 1H), 7.27-7.34 (m, 2H), 7.43-7.49 (m, 2H), 7.56-7.59 (d, 1H), 8.20 (s, 1H).
ESI/MS (m/e, %): 205 [(M+1)$^+$, 100].

Intermediate 50

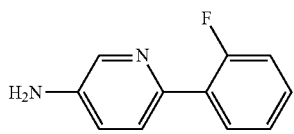

6-(2-Fluorophenyl)pyridin-3-amine

Obtained (0.210 g, yield 31%) following the procedure described in Intermediate 39, starting with 6-chloropyridin-3-amine (3.50 mmol, 0.45 g), 2-fluorophenylboronic acid (6.94 mmol, 0.97 g).

ESI/MS (m/e, %): 189 [(M+1)$^+$, 100].

Intermediate 51

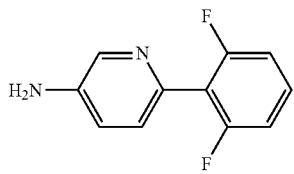 [SMILES: Nc1ccc(-c2c(F)cccc2F)nc1]

6-(2,6-Difluorophenyl)pyridin-3-amine

In a three neck round bottle flask, to a mixture of 1,3-difluorobenzene (23.24 mmol, 2.29 ml) in THF (30 ml) at −78° C. under argon atmosphere, a solution of n-BuLi (10.2 ml) in THF (2.5M) was added. The mixture was stirred at −78° C. for 30 minutes and then it was heated to −50° C. A solution of ZnCl$_2$ (51 ml) in THF (0.5M) was added drop wise and the mixture was stirred at this temperature for 20 minutes. A solution of 6-bromopyridin-3-amine (11.56 mmol, 2.0 g) in THF (20 ml) and Pd(PPh$_3$)$_4$ (1.16 mmol, 1.3 g) were added respectively and the crude mixture was heated at 40° C. overnight. The solvent was evaporated and the crude mixture was purified by reverse phase chromatography eluting with a water-MeOH/AcN system affording 0.72 g (yield 30%) of the expected product.

δ $^1$H NMR (200 MHz, CDCl$_3$): 3.83 (s, 2H), 6.95-7.00 (m, 2H), 7.06-7.09 (d, 1H), 7.23-7.32 (m, 2H), 8.24 (s, 1H).

ESI/MS (m/e, %): 207 [(M+1)$^+$, 100].

Intermediate 52

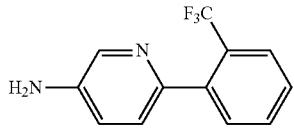

6-(2-(Trifluoromethyl)phenyl)pyridin-3-amine

Obtained (2.05 g, yield 59%) following the procedure described in Intermediate 27, starting with 6-bromopyridin-3-amine, 2-(trifluoromethyl)phenylboronic acid.

ESI/MS (m/e, %): 239 [(M+1)$^+$, 100].

Intermediate 53

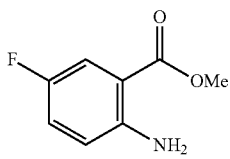

Methyl 2-amino-5-fluorobenzoate

A solution of 2-amino-5-fluorobenzoic acid (9.29 mmol, 1.440 g) in a mixture of HCl/MeOH (3N, 30 ml) was heated at 100° C. overnight. The solvent was evaporated and the crude mixture was extracted between DCM and K$_2$CO$_3$ saturated aqueous solution. The organic phase was evaporated and the crude mixture was purified by chromatography over SiO$_2$ with hexane/ethyl acetate mixtures affording 0.650 g (yield 42%) of the expected product.

δ $^1$H NMR (200 MHz, CDCl$_3$): 3.9 (s, 3H), 5.6 (s, 2H), 6.6 (dd, J=9.0, 4.7 Hz, 1H), 7.0 (m, 1H), 7.5 (dd, J=9.8, 3.1 Hz, 1H).

ESI/MS (m/e, %): 170 [(M+1)$^+$, 100].

Intermediate 54

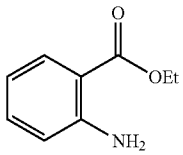 [SMILES: CCOC(=O)c1ccccc1N]

Ethyl 2-aminobenzoate

To a solution of 2-aminobenzoic acid (7.29 mmol, 1.0 g) in ethanol (20 ml), H$_2$SO$_4$ (45 mmol, 2.5 ml) was added and the mixture was refluxed for 20 hours. The solvent was evaporated and the crude residue was dissolved in water. The solution neutralised with 6N NaOH aqueous solution and extracted with CHCl$_3$. The organic phase was evaporated affording 0.939 g (yield 78%) of the expected product.

$^1$H NMR (300 MHz, CDCl$_3$): 1.38 (t, 3H), 4.33 (q, 2H), 5.74 (s, 2H), 6.61-6.66 (m, 2H), 7.26 (t, 1H), 7.88 (d, 1H).

Intermediate 55

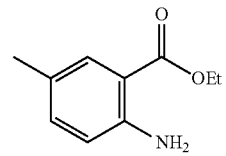

Ethyl 2-amino-5-methylbenzoate

Obtained (5.83 g, yield 88%) following the procedure described in Intermediate 54, starting with 2-amino-5-methylbenzoic acid (151.16 mmol, 5.58 g).

δ $^1$H NMR (300 MHz, CDCl$_3$): 1.38 (t, 3H), 2.23 (s, 3H), 4.33 (q, 2H), 5.55 (s, 2H), 6.59 (d, 1H), 7.09 (dd, 1H), 7.67 (d, 1H).

ESI/MS (m/e, %): 180 [(M+1)$^+$, 100].

Intermediate 56

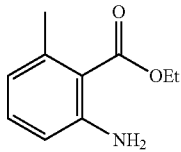

Ethyl 2-amino-6-methylbenzoate

Obtained (0.342 g, yield 12%) following the procedure described in Intermediate 55, starting with 2-amino-6-methylbenzoic acid (13.23 mmol, 2 g).

δ $^1$H NMR (300 MHz, CDCl$_3$): 1.37-1.42 (t, 3H), 2.44 (s, 3H), 4.33-4.41 (q, 2H), 5.08 (bs, 2H), 6.52-6.54 (m, 2H), 7.05-7.10 (t, 1H).
ESI/MS (m/e, %): 180 [(M+1)$^+$, 100].

Intermediate 57

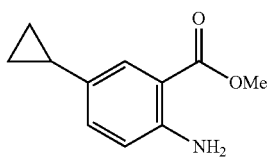 [SMILES: COC(=O)c1cc(C2CC2)ccc1N]

Methyl 2-amino-5-cyclopropylbenzoate

In a schlenck tube, a mixture of methyl 2-amino-5-bromobenzoate (43.47 mmol, 10 g), cyclopropylboronic acid (112.92 mmol, 9.700 g), K$_3$PO$_4$ (144.16 mmol, 30.6 g), Pd(AcO)$_2$ (3.47 mmol, 0.780 g), P(Cy)$_3$ (7.85 mmol, 2.2 g) in toluene (170 ml) and water (10 ml) was heated for 2 hours at 100° C., under nitrogen atmosphere. The reaction mixture was filtered through celite and the organic phase was separated and evaporated affording 7.34 g (yield 77%) of the expected product.

δ $^1$H NMR (300 MHz, CDCl$_3$): 0.48-0.66 (m, 2H) 0.75-0.95 (m, 2H), 1.80 (s, 1H), 3.86 (s, 3H), 5.56 (s, 2H), 6.59 (d, J=8.50 Hz, 1H), 7.03 (dd, J=8.50, 2.15 Hz, 1H), 7.60 (s, 1H).
ESI/MS (m/e, %): 192 [(M+1)$^+$, 87].

Intermediate 58

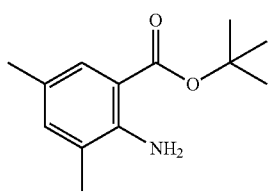 [SMILES: Cc1cc(C)c(N)c(C(=O)OC(C)(C)C)c1]

tert-Butyl 2-amino-3,5-dimethylbenzoate

A. 3,5-Dimethyl-2-(2,2,2-trifluoroacetamido)benzoic acid

Obtained (3.44 g, yield 72%) following the procedure described in Intermediate 11 (step A) starting with 2-amino-3,5-dimethylbenzoic acid (18.16 mmol, 3 g).

δ $^1$H NMR (200 MHz, DMSO-d$_6$): 2.16 (s, 3H), 2.33 (s, 3H), 7.36 (d, J=1.95 Hz, 1H), 7.54 (d, J=1.95 Hz, 1H), 10.87 (s, 1H) 12.98 (s, 1H).
ESI/MS (m/e, %): 262 [(M+1)$^+$, 100].

B. tert-Butyl 3,5-dimethyl-2-(2,2,2-trifluoroacetamido)benzoate

Obtained (2.10 g, yield 50%) following the procedure described in Intermediate 11 (step B) starting with 3,5-dimethyl-2-(2,2,2-trifluoroacetamido)benzoic acid (13.17 mmol, 3.44 g).

δ $^1$H NMR (200 MHz, DMSO-d$_6$): 1.47 (s, 9H), 2.16 (s, 3H), 2.32 (s, 3H), 7.34 (d, J=1.95 Hz, 1H), 7.41 (d, J=1.95 Hz, 1H), 10.93 (s, 1H).
ESI/MS (m/e, %): 318 [(M+1)$^+$, 100].

C. tert-Butyl 2-amino-3,5-dimethylbenzoate

Obtained (1.37 g, yield 83%) following the procedure described in Intermediate 11 (step C) starting with tert-butyl 3,5-dimethyl-2-(2,2,2-trifluoroacetamido)benzoate (6.62 mmol, 2.10 g).

δ $^1$H NMR (200 MHz, CDCl$_3$): 1.53 (s, 9H) 2.07 (s, 3H), 2.13 (s, 3H), 6.24 (s, 2H), 7.00 (s, 1H), 7.37 (s, 1H).
ESI/MS (m/e, %): 222 [(M+1)$^+$, 83].

Intermediate 59

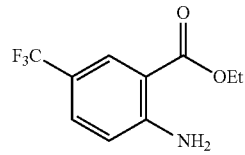

Ethyl 2-amino-5-(trifluoromethyl)benzoate

A. Tert-butyl 4-(trifluoromethyl)phenylcarbamate

A mixture of 4-trifluoromethylaniline (40 mmol, 5 ml), di-tert-butylcarbonate (40 mmol, 8.7 g), 1N solution of aqueous NaOH (20 ml) in THF (20 ml) was stirred at room temperature for 12 hours. di-tert-butylcarbonate (20 mmol, 4.2 g), 1N solution of aqueous NaOH (20 ml) were added and the mixture was stirred at room temperature for 24 hours. The solvent was evaporated and EtOAc was added. The solution was washed with 2N HCl aqueous solution and brine and then evaporated. The crude mixture was purified by chromatography over SiO2 eluting with hexane/EtOAc mixtures and affording 9.3 g (yield 90%) of the expected product.

δ $^1$H NMR (300 MHz, DMSO-d$_6$): 1.46 (s, 9H), 7.69-7.72 (d, 1H), 8.22 (s, 1H), 8.35-8.38 (d, 1H).
ESI/MS (m/e, %): 263 [(M+1)$^+$, 100].

B. 2-(tert-butoxycarbonylamino)-5-(trifluoromethyl) benzoic acid

In at three round bottle neck flask, a mixture of tert-butyl 4-(trifluoromethyl)phenyl-carbamate (11.5 mmol, 3.0 g) and TMDEA (34.4 mmol, 5.2 ml) in anhydrous ethyl ether (70 ml) was cooled at −78° C. A solution of n-BuLi 2.5M (34.4 mmol, 13.8 ml) in hexanes was slowly added over 20 minutes at −65° C. After 10 minutes at −78° C., the mixture was heated at −10° C. and stirred for 2 hours. The solution was cooled to −78° C. and dried $CO_2$ was bubbled for 1 hour and then heated to room temperature. Saturated $NH_4Cl$ aqueous solution (35 ml) was added and extracted with diethyl ether. The organic phase was evaporated and the crude mixture was purified by $SiO_2$ eluting with DCM/MeOH mixtures affording 2.2 g (yield 85%) of the expected product.

δ $^1$H NMR (300 MHz, $CDCl_3$): 1.52 (s, 9H), 3.54 (s, 1H), 7.73-7.76 (m, 1H), 8.35 (s, 1H), 8.57-8.61 (m, 1H), 10.30 (bs, 1H).

ESI/MS (m/e, %): 306 [(M+1)$^+$, 100].

C. Ethyl 2-amino-5-(trifluoromethyl)benzoate

A mixture of 2-(tert-butoxycarbonylamino)-5-(trifluoromethyl)benzoic acid (7.21 mmol, 2.2 g), $H_2SO_4$ (36 mmol, 1.92 ml) in ethanol (25 ml) was stirred at 100° C. for 16 hours. The solvent was evaporated, water was added, pH was taken to 6 and extracted with $CHCl_3$. The crude mixture was purified by chromatography over $SiO_2$ eluting with DCM/MeOH mixtures and affording 0.69 g (yield 41%) of the expected product.

δ $^1$H NMR (300 MHz, $CDCl_3$): 1.38-1.43 (t, 3H), 4.32-4.39 (q, 2H), 6.10 (bs, 2H), 6.68-6.71 (d, 1H), 6.44-6.47 (d, 1H), 8.14 (s, 1H).

ESI/MS (m/e, %): 234 [(M+1)$^+$, 100].

Intermediate 60

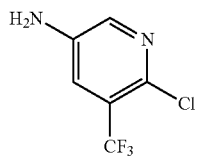

6-Chloro-5-(trifluoromethyl)pyridin-3-amine

A. 2-Chloro-3-iodo-5-nitropyridine

A mixture of 3-iodo-5-nitropyridin-2-ol (37.60 mmol, 10 g), $POCl_3$ (86.47 mmol, 7.94 ml) and $PCl_5$ (48.87 mmol, 10.2 g) was heated at 140° C. for 45 minutes under argon atmosphere. The mixture was cooled at room temperature, poured slowly over iced-water and extracted with dichloromethane. The organic phase was washed with water, $NaHCO_3$ aqueous solution and brine. The solvent was evaporated and the crude mixture was purified by chromatography over $SiO_2$ eluting hexane/DCM mixtures affording 7.32 g (yield 69%) of the expected product.

δ $^1$H NMR (300 MHz, $CDCl_3$): 8.90 (s, 1H), 9.19 (s, 1H).

B. 2-Chloro-5-nitro-3-(trifluoromethyl)pyridine

In a schlenk tube, a mixture of 2-chloro-3-iodo-5-nitropyridine (17.58 mmol, 5.00 g), methyl 2,2-difluoro-2-(fluorosulfonyl)acetate (8.79 mmol, 1.12 ml) and CuI (2.64 mmol, 0.5 g) in DMF (30 ml) was heated at 70° C. for 3 hours under argon atmosphere. Methyl 2,2-difluoro-2-(fluorosulfonyl)acetate (4.40 mmol, 0.6 ml) was added and the mixture was heated at 70° C. for 16 hours. The solvent was evaporated and the crude mixture was extracted between ethyl acetate and water. The crude mixture was purified by chromatography over $SiO_2$ eluting with hexane/DCM mixtures affording 1.19 g (yield 30%) of the expected product.

δ $^1$H NMR (300 MHz, $CDCl_3$): 8.82 (s, 1H), 9.41 (s, 1H).

C. 6-Chloro-5-(trifluoromethyl)pyridin-3-amine

A mixture of 2-chloro-5-nitro-3-(trifluoromethyl)pyridine (5.25 mmol, 1.19 g), $ZnBr_2$ (1.05 mmol, 0.200 g) and 5% Pt © (1.58 mmol, 0.31 g) in ethyl acetate (50 ml) was stirred for 20 hours under hydrogen atmosphere. The catalyst was filtered off and the solid was washed with warmed ethanol. The solvent was evaporated affording the expected product (0.95 g, yield 92%).

δ $^1$H NMR (300 MHz, DMSO-$d_6$): 5.59 (bs, 1H), 7.37 (s, 1H), 7.92 (s, 1H).

Intermediate 61

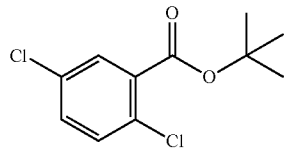

tert-Butyl 2,5-dichlorobenzoate

Obtained (1.64 g, yield 61%) following the procedure described in Intermediate 11 (step B starting with 2,5-dichlorobenzoic acid (10.5 mmol, 2.0 g).

δ $^1$H NMR (200 MHz, $CDCl_3$): 1.6 (s, 12H), 7.3 (m, 2H), 7.7 (m, 1H).

ESI/MS (m/e, %): 247 [(M+1)$^+$, 100], 249 [(M+1)$^+$, 64].

Intermediate 62

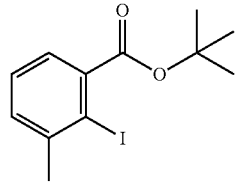

tert-Butyl 2-iodo-3-methylbenzoate

Obtained (1.05 g, yield 86%) following the procedure described in Intermediate 61 starting with 2-iodo-3-methylbenzoic acid (3.82 mmol, 1.0 g).

δ $^1$H NMR (200 MHz, DMSO-$d_6$): 1.49-1.62 (m, 9H), 2.43 (s, 3H), 7.06-7.53 (m, 3H).

ESI/MS (m/e, %): 319 [(M+1)$^+$, 100].

Intermediate 63

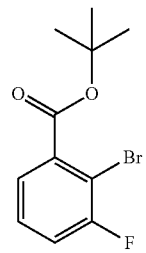

tert-Butyl 2-bromo-3-fluorobenzoate

Obtained (1.39 g, yield 49%) following the procedure described in Intermediate 61 starting with 2-bromo-3-fluorobenzoic acid (10.36 mmol, 2.27 g).

ESI/MS (m/e, %): 275 [(M+1)$^+$, 100], 277 [(M+1)$^+$, 97].

Intermediate 64

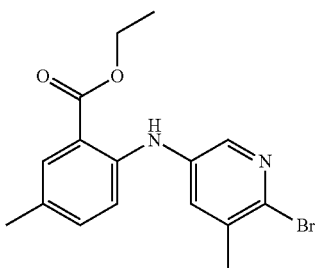 [SMILES: CCOC(=O)c1cc(C)ccc1Nc1cnc(Br)c(C)c1]

Ethyl 2-(6-bromo-5-methylpyridin-3-ylamino)-5-methylbenzoate

Obtained (0.050 g, yield 25%) following the procedure described in Intermediate 16 starting with ethyl 2-amino-5-methylbenzoate (0.56 mmol, 0.100 g) and 2-bromo-5-iodo-3-methylpyridine (1.0 mmol, 0.166 g).
ESI/MS (m/e, %): 349 [(M+1)$^+$, 100], 351 [(M+1)$^+$, 100].

Intermediate 65

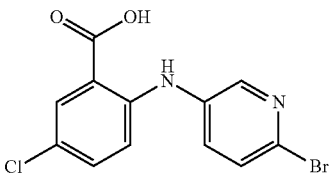 [SMILES: O=C(O)c1cc(Cl)ccc1Nc1ccc(Br)nc1]

2-(6-Bromopyridin-3-ylamino)-5-chlorobenzoic acid

A mixture of 6-bromopyridin-3-amine (27.27 mmol, 4.70 g), 2,5-dichlorobenzoic acid (54.34 mmol, 10.38 g), Cu (2.71 mmol, 0.2 g), Cu$_2$O (1.36 mmol, 0.2 g) and K$_2$CO$_3$ (54.27 mmol, 7.5 g) in 1,2-dimethoxiethane (40 ml) was heated in a microwave oven at 130° C. for 14 hours, under nitrogen atmosphere. Water was added and the mixture was filtered through celite and extracted with AcOEt. The organic phase was washed with saturated K$_2$CO$_3$ aqueous solution and brine. The solvent was evaporated to afford 3.08 g (yield 31%) of the expected product.
ESI/MS (m/e, %): 327 [(M+1)$^+$, 77], 329 [(M+1)$^+$, 100], 331 [(M+1)$^+$, 24].

Intermediate 66

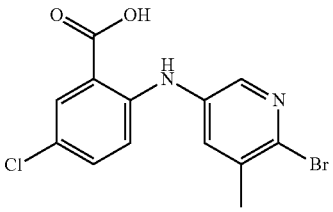 [SMILES: Cc1cc(Nc2ccc(Cl)cc2C(=O)O)cnc1Br]

2-(6-bromo-5-methylpyridin-3-ylamino)-5-chlorobenzoic acid

Obtained (0.51 g, yield 24%) following the procedure described in Intermediate 13 starting with 6-bromo-5-methylpyridin-3-amine (5.35 mmol, 1.0 g) and 2,5-dichlorobenzoic acid (10.68 mmol, 2.04 g).
ESI/MS (m/e, %): 341 [(M+1)$^+$, 77], 343 [(M+1)$^+$, 100], 345 [(M+1)$^+$, 24].

Intermediate 67

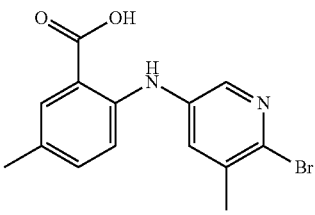 [SMILES: Cc1ccc(Nc2cnc(Br)c(C)c2)c(C(=O)O)c1]

2-(6-Bromo-5-methylpyridin-3-ylamino)-5-methylbenzoic acid

Obtained (0.51 g, yield 20%) following the procedure described in Intermediate 13 starting with 6-bromo-5-methylpyridin-3-amine (7.70 mmol, 1.44 g) and 2-chloro-5-methylbenzoic acid (15.36 mmol, 2.62 g).
ESI/MS (m/e, %): 321 [(M+1)$^+$, 100], 323 [(M+1)$^+$, 97].

Intermediate 68

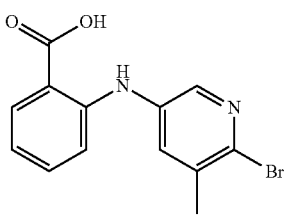 [SMILES: Cc1cc(Nc2ccccc2C(=O)O)cnc1Br]

2-(6-Bromo-5-methylpyridin-3-ylamino)benzoic acid

Obtained (0.17 g, yield 14%) following the procedure described in Intermediate 13 starting with 6-bromo-5-methylpyridin-3-amine (2.70 mmol, 0.5 g) and 2-bromobenzoic acid (4.03 mmol, 0.81 g).
ESI/MS (m/e, %): 307 [(M+1)$^+$, 100], 309 [(M+1)$^+$, 97].

Intermediate 69

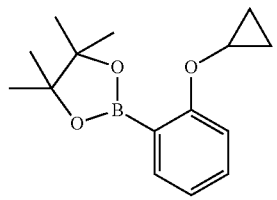 [SMILES: CC1(C)OB(c2ccccc2OC2CC2)OC1(C)C]

2-(2-Cyclopropoxyphenyl)-4,4,5,5-tetramethyl-1,3,2-dioxaborolane

A. 1-Bromo-2-cyclopropoxybenzene

Obtained (1.86 g, yield 75%) following the procedure described in Intermediate 25 (step A) starting with 2-bromophenol (9.25 mmol, 1.60 g).

B. 2-Cyclopropoxyphenylboronic acid

Obtained (0.245 g, yield 14%) following the procedure described in Intermediate 25 (step B) starting with 1-bromo-2-cyclopropoxybenzene (6.90 mmol, 1.86 g).
$^1$H NMR (200 MHz, CDCl$_3$) δ ppm 0.8 (m, 4H) 1.3 (s, 12H) 3.8 (none, 2H) 3.8 (m, 1H) 6.9 (m, 1H) 7.2 (d, J=9.0 Hz, 1H) 7.4 (m, 1H) 7.6 (m, 1H)
ESI/MS (m/e, %): 261 [(M+1)$^+$, 100]

Intermediate 70

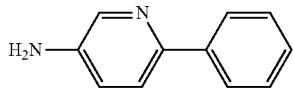 [SMILES: Nc1ccc(-c2ccccc2)nc1]

6-phenylpyridin-3-amine

Obtained (71% yield) following the procedure described in Intermediate 39, starting with 6-bromopyridin-3-amine and phenylboronic acid.

ESI/MS (m/e, %): 171 [(M+1)⁺, 100].

Intermediate 71

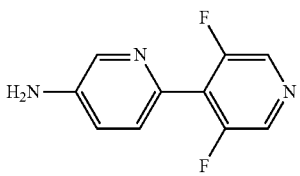 [SMILES: Nc1ccc(-c2c(F)cncc2F)nc1]

3',5'-difluoro-2,4'-bipyridin-5-amine

Obtained (50% yield) following the procedure described in example 34 (step A), starting with 6-bromopyridin-3-amine and 3,5-difluoro-4-(tributylstannyl)pyridine.

ESI/MS (m/e, %): 208 [(M+1)⁺, 100].

Intermediate 72

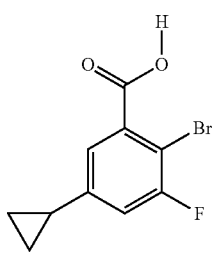 [SMILES: O=C(O)c1cc(C2CC2)cc(F)c1Br]

2-bromo-5-cyclopropyl-3-fluorobenzoic acid

A. 3-cyclopropyl-5-fluorobenzoic acid

Obtained (16% yield) following the procedure described in intermediate 8 (step A), starting from 3-chloro-5-fluorobenzoic acid.

ESI/MS (m/e, %): 179 [(M−1)⁻, 100].

B. 2-bromo-5-cyclopropyl-3-fluorobenzoic acid

To a solution of TMDA (1.3 ml, 8.61 mmol) in dry THF (9 mL) under inert atmosphere at −65° C., a 1.4M solution of sec-BuLi (8 ml, 11.20 mmol) was added dropwise. Then a solution of 3-cyclopropyl-5-fluorobenzoic acid (0.69 g, 3.83 mmol) in dry THF (3 mL) was added dropwise and stirred for 1 h. Then a solution of 1,2-dibromotetrachloroethane (5 g, 15.48 mmol) in dry THF (11 mL) was added dropwise for 1 h and stirred for additional 20 min. A white suspension was obtained. The cooling bath was removed and at −20° C. water (30 mL) and diethyl ether (30 mL) were added. The organic layer was separated and the aqueous phase was acidified (until pH: 1) using a 2N aqueous solution of HCl (13 mL needed) and extracted with diethyl ether. The organic phase was washed with water and brine, dried, filtered and concentrated in vacuo to afford a mixture 1:1 of the expected compound and starting material (38% yield), which was used without further purification ESI/MS (m/e, %): 257 [(M−1)⁻, 100], 259 [(M−1)⁻, 97].

Intermediate 73

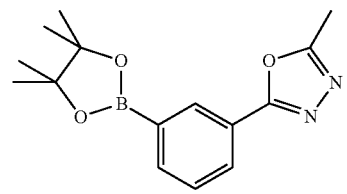 [SMILES: Cc1nnc(-c2cccc(B3OC(C)(C)C(C)(C)O3)c2)o1]

2-methyl-5-(3-(4,4,5,5-tetramethyl-1,3,2-dioxaborolan-2-yl)phenyl)-1,3,4-oxadiazole

A. Ethyl 3-iodobenzoate

Obtained (75% yield) following the procedure described in intermediate 10, starting from 3-iodobenzoic acid.

ESI/MS (m/e, %): 277 [(M+1)⁺, 100]

B. 3-iodobenzohydrazide

In a schlenck tube, a mixture of ethyl 3-iodobenzoate (1.80 g, 6.52 mmol) and hidrazine hydrate (3.18 ml, 65.2 mmol) in ethanol (25 ml) was heated at 80° C. overnight. The solvent was evaporated and the crude redissolved in DCM and washed with water and brine. The organic layer was dried, filtered and concentrated under vacuum to give the title compound as a white solid (88% yield).

ESI/MS (m/e, %): 263 [(M+1)⁺, 100]

C. 2-(3-iodophenyl)-5-methyl-1,3,4-oxadiazole

In a schlenck tube, a mixture of 3-iodobenzohydrazide (510 mg, 1.95 mmol) and 1,1,1-triethoxyethane (1.14 ml, 6.23 mmol) in acetic acid (15 ml) was heated at 150° C. for 3 h. The solvent was evaporated and the crude redissolved in ethyl acetate and washed with 4% solution of NaHCO₃, water and brine. The organic layer was dried, filtered and concentrated under vacuum to give the title compound as a white solid (92% yield).

ESI/MS (m/e, %): 287 [(M+1)⁺, 100]

D. 2-methyl-5-(3-(4,4,5,5-tetramethyl-1,3,2-dioxaborolan-2-yl)phenyl)-1,3,4-oxadiazole Obtained (62% yield) following the procedure described in Intermediate 25 (step B) starting with 2-(3-iodophenyl)-5-methyl-1,3,4-oxadiazole.

1H NMR (300 MHz, CDCl₃) δ ppm 1.4 (s, 12H) 2.6 (s, 3H) 7.5 (t, J=7.7 Hz, 1H) 8.0 (t, J=7.4 Hz, 1H) 8.2 (m, 1H) 8.4 (s, 1H)

Intermediate 74

5-bromo-2-(2-(trifluoromethyl)phenyl)pyrimidine

Obtained (52% yield) following the procedure described in Intermediate 21, starting with 5-bromo-2-iodopyrimidine and 2-(trifluoromethyl)phenylboronic acid.

ESI/MS (m/e, %): 303 [(M+1)$^+$, 100], 305[(M+1)$^+$, 97].

EXAMPLES

Example 1

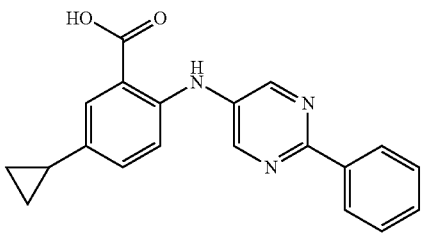 [SMILES: O=C(O)c1cc(C2CC2)ccc1Nc1cnc(-c2ccccc2)nc1]

5-cyclopropyl-2-(2-phenylpyrimidin-5-ylamino)benzoic acid

In a schlenck tube, a mixture of Intermediate 8 (0.20 g, 1.15 mmol), Intermediate 21 (0.30, 1.15 mmol), potassium carbonate (1.72 mmol, 0.238 g), Cu$_2$O (0.06 mmol, 0.008 g) and Cu (0.11 mmol, 0.007 g) in DME (5 ml) was heated at 130° C. overnight, under argon atmosphere. The solvent was evaporated and the crude mixture was purified over SiO$_2$ eluting with CH$_2$Cl$_2$/MeOH mixtures affording 0.120 g (57% of yield) of the expected compound.

$^1$H NMR (400 MHz, DMSO-d6) δ ppm 0.6 (s, 2H) 0.9 (m, 2H) 1.9 (m, 1H) 7.2 (d, J=8.6 Hz, 1H) 7.3 (d, J=8.2 Hz, 1H) 7.5 (m, 2H) 7.7 (m, 1H) 8.3 (d, J=7.0 Hz, 2H) 8.5 (m, 1H) 8.8 (s, 2H) 9.4 (s, 1H) 13.3 (m, 1H).

ESI/MS (m/e, %): 332 [(M+1)$^+$, 100]

Example 2

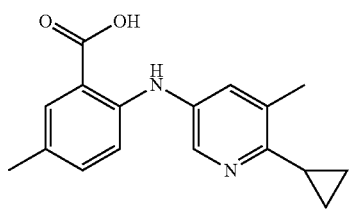 [SMILES: Cc1ccc(Nc2cnc(C3CC3)c(C)c2)c(C(=O)O)c1]

2-(6-Cyclopropyl-5-methylpyridin-3-ylamino)-5-methylbenzoic acid

A. tert-Butyl 2-(6-cyclopropyl-5-methylpyridin-3-ylamino)-5-methylbenzoate

In a schlenck tube, a mixture of Intermediate 16 (1.33 mmol, 0.502 g), cyclopropylboronic acid (1.83 mmol, 0.157 g), K$_3$PO$_4$ (4.52 mmol, 0.960 g), PCy$_3$ (0.14 mmol, 0.040 g) and Pd(AcO)$_2$ (0.07 mmol, 0.015 g) in a mixture of toluene/water 20:1 (25 ml) was heated at 110° C. for 72 hours, under argon atmosphere. The crude mixture was poured into water and extracted with ethyl acetate. The organic phase was dried over MgSO$_4$, filtered and the solvent removed to afford 0.514 g (83% of the yield) of the expected product.

ESI/MS (m/e, %): 339 [(M+1)$^+$, 100]

B. 2-(6-Cyclopropyl-5-methylpyridin-3-ylamino)-5-methylbenzoic acid

A solution of tert-butyl 2-(6-cyclopropyl-5-methylpyridin-3-ylamino)-5-methylbenzoate (1.52 mmol, 0.514 g) in TFA (5 ml) was stirred at room temperature for 30 minutes. The solvent was reduced under reduced pressure and the crude mixture was purified by reverse phase chromatography using a 30% to 100% (Water-ACN) gradient and affording 0.150 g (35% of yield) of the expected product.

$^1$H NMR (400 MHz, DMSO-d$_6$) δ ppm: 0.75-1.06 (m, 4H), 2.05 (m, 1H), 2.22 (s, 3H), 2.37 (s, 3H) 7.03 (d, J=8.61 Hz, 1H), 7.22 (d, J=8.61 Hz, 1H), 7.40 (s, 1H), 7.71 (s, 1H), 8.15 (s, 1H) 9.35 (s, 1H).

ESI/MS (m/e, %): 283 [(M+1)$^+$, 100]

Example 3

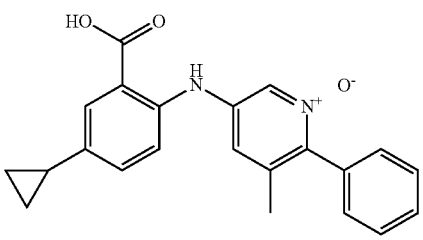

5-(2-Carboxy-4-cyclopropylphenylamino)-3-methyl-2-phenylpyridine 1-oxide

A. Ethyl 5-cyclopropyl-2-(5-methyl-6-phenylpyridin-3-ylamino)benzoate

In a schlenck tube, a mixture of Intermediate 9 (0.67 mmol, 0.150 g), Intermediate 2 (0.67 mmol, 0.123 g), Cs$_2$CO$_3$ (0.94 mmol, 0.3 g), xanthpos (0.13 mmol, 0.077 g) and Pd$_2$(dba)$_3$ (0.07 mmol, 0.061 g) in dioxane (2.5 ml) was heated at 110° C. for 12 hours, under argon atmosphere. The solvent was evaporated and the crude mixture was extracted between water and ethyl acetate. The organic phase was evaporated affording 0.245 g (yield 99%) of the expected product.

ESI/MS (m/e, %): 373 [(M+1)$^+$, 100].

B. 5-Cyclopropyl-2-(5-methyl-6-phenylpyridin-3-ylamino)benzoic acid

The solid residue obtained in step A was dissolved in ethanol (5 ml) and aqueous solution 2N NaOH (0.67 ml) was added. The mixture was heated at 60° C. for 2 hours, the solvent was evaporated and the solid obtained was suspended in water. The pH was taken to 6.5 and extracted with CHCl$_3$. The crude mixture was purified over a SCX cartridge eluting with MeOH/NH$_3$ 10:1 affording 0.070 g (yield 29%) of the expected product.

$^1$H NMR (300 MHz, CDCl$_3$) δ ppm: 0.63 (q, 2H), 0.90 (q, 2H), 1.84 (m, 1H), 2.33 (s, 3H), 7.12 (d, 1H), 7.24 (s, 1H), 7.38-7.58 (m, 6H), 7.73 (s, 1H), 8.51 (s, 1H).

ESI/MS (m/e, %): 345 [(M+1)$^+$, 100].

C. 5-(2-Carboxy-4-cyclopropylphenylamino)-3-methyl-2-phenylpyridine 1-oxide

To a stirred solution of 5-cyclopropyl-2-(5-methyl-6-phenylpyridin-3-ylamino)benzoic acid (0.29 mmol, 0.1 g) in 4 ml of dichloromethane was added mCPBA in portions, at 0° and under argon atmosphere. After the addition the mixture was stirred overnight at room temperature. The solvent was evaporated and the solid residue was triturated with a water/ethyl acetate mixture. The solid was filtered off affording 0.035 g (33% of yield) of the expected product.

$^1$H NMR (300 MHz, DMSO-$d_6$) δ ppm: 0.62 (d, 2H), 0.92 (d, 2H), 1.28 (m, 1H), 1.99 (s, 3H), 7.16 (s, 1H), 7.23 (s, 1H), 7.31 (s, 3H), 7.46 (s, 3H), 7.66 (s, 1H), 8.10 (s, 1H).

ESI/MS (m/e, %): 361 [(M+1)$^+$, 100].

Example 4

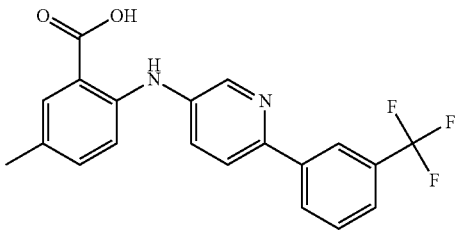 [SMILES: Cc1ccc(Nc2ccc(-c3cccc(C(F)(F)F)c3)nc2)c(C(=O)O)c1]

5-Methyl-2-(6-(3-(trifluoromethyl)phenyl)pyridin-3-ylamino)benzoic acid

In a schlenck tube, a mixture of Intermediate 13 (0.57 mmol, 0.150 g), 3-(trifluoromethyl)phenylboronic acid (0.63 mmol, 0.119 g), cessium carbonate (1.71 mmol, 0.558 g) and PdCl$_2$dppf.CH$_2$Cl$_2$ (0.006 mmol, 0.047 g) in dioxane/water 3:1 (4 ml) was heated at 120° C. overnight, under argon atmosphere. The solvent was evaporated and the crude mixture was purified over SiO$_2$ eluting with CH$_2$Cl$_2$/MeOH mixtures affording 0.120 g (56% of yield) of the expected compound.

$^1$H NMR (300 MHz, DMSO-$d_6$) δ ppm: 2.27 (s, 3H), 7.31-7.33 (m, 3H), 7.73-7.76 (m, 4H), 8.04-8.22 (m, 1H), 8.33-8.38 (m, 2H), 8.60 (s, 1H), 9.64 (bs, 1H).

ESI/MS (m/e, %): 373 [(M+1)$^+$, 100].

Example 5

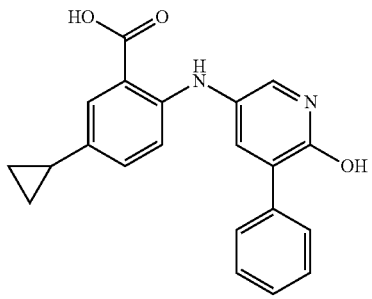 [SMILES: O=C(O)c1cc(C2CC2)ccc1Nc1cnc(O)c(-c2ccccc2)c1]

5-Cyclopropyl-2-(6-hydroxy-5-phenylpyridin-3-ylamino)benzoic acid

A. 2-(6-(Benzyloxy)-5-phenylpyridin-3-ylamino)-5-cyclopropylbenzoic acid

Obtained (0.155 g, 42% of yield) following the procedure described in example 3 (step A) starting with Intermediate 9 (0.78 mmol, 0.175 g) and Intermediate 26 (0.78 mmol, 0.215 g).

ESI/MS (m/e, %): 437 [(M+1)$^+$, 100].

B. 5-Cyclopropyl-2-(6-hydroxy-5-phenylpyridin-3-ylamino)benzoic acid

A solution of methyl 2-(6-(benzyloxy)-5-phenylpyridin-3-ylamino)-5-cyclopropylbenzoate (0.34 mmol, 0.155 g) in TFA (1.3 ml) was stirred at 45° C. for 30 minutes. The solvent was removed under reduced pressure. The crude mixture was solved in ethanol (2 ml), 2N aqueous NaOH were added and stirred at room temperature for 16 hours. The solvent was removed and the crude was neutralised with 2N aqueous HCl and extracted with CHCl$_3$. The crude mixture was purified by ionic exchange through a SCX cartridge affording 0.060 g (50% of yield).

ESI/MS (m/e, %): 347 [(M+1)$^+$, 100].

Example 6

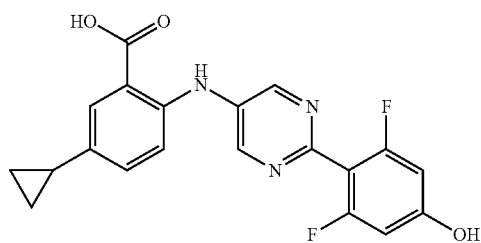 [SMILES: O=C(O)c1cc(C2CC2)ccc1Nc1cnc(-c2c(F)cc(O)cc2F)nc1]

5-cyclopropyl-2-(2-(2,6-difluoro-4-hydroxyphenyl)pyrimidin-5-ylamino)benzoic acid Obtained (0.52 g, yield 51%) following the procedure described in example 1, starting from Intermediate 8 (0.491 g, 2.77 mmol) and Intermediate 22 (2.5 mmol, 0.817 g).

$^1$H NMR (200 MHz, DMSO-$d_6$) δ ppm: 0.6 (m, 2H) 0.9 (m, 2H) 1.9 (m, 1H) 6.6 (d, J=9.4 Hz, 2H) 7.1 (d, J=9.0 Hz, 1H) 7.3 (m, 1H) 7.7 (s, 1H) 8.8 (s, 2H) 10.9 (s, 1H).

ESI/MS (m/e, %): 384 [(M+1)$^+$, 100]

Example 7

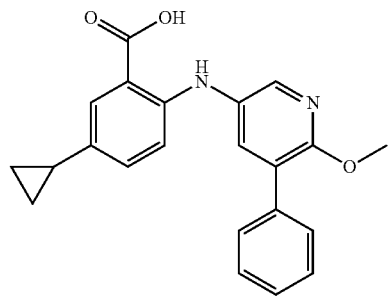 [SMILES: COc1ncc(Nc2ccc(C3CC3)cc2C(=O)O)cc1-c1ccccc1]

5-Cyclopropyl-2-(6-methoxy-5-phenylpyridin-3-ylamino)benzoic acid

A. Ethyl 5-cyclopropyl-2-(6-methoxy-5-phenylpyridin-3-ylamino)benzoate

In a schlenck tube, a mixture of Intermediate 9 (0.45 mmol, 0.1 g), Intermediate 3 (0.42 mmol, 0.085 g), Pd$_2$dba$_3$ (0.04 mmol, 0.041 g), xantphos (0.09 mmol, 0.052 g) and Cs₂CO₃ (0.62 mmol, 0.2 g) in dioxane (3 ml) was heated at 120° C. for 18 hours, under argon atmosphere. The solvent was evaporated and the crude mixture was extracted between water and ethyl acetate. The solid residue was purified by chromatography over SiO₂ eluting with dichloromethane/methanol mixtures affording 0.035 g of the corresponding ester derivative.

ESI/MS (m/e, %): 389 [(M+1)⁺, 100].

B. 5-Cyclopropyl-2-(6-methoxy-5-phenylpyridin-3-ylamino)benzoic acid

The solid residue obtained in step A was dissolved in 2.5 ml of ethanol and 0.180 ml of aqueous solution 2N NaOH were added. The mixture was heated at 60° C. for 2 hours, the solvent was evaporated and the solid obtained was suspended in water. The pH was taken to 6.5 and extracted with CHCl₃. The crude mixture was purified over a SCX cartridge eluting with MeOH/NH3 10:1 affording 0.025 g (yield 77%) of the expected product.

¹H NMR (300 MHz, CDCl₃) δ ppm: 0.63 (m, 2H) 0.79-1.16 (m, 2H) 1.64-2.09 (m, 1H) 3.81-4.34 (m, 3H) 6.69-7.03 (m, 1H) 7.11 (s, 1H) 7.21-8.01 (m, 7H) 8.08 (s, 1H).

ESI/MS (m/e, %): 361 [(M+1)⁺, 100].

Example 8

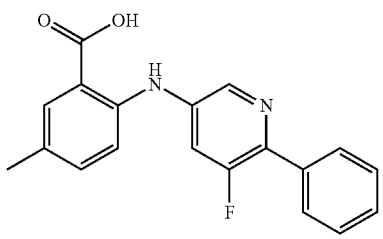 [SMILES: Cc1ccc(Nc2cnc(-c3ccccc3)c(F)c2)c(C(=O)O)c1]

2-(5-Fluoro-6-phenylpyridin-3-ylamino)-5-methyl-benzoic acid

A. tert-Butyl 2-(5-fluoro-6-phenylpyridin-3-ylamino)-5-methylbenzoate

In a schlenck tube, a mixture of Intermediate 19 (0.99 mmol, 0.332 g), phenylboronic acid (1.48 mmol, 0.180 g), potassium carbonate (3.15 mmol, 0.436 g) and Pd(PPh₃)₄ (0.10 mmol, 0.114 g) in DMF (10 ml) was heated at 120° C. for 5 hours in a microwave oven. The crude mixture was poured into water and extracted with ethyl acetate. The organic phase was dried over MgSO₄ and filtered and the solvent was removed. The crude mixture was purified over SiO₂ eluting with mixtures of hexane and ethyl acetate affording 0.313 g (68% of yield) of the expected product.

ESI/MS (m/e, %): 384 [(M+1-1)⁺, 100]

B. 2-(5-Fluoro-6-phenylpyridin-3-ylamino)-5-methylbenzoic acid

A solution of tert-butyl 2-(5-fluoro-6-phenylpyridin-3-ylamino)-5-methylbenzoate (0.83 mmol, 0.313 g) in TFA (5 ml) was stirred at room temperature for 30 minutes. The solvent was reduced under reduced pressure and the crude mixture was purified by reverse phase chromatography using a 30% to 100% (Water-ACN) gradient and affording 0.119 g (40% of yield) of the expected product.

¹H NMR (400 MHz, DMSO-d₆) δ ppm: 2.29 (s, 3H) 7.29-7.55 (m, 6H) 7.64 (d, J=13.69 Hz, 1H) 7.77 (s, 1H) 7.88 (d, J=7.04 Hz, 1H) 8.45 (s, 1H) 9.56-9.76 (m, 1H)

ESI/MS (m/e, %): 323 [(M+1)⁺, 100]

Example 9

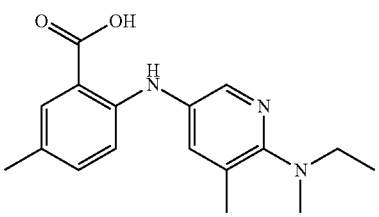 [SMILES: CCN(C)c1ncc(Nc2ccc(C)cc2C(=O)O)cc1C]

2-(6-(Ethyl(methyl)amino)-5-methylpyridin-3-ylamino)-5-methylbenzoic acid

To a solution of Intermediate 16 (1.06 mmols, 0.4 g) in dry dioxane (3.5 ml), N-methylethanamine (0.1 ml, 1.16 mmols) and K'BuO (1.67 mmols, 0.187 g) were added. Nitrogen was bubbled through. Pd₂(dba)₃ (0.01 mmols, 0.01 g) and 1,3-bis(2,6-diisopropylphenyl)imidazolium chloride (0.03 mmols, 0.014 g) were added and the inert gas was bubbled again. It was heated in the microwave at 120° C. for 5 h. 0.207 ml (2.40 mmols) more of amine, 560 mg (5.00 mmols) of K'BuO, 30 mg (0.03 mmols) of Pd₂(dba)₃, 42 mg (0.09 mmols) of 1,3-bis(2,6-diisopropylphenyl)imidazolium chloride and 1 ml more of solvent were added. The inert atmosphere was re-established. It was heated in the microwave for 5 h more under the previous conditions. It was poured in water and washed with diethyl ether. The basic aqueous organic phase was acidified up to pH: 1-3 and it was extracted with diethyl ether. The organic phase was dried, filtered and concentrated in vacuo. The crude was purified by chromatography (SiO₂, dichloromethane:methanol 10:0.5) affording 0.08 g (2% of yield) of the expected compound.

¹H NMR (200 MHz, DMSO-d₆) δ ppm: 1.08 (t, J=7.19 Hz, 3H), 2.21 (s, 3H), 2.22 (s, 3H), 2.72 (s, 3H), 3.05 (q, J=7.19 Hz, 2H), 6.90 (d, J=8.40 Hz, 1H), 7.17 (dd, J=8.40, 1.95 Hz, 1H), 7.39 (d, J=1.95 Hz, 1H), 7.68 (d, J=1.95 Hz, 1H), 7.99 (d, J=1.95 Hz, 1H).

ESI/MS (m/e, %): 300 [(M+1)⁺, 100]

Example 10

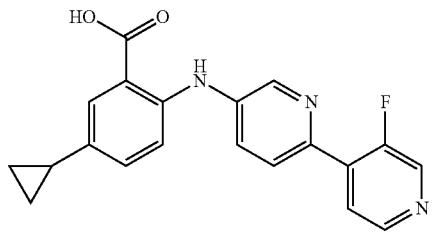 [SMILES: O=C(O)c1cc(C2CC2)ccc1Nc1ccc(-c2ccncc2F)nc1]

5-Cyclopropyl-2-(3'-fluoro-2,4'-bipyridin-5-ylamino)benzoic acid

In a schlenck tube, a mixture of Intermediate 14 (1.66 mmol, 0.676 g), 3-fluoro-4-(tributylstannyl)pyridine (1.66 mmol, 0.642 g), PdCl₂dppf.DCM (0.17 mmol, 0.136 g) and CuI (0.33 mmol, 0.063 g) in DMF (12 ml) was heated at 120° C. overnight. The mixture was filtered through celite and the solvent was evaporated. The crude mixture was extracted between ethyl ether and water. The organic phase was evaporated and the crude residue was purified over a SiO₂ eluting with hexane/ethyl acetate mixtures and affording 0.049 g (9% of yield) of the expected product.

¹H NMR (400 MHz, DMSO-d₆) δ ppm: 0.6 (m, 2H), 0.9 (m, 2H), 1.9 (m, 1H), 7.2 (dd, J=8.6, 2.3 Hz, 1H), 7.4 (d, J=8.6 Hz, 1H), 7.7 (d, J=2.3 Hz, 1H), 7.8 (dd, J=8.6, 2.7 Hz, 1H), 7.9 (d, J=8.2 Hz, 1H), 8.0 (dd, J=6.7, 5.1 Hz, 1H), 8.5 (d, J=4.3 Hz, 1H), 8.6 (m, 2H) 9.6 (m, 1H).

ESI/MS (m/e, %): 350 [(M+1)⁺, 100].

Example 11

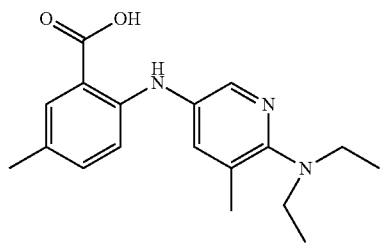 [SMILES: CCN(CC)c1ncc(Nc2ccc(C)cc2C(=O)O)cc1C]

2-(6-(Diethylamino)-5-methylpyridin-3-ylamino)-5-methylbenzoic acid

Obtained following the procedure described in Example 9 starting with Intermediate 16 (400 mg, 1.06 mmols) and diethylamine (0.12 ml, 1.17 mmols). After purification, 0.040 g (10% of yield) were obtained of the expected product.

¹H NMR (200 MHz, DMSO-d₆) δ ppm: 1.00 (t, J=7.03 Hz, 6H), 2.20 (s, 3H), 2.22 (s, 3H), 3.11 (q, J=7.03 Hz, 4H), 6.93 (d, J=8.59 Hz, 1H), 7.13-7.25 (m, 1H), 7.44 (d, J=2.00 Hz, 1H), 7.69 (s, 1H), 8.02 (d, J=2.73 Hz, 1H), 9.25 (s, 1H), 12.98 (s, 1H).

ESI/MS (m/e, %): 314 [(M+1)⁺, 100].

Example 12

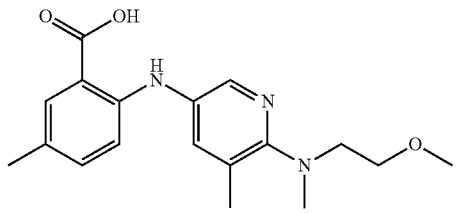

2-(6-((2-Methoxyethyl)(methyl)amino)-5-methylpyridin-3-ylamino)-5-methylbenzoic acid Obtained following the procedure described in Example 9 starting with Intermediate 16 (400 mg, 1.06 mmols) and 2-methoxy-N-methylethanamine (0.14 ml, 1.51 mmols). After purification, 0.040 g (10% of yield) were obtained of the expected product.

¹H NMR (200 MHz, DMSO-d₆) δ ppm: 2.21 (s, 3H), 2.23 (s, 3H), 2.79 (s, 3H), 3.07-3.27 (m, 5H), 3.51 (t, J=6.05 Hz, 2H), 6.90 (d, J=8.59 Hz, 1H), 7.06-7.24 (m, 1H), 7.39 (s, 1H), 7.68 (s, 1H), 7.87-8.19 (m, 1H), 8.73-10.03 (m, 1H).

ESI/MS (m/e, %): 330 [(M+1)⁺, 100].

Example 13

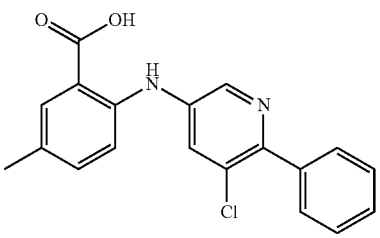

2-(5-Chloro-6-phenylpyridin-3-ylamino)-5-methylbenzoic acid

A. tert-Butyl 2-(5-chloro-6-phenylpyridin-3-ylamino)-5-methylbenzoate

Obtained (0.005 g, 3% of yield) following the procedure described in Example 8 (step A) starting with 0.230 g (0.58 mmol) of Intermediate 20A and 0.106 g (0.87 mmol) of phenylboronic acid.

ESI/MS (m/e, %): 395 [(M−1)⁺, 100]

B. 2-(5-Chloro-6-phenylpyridin-3-ylamino)-5-methylbenzoic acid

Obtained (0.005 g, 87% of yield) following the procedure described in Example 8 (step B) starting with 0.006 g (0.02 mmol) of tert-Butyl 2-(5-chloro-6-phenylpyridin-3-ylamino)-5-methylbenzoate in 1 ml of TFA.

¹H NMR (400 MHz, DMSO-d₆) δ ppm: 2.20 (s, 3H), 7.02-7.54 (m, 7H), 7.63 (s, 1H), 8.23 (d, J=17.22 Hz, 1H) 8.63 (s, 1H).

ESI/MS (m/e, %): 337 [(M−1)−, 100]

Example 14

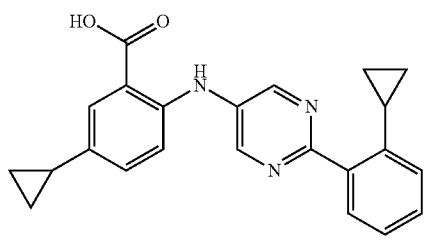 [SMILES: O=C(O)c1cc(C2CC2)ccc1Nc1cnc(-c2ccccc2C2CC2)nc1]

5-Cyclopropyl-2-(2-(2-cyclopropylphenyl)pyrimidin-5-ylamino)benzoic acid

A. Methyl 2-(2-(2-chlorophenyl)pyrimidin-5-ylamino)-5-cyclopropylbenzoate

In a schlenck tube, a mixture of methyl 2-amino-5-cyclopropylbenzoate (described in Intermediate 8 (step A)) (0.75 mmol, 0.165 g), Intermediate 23 (5-bromo-2-(2-chlorophenyl)pyrimidine) (0.75 mmol, 0.202 g), Cs₂CO₃ (1.06 mmol, 0.345 g), xanthpos (0.15 mmol, 0.089 g) and Pd₂(dba)₃ (0.08 mmol, 0.074 g) in dioxane (4 ml) was heated at 110° C. for 12 hours, under argon atmosphere. After filtration over celite, the solvent was evaporated and the crude mixture was purified over SiO₂ eluting with hexane/ethyl acetate affording 0.210 g (72% of yield) of the corresponding ester derivative.

ESI/MS (m/e, %): 380 [(M+1)⁺, 100], 382 [(M+1)⁺, 35].

B. 2-(2-(2-Chlorophenyl)pyrimidin-5-ylamino)-5-cyclopropylbenzoic acid

The solid residue obtained in step A was dissolved in methanol (3 ml) and aqueous solution 2N NaOH (1 ml) was added. The mixture was heated at 60° C. for 2 hours, the solvent was evaporated and the solid obtained was suspended in water. The pH was taken to 6.5 and extracted with $CHCl_3$. The crude mixture was purified over a $SiO_2$ eluting with DCM/MeOH 2% affording 0.170 g (yield 81%) of the expected product.

$^1$H NMR (300 MHz, DMSO-$d_6$) δ ppm: 1.2 (m, 2H), 1.5 (m, 2H), 2.5 (m, 1H), 7.8 (dd, J=8.6, 2.3 Hz, 1H), 7.9 (d, J=8.6 Hz, 1H), 8.0 (m, 2H), 8.1 (m, 1H), 8.2 (d, J=2.3 Hz, 1H), 8.3 (m, 1H), 9.4 (s, 2H), 10.0 (s, 1H), 13.8 (s, 1H).

ESI/MS (m/e, %): 366 [(M+1)$^+$, 100], 368 [(M+1)$^+$, 35].

C. 5-Cyclopropyl-2-(2-(2-cyclopropylphenyl)pyrimidin-5-ylamino)benzoic acid

In a schlenck tube, a mixture of 2-(2-(2-chlorophenyl)pyrimidin-5-ylamino)-5-cyclopropylbenzoic acid (0.55 mmol, 0.200 g), cyclopropylboronic acid (0.71 mmol, 0.061 g), $K_3PO_4$ (1.86 mmol, 0.395 g), $PCy_3$ (0.05 mmol, 0.015 g) and Pd(AcO)$_2$ (0.03 mmol, 0.006 g) in a mixture of toluene/water 6:1 (6 ml) was heated at 110° C. for 72 hours, under argon atmosphere. The crude mixture was poured into water and extracted with ethyl acetate. The organic phase was dried over $MgSO_4$, filtered and the solvent removed. The crude mixture was purified by reverse phase chromatography eluting with a gradient of 100% water to 100% MeOH/AcN 1:1 affording 0.016 g (71% of yield).

$^1$H NMR (400 MHz, DMSO-$d_6$) δ ppm: 0.6 (m, 4H), 0.9 (m, 4H), 1.9 (m, 2H), 7.0 (d, J=7.0 Hz, 1H), 7.3 (m, 3H), 7.5 (s, 1H), 7.6 (m, J=2.0 Hz, 1H), 8.3 (s, 1H), 8.8 (s, 2H), 9.5 (s, 1H), 13.2 (s, 1H).

ESI/MS (m/e, %): 372 [(M+1)$^+$, 100].

Example 15

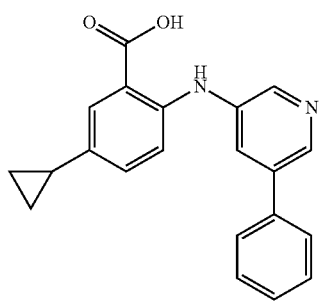 [SMILES: O=C(O)c1cc(C2CC2)ccc1Nc1cncc(-c2ccccc2)c1]

5-cyclopropyl-2-(5-phenylpyridin-3-ylamino)benzoic acid

A. Ethyl 5-cyclopropyl-2-(5-phenylpyridin-3-ylamino)benzoate

Obtained (0.084 g, 79% of yield) following the procedure described in Example 7 (step A) starting with Intermediate 9 (0.29 mmol, 0.066 g) and Intermediate 4 (0.29 mmol, 0.05 g).
ESI/MS (m/e, %): 359 [(M+1)$^+$, 100].

B. 5-cyclopropyl-2-(5-phenylpyridin-3-ylamino)benzoic acid

Obtained (0.07 g, 87% of yield) following the procedure describes in Example 7 (step B) starting with 0.084 g of ethyl 5-cyclopropyl-2-(5-phenylpyridin-3-ylamino)benzoate.
$^1$H NMR (300 MHz, DMSO-$d_6$) δ ppm: 0.58 (m, 2H) 0.76-0.99 (m, 2H) 1.76-2.06 (m, 1H) 6.92-8.09 (m, 9H) 8.22-8.68 (m, 2H).
ESI/MS (m/e, %): 331 [(M+1)$^+$, 100].

Example 16

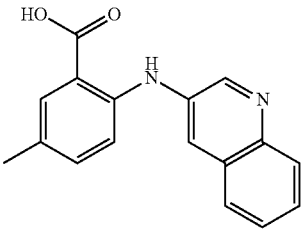 [SMILES: Cc1ccc(Nc2cnc3ccccc3c2)c(C(=O)O)c1]

5-methyl-2-(quinolin-3-ylamino)benzoic acid

A. Ethyl 5-methyl-2-(quinolin-3-ylamino)benzoate

Obtained (0.845 g, 97% of yield) following the procedure described in Example 14 (step B) starting from ethyl 2-amino-5-methylbenzoate (0.395 g, 2.20 mmol) and 3-bromoquinoline (0.46 g, 2.20 mmol).
ESI/MS (m/e, %): 307 [(M+1)$^+$, 100].

B. 5-methyl-2-(quinolin-3-ylamino)benzoic acid

Obtained (0.542 g, yield 86%) following the procedure described in Example 14 (step B) starting from ethyl 5-methyl-2-(quinolin-3-ylamino)benzoate (0.845 g, 2.1 mmol).
$^1$H NMR (400 MHz, DMSO-$d_6$) δ ppm: 2.3 (s, 3H), 7.3 (dd, J=8.6, 2.3 Hz, 1H), 7.4 (m, 1H), 7.6 (m, 2H), 7.8 (s, 1H), 7.9 (d, J=7.8 Hz, 1H), 7.9 (d, J=7.8 Hz, 1H), 8.1 (d, J=2.3 Hz, 1H), 8.8 (d, J=2.7 Hz, 1H), 9.7 (s, 1H), 13.2 (s, 1H).
ESI/MS (m/e, %): 279 [(M+1)$^+$, 100].

Example 17

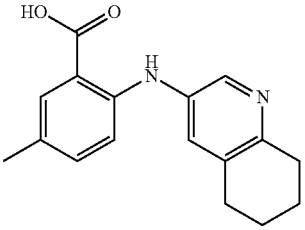 [SMILES: Cc1ccc(Nc2cnc3c(c2)CCCC3)c(C(=O)O)c1]

5-methyl-2-(5,6,7,8-tetrahydroquinolin-3-ylamino)benzoic acid

A solution of 5-methyl-2-(quinolin-3-ylamino)benzoic acid (Example 16) (1.08 mmol, 0.30 g) in TFA (2.5 ml) was hydrogenated under pressure (58 psi) with $PtO_2$ (0.11 mmol, 0.028 g) as catalyst until all starting material disappeared. After that the reaction mixture was filtered, concentrated and redissolved in water. The pH was adjusted to 4-5 by addition of 2N NaOH and a solid was formed. This yellow solid formed was the desired compound (0.249 mg, 79% of yield).
$^1$H NMR (400 MHz, DMSO-$d_6$) δ ppm: 1.8 (m, 4H), 2.3 (s, 3H), 2.8 (t, J=6.0 Hz, 2H), 2.9 (t, J=6.2 Hz, 2H), 7.2 (d, J=8.5 Hz, 1H), 7.3 (m, 1H), 7.7 (s, 1H), 7.9 (s, 1H), 8.4 (d, J=1.7 Hz, 1H), 9.4 (s, 1H), 13.3 (s, 1H).
ESI/MS (m/e, %): 283 [(M+1)$^+$, 100].

Example 18

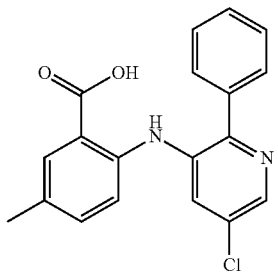 [SMILES: Cc1ccc(Nc2cc(Cl)cnc2-c2ccccc2)c(C(=O)O)c1]

2-(5-Chloro-2-phenylpyridin-3-ylamino)-5-methyl-benzoic acid

A. tert-Butyl 2-(5-chloro-2-phenylpyridin-3-ylamino)-5-methylbenzoate

Obtained (0.008 g, 3% of yield) following the procedure described in Example 8 (step A) starting with Intermediate 20B (0.58 mmol, 0.230 g) and phenylboronic acid (0.87 mmol, 0.106 g).
ESI/MS (m/e, %): 395 [(M+1)+, 100]

B. 2-(5-Chloro-2-phenylpyridin-3-ylamino)-5-methylbenzoic acid

Obtained (0.025 g, 34% of yield) following the procedure described in Example 8 (step B) starting with tert-butyl 2-(5-chloro-2-phenylpyridin-3-ylamino)-5-methylbenzoate (0.17 mmol, 0.068 g).
$^1$H NMR (400 MHz, DMSO-$d_6$) δ ppm: 2.20 (s, 3H), 7.19-7.71 (m, 8H), 7.88 (s, 1H), 8.32 (s, 1H), 9.48 (s, 1H).
ESI/MS (m/e, %): 339 [(M+1)+, 100]

Example 19

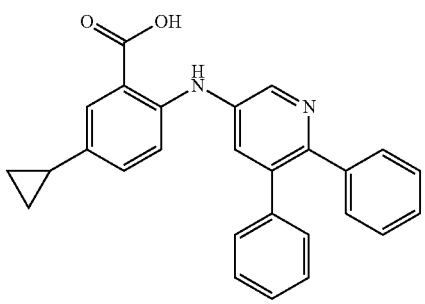 [SMILES: O=C(O)c1cc(C2CC2)ccc1Nc1cnc(-c2ccccc2)c(-c2ccccc2)c1]

5-Cyclopropyl-2-(5,6-diphenylpyridin-3-ylamino)benzoic acid

A. Ethyl 5-cyclopropyl-2-(5,6-diphenylpyridin-3-ylamino)benzoate

Obtained (0.09 g, 38% of yield) following the procedure described in Example 7 (step A) starting with Intermediate 9 (0.71 mmol, 0.16 g) and Intermediate 5 (0.55 mmol, 0.135 g).
ESI/MS (m/e, %): 435 [(M+1)+, 100].

B. 5-Cyclopropyl-2-(5,6-diphenylpyridin-3-ylamino)benzoic acid

Obtained (0.035 g, 42% of yield) following the procedure described in Example 7 (step B) starting with 0.090 g (0.21 mmol) of ethyl 5-cyclopropyl-2-(5,6-diphenylpyridin-3-ylamino)benzoate.
$^1$H NMR (300 MHz, CDCl$_3$) δ ppm: 0.65 (d, 2H) 0.90 (d, 2H) 1.75-1.99 (m, 1H) 7.06-7.41 (m, 12H) 7.61 (s, 1H) 7.78 (s, 1H) 8.62 (s, 1H).
ESI/MS (m/e, %): 407 [(M+1)+, 100].

Example 20

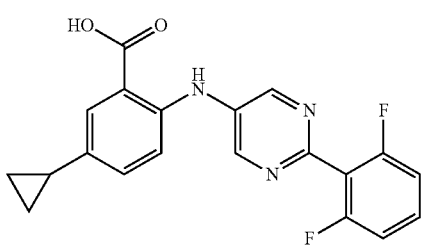 [SMILES: O=C(O)c1cc(C2CC2)ccc1Nc1cnc(-c2c(F)cccc2F)nc1]

5-cyclopropyl-2-(2-(2,6-difluorophenyl)pyrimidin-5-ylamino)benzoic acid

In a schlenck tube, a mixture of Intermediate 8 (0.90 g, 5.77 mmol) and Intermediate 24 (1.38 g, 5.09 mmol), Cs$_2$CO$_3$ (12.18 mmol, 3.97 g), xanthpos (1.02 mmol, 0.59 g) and Pd$_2$(dba)$_3$ (0.51 mmol, 0.47 g) in dioxane (30 ml) was heated at 110° C. for 12 hours, under argon atmosphere.

The solvent was evaporated and the crude mixture was extracted between acidulated water and ethyl acetate. The organic phase was dried over MgSO$_4$, filtered and the solvent removed. The crude mixture was triturated with DCM to give 1.145 g (61% of yield) of the expected product.
$^1$H NMR (200 MHz, DMSO-$d_6$) δ ppm: 0.6 (m, 2H) 0.9 (m, 2H) 1.9 (m, 1H) 7.2 (m, 3H) 7.4 (m, 1H) 7.6 (m, 1H) 7.7 (d, J=2.3 Hz, 1H) 8.8 (s, 2H) 9.5 (s, 1H) 13.3 (s, 1H).
ESI/MS (m/e, %): 368 [(M+1)+, 100].

Example 21

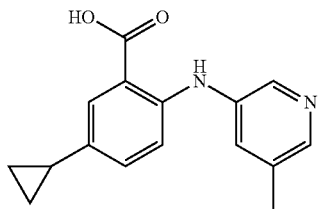 [SMILES: Cc1cncc(Nc2ccc(C3CC3)cc2C(=O)O)c1]

5-Cyclopropyl-2-(5-methylpyridin-3-ylamino)benzoic acid

A. Ethyl 5-cyclopropyl-2-(5-methylpyridin-3-ylamino)benzoate

Obtained (0.11 g, 42% of yield) following the procedure described in Example 7 (step A) starting with Intermediate 9 (0.89 mmol, 0.2 g) and 5-methylpyridin-3-amine (0.89 mmol, 0.096 g).
ESI/MS (m/e, %): 297 [(M+1)+, 100].

B. 5-Cyclopropyl-2-(5-methylpyridin-3-ylamino)benzoic acid

The solid residue obtained in step A was dissolved in 4 ml of ethanol and 0.4 ml of aqueous solution 2N NaOH were added. The mixture was stirred at 25° C. for 16 hours, the solvent was evaporated and the solid obtained was suspended in water. The pH was taken to 6.5 and extracted with $CHCl_3$ affording 0.06 g (yield 60%) of the expected product.

$^1$H NMR (300 MHz, DMSO-$d_6$): 0.59 (d, 2H), 0.90 (d, 2H), 1.89 (m, 1H), 2.27 (s, 3H), 7.16 (s, 2H), 7.46 (s, 1H), 7.64 (s, 1H), 8.05 (s, 1H), 8.26 (s, 1H).

ESI/MS (m/e, %): 269 [(M+1)$^+$, 100].

Example 22

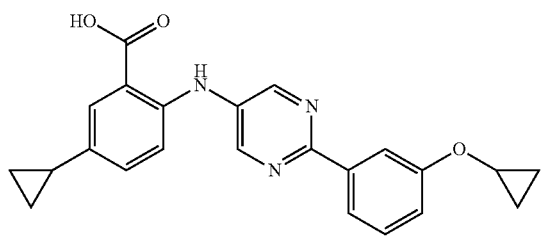 [SMILES: O=C(O)c1cc(C2CC2)ccc1Nc1cnc(-c2cccc(OC3CC3)c2)nc1]

2-(2-(3-Cyclopropoxyphenyl)pyrimidin-5-ylamino)-5-cyclopropylbenzoic acid

A. Methyl 2-(2-(3-cyclopropoxyphenyl)pyrimidin-5-ylamino)-5-cyclopropylbenzoate In a schlenck tube, a mixture of Intermediate 17 (0.305 g, 1 mmol) and Intermediate 25 (0.260 g, 1 mmol), 2M $K_2CO_3$ (1.98 mmol, 1 ml) and Pd(PPh$_3$)$_4$ (0.1 mmol, 0.114 g) in dioxane (7 ml) was heated at 110° C. for 12 hours, under argon atmosphere. The solvent was evaporated and the crude mixture was extracted between water and ethyl acetate. The organic phase was dried over $MgSO_4$, filtered and the solvent removed. The crude mixture was purified by chromatography over $SiO_2$ eluting with hexane/ethyl acetate mixtures affording 0.205 g (49% of yield) of the expected product.

ESI/MS (m/e, %): 402 [(M+1)$^+$, 100].

B. 2-(2-(3-Cyclopropoxyphenyl)pyrimidin-5-ylamino)-5-cyclopropylbenzoic acid Obtained (0.136 g, yield 64%) following the procedure described in example 21 (step B) starting from methyl 2-(2-(3-cyclopropoxyphenyl)pyrimidin-5-ylamino)-5-cyclopropylbenzoate.

$^1$H NMR (400 MHz, DMSO-$d_6$) δ ppm: 0.7 (m, 4H), 0.9 (m, 4H), 1.9 (m, 1H), 3.9 (m, 1H), 7.1 (d, J=6.7 Hz, 1H), 7.2 (d, J=7.8 Hz, 1H), 7.3 (d, J=7.8 Hz, 1H), 7.4 (t, J=7.4 Hz, 1H), 7.7 (s, 1H), 7.9 (d, J=7.4 Hz, 1H), 8.0 (s, 1H), 8.8 (m, 2H), 9.6 (s, 1H), 13.2 (s, 1H).

ESI/MS (m/e, %): 388 [(M+1)$^+$, 100].

Example 23

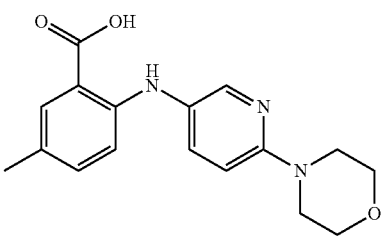 [SMILES: Cc1ccc(Nc2ccc(N3CCOCC3)nc2)c(C(=O)O)c1]

5-Methyl-2-(6-morpholinopyridin-3-ylamino)benzoic acid

A. tert-Butyl 5-methyl-2-(6-morpholinopyridin-3-ylamino)benzoate

To a solution of Intermediate 15 (0.28 mmol, 0.1 g) in ethoxyethanol (1 ml), morpholine (0.55 mmol, 0.050 g) was added. The mixture was heated at 130° C. for 16 hours in a sealed tube. 0.050 g (0.55 mmol) of morpholine were added and the mixture was heated at 130° C. for further 24 hours. The solvent was evaporated and the crude mixture was purified by $SiO_2$ eluting with mixtures of hexane/ethyl acetate affording 0.056 g (55% of yield) of the expected product.

ESI/MS (m/e, %): 370 [(M+1)$^+$, 100]

B. 5-Methyl-2-(6-morpholinopyridin-3-ylamino)benzoic acid

A solution of 5-methyl-2-(6-morpholinopyridin-3-ylamino)benzoate tert-butyl ester in TFA (0.6 ml, 7.58 mmol) was stirred at room temperature for 1 hour. The solvent was evaporated and the residue was triturated in diethyl ether. The solid formed was filtered off to afford 0.047 g (73% of yield) of the expected product.

ESI/MS (m/e, %): 314 [(M+1)$^+$, 100]

Example 24

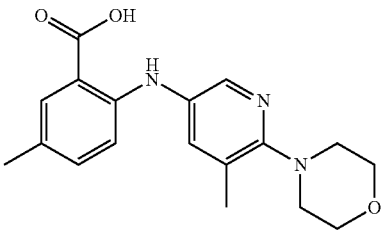 [SMILES: Cc1ccc(Nc2cnc(N3CCOCC3)c(C)c2)c(C(=O)O)c1]

5-Methyl-2-(5-methyl-6-morpholinopyridin-3-ylamino)benzoic acid

Obtained (0.060 g, 17% of yield) following the procedure described in Example 9 starting with Intermediate 16 (1.06 mmols, 0.400 g) and morpholine (1.17 mmols, 0.102 ml).

$^1$H NMR (200 MHz, DMSO-$d_6$) δ ppm: 2.19 (s, 3H), 2.23 (s, 3H), 2.99 (m, 4H), 3.54-3.91 (m, 4H), 6.93 (d, J=8.59 Hz, 1H), 7.14 (d, J=8.59 Hz, 1H), 7.40 (s, 1H), 7.67 (s, 1H), 8.01 (s, 1H), 8.62-10.25 (s, 1H).

ESI/MS (m/e, %): 328 [(M+1)$^+$, 100]

Example 25

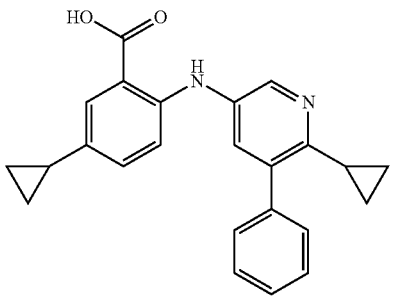 [SMILES: O=C(O)c1cc(C2CC2)ccc1Nc1cnc(C2CC2)c(-c2ccccc2)c1]

5-cyclopropyl-2-(6-cyclopropyl-5-phenylpyridin-3-ylamino)benzoic acid

A. Ethyl 5-cyclopropyl-2-(6-cyclopropyl-5-phenylpyridin-3-ylamino)benzoate

Obtained (0.025 g, 44% of yield) following the procedure described in Example 7 (step A) starting with Intermediate 9 (0.16 mmol, 0.035 g) and Intermediate 6 (0.14 mmol, 0.03 g).
ESI/MS (m/e, %): 399 [(M+1)$^+$, 100].

B. 5-Cyclopropyl-2-(6-cyclopropyl-5-phenylpyridin-3-ylamino)benzoic acid

Obtained (0.005 g, 22% of yield) following the procedure described in Example 7 (step B) starting with ethyl 5-cyclopropyl-2-(6-cyclopropyl-5-phenylpyridin-3-ylamino)benzoate (0.025 g, 0.06 mmol).
$^1$H NMR (300 MHz, CDCl$_3$) δ ppm: 0.55-0.71 (m, 2H), 0.78-0.99 (m, 4H), 1.07-1.20 (m, 2H), 1.76-1.93 (m, 1H), 1.96-2.23 (m, 1H), 7.12 (s, 2H), 7.33-7.56 (m, 6H), 7.78 (s, 1H), 8.28-8.57 (s, 1H).
ESI/MS (m/e, %): 371 [(M+1)$^+$, 100].

Example 26

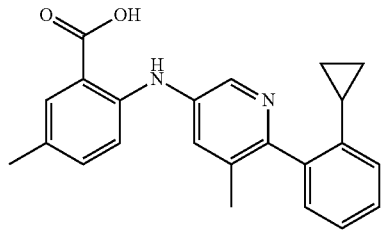 [SMILES: Cc1ccc(Nc2cnc(-c3ccccc3C3CC3)c(C)c2)c(C(=O)O)c1]

2-(6-(2-Cyclopropylphenyl)-5-methylpyridin-3-ylamino)-5-methylbenzoic acid

A. tert-Butyl 2-(6-(2-chlorophenyl)-5-methylpyridin-3-ylamino)-5-methylbenzoate Obtained (0.150 g, yield 95%) following the procedure described in Example 22 (step A) starting with Intermediate 16 (0.53 mmol, 0.200 g) and 2-chlorophenylboronic acid (0.79 mmol, 0.124 g).
$^1$H NMR (200 MHz, CDCl$_3$) δ ppm: 1.62 (s, 9H), 2.14 (s, 3H), 2.30 (s, 3H), 6.90-7.59 (m, 7H), 7.74 (m, 1H), 8.45 (d, J=2.34 Hz, 1H), 9.48 (s, 1H).
ESI/MS (m/e, %): 409 [(M+1)$^+$, 96].

B. tert-Butyl 2-(6-(2-cyclopropylphenyl)-5-methylpyridin-3-ylamino)-5-methylbenzoate Obtained (0.152 g, 63% of yield) following the procedure described in Example 14 (step C) starting with tert-butyl 2-(6-(2-chlorophenyl)-5-methylpyridin-3-ylamino)-5-methylbenzoate (0.49 mmol, 0.200 g) and cyclopropylboronic acid (1.47 mmol, 0.126 g).
ESI/MS (m/e, %): 409 [(M+1)$^+$, 96].

C. 2-(6-(2-Cyclopropylphenyl)-5-methylpyridin-3-ylamino)-5-methylbenzoic acid Obtained (0.012 g, 10% of yield) following the procedure described in Example 8 (step B) starting with tert-Butyl 2-(6-(2-cyclopropylphenyl)-5-methylpyridin-3-ylamino)-5-methylbenzoate (0.150 g, 0.37 mmol).
$^1$H NMR (400 MHz, DMSO-d$_5$) δ ppm: 0.59-0.68 (m, 2H), 0.78 (d, J=8.61 Hz, 2H), 1.47-1.60 (m, 1H), 2.07 (s, 3H), 2.25 (s, 3H), 6.91 (d, J=7.83 Hz, 1H), 7.12 (dd, J=7.43, 1.17 Hz, 1H), 7.20 (t, J=6.85 Hz, 1H), 7.25-7.35 (m, 3H), 7.58 (d, J=2.35 Hz, 1H), 7.75 (s, 1H), 8.36 (d, J=2.74 Hz, 1H).
ESI/MS (m/e, %): 359 [(M+1)$^+$, 100]

Example 27

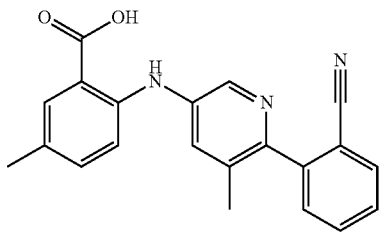 [SMILES: Cc1ccc(Nc2cnc(-c3ccccc3C#N)c(C)c2)c(C(=O)O)c1]

2-(6-(2-Cyanophenyl)-5-methylpyridin-3-ylamino)-5-methylbenzoic acid

A. tert-Butyl 2-(6-(2-cyanophenyl)-5-methylpyridin-3-ylamino)-5-methylbenzoate Obtained (0.164 g, 34% of yield) following the procedure described in Example 8 (step A) starting with Intermediate 16 (1.06 mmols, 0.400 g) and 2-cyanophenylboronic acid (1.59 mmol, 0.233 g).
$^1$H NMR (200 MHz, DMSO-d$_6$) δ ppm: 1.29-1.70 (s, 9H), 2.18 (s, 3H), 2.29 (s, 3H), 7.33 (s, 1H), 7.43-8.07 (m, 6H), 8.40 (d, J=2.34 Hz, 1H), 9.22 (s, 1H).
ESI/MS (m/e, %): 400 [(M+1)$^+$, 100]

B. 2-(6-(2-Cyanophenyl)-5-methylpyridin-3-ylamino)-5-methylbenzoic acid

Obtained (0.013 g, 10% of yield) following the procedure described in Example 8 (step B) starting with tert-Butyl 2-(6-(2-cyanophenyl)-5-methylpyridin-3-ylamino)-5-methylbenzoate (0.164 g, mmol).

¹H NMR (200 MHz, DMSO-d₆) δ ppm: 2.19 (s, 3H), 2.27 (s, 3H), 7.31 (m, 2H), 7.50-7.7 (m, 3H), 7.70-7.87 (m, 2H), 7.90-8.00 (m, 1H) 8.39 (s, 1H).
ESI/MS (m/e, %): 344 [(M+1)⁺, 100]

Example 28

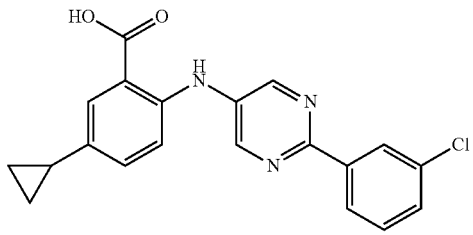 [SMILES: O=C(O)c1cc(C2CC2)ccc1Nc1cnc(-c2cccc(Cl)c2)nc1]

2-(2-(3-Chlorophenyl)pyrimidin-5-ylamino)-5-cyclopropylbenzoic acid

A. Methyl 2-(2-(3-chlorophenyl)pyrimidin-5-ylamino)-5-cyclopropylbenzoate

Obtained (0.433 g, 61% of yield) following the procedure described in Example 22 (step A) starting with Intermediate 17 (0.99 mmol, 0.300 g) and 3-chlorophenylboronic acid (0.99 mmol, 0.155 g).
ESI/MS (m/e, %): 380 [(M+1)⁺, 100], 368 [(M+1)⁺, 35]

B. 2-(2-(3-Chlorophenyl)pyrimidin-5-ylamino)-5-cyclopropylbenzoic acid

Obtained (0.217 g, yield 60%) following the procedure described in example 22 (step B) starting from methyl 2-(2-(3-chlorophenyl)pyrimidin-5-ylamino)-5-cyclopropylbenzoate (0.433 g, 0.60 mmol).
¹H NMR (400 MHz, DMSO-d₆) δ ppm: 0.6 (m, 2H), 0.9 (m, 2H), 1.9 (m, 1H), 7.3 (m, 2H), 7.6 (m, 3H), 8.3 (m, 2H), 8.8 (s, 2H), 9.5 (s, 1H), 13.3 (s, 1H).
ESI/MS (m/e, %): 366 [(M+1)⁺, 100], 368 [(M+1)⁺, 35]

Example 29

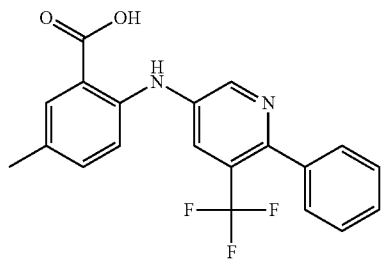 [SMILES: Cc1ccc(Nc2cnc(-c3ccccc3)c(C(F)(F)F)c2)c(C(=O)O)c1]

5-Methyl-2-(6-phenyl-5-(trifluoromethyl)pyridin-3-ylamino)benzoic acid

In a schlenck tube, a mixture of 2-bromo-5-methylbenzoic acid (0.57 mmol, 0.120 g), Intermediate 1 (1.12 mmol, 0.265 g), potassium carbonate (1.12 mmol, 0.153 g), Cu₂O (0.06 mmol, 0.008 g) and Cu (0.06 mmol, 0.004 g) in DME (2 ml) was heated at 130° C. overnight, under argon atmosphere. The solvent was evaporated and the crude mixture was purified over SiO₂ eluting with CH₂Cl₂/MeOH mixtures affording 0.120 g (57% of yield) of the expected compound.
ESI/MS (m/e, %): 373 [(M+1)⁺, 100]

Example 30

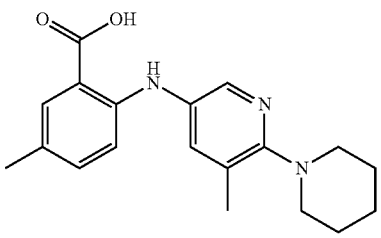 [SMILES: Cc1ccc(Nc2cnc(N3CCCCC3)c(C)c2)c(C(=O)O)c1]

5-Methyl-2-(5-methyl-6-(piperidin-1-yl)pyridin-3-ylamino)benzoic acid

Obtained (0.163 g, 47% of yield) following the procedure described in Example 9 starting with Intermediate 16 (1.06 mmol, 0.400 g) and piperidine (1.16 mmol, 0.115 ml).
¹H NMR (200 MHz, DMSO-d₆) δ ppm: 1.43-1.78 (m, 6H), 2.07-2.30 (m, 6H), 2.74-3.11 (m, 4H), 6.92 (d, J=8.69 Hz, 1H), 7.19 (dd, J=8.69, 2.15 Hz, 1H), 7.41 (d, J=1.95 Hz, 1H), 7.68 (s, 1H), 8.01 (d, J=2.73 Hz, 1H).
ESI/MS (m/e, %): 326 [(M+1)⁺, 100]

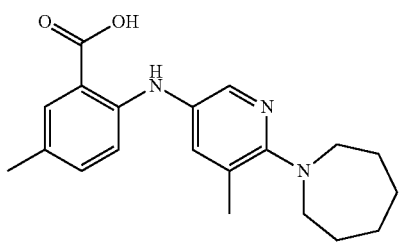 [SMILES: Cc1ccc(Nc2cnc(N3CCCCCC3)c(C)c2)c(C(=O)O)c1]

Example 31

2-(6-(Azepan-1-yl)-5-methylpyridin-3-ylamino)-5-methylbenzoic acid

Obtained (0.089 g, 21% of yield) following the procedure described in Example 9 starting with Intermediate 16 (1.06 mmol, 0.400 g) and azepane (1.17 mmol, 0.132 g)
¹H NMR (200 MHz, DMSO-d₆) δ ppm: 1.49-1.84 (m, 8H), 2.20 (s, 3H), 2.23 (s, 3H), 3.00-3.63 (m, 4H), 6.84 (d, J=8.59 Hz, 1H), 7.17 (dd, J=8.59, 1.95 Hz, 1H), 7.34 (d, J=2.73 Hz, 1H), 7.59-7.72 (m, 1H), 7.82-8.05 (m, 1H), 9.20 (s, 1H).
ESI/MS (m/e, %): 340 [(M+1)⁺, 100]

Example 32

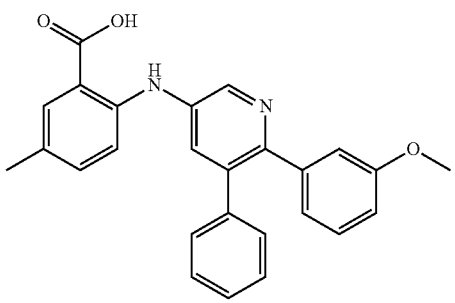

2-(6-(3-Methoxyphenyl)-5-phenylpyridin-3-ylamino)-5-methylbenzoic acid

A. Ethyl 2-(6-(3-methoxyphenyl)-5-phenylpyridin-3-ylamino)-5-methylbenzoate

Obtained (0.100 g, 29% of yield) following the procedure described in Example 7 (step A) starting with Intermediate 10 (0.81 mmol, 0.161 g) and Intermediate 7 (0.81 mmol, 0.223 g).
ESI/MS (m/e, %): 439 [(M+1)$^+$, 100]

B. 2-(6-(3-Methoxyphenyl)-5-phenylpyridin-3-ylamino)-5-methylbenzoic acid

Obtained (0.060 g, 64% of yield) following the procedure described in Example 7 (step B) starting with (0.23 mmol, 0.100 g) of ethyl 2-(6-(3-methoxyphenyl)-5-phenylpyridin-3-ylamino)-5-methylbenzoate.
$^1$H NMR (300 MHz, DMSO-d$_6$) δ ppm: 2.24 (s, 3H), 3.56 (s, 3H), 6.76-6.84 (m, 3H), 7.09-7.14 (t, 1H), 7.21-7.38 (m, 7H), 7.56-7.58 (d, 1H), 7.74 (s, 1H), 8.55-8.57 (d, 1H), 9.53 (bs, 1H).
ESI/MS (m/e, %): 411 [(M+1)$^+$, 100]

Example 33

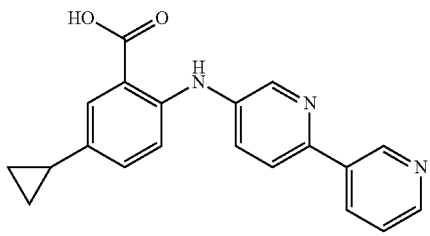 [SMILES: O=C(O)c1cc(C2CC2)ccc1Nc1ccc(-c2cccnc2)nc1]

2-(2,3'-bipyridin-5-ylamino)-5-cyclopropylbenzoic acid

A. Methyl 2-(2,3'-bipyridin-5-ylamino)-5-cyclopropylbenzoate

Obtained (0.067 g, 49% of yield) following the procedure described in Example 22 (step A) starting with Intermediate 18 (0.45 mmol, 0.155 g) and pyridin-3-ylboronic acid (0.67 mmol, 0.082 g).
ESI/MS (m/e, %): 346 [(M+1)$^+$, 100]

B. 2-(2,3'-bipyridin-5-ylamino)-5-cyclopropylbenzoic acid

Obtained (0.064 g, yield 79%) following the procedure described in Example 22 (step B) starting from methyl 2-(2,3'-bipyridin-5-ylamino)-5-cyclopropylbenzoate (0.067 g, 0.19 mmol).
$^1$H NMR (400 MHz, DMSO-d$_6$) δ ppm: 0.6 (m, 2H), 0.9 (m, 2H), 1.9 (m, 1H), 7.2 (d, J=8.7 Hz, 1H), 7.3 (d, J=8.7 Hz, 1H), 7.5 (dd, J=7.7, 4.8 Hz, 1H), 7.7 (s, 1H), 7.7 (dd, J=8.5, 2.7 Hz, 1H), 8.0 (d, J=8.7 Hz, 1H), 8.4 (d, J=7.9 Hz, 1H), 8.6 (m, 2H), 9.2 (s, 1H), 9.6 (s, 1H), 13.2 (s, 1H).
ESI/MS (m/e, %): 332 [(M+1)$^+$, 100]

Example 34

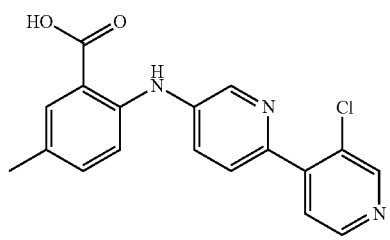

2-(3'-chloro-2,4'-bipyridin-5-ylamino)-5-methylbenzoic acid

A. tert-butyl 2-(3'-chloro-2,4'-bipyridin-5-ylamino)-5-methylbenzoate

In a schlenck tube, a mixture of Intermediate 15 (0.77 mmol, 0.28 g), 3-chloro-4-(tributylstannyl)pyridine (0.86 mmol, 0.345 g), PdCl$_2$(PPh$_3$)$_2$ (0.08 mmol, 0.055 g) and CuI (0.16 mmol, 0.03 g) in dioxane (4 ml) was heated at 120° C. for 18 hours, under argon atmosphere. The solvent was evaporated and the crude mixture was extracted between water and ethyl acetate. The organic phase was evaporated and the crude residue was purified over a SiO$_2$ eluting with dichloromethane/methanol mixtures and affording 0.3 g (yield 98%) of the corresponding ester derivative.
ESI/MS (m/e, %): 396[(M+1)$^+$, 100].

B. 2-(3'-Chloro-2,4'-bipyridin-5-ylamino)-5-methylbenzoic acid

The solid residue obtained in step A was dissolved in 3 ml of trifluoroacetic acid and stirred for 1 hour at room temperature. The solvent was evaporated and the solid residue was triturated with an isopropyl ether/hexane mixture. The solid was filtered off affording 0.16 g (yield 62%) of the expected product.
$^1$H NMR (300 MHz, DMSO-d$_6$) δ ppm: 2.28 (s, 3H), 7.25-7.44 (m, 3H), 7.65-7.72 (m, 1H), 7.72-7.83 (m, 3H), 8.53-8.67 (m, 2H).
ESI/MS (m/e, %): 340 [(M+1)$^+$, 100].

Example 35

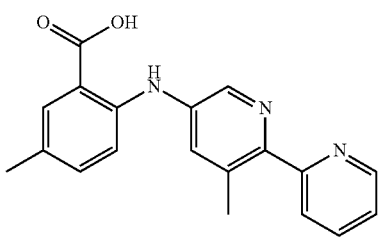 [SMILES: Cc1ccc(Nc2cnc(-c3ccccn3)c(C)c2)c(C(=O)O)c1]

5-Methyl-2-(3-methyl-2,2'-bipyridin-5-ylamino)benzoic acid

To a solution of Intermediate 16 (1.07 mmol, 0.403 g) in DMF (7 ml) 2-(tributylstannyl)pyridine (1.56 mmol, 0.574 g) was added. Nitrogen was bubbled through and Pd(PPh$_3$)$_4$ (0.08 mmol, 0.091 g) was added. It was heated in the microwave at 120° C. for 5 h. It was allowed to cool dawn to room temperature and poured into water. It was extracted with ethyl acetate and the organic phase was washed with water and brine. It was dried, filtered and concentrated in vacuo. The crude was purified by column chromatography (SiO$_2$, hexane:ethyl acetate 1:1) affording 0.310 g (77% of yield) of the expected product.

$^1$H NMR (200 MHz, DMSO-d$_6$) δ ppm: 1.50 (s, 9H), 2.27 (s, 3H), 2.50 (s, 3H), 7.23-7.43 (m, 3H), 7.52 (d, J=1.95 Hz, 1H), 7.68 (s, 1H), 7.89 (d, J=3.51 Hz, 2H), 8.39 (d, J=2.34 Hz, 1H), 8.63 (d, J=5.08 Hz, 1H), 9.22 (s, 1H).

ESI/MS (m/e, %): 320 [(M+1)$^+$, 100]

Example 36

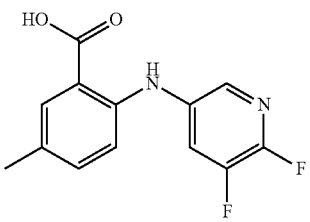 [SMILES: Cc1ccc(Nc2cnc(F)c(F)c2)c(C(=O)O)c1]

2-(5,6-Difluoropyridin-3-ylamino)-5-methylbenzoic acid

A. tert-butyl 2-(5,6-difluoropyridin-3-ylamino)-5-methylbenzoate

Obtained (0.13 g, yield 84%) following the procedure described in Example 7 (step A) starting with Intermediate 11 (0.48 mmol, 0.1 g) and 5-chloro-2,3-difluoropyridine (0.48 mmol, 0.072 g).

ESI/MS (m/e, %): 321[(M+1)$^+$, 100].

B. 2-(5,6-diflouropyridin-3-ylamino)-5-methylbenzoic acid

The solid residue obtained in step A was dissolved in 0.78 ml of trifluoroacetic acid and stirred for 1 hour at room temperature. The solvent was evaporated and the solid residue was triturated with an isopropyl ether/hexane mixture. The solid was filtered off affording 0.01 g (yield 15%) of the expected product.

$^1$H NMR (200 MHz, CDCl$_3$) δ ppm: 2.32 (s, 3H) 6.86-7.15 (m, 1H) 7.37-7.68 (m, 1H) 7.88 (s, 2H) 9.22 (s, 1H).

ESI/MS (m/e, %): 325 [(M+1)$^+$, 100].

Example 37

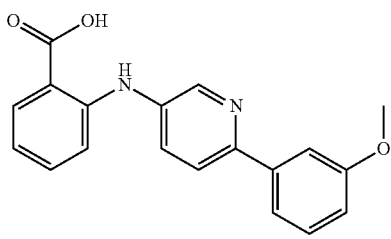 [SMILES: COc1cccc(-c2ccc(Nc3ccccc3C(=O)O)cn2)c1]

2-(6-(3-Methoxyphenyl)pyridin-3-ylamino)benzoic acid

In a schlenck tube, a mixture of 5-bromo-2-(3-methoxyphenyl)pyridine (Intermediate 27, 0.91 mmol, 0.23 g), ethyl 2-aminobenzoate (Intermediate 33, 0.91 mmol, 0.15 g), BINAP (0.05 mmol, 0.028 g), Pd$_2$(dba)$_3$ (0.05 mmol, 0.042 g) and NaO$^t$Bu (1.82 mmol, 0.175 g) in toluene (4 ml) was heated at 110° C. for 12 hours, under argon atmosphere. The solvent was evaporated and the solid residue was triturated with aqueous solution of 2N HCl and extracted with CHCl$_3$. The crude mixture was purified by flash chromatography over SiO$_2$ eluting with mixtures of hexane/ethyl acetate affording 0.078 g (yield 26%) of the expected compound.

δ $^1$H NMR (300 MHz, CDCl$_3$): 3.93 (s, 3H), 6.84-6.90 (m, 1H), 6.97-7.01 (m, 1H), 7.27-7.32 (m, 2H), 7.40-7.45 (m, 2H), 7.51-7.57 (m, 2H), 7.71-7.77 (m, 2H), 8.09-8.12 (d, 1H), 8.72 (s, 1H), 9.67 (bs, 1H).

ESI/MS (m/e, %): 321 [(M+1)$^+$, 100].

Example 38

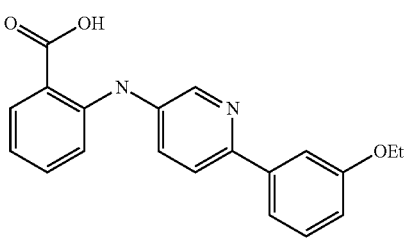 [SMILES: CCOc1cccc(-c2ccc(Nc3ccccc3C(=O)O)cn2)c1]

2-(6-(3-Ethoxyphenyl)pyridin-3-ylamino)benzoic acid

Obtained (0.070 g, yield 19%) following the procedure described in Example 37 starting with Intermediate 54 (1.09 mmol, 0.180 g) and Intermediate 28 (1.09 mmol, 0.303 g).

δ $^1$H NMR (300 MHz, CDCl$_3$): 1.42-1.47 (t, 3H), 4.11-4.16 (q, 2H), 6.82-6.86 (t, 1H), 6.94-6.97 (d, 1H), 7.25-7.30 (m, 1H), 7.38-7.41 (m, 2H), 7.47-7.53 (m, 2H), 7.68-7.76 (m, 2H), 8.07-8.10 (d, 1H), 8.70 (s, 1H), 9.72 (bs, 1H).

ESI/MS (m/e, %): 335 [(M+1)$^+$, 100].

Example 39

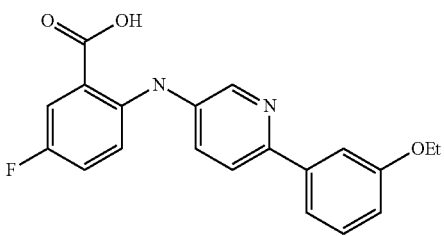 [SMILES: CCOc1cccc(-c2ccc(Nc3ccc(F)cc3C(=O)O)cn2)c1]

2-(6-(3-Ethoxyphenyl)pyridin-3-ylamino)-5-fluorobenzoic acid

Obtained (0.090 g, yield 43%) following the procedure described in Example 37 starting with Intermediate 53 (0.59 mmol, 0.100 g) and Intermediate 28 (0.59 mmol, 0.164 g).

δ $^1$H NMR (300 MHz, DMSO-d$_6$): 1.32-1.37 (t, 3H), 4.05-4.12 (q, 2H), 6.91-6.95 (m, 1H), 7.32-7.37 (m, 3H), 7.58-7.65 (m, 3H), 7.69-7.72 (m, 1H), 7.90-7.93 (d, 1H), 8.54-8.56 (m, 1H), 9.52 (bs, 1H).

ESI/MS (m/e, %): 353 [(M+1)$^+$, 100].

Example 40

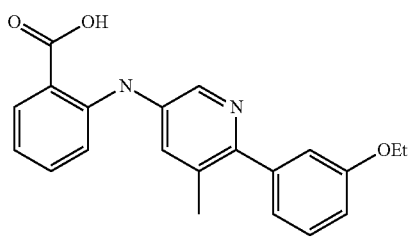 [SMILES: CCOc1cccc(-c2ncc(Nc3ccccc3C(=O)O)cc2C)c1]

2-(6-(3-Ethoxyphenyl)-5-methylpyridin-3-ylamino)benzoic acid

Obtained (0.050 g, yield 20%) following the procedure described in Example 37 starting with Intermediate 54 (0.91 mmol, 0.165 g) and Intermediate 29 (0.91 mmol, 0.265 g).

δ $^1$H NMR (300 MHz, CDCl$_3$): 1.40-1.44 (t, 3H), 2.36 (s, 3H), 4.08-4.13 (q, 2H), 6.79-6.83 (t, 1H), 6.94-6.97 (m, 1H), 7.08-7.10 (m, 2H), 7.34-7.41 (m, 3H), 7.64 (s, 1H), 8.00-8.03 (m, 1H), 8.55 (s, 1H), 9.79 (bs, 1H).

ESI/MS (m/e, %): 349 [(M+1)$^+$, 100].

Example 41

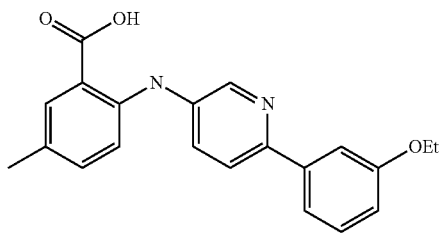 [SMILES: CCOc1cccc(-c2ccc(Nc3ccc(C)cc3C(=O)O)cn2)c1]

2-(6-(3-Ethoxyphenyl)pyridin-3-ylamino)-5-methylbenzoic acid

Obtained (0.150 g, yield 51%) following the procedure described in Example 37 starting with Intermediate 55 (0.84 mmol, 0.150 g) and Intermediate 28 (0.91 mmol, 0.233 g).

δ $^1$H NMR (300 MHz, CDCl$_3$): 1.45 (t, 3H), 2.31 (s, 3H), 4.15 (q, 2H), 6.95 (d, 1H), 7.24 (s, 2H), 7.37 (t, 1H), 7.50 (d, 1H), 7.54 (s, 1H), 7.68 (s, 2H), 7.88 (s, 1H), 8.65 (s, 1H).

ESI/MS (m/e, %): 349 [(M+1)$^+$, 100].

Example 42

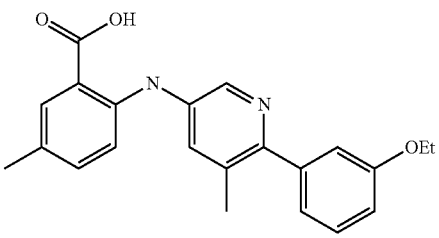 [SMILES: CCOc1cccc(-c2ncc(Nc3ccc(C)cc3C(=O)O)cc2C)c1]

2-(6-(3-Ethoxyphenyl)-5-methylpyridin-3-ylamino)-5-methylbenzoic acid

Obtained (0.036 g, yield 18%) following the procedure described in Example 37 starting with Intermediate 55 (0.56 mmol, 0.100 g) and Intermediate 29 (0.56 mmol, 0.163 g).

δ $^1$H NMR (300 MHz, CDCl$_3$): 1.38-1.43 (t, 3H), 2.26 (s, 3H), 2.32 (s, 3H), 4.07-4.12 (q, 2H), 6.93-6.96 (d, 1H), 7.07-7.09 (m, 2H), 7.17-7.20 (m, 1H), 7.25-7.28 (m, 1H), 7.33-7.37 (t, 1H), 7.60 (s, 1H), 7.81 (s, 1H), 8.54 (s, 1H), 9.10 (bs, 1H).

ESI/MS (m/e, %): 363 [(M+1)$^+$, 100].

Example 43

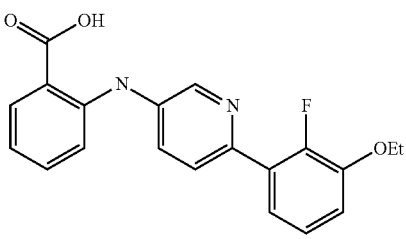 [SMILES: CCOc1cccc(-c2ccc(Nc3ccccc3C(=O)O)cn2)c1F]

2-(6-(3-Ethoxy-2-fluorophenyl)pyridin-3-ylamino)benzoic acid

Obtained (0.150 g, yield 46%) following the procedure described in Example 37 starting with Intermediate 54 (0.91 mmol, 0.165 g) and Intermediate 31 (0.91 mmol, 0.269 g).

δ $^1$H NMR (300 MHz, CDCl$_3$): 1.49 (t, 3H), 4.16 (q, 2H), 6.85 (t, 1H), 7.00 (t, 1H), 7.16 (t, 1H), 7.32-7.49 (m, 3H), 7.69 (dd, 1H), 7.76 (dd, 1H), 8.05 (d, 1H), 8.63 (d, 1H).

ESI/MS (m/e, %): 353 [(M+1)$^+$, 100].

Example 44

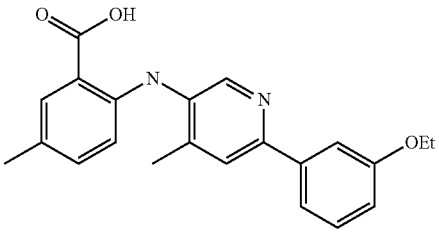 [SMILES: CCOc1cccc(-c2cc(C)c(Nc3ccc(C)cc3C(=O)O)cn2)c1]

2-(6-(3-Ethoxyphenyl)-4-methylpyridin-3-ylamino)-5-methylbenzoic acid

Obtained (0.158 g, yield 78%) following the procedure described in Example 37 starting with Intermediate 55 (0.56 mmol, 0.100 g) and Intermediate 30 (0.56 mmol, 0.292 g).

δ $^1$H NMR (300 MHz, DMSO-d$_6$): 1.32-1.37 (t, 3H), 2.22 (s, 3H), 2.26 (s, 3H), 4.07-4.12 (q, 2H), 6.86-6.94 (m, 2H), 7.20-7.23 (d, 1H), 7.32-7.38 (t, 1H), 7.61-7.65 (m, 2H), 7.72 (s, 1H), 7.93 (s, 1H), 8.55 (s, 1H), 9.47 (bs, 1H).

ESI/MS (m/e, %): 363[(M+1)$^+$, 100].

Example 45

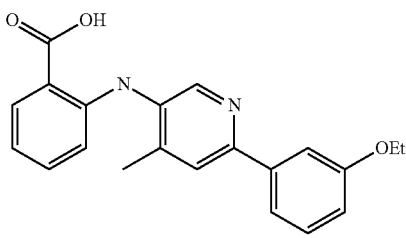 [SMILES: CCOc1cccc(-c2cc(C)c(Nc3ccccc3C(=O)O)cn2)c1]

2-(6-(3-Ethoxyphenyl)-4-methylpyridin-3-ylamino) benzoic acid

Obtained (0.070 g, yield 33%) following the procedure described in Example 37 starting with Intermediate 54 (0.61 mmol, 0.100 g) and Intermediate 30 (0.61 mmol, 0.176 g).

δ $^1$H NMR (300 MHz, CDCl$_3$): 1.43-1.48 (t, 3H), 2.35 (s, 3H), 4.12-4.19 (q, 2H), 6.77-6.82 (t, 1H), 6.89-6.97 (m, 2H), 7.33-7.41 (m, 2H), 7.52 (s, 1H), 7.55-7.57 (m, 1H), 7.65 (s, 1H), 8.06-8.08 (d, 1H), 8.69 (s, 1H), 9.31 (bs, 1H).

ESI/MS (m/e, %): 349 [(M+1)$^+$, 100].

Example 46

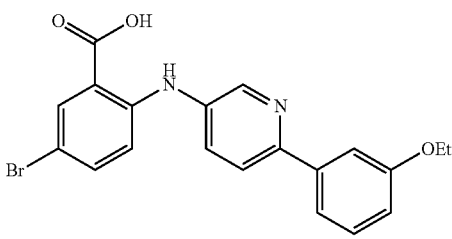

5-Bromo-2-(6-(3-ethoxyphenyl)pyridin-3-ylamino) benzoic acid

Obtained (0.072 g, yield 40%) following the procedure described in Example 37 starting with methyl 2-amino-5-bromobenzoate (0.43 mmol, 0.100 g) and Intermediate 28 (0.43 mmol, 0.121 g).

δ $^1$H NMR (300 MHz, MeOD): 1.30-1.34 (t, 3H), 3.98-4.05 (q, 2H), 6.84-6.87 (m, 1H), 7.12-7.15 (d, 1H), 7.13-7.26 (t, 1H), 7.35-7.41 (m, 3H), 7.68-7.73 (m, 2H), 8.00-8.02 (m, 1H), 8.39 (s, 1H).

ESI/MS (m/e, %): 413 [(M+1)$^+$, 100]; 415 [(M+1)$^+$, 97.4].

Example 47

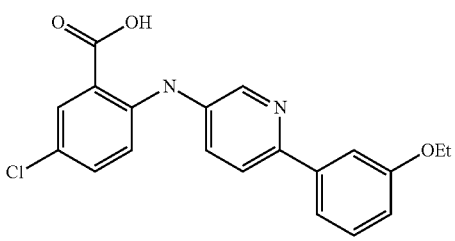 [SMILES: CCOc1cccc(-c2ccc(Nc3ccc(Cl)cc3C(=O)O)cn2)c1]

5-Chloro-2-(6-(3-ethoxyphenyl)pyridin-3-ylamino) benzoic acid

Obtained (0.081 g, yield 41%) following the procedure described in Example 37 starting with methyl 2-amino-5-chlorobenzoate (0.54 mmol, 0.100 g) and Intermediate 28 (0.54 mmol, 0.150 g).

δ $^1$H NMR (300 MHz, DMSO-d$_6$): 1.32-1.37 (t, 3H), 4.05-4.13 (q, 2H), 6.93-6.96 (d, 1H), 7.26-7.28 (d, 1H), 7.33-7.39 (t, 1H), 7.44-7.47 (d, 1H), 7.59-7.61 (m, 2H), 7.74-7.77 (m, 1H), 7.85 (s, 1H), 7.93-7.96 (d, 1H), 8.57 (s, 1H), 9.71 (bs, 1H).

ESI/MS (m/e, %): [369 (M+1)$^+$, 100; 371 (M+1)$^+$, 32].

Example 48

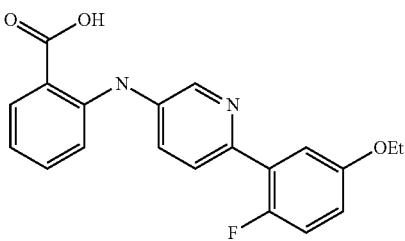 [SMILES: CCOc1ccc(F)c(-c2ccc(Nc3ccccc3C(=O)O)cn2)c1]

2-(6-(5-Ethoxy-2-fluorophenyl)pyridin-3-ylamino) benzoic acid

Obtained (0.040 g, yield 19%) following the procedure described in Example 37 starting with Intermediate 54 (0.61 mmol, 0.100 g) and Intermediate 32 (0.61 mmol, 0.179 g).

δ $^1$H NMR (300 MHz, CDCl$_3$): 1.43 (t, 3H), 4.10 (q, 2H), 6.82-6.90 (m, 2H), 7.07 (dd, 1H), 7.34 (s, 1H), 7.39 (dd, 1H), 7.48 (m, 1H), 7.67 (dd, 1H), 7.78 (dd, 1H), 8.06 (d, 1H), 8.62 (s, 1H).

ESI/MS (m/e, %): 353 [(M+1)$^+$, 100].

Example 49

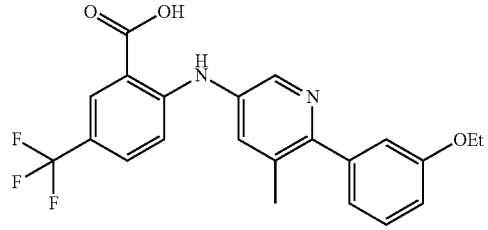 [SMILES: CCOc1cccc(-c2ncc(Nc3ccc(C(F)(F)F)cc3C(=O)O)cc2C)c1]

2-(6-(3-Ethoxyphenyl)-5-methylpyridin-3-ylamino)-5-(trifluoromethyl)benzoic acid In a schlenck tube, a mixture of Intermediate 29 (0.66 mmol, 0.194 g), Intermediate 59 (0.66 mmol, 0.155 g), BINAP (0.07 mmol, 0.041 g), Pd$_2$(dba)$_3$ (0.03 mmol, 0.030 g)

and NaO'Bu (1.66 mmol, 0.159 g) in toluene (4 ml) was heated at 110° C. for 12 hours, under argon atmosphere. The solvent was evaporated and the solid residue was triturated with aqueous solution of 2N HCl and extracted with CHCl₃. The crude mixture was dissolved in ethanol (3 ml) and 0.2 ml of aqueous 2N NaOH were added and stirred at room temperature overnight. The solid residue was triturated with water, neutralised with aqueous solution of 2N HCl and extracted with CHCl₃. The crude mixture was purified by flash chromatography over SiO₂ eluting with mixtures of hexane/ethyl acetate affording 0.061 g (yield 21%) of the expected compound.

δ ¹H NMR (300 MHz, DMSO-d₆): 1.31-1.35 (t, 3H), 2.32 (s, 3H), 4.02-4.06 (q, 2H), 6.91-6.94 (d, 1H), 7.04-7.09 (m, 2H), 7.32-7.35 (m, 2H), 7.48-7.50 (m, 1H), 7.59 (s, 1H), 8.24 (s, 1H), 8.34 (s, 1H), 12.42 (bs, 1H).

ESI/MS (m/e, %): 417 [(M+1)⁺, 100].

Example 50

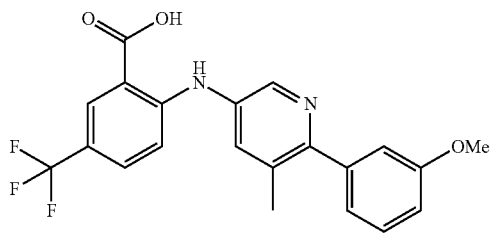 [SMILES: COc1cccc(-c2ncc(Nc3ccc(C(F)(F)F)cc3C(=O)O)cc2C)c1]

2-(6-(3-Methoxyphenyl)-5-methylpyridin-3-ylamino)-5-(trifluoromethyl)benzoic acid Obtained (0.050 g, yield 27%) following the procedure described in Example 49 starting with Intermediate 59 (0.43 mmol, 0.100 g) and Intermediate 33 (0.43 mmol, 0.12 g).

δ ¹H NMR (300 MHz, DMSO-d₆): 2.32 (s, 3H), 3.78 (s, 3H), 6.93-6.96 (d, 1H), 7.07-7.11 (m, 2H), 7.32-7.35 (m, 2H), 7.50-7.53 (m, 1H), 7.61 (s, 1H), 8.22 (s, 1H), 8.37 (s, 1H), 12.15 (bs, 1H).

ESI/MS (m/e, %): 403 [(M+1)⁺, 100].

Example 51

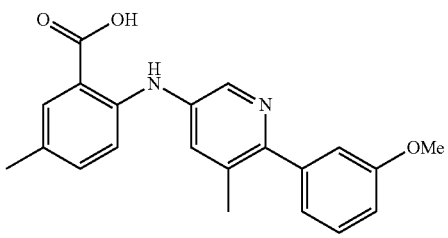 [SMILES: COc1cccc(-c2ncc(Nc3ccc(C)cc3C(=O)O)cc2C)c1]

2-(6-(3-Methoxyphenyl)-5-methylpyridin-3-ylamino)-5-methylbenzoic acid

In a schlenck tube, a mixture of Intermediate 33 (2.55 mmol, 0.71 g), Intermediate 55 (2.57 mmol, 0.46 g), BINAP (0.25 mmol, 0.158 g), Pd₂(dba)₃ (0.13 mmol, 0.116 g) and NaO'Bu (6.35 mmol, 0.610 g) in toluene (20 ml) was heated at 110° C. for 12 hours, under argon atmosphere. The solvent was evaporated, the solid residue was suspended in water, the pH was taken to 6.5 and extracted with CHCl₃. The crude mixture was purified by flash chromatography over SiO₂ eluting with mixtures of hexane/ethyl acetate affording 0.580 g (yield 65%) of the expected compound.

δ ¹H NMR (300 MHz, CDCl₃): 2.28 (s, 3H), 2.34 (s, 3H), 3.85 (s, 3H), 6.95 (d, 1H), 7.08 (s, 2H), 7.23 (d, 1H), 7.36 (t, 1H), 7.58 (s, 1H), 7.83 (s, 1H), 8.51 (s, 1H).

ESI/MS (m/e, %): 349 [(M+1)⁺, 100].

Example 52

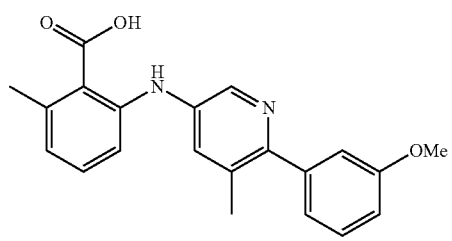 [SMILES: COc1cccc(-c2ncc(Nc3cccc(C)c3C(=O)O)cc2C)c1]

2-(6-(3-Methoxyphenyl)-5-methylpyridin-3-ylamino)-6-methylbenzoic acid

Obtained (0.085 g, yield 32%) following the procedure described in Example 51 starting with Intermediate 56 (0.76 mmol, 0.212 g) and Intermediate 33 (0.76 mmol, 0.136 g).

δ ¹H NMR (300 MHz, CDCl₃): 2.29 (s, 3H), 2.35 (s, 3H), 3.82 (s, 3H), 6.74-6.76 (m, 1H), 6.92-6.95 (m, 1H), 7.03-7.07 (m, 2H), 7.17-7.19 (m, 2H), 7.32-7.36 (t, 1H), 7.59 (s, 1H), 8.43 (s, 1H).

ESI/MS (m/e, %): 349[(M+1)⁺, 100].

Example 53

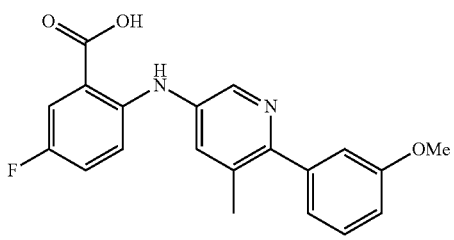 [SMILES: COc1cccc(-c2ncc(Nc3ccc(F)cc3C(=O)O)cc2C)c1]

5-Fluoro-2-(6-(3-methoxyphenyl)-5-methylpyridin-3-ylamino)benzoic acid

Obtained (0.043 g, yield 22%) following the procedure described in Example 51 starting with Intermediate 53 (0.53 mmol, 0.148 g) and Intermediate 33 (0.53 mmol, 0.090 g).

δ ¹H NMR (300 MHz, DMSO-d₆): 2.31 (s, 3H), 3.78 (S, 3H), 6.93-6.96 (m, 1H), 7.05-7.10 (m, 2H), 7.31-7.36 (m, 3H), 7.58 (s, 1H), 7.62-7.65 (d, 1H), 8.38 (s, 1H).

ESI/MS (m/e, %): 353 [(M+1)⁺, 100].

Example 54

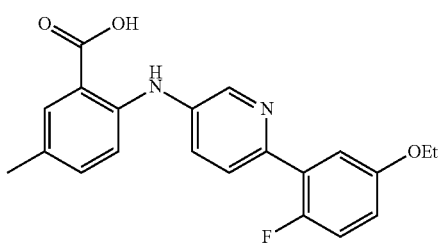 [SMILES: CCOc1ccc(F)c(-c2ccc(Nc3ccc(C)cc3C(=O)O)cn2)c1]

2-(6-(5-Ethoxy-2-fluorophenyl)pyridin-3-ylamino)-5-methylbenzoic acid

Obtained (0.110 g, yield 37%) following the procedure described in Example 51 starting with Intermediate 55 (0.81 mmol, 0.240 g) and Intermediate 32 (0.82 mmol, 0.147 g).

δ $^1$H NMR (300 MHz, DMSO-$d_6$): 1.39 (t, 3H), 2.32 (s, 3H), 4.12 (q, 2H), 7.01 (m, 1H), 7.29 (dd, 1H), 7.36 (s, 2H), 7.52 (dd, 1H), 7.80 (m, 3H), 8.64 (s, 1H).

ESI/MS (m/e, %): 367 [(M+1)$^+$, 100].

Example 55

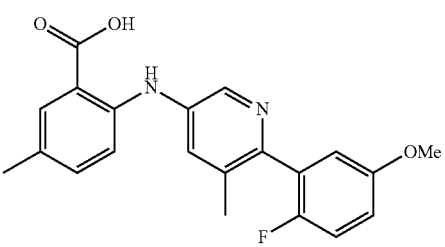 [SMILES: COc1ccc(F)c(-c2ncc(Nc3ccc(C)cc3C(=O)O)cc2C)c1]

2-(6-(2-Fluoro-5-methoxyphenyl)-5-methylpyridin-3-ylamino)-5-methylbenzoic acid

A. Ethyl 2-(6-(2-fluoro-5-methoxyphenyl)-5-methylpyridin-3-ylamino)-5-methylbenzoate In a schlenck tube, a mixture of Intermediate 64 (0.14 mmol, 0.050 g), 2-fluoro-5-methoxyphenylboronic acid (0.14 mmol, 0.024 g), PdCl$_2$dppf.DCM (0.01 mmol, 0.012 g) and Cs$_2$CO$_3$ (0.43 mmol, 0.140 g) in a 4:1 dioxane/water mixture (1.5 ml) was heated at 110° C. for 12 hours, under argon atmosphere. The solvent was evaporated and the crude mixture was purified over a SCX cartridge eluting with MeOH:NH$_3$ 10:1 and affording 0.048 g of the corresponding ester derivative.

ESI/MS (m/e, %): 395 [(M+1)$^+$, 100].

B. 2-(6-(2-Fluoro-5-methoxyphenyl)-5-methylpyridin-3-ylamino)-5-methylbenzoic acid The solid residue obtained in step A was dissolved in 2 ml of ethanol and 0.150 ml of aqueous solution 2N NaOH were added. The mixture was heated at 60° C. for 2 hours, the solvent was evaporated and the solid obtained was suspended in water. The pH was taken to 6.5 and extracted with CHCl$_3$. The crude mixture was purified over a SCX cartridge eluting with MeOH/NH$_3$ 10:1 affording 0.030 g (yield 67%) of the expected product.

δ $^1$H NMR (300 MHz, CDCl$_3$): 2.25 (s, 3H), 2.29 (s, 3H), 3.81 (s, 3H), 6.91-6.99 (m, 2H), 7.07 (t, 1H), 7.21-7.31 (m, 2H), 7.58 (s, 1H), 7.84 (s, 1H), 8.51 (s, 1H).

ESI/MS (m/e, %): 367 [(M+1)$^+$, 100].

Example 56

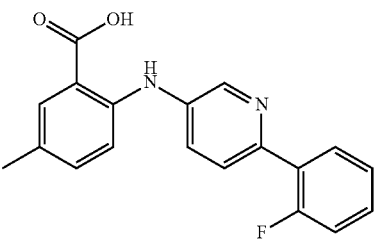 [SMILES: Cc1ccc(Nc2ccc(-c3ccccc3F)nc2)c(C(=O)O)c1]

2-(6-(2-Fluorophenyl)pyridin-3-ylamino)-5-methylbenzoic acid

Obtained (0.08 g, yield 28%) following the procedure described in Example 51 starting with Intermediate 55 (0.85 mmol, 0.213 g) and Intermediate 34 (0.0.85 mmol, 0.140 g).

δ $^1$H NMR (300 MHz, CDCl$_3$): 2.25 (s, 3H), 7.27-7.35 (m, 4H), 7.40-7.44 (m, 1H), 7.70-7.75 (m, 3H), 7.92-7.97 (m, 1H), 8.58 (s, 1H).

ESI/MS (m/e, %): 323 [(M+1)$^+$, 100].

Example 57

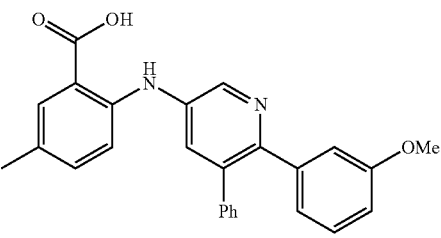 [SMILES: COc1cccc(-c2ncc(Nc3ccc(C)cc3C(=O)O)cc2-c2ccccc2)c1]

2-(6-(3-Methoxyphenyl)-5-phenylpyridin-3-ylamino)-5-methylbenzoic acid

A. Ethyl 2-(6-(3-methoxyphenyl)-5-phenylpyridin-3-ylamino)-5-methylbenzoate

In a schlenck tube, a mixture of Intermediate 10 (0.81 mmol, 0.161 g), Intermediate 7 (0.81 mmol, 0.223 g), Cs$_2$CO$_3$ (1.13 mmol, 0.369 g), xanthpos (0.16 mmol, 0.094 g) and Pd$_2$(dba)$_3$ (0.08 mmol, 0.074 g) in dioxane (3 ml) was heated at 110° C. for 12 hours, under argon atmosphere. After filtration over celite, the solvent was evaporated and the crude mixture was purified over SiO$_2$ eluting with hexane/ethyl acetate affording 0.100 g (yield 28%) of the corresponding ester derivative.

δ $^1$H NMR (300 MHz, CDCl$_3$): 1.41-1.46 (t, 3H), 2.31 (s, 3H), 3.63 (s, 3H), 4.35-4.42 (q, 2H), 6.77-6.80 (d, 1H), 6.88

(s, 1H), 6.92-6.94 (d, 1H), 7.11-7.14 (s, 1H), 7.19-7.35 (m, 7H), 7.59-7.61 (d, 1H), 7.83 (s, 1H), 7.61-7.63 (d, 1H), 9.52 (s, 1H).

ESI/MS (m/e, %): 439 [(M+1)$^+$, 100].

B. 2-(6-(3-Methoxyphenyl)-5-phenylpyridin-3-ylamino)-5-methylbenzoic acid

The solid residue obtained in step A was dissolved in ethanol (5 ml) and aqueous solution 2N NaOH (0.250 ml) was added. The mixture was heated at 60° C. for 2 hours, the solvent was evaporated and the solid obtained was suspended in water. The pH was taken to 6.5 and extracted with CHCl$_3$. The crude mixture was purified over a SiO$_2$ eluting with DCM/MeOH 2% affording 0.060 g (yield 63%) of the expected product.

δ $^1$H NMR (300 MHz, DMSO-d$_6$): 2.24 (s, 3H), 3.56 (s, 3H), 6.75-6.84 (m, 2H), 7.09-7.15 (t, 1H), 7.20-7.24 (m, 3H), 7.32-7.38 (m, 5H), 7.56 (s, 1H), 7.74 (s, 1H), 8.55 (s, 1H), 9.60 (bs, 1H).

ESI/MS (m/e, %): 411 [(M+1)$^+$, 100].

Example 58

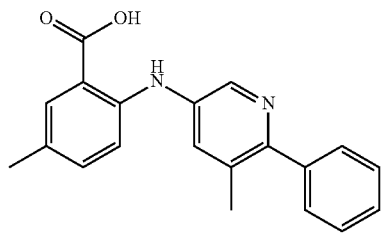 [SMILES: Cc1ccc(Nc2cnc(-c3ccccc3)c(C)c2)c(C(=O)O)c1]

5-Methyl-2-(5-methyl-6-phenylpyridin-3-ylamino)benzoic acid

A. Ethyl 5-methyl-2-(5-methyl-6-phenylpyridin-3-ylamino)benzoate

Obtained (1 g, yield 57%) following the procedure described in Example 57 (step A) starting with Intermediate 10 (5.03 mmol, 1 g) and Intermediate 2 (5.05 mmol, 0.93 g).

ESI/MS (m/e, %): 347 [(M+1)$^+$, 100].

B. 5-Methyl-2-(5-methyl-6-phenylpyridin-3-ylamino)benzoic acid

Obtained (0.51 g, yield 52%) following the procedure described in Example 57 (step B) starting with ethyl 5-methyl-2-(5-methyl-6-phenylpyridin-3-ylamino)benzoate (1 g, 3.18 mmol).

δ $^1$H NMR (300 MHz, CDCl$_3$): 2.27 (s, 3H), 2.32 (s, 3H), 7.20 (s, 1H), 7.23 (s, 1H), 7.39-7.56 (m, 6H), 7.82 (s, 1H), 8.50 (s, 1H).

ESI/MS (m/e, %): 319 [(M+1)$^+$, 100].

Example 59

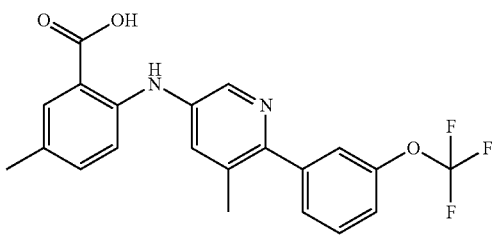 [SMILES: Cc1ccc(Nc2cnc(-c3cccc(OC(F)(F)F)c3)c(C)c2)c(C(=O)O)c1]

5-Methyl-2-(5-methyl-6-(3-(trifluoromethoxy)phenyl)pyridin-3-ylamino)benzoic acid

A. Ethyl 5-methyl-2-(5-methyl-6-(3-(trifluoromethoxy)phenyl)pyridin-3-ylamino)benzoate Obtained (0.083 g, yield 38%) following the procedure described in Example 57 (step A) starting with Intermediate 10 (0.50 mmol, 0.1 g) and Intermediate 41 (0.50 mmol, 0.135 g).

ESI/MS (m/e, %): 431 [(M+1)$^+$, 100].

B. 5-Methyl-2-(5-methyl-6-(3-(trifluoromethoxy)phenyl)pyridin-3-ylamino)benzoic acid Obtained (0.50 g, yield 64%) following the procedure described in Example 57 (step B) starting with ethyl 5-methyl-2-(5-methyl-6-(3-(trifluoromethoxy)phenyl)pyridin-3-ylamino)benzoate (0.083 g, 0.19 mmol).

δ $^1$H NMR (300 MHz, DMSO-d$_6$): 2.30 (s, 3H), 2.39 (s, 3H), 7.34 (s, 2H), 7.44 (m, 1H), 7.57 (s, 1H), 7.63-7.65 (m, 3H), 7.80 (s, 1H), 8.46 (d, 1H).

ESI/MS (m/e, %): 403 [(M+1)$^+$, 100].

Example 60

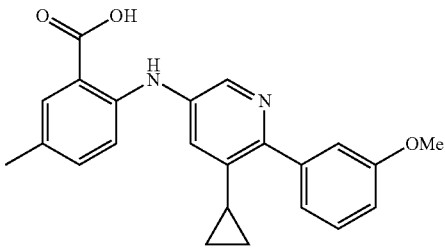 [SMILES: COc1cccc(-c2ncc(Nc3ccc(C)cc3C(=O)O)cc2C2CC2)c1]

2-(5-Cyclopropyl-6-(3-methoxyphenyl)pyridin-3-ylamino)-5-methylbenzoic acid

A. Ethyl 2-(5-Cyclopropyl-6-(3-methoxyphenyl)pyridin-3-ylamino)-5-methylbenzoate Obtained (0.047 g, yield 27%) following the procedure described in Example 57 (step A) starting with Intermediate 10 (0.42 mmol, 0.082 g) and Intermediate 42 (0.42 mmol, 0.100

δ ¹H NMR (300 MHz, CDCl₃): 0.68-0.73 (m, 2H), 0.93-0.98 (m, 2H), 1.42-1.46 (t, 3H), 1.99-2.07 (m, 1H), 2.31 (s, 3H), 3.88 (s, 3H), 4.35-4.42 (q, 2H), 6.93-6.96 (m, 1H), 7.08-7.10 (m, 1H), 7.20-7.27 (m, 3H), 7.35-7.40 (m, 1H), 7.82 (s, 1H), 7.42-7.44 (m, 1H), 9.38 (s, 1H).
ESI/MS (m/e, %): 403 [(M+1)⁺, 100].

B. 2-(5-Cyclopropyl-6-(3-methoxyphenyl)pyridin-3-ylamino)-5-methylbenzoic acid

Obtained (0.32 g, yield 73%) following the procedure described in Example 57 (step B) starting with ethyl 2-(5-Cyclopropyl-6-(3-methoxyphenyl)pyridin-3-ylamino)-5-methylbenzoate (0.047 g, 0.12 mmol).
δ ¹H NMR (300 MHz, DMSO-d₆): 0.72-0.76 (m, 2H), 0.90-0.93 (m, 2H), 1.91-1.96 (m, 1H), 2.23 (s, 3H), 3.32 (s, 3H), 6.93-6.96 (d, 1H), 7.15-7.23 (m, 4H), 7.25-7.28 (m, 1H), 7.34-7.38 (t, 1H), 7.72 (s, 1H), 8.34 (s, 1H), 9.45 (bs, 1H).
ESI/MS (m/e, %): 375 [(M+1)⁺, 100].

Example 61

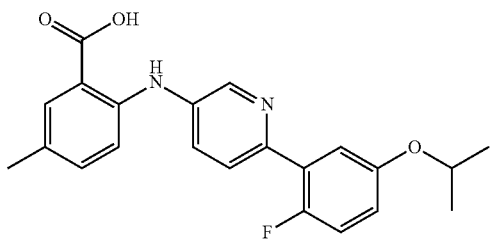 [SMILES: Cc1ccc(Nc2ccc(-c3cc(OC(C)C)ccc3F)nc2)c(C(=O)O)c1]

2-(6-(2-Fluoro-5-isopropoxyphenyl)pyridin-3-ylamino)-5-methylbenzoic acid

Obtained (0.065 g, yield 17%) following the procedure described in Example 51 starting with Intermediate 55 (1 mmol, 0.180 g) and Intermediate 35 (1 mmol, 0.311 g).
δ ¹H NMR (300 MHz, CDCl₃): 1.34-1.36 (d, 6H), 2.30 (s, 3H), 4.55-4.64 (m, 1H), 6.85-6.90 (m, 1H), 7.04-7.10 (t, 1H), 7.22-7.30 (m, 2H), 7.44-7.47 (m, 1H), 7.71-7.75 (m, 2H), 7.88 (s, 1H), 8.71 (s, 1H), 9.62 (bs, 1H).
ESI/MS (m/e, %): 381[(M+1)⁺, 100].

Example 62

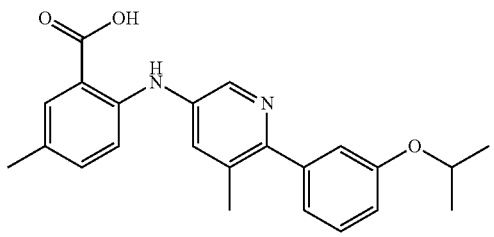 [SMILES: Cc1ccc(Nc2cnc(-c3cccc(OC(C)C)c3)c(C)c2)c(C(=O)O)c1]

2-(6-(3-Isopropoxyphenyl)-5-methylpyridin-3-ylamino)-5-methylbenzoic acid

A. Ethyl 2-(6-(3-Isopropoxyphenyl)-5-methylpyridin-3-ylamino)-5-methylbenzoate

Obtained (0.204 g, yield 67%) following the procedure described in Example 57 (step A) starting with Intermediate 10 (0.76 mmol, 0.183 g) and Intermediate 43 (0.76 mmol, 0.150 g).

δ ¹H NMR (300 MHz, CDCl₃): 1.34-1.36 (d, 6H), 1.41-1.45 (t, 3H), 2.30 (s, 3H), 2.35 (s, 3H), 4.34-4.41 (q, 2H), 4.57-4.65 (m, 1H), 6.89-6.92 (d, 1H), 7.06-7.09 (m, 2H), 7.21-7.26 (m, 2H), 7.31-7.35 (t, 1H), 7.44 (s, 1H), 7.81 (s, 1H), 8.44 (s, 1H), 9.39 (s, 1H).
ESI/MS (m/e, %): 405 (M+1)⁺, 100].

B. 2-(6-(3-Isopropoxyphenyl)-5-methylpyridin-3-ylamino)-5-methylbenzoic acid

Obtained (0.140 g, yield 73%) following the procedure described in Example 57 (step B) starting with ethyl 2-(6-(3-isopropoxyphenyl)-5-methylpyridin-3-ylamino)-5-methylbenzoate (0.204 g, 0.50 mmol).
δ ¹H NMR (300 MHz, DMSO-d₆): 1.26-1.28 (d, 6H), 2.24 (s, 3H), 2.30 (s, 3H), 4.60-4.68 (m, 1H), 6.89-6.93 (d, 1H), 7.01-7.06 (m, 2H), 7.23-7.34 (m, 4H), 7.56 (s, 1H), 7.73 (s, 1H), 8.36 (s, 1H), 9.52 (bs, 1H).
ESI/MS (m/e, %): 377 [(M+1)⁺, 100].

Example 63

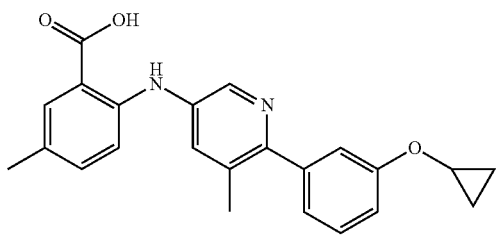 [SMILES: Cc1ccc(Nc2cnc(-c3cccc(OC4CC4)c3)c(C)c2)c(C(=O)O)c1]

2-(6-(3-Cyclopropoxyphenyl)-5-methylpyridin-3-ylamino)-5-methylbenzoic acid

A. Tert-butyl 2-(6-(3-cyclopropoxyphenyl)-5-methylpyridin-3-ylamino)-5-methylbenzoate A mixture of Intermediate 16 (0.66 mmol, 0.250 g), Intermediate 25 (0.99 mmol, 0.257 g), Pd(PPh₃)₄ (0.06 mmol, 0.075 g) and K₂CO₃ (2.32 mmol, 0.320 g) in DMF (7 ml) was heated at 130° C. for 2 hours in a microwave oven. The mixture was filtered through celite and the solvent was evaporated. The crude mixture was purified over a SiO₂ eluting with hexane/ethyl acetate mixtures and affording 0.110 g (yield 92%) of the corresponding ester derivative.
δ ¹H NMR (200 MHz, DMSO-d₆): 0.74-0.79 (m, 2H), 0.79-0.86 (m, 2H), 1.62 (s, 9H), 2.30 (s, 3H), 2.35 (s, 3H), 3.57-3.90 (m, 1H), 6.97-7.24 (m, 4H), 7.27-7.49 (m, 3H), 7.68-7.81 (m, 1H), 8.46 (d, J=2.34 Hz, 1H), 9.44 (s, 1H).
ESI/MS (m/e, %): 431 [(M+1)⁺, 92].

B. 2-(6-(3-Cyclopropoxyphenyl)-5-methylpyridin-3-ylamino)-5-methylbenzoic acid

The solid residue obtained in step A was dissolved in 1.5 ml of trifluoroacetic acid and stirred for 45 minutes at room temperature. The solvent was evaporated and the solid residue was tritured with a diethyl ether/hexane mixture. The solid was filtered off affording 0.093 g (yield 74%) of the expected product.
δ ¹H NMR (200 MHz, DMSO-d₆): 0.69 (m, 2H), 0.75-0.89 (m, H), 2.29 (s, 3H), 2.34 (s, 3H), 3.90 (m, 1H), 7.15-7.57 (m, 5H), 7.78 (s, 1H), 7.91 (s, 1H), 8.45 (s, 1H), 9.55 (s, 1H).
ESI/MS (m/e, %): 375 [(M+1)⁺, 100].

Example 64

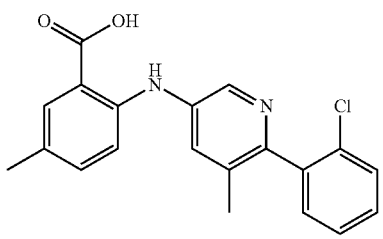 [SMILES: Cc1ccc(Nc2cnc(-c3ccccc3Cl)c(C)c2)c(C(=O)O)c1]

2-(6-(2-Chlorophenyl)-5-methylpyridin-3-ylamino)-5-methylbenzoic acid

A. Tert-butyl 2-(6-(2-chlorophenyl)-5-methylpyridin-3-ylamino)-5-methylbenzoate

Obtained (0.150 g, yield 95%) following the procedure described in Example 63 (step A) starting with Intermediate 16 (0.53 mmol, 0.200 g) and 2-chlorophenylboronic acid (0.79 mmol, 0.124 g).

δ $^1$H NMR (200 MHz, CDCl$_3$): 1.62 (s, 9H), 2.14 (s, 3H), 2.30 (s, 3H), 6.90-7.59 (m, 7H), 7.74 (m, 1H), 8.45 (d, J=2.34 Hz, 1H), 9.48 (s, 1H).
ESI/MS (m/e, %): 409 [(M+1)$^+$, 96].

B. 2-(6-(2-Chlorophenyl)-5-methylpyridin-3-ylamino)-5-methylbenzoic acid

Obtained (0.088 g, yield 51%) following the procedure described in Example 63 (step B) starting with tert-butyl 2-(6-(2-chlorophenyl)-5-methylpyridin-3-ylamino)-5-methylbenzoate (0.150 g, 0.37 mmol).

δ $^1$H NMR (200 MHz, DMSO-d$_6$): 2.10 (s, 3H), 2.29 (s, 3H), 7.16-7.70 (m, 6H), 7.70-7.89 (m, 2H), 8.44 (m, 1H), 9.56 (s, 1H).
ESI/MS (m/e, %): 353 [(M+1)$^+$, 100].

Example 65

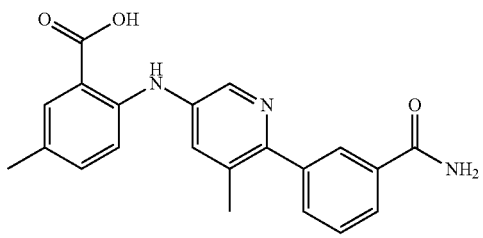 [SMILES: Cc1ccc(Nc2cnc(-c3cccc(C(N)=O)c3)c(C)c2)c(C(=O)O)c1]

2-(6-(3-Carbamoylphenyl)-5-methylpyridin-3-ylamino)-5-methylbenzoic acid

A. Ethyl 2-(6-(3-carbamoylphenyl)-5-methylpyridin-3-ylamino)-5-methylbenzoate

Obtained (0.210 g, yield 91%) following the procedure described in Example 63 (step A) starting with Intermediate 10 (0.60 mmol, 0.120 g) and Intermediate 44 (0.59 mmol, 0.135 g).
ESI/MS (m/e, %): 390 [(M+1)$^+$, 100].

B. 2-(6-(3-Carbamoylphenyl)-5-methylpyridin-3-ylamino)-5-methylbenzoic acid

Obtained (0.140 g, yield 64%) following the procedure described in Example 63 (step B) starting with ethyl ethyl 2-(6-(3-carbamoylphenyl)-5-methylpyridin-3-ylamino)-5-methylbenzoate (0.235 g, 0.6 mmol).

δ $^1$H NMR (300 MHz, DMSO-d$_6$): 2.30 (s, 3H), 2.37 (s, 3H), 7.26-7.33 (m, 2H), 7.45 (m, 1H), 7.57 (m, 1H), 7.62 (m, 1H), 7.74 (d, 1H), 7.80 (s, 1H), 7.93 (d, 1H), 8.09 (s, 1H), 8.43 (m, 1H).
ESI/MS (m/e, %): 362 [(M+1)$^+$, 100].

Example 66

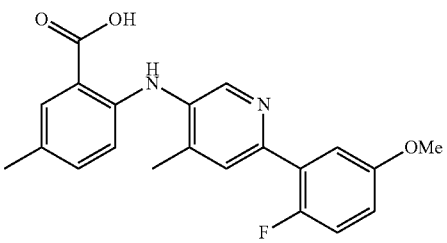 [SMILES: COc1ccc(F)c(-c2cc(C)c(Nc3ccc(C)cc3C(=O)O)cn2)c1]

2-(6-(2-Fluoro-5-methoxyphenyl)-4-methylpyridin-3-ylamino)-5-methylbenzoic acid

A. Ethyl 2-(6-(2-Fluoro-5-methoxyphenyl)-4-methylpyridin-3-ylamino)-5-methylbenzoate Obtained (0.150 g, yield 54%) following the procedure described in Example 57 (step A) starting with Intermediate 10 (0.76 mmol, 0.150 g) and Intermediate 46 (0.76 mmol, 0.175 g).
ESI/MS (m/e, %): 395 [(M+1)$^+$, 100].

B. 2-(6-(2-Fluoro-5-methoxyphenyl)-4-methylpyridin-3-ylamino)-5-methylbenzoic acid Obtained (0.076 g, yield 55%) following the procedure described in Example 57 (step B) starting with ethyl 2-(6-(2-fluoro-5-methoxyphenyl)-4-methylpyridin-3-ylamino)-5-methylbenzoate (0.150 g, 0.38 mmol).
ESI/MS (m/e, %): 367 [(M+1)$^+$, 100].

Example 67

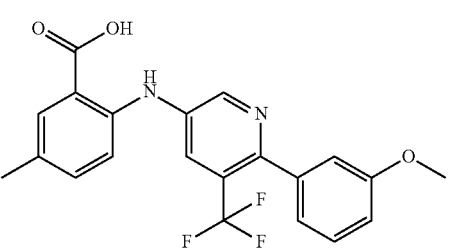

2-(6-(3-Methoxyphenyl)-5-(trifluoromethyl)pyridin-3-ylamino)-5-methylbenzoic acid A. Ethyl 2-(6-(3-Methoxyphenyl)-5-(trifluoromethyl)pyridin-3-ylamino)-5-methylbenzoate Obtained (0.055 g, yield 43%) following the procedure described in Example 57 (step A) starting with Intermediate 10 (0.29 mmol, 0.058 g) and Intermediate 45 (0.29 mmol, 0.078 g).

δ $^1$H NMR (300 MHz, CDCl$_3$): 1.42-1.46 (t, 3H), 2.34 (s, 3H), 3.85 (s, 3H), 4.36-4.43 (q, 2H), 6.97-7.00 (d, 1H), 7.06

(s, 1H), 7.08-7.11 (d, 1H), 7.27-7.38 (m, 3H), 7.86 (s, 1H), 7.88-7.90 (d, 1H), 8.71 (s, 1H), 9.39 (s, 1H).
ESI/MS (m/e, %): 431 [(M+1)⁺, 100].

B. 2-(6-(3-Methoxyphenyl)-5-(trifluoromethyl)pyridin-3-ylamino)-5-methylbenzoic acid Obtained (0.022 g, yield 42%) following the procedure described in Example 57 (step B) starting with ethyl 2-(6-(3-methoxyphenyl)-5-(trifluoromethyl)pyridin-3-ylamino)-5-methylbenzoate (0.055 g, 0.13 mmol).
δ ¹H NMR (300 MHz, DMSO-d₆): 2.25 (s, 3H), 3.76 (s, 3H), 6.96-7.01 (m, 3H), 7.20-7.23 (d, 1H), 7.29-7.37 (m, 2H), 7.78 (s, 1H), 7.86-7.88 (m, 1H), 8.67 (s, 1H).
ESI/MS (m/e, %): 403 [(M+1)⁺, 100].

Example 68

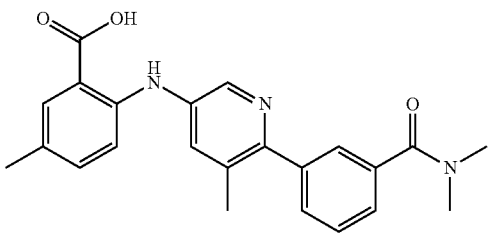

2-(6-(3-(Dimethylcarbamoyl)phenyl)-5-methylpyridin-3-ylamino)-5-methylbenzoic acid A. Ethyl 2-(6-(3-(dimethylcarbamoyl)phenyl)-5-methylpyridin-3-ylamino)-5-methylbenzoate Obtained (0.125 g, yield 40%) following the procedure described in Example 57 (step A) starting with Intermediate 10 (0.76 mmol, 0.150 g) and Intermediate 47 (0.76 mmol, 0.195 g).
ESI/MS (m/e, %): 418 [(M+1)⁺, 100].

B. 2-(6-(3-(Dimethylcarbamoyl)phenyl)-5-methylpyridin-3-ylamino)-5-methylbenzoic acid Obtained (0.060 g, yield 50%) following the procedure described in Example 57 (step B) starting with ethyl 2-(6-(3-(dimethylcarbamoyl)phenyl)-5-methylpyridin-3-ylamino)-5-methylbenzoate (0.125 g, 0.30 mmol).
δ ¹H NMR (300 MHz, CDCl₃): 2.28 (s, 3H), 2.32 (s, 3H), 3.04 (s, 3H), 3.14 (s, 3H), 7.20-7.28 (m, 3H), 7.46-7.60 (m, 4H), 7.78 (m, 1H), 8.52 (m, 1H).
ESI/MS (m/e, %): 390 [(M+1)⁺, 100].

Example 69

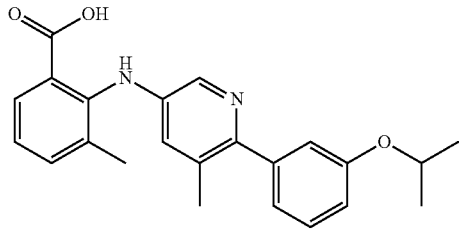 [SMILES: Cc1cc(Nc2c(C)cccc2C(=O)O)cnc1-c1cccc(OC(C)C)c1]

2-(6-(3-Isopropoxyphenyl)-5-methylpyridin-3-ylamino)-3-methylbenzoic acid

A. Tert-butyl 2-(6-(3-isopropoxyphenyl)-5-methylpyridin-3-ylamino)-3-methylbenzoate Obtained (0.25 g, yield 94) following the procedure described in Example 57 (step A) starting with intermediate 62 (0.62 mmol, 0.197 g) and Intermediate 43 (0.62 mmol, 0.150 g).
δ ¹H NMR (300 MHz, CDCl₃): 1.31 (d, 3H), 1.34 (d, 3H), 1.56 (s, 9H), 2.12 (s, 3H), 2.27 (s, 3H), 4.33-4.71 (m, 1H), 6.65-6.91 (m, 2H), 6.98-7.13 (m, 3H), 7.27-7.41 (m, 2H), 7.82 (dd, J=7.81 Hz, 1H), 8.03 (d, J=2.73 Hz, 1H), 8.66 (s, 1H).
ESI/MS (m/e, %): 433 [(M+1)⁺, 90].

B. 2-(6-(3-Isopropoxyphenyl)-5-methylpyridin-3-ylamino)-3-methylbenzoic acid

Obtained (0.092 g, yield 28%) following the procedure described in Example 63 (step B) starting with tert-butyl 2-(6-(3-isopropoxyphenyl)-5-methylpyridin-3-ylamino)-3-methylbenzoate (0.25 g, 0.65 mmol).
δ ¹H NMR (400 MHz, DMSO-d₆): 1.28 (s, 3H), 1.29 (s, 3H), 2.18 (s, 3H), 2.28 (s, 3H), 4.53-4.78 (m, 1H), 6.93-7.14 (m, 3H), 7.19 (s, 1H), 7.32 (t, J=7.44 Hz, 1H), 7.42 (t, J=7.44 Hz, 1H), 7.57 (d, J=7.04 Hz, 1H), 7.77 (d, J=7.04 Hz, 1H), 7.86 (s, 1H) 8.80 (s, 1H).
ESI/MS (m/e, %): 377 [(M+1)⁺, 100].

Example 70

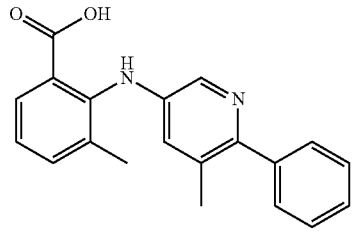 [SMILES: Cc1cc(Nc2c(C)cccc2C(=O)O)cnc1-c1ccccc1]

3-Methyl-2-(5-methyl-6-phenylpyridin-3-ylamino)benzoic acid

A. Tert-butyl 3-Methyl-2-(5-methyl-6-phenylpyridin-3-ylamino)benzoate

Obtained (0.280 g, yield 90%) following the procedure described in Example 57 (step A) starting with Intermediate 62 (0.82 mmol, 0.260 g) and Intermediate 2 (0.81 mmol, 0.150 g).
δ ¹H NMR (300 MHz, CDCl₃): 1.58 (s, 9H), 2.14 (s, 3H), 2.29 (s, 3H), 6.84 (d, J=2.73 Hz, 1H), 6.97-7.15 (m, J=7.61, 7.61 Hz, 1H), 7.28-7.58 (m, 6H), 7.86 (m, 1H), 8.06 (d, J=2.73 Hz, 1H), 8.68 (s, 1H).
ESI/MS (m/e, %): 375 [(M+1)⁺, 90].

B. 3-Methyl-2-(5-methyl-6-phenylpyridin-3-ylamino)benzoic acid

Obtained (0.120 g, yield 42%) following the procedure described in Example 63 (step B) starting with tert-butyl 3-Methyl-2-(5-methyl-6-phenylpyridin-3-ylamino)benzoate (0.25 g, 0.67 mmol).
δ ¹H NMR (400 MHz, DMSO-d₆): 2.19 (s, 3H), 2.27 (s, 3H), 7.18 (s, 1H), 7.31 (t, J=7.63 Hz, 1H), 7.47-7.61 (m, 6H), 7.77 (d, J=6.65 Hz, 1H), 7.89 (d, J=2.74 Hz, 1H), 8.79 (s, 1H).

Example 71

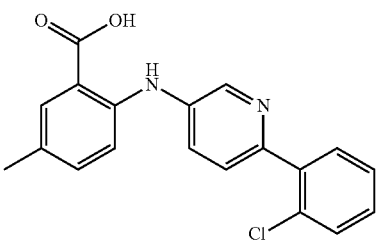 [SMILES: Cc1ccc(Nc2ccc(-c3ccccc3Cl)nc2)c(C(=O)O)c1]

2-(6-(2-Chlorophenyl)pyridin-3-ylamino)-5-methyl-benzoic acid

A. Tert-butyl 2-(6-(2-chlorophenyl)pyridin-3-ylamino)-5-methylbenzoate

Obtained (0.043 g, yield 43%) following the procedure described in Example 63 (step A) starting with Intermediate 15 (0.25 mmol, 0.090 g) and 2-chlorophenylboronic acid (0.37 mmol, 0.058 g).

δ $^1$H NMR (300 MHz, CDCl$_3$): 1.62 (s, 9H), 2.31 (s, 3H), 7.18-7.21 (m, 1H), 7.29-7.36 (m, 3H), 7.46-7.49 (m, 1H), 7.61-7.65 (m, 3H), 7.74 (s, 1H), 8.62 (s, 1H), 9.54 (s, 1H).

ESI/MS (m/e, %): 395 [(M+1)$^+$, 100].

B. 2-(6-(2-Chlorophenyl)pyridin-3-ylamino)-5-methylbenzoic acid

Obtained (0.020 g, yield 54%) following the procedure described in Example 63 (step B) starting with tert-butyl 2-(6-(2-chlorophenyl)pyridin-3-ylamino)-5-methylbenzoate (0.042 g, 0.11 mmol).

δ $^1$H NMR (300 MHz, DMSO-d$_6$): 2.27 (s, 3H), 7.30-7.32 (m, 2H), 7.42-7.46 (m, 2H), 7.56-7.64 (m, 3H), 7.73-7.75 (m, 1H), 7.77 (s, 1H), 8.56-8.58 (d, 1H), 9.58 (bs, 1H).

ESI/MS (m/e, %): 339 [(M+1)$^+$, 100].

Example 72

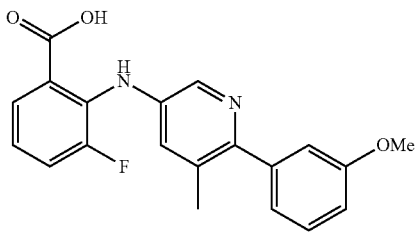 [SMILES: COc1cccc(-c2ncc(Nc3c(F)cccc3C(=O)O)cc2C)c1]

3-Fluoro-2-(6-(3-methoxyphenyl)-5-methylpyridin-3-ylamino)benzoic acid

A. Tert-butyl 3-fluoro-2-(6-(3-methoxyphenyl)-5-methylpyridin-3-ylamino)benzoate Obtained (0.310 g, yield 80%) following the procedure described in Example 57 (step A) starting with Intermediate 63 (0.91 mmol, 0.250 g) and Intermediate 48 (0.91 mmol, 0.195 g).

δ $^1$H NMR (300 MHz, CDCl$_3$): 1.60 (s, 9H), 2.33 (s, 3H), 3.85 (s, 3H), 6.90-7.38 (m, 7H), 7.78 (d, J=7.81 Hz, 1H), 8.06-8.45 (m, 1H), 9.05 (s, 1H).

ESI/MS (m/e, %): 409 [(M+1)$^+$, 97].

B. 3-Fluoro-2-(6-(3-methoxyphenyl)-5-methylpyridin-3-ylamino)benzoic acid

Obtained (0.258 g, yield 74%) following the procedure described in Example 63 (step B) starting with tert-butyl 3-fluoro-2-(6-(3-methoxyphenyl)-5-methylpyridin-3-ylamino)benzoate (0.300 g, 0.73 mmol).

δ $^1$H NMR (200 MHz, DMSO-d$_6$): 2.31 (s, 3H), 3.81 (s, 3H), 6.93-7.69 (m, 7H) 7.81 (d, J=7.81 Hz, 1H), 8.20 (s, 1H), 9.08 (s, 1H).

ESI/MS (m/e, %): 353 [(M+1)$^+$, 100].

Example 73

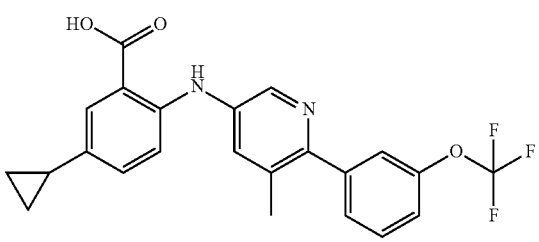 [SMILES: Cc1cc(Nc2ccc(C3CC3)cc2C(=O)O)cnc1-c1cccc(OC(F)(F)F)c1]

5-Cyclopropyl-2-(5-methyl-6-(3-(trifluoromethoxy)phenyl)pyridin-3-ylamino)benzoic acid

A. Ethyl 5-cyclopropyl-2-(5-methyl-6-(3-(trifluoromethoxy)phenyl)pyridin-3-ylamino)benzoate Obtained (0.300 g, yield 99%) following the procedure described in Example 57 (step A) starting with Intermediate 9 (0.67 mmol, 0.150 g) and Intermediate 41 (0.67 mmol, 0.179 g).

ESI/MS (m/e, %): 457 [(M+1)$^+$, 100].

B. 5-Cyclopropyl-2-(5-methyl-6-(3-(trifluoromethoxy)phenyl)pyridin-3-ylamino)benzoic acid Obtained (0.300 g, yield 68%) following the procedure described in Example 57 (step B) starting with ethyl 5-cyclopropyl-2-(5-methyl-6-(3-(trifluoromethoxy)phenyl)pyridin-3-ylamino)benzoate (0.125 g, 0.30 mmol).

δ $^1$H NMR (300 MHz, CDCl$_3$): 0.63 (qd, 2H), 0.90 (qd, 2H), 1.84 (m, 1H), 2.30 (s, 3H), 7.12 (dd, 1H), 7.24 (m, 2H), 7.39 (m, 1H), 7.44-7.50 (m, 3H), 7.76 (m, 1H), 8.46 (m, 1H).

ESI/MS (m/e, %): 429 [(M+1)$^+$, 100].

Example 74

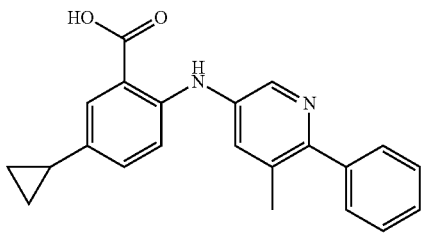 [SMILES: Cc1cc(Nc2ccc(C3CC3)cc2C(=O)O)cnc1-c1ccccc1]

5-Cyclopropyl-2-(5-methyl-6-phenylpyridin-3-ylamino)benzoic acid

A. Ethyl 5-cyclopropyl-2-(5-methyl-6-phenylpyridin-3-ylamino)benzoate

Obtained (0.245 g, yield 99%) following the procedure described in Example 57 (step A) starting with Intermediate 9 (0.67 mmol, 0.150 g) and Intermediate 2 (0.67 mmol, 0.123 g).

ESI/MS (m/e, %): 373 [(M+1)$^+$, 100].

B. 5-Cyclopropyl-2-(5-methyl-6-phenylpyridin-3-ylamino)benzoic acid

Obtained (0.070 g, yield 29%) following the procedure described in Example 57 (step B) starting with ethyl 5-cyclopropyl-2-(5-methyl-6-phenylpyridin-3-ylamino)benzoate (0.245 g, 0.67 mmol).

δ $^1$H NMR (300 MHz, CDCl$_3$): 0.63 (q, 2H), 0.90 (q, 2H), 1.84 (m, 1H), 2.33 (s, 3H), 7.12 (d, 1H), 7.24 (s, 1H), 7.38-7.58 (m, 6H), 7.73 (s, 1H), 8.51 (s, 1H).

ESI/MS (m/e, %): 345 [(M+1)$^+$, 100].

Example 75

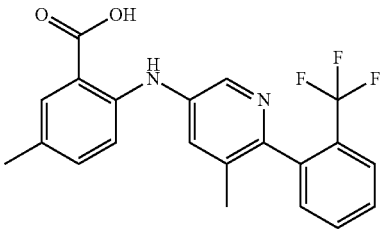 [SMILES: Cc1ccc(Nc2cnc(-c3ccccc3C(F)(F)F)c(C)c2)c(C(=O)O)c1]

5-Methyl-2-(5-methyl-6-(2-(trifluoromethyl)phenyl)pyridin-3-ylamino)benzoic acid A. Tert-butyl 5-methyl-2-(5-methyl-6-(2-(trifluoromethyl)phenyl)pyridin-3-ylamino)benzoate Obtained (0.032 g, yield 14%) following the procedure described in Example 63 (step A) starting with Intermediate 16 (0.53 mmol, 0.200 g) and 2-(trifluoromethyl)-phenyl boronic acid (0.53 mmol, 0.151 g).

B. 5-Methyl-2-(5-methyl-6-(2-(trifluoromethyl)phenyl)pyridin-3-ylamino)benzoic acid Obtained (0.016 g, yield 55%) following the procedure described in Example 63 (step B) starting with tert-butyl 5-methyl-2-(5-methyl-6-(2-(trifluoromethyl)phenyl)pyridin-3-ylamino)benzoate (0.032 g, 0.072 mmol).

δ $^1$H NMR (200 MHz, DMSO-d$_6$): 2.01 (s, 3H), 2.28 (s, 3H), 7.28-7.37 (m, 1H), 7.46 (d, J=6.25 Hz, 1H), 7.59-8.02 (m, 5H), 8.37 (d, J=1.95 Hz, 1H), 9.54 (s, 1H).

ESI/MS (m/e, %): 387 [(M+1)$^+$, 96].

Example 76

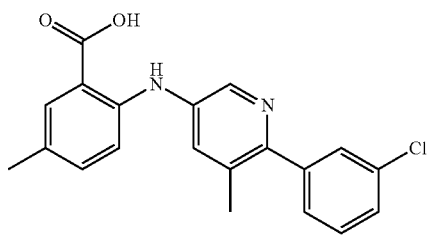 [SMILES: Cc1ccc(Nc2cnc(-c3cccc(Cl)c3)c(C)c2)c(C(=O)O)c1]

2-(6-(3-Chlorophenyl)-5-methylpyridin-3-ylamino)-5-methylbenzoic acid

A. Tert-butyl 2-(6-(3-chlorophenyl)-5-methylpyridin-3-ylamino)-5-methylbenzoate

Obtained (0.165 g, yield 76%) following the procedure described in Example 63 (step A) starting with Intermediate 16 (0.53 mmol, 0.200 g) and 3-chlorophenylboronic acid (0.53 mmol, 0.124 g).

B. 2-(6-(3-Chlorophenyl)-5-methylpyridin-3-ylamino)-5-methylbenzoic acid

Obtained (0.118 g, yield 83%) following the procedure described in Example 63 (step B) starting with tert-butyl 2-(6-(3-chlorophenyl)-5-methylpyridin-3-ylamino)-5-methylbenzoate (0.165 g, 0.40 mmol).

δ $^1$H NMR (200 MHz, DMSO-d$_6$): 2.28 (s, 3H), 2.34 (s, 3H), 7.23-7.42 (m, 1H), 7.43-7.83 (m, 7H), 8.43 (d, J=2.73 Hz, 1H), 9.53 (s, 1H).

ESI/MS (m/e, %): 353 [(M+1)$^+$, 94].

Example 77

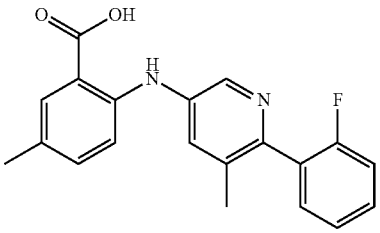 [SMILES: Cc1ccc(Nc2cnc(-c3ccccc3F)c(C)c2)c(C(=O)O)c1]

2-(6-(2-Fluorophenyl)-5-methylpyridin-3-ylamino)-5-methylbenzoic acid

A. Tert-butyl 2-(6-(2-fluorophenyl)-5-methylpyridin-3-ylamino)-5-methylbenzoate

Obtained (0.310 g, yield 74%) following the procedure described in Example 63 (step A) starting with Intermediate 16 (1.06 mmol, 0.400 g) and 2-fluorophenylboronic acid (1.60 mmol, 0.224 g).

B. 2-(6-(2-Fluorophenyl)-5-methylpyridin-3-ylamino)-5-methylbenzoic acid

Obtained (0.262 g, yield 74%) following the procedure described in Example 63 (step B) starting with tert-butyl 2-(6-(2-fluorophenyl)-5-methylpyridin-3-ylamino)-5-methylbenzoate (0.310 g, 0.79 mmol).

δ $^1$H NMR (200 MHz, DMSO-d$_5$): 2.18 (s, 3H), 2.28 (s, 3H), 7.14-7.65 (m, 6H), 7.68-7.92 (m, 2H), 8.45 (d, J=2.34 Hz, 1H), 9.55 (s, 1H).

ESI/MS (m/e, %): 337 [(M+1)$^+$, 96].

Example 78

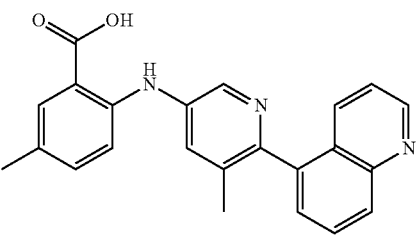 [SMILES: Cc1ccc(Nc2cnc(-c3cccc4ncccc34)c(C)c2)c(C(=O)O)c1]

5-Methyl-2-(5-methyl-6-(quinolin-5-yl)pyridin-3-ylamino)benzoic acid

A. Tert-butyl 5-methyl-2-(5-methyl-6-(quinolin-5-yl)pyridin-3-ylamino)benzoate

Obtained (0.683 g, yield 94%) following the procedure described in Example 63 (step A) starting with Intermediate 16 (1.46 mmol, 0.550 g) and quinolin-5-ylboronic acid (2.19 mmol, 0.378 g).

B. 5-Methyl-2-(5-methyl-6-(quinolin-5-yl)pyridin-3-ylamino)benzoic acid

Obtained (0.562 g, yield 85%) following the procedure described in Example 63 (step B) starting with tert-butyl 5-methyl-2-(5-methyl-6-(quinolin-5-yl)pyridin-3-ylamino)benzoate (0.583 g, 1.37 mmol).

Example 79

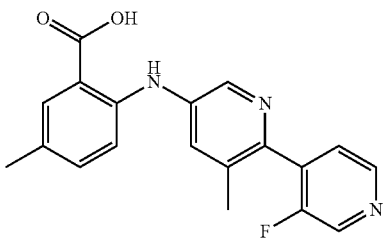 [SMILES: Cc1ccc(Nc2cnc(-c3ccncc3F)c(C)c2)c(C(=O)O)c1]

2-(3'-Fluoro-3-methyl-2,4'-bipyridin-5-ylamino)-5-methylbenzoic acid

A. Tert-butyl 2-(3'-fluoro-3-methyl-2,4'-bipyridin-5-ylamino)-5-methylbenzoate

In a schlenck tube, a mixture of Intermediate 16 (1.46 mmol, 0.550 g), 3-fluoro-4-(tributylstannyl)pyridine (1.46 mmol, 0.564 g), PdCl$_2$dppf.DCM (0.15 mmol, 0.120 g) and CuI (0.42 mmol, 0.080 g) in DMF (10 ml) was heated at 120° C. for 4.5. The mixture was filtered through celite and the solvent was evaporated. The crude mixture was extracted between ethyl acetate and water. The organic phase was evaporated and the crude residue was purified over a SiO2 eluting with hexane/ethyl acetate mixtures and affording 0.360 g (yield 62%) of the corresponding ester derivative.
ESI/MS (m/e, %): 394 [(M+1)$^+$, 100].

B. 2-(3'-Fluoro-3-methyl-2,4'-bipyridin-5-ylamino)-5-methylbenzoic acid

Obtained (0.291 g, yield 72%) following the procedure described in Example 63 (step B) starting with tert-butyl 2-(3'-fluoro-3-methyl-2,4'-bipyridin-5-ylamino)-5-methylbenzoate (0.351 g, 0.89 mmol).
δ $^1$H NMR (300 MHz, DMSO-d$_5$): 2.29 (s, 3H), 7.32-7.40 (m, 2H), 7.75-7.79 (m, 2H), 7.89 (d, 1H), 8.01 (dd, 1H), 8.52 (d, 1H), 8.65-8.67 (m, 2H).
ESI/MS (m/e, %): 322 [(M+1)$^+$, 100].

Example 80

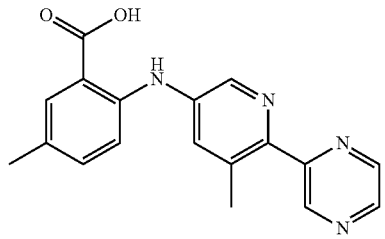 [SMILES: Cc1ccc(Nc2cnc(-c3cnccn3)c(C)c2)c(C(=O)O)c1]

5-Methyl-2-(5-methyl-6-(pyrazin-2-yl)pyridin-3-ylamino)benzoic acid

A. Tert-butyl 5-methyl-2-(5-methyl-6-(pyrazin-2-yl)pyridin-3-ylamino)benzoate

Obtained (0.100 g, yield 50%) following the procedure described in Example 79 (step A) starting with Intermediate 16 (0.53 mmol, 0.200 g) and 2-(tributylstannyl)pyrazine (0.53 mmol, 0.196 g).

B. 5-Methyl-2-(5-methyl-6-(pyrazin-2-yl)pyridin-3-ylamino)benzoic acid

Obtained (0.048 g, yield 56%) following the procedure described in Example 63 (step B) starting with tert-butyl 5-methyl-2-(5-methyl-6-(pyrazin-2-yl)pyridin-3-ylamino)benzoate (0.100 g, 0.25 mmol).
δ $^1$H NMR (300 MHz, DMSO-d$_6$): 2.20 (s, 3H), 2.28 (s, 3H), 7.20-7.40 (m, 2H), 7.54 (dd, J=6.44, 4.88 Hz, 1H), 7.66 (d, J=1.95 Hz, 1H), 7.77 (s, 1H), 8.44 (d, J=3.12 Hz, 1H), 8.55 (d, J=4.68 Hz, 1H), 8.70 (d, J=1.95 Hz, 1H), 9.54 (s, 1H).
ESI/MS (m/e, %): 338 [(M+1)$^+$, 98].

Example 81

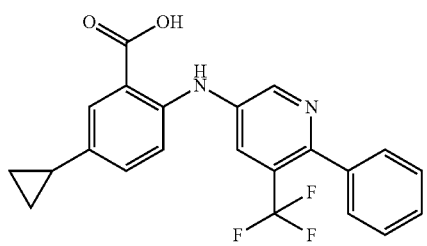 [SMILES: O=C(O)c1cc(C2CC2)ccc1Nc1cnc(-c2ccccc2)c(C(F)(F)F)c1]

5-Cyclopropyl-2-(6-phenyl-5-(trifluoromethyl)pyridin-3-ylamino)benzoic acid

A. Ethyl 5-cyclopropyl-2-(6-phenyl-5-(trifluoromethyl)pyridin-3-ylamino)benzoate Obtained (0.043 g, yield 28%) following the procedure described in Example 57 (step A) starting with Intermediate 9 (0.36 mmol, 0.080 g) and Intermediate 1 (0.43 mmol, 0.084 g).
ESI/MS (m/e, %): 427 [(M+1)$^+$, 100].

B. 5-Cyclopropyl-2-(6-phenyl-5-(trifluoromethyl)pyridin-3-ylamino)benzoic acid

Obtained (0.028 g, yield 70%) following the procedure described in Example 57 (step B) starting with ethyl 5-cyclopropyl-2-(6-phenyl-5-(trifluoromethyl)pyridin-3-ylamino)benzoate (0.043 g, 0.10 mmol).
ESI/MS (m/e, %): 399 [(M+1)$^+$, 100].

Example 82

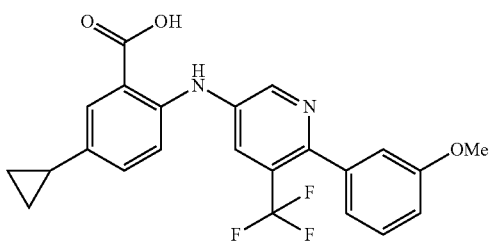 [SMILES: COc1cccc(-c2ncc(Nc3ccc(C4CC4)cc3C(=O)O)cc2C(F)(F)F)c1]

5-Cyclopropyl-2-(6-(3-methoxyphenyl)-5-(trifluoromethyl)pyridin-3-ylamino)benzoic acid A. Ethyl 5-cyclopropyl-2-(6-(3-methoxyphenyl)-5-(trifluoromethyl)pyridin-3-ylamino)benzoate Obtained (0.518 g, yield 55%) following the procedure described in Example 57 (step A) starting with Intermediate 9 (1.1 mmol, 0.250 g) and Intermediate 45 (1.12 mmol, 0.300 g).
ESI/MS (m/e, %): 457 [(M+1)$^+$, 100].

B. 5-Cyclopropyl-2-(6-(3-methoxyphenyl)-5-(trifluoromethyl)pyridin-3-ylamino)benzoic acid Obtained (0.070 g, yield 27%) following the procedure described in Example 57 (step B) starting with ethyl 5-cyclopropyl-2-(6-(3-methoxyphenyl)-5-(trifluoromethyl)pyridin-3-ylamino)benzoate (0.518 g, 0.61 mmol).

δ $^1$H NMR (300 MHz, CDCl$_3$): 0.65 (q, 2H), 0.94 (q, 2H), 1.86 (m, 1H), 3.84 (s, 3H), 6.98-7.09 (m, 3H), 7.20 (m, 1H), 7.28 (m, 1H), 7.36 (t, 1H), 7.78 (m, 1H), 7.93 (m, 1H), 8.73 (m, 1H).
ESI/MS (m/e, %): 429 [(M+1)$^+$, 100].

Example 83

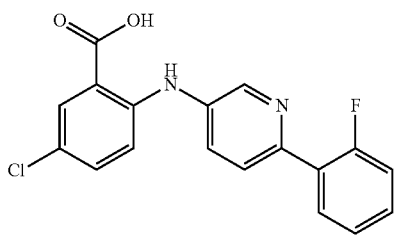 [SMILES: O=C(O)c1cc(Cl)ccc1Nc1ccc(-c2ccccc2F)nc1]

5-Chloro-2-(6-(2-fluorophenyl)pyridin-3-ylamino) benzoic acid

In a schlenck tube, a mixture of Intermediate 65 (0.92 mmol, 0.300 g), 2-fluorophenyl boronic acid (1.10 mmol, 0.154 g), Pd(PPh$_3$)$_4$ (0.06 mmol, 0.064 g) and K$_2$CO$_3$ (2.56 mmol, 0.354 g) in a toluene/methanol mixture (12.5 ml, 4:1) was heated at 80° C. for 14 hours, under nitrogen atmosphere. The mixture was diluted with water and extracted with ethyl acetate. The organic phase was evaporated. The crude mixture was purified over by reverse phase using a water/acetonitril/methanol solvent gradient affording 0.157 g (yield 49%) of the expected product.
$^1$H NMR (400 MHz, DMSO-d$_6$): 7.4 (m, 5H), 7.9 (m, 4H), 8.7 (s, 1H), 9.7 (s, 1H), 13.6 (s, 1H).
ESI/MS (m/e, %): 343 [(M+1)$^+$, 100], 345 [(M+1)$^+$, 35]

Example 84

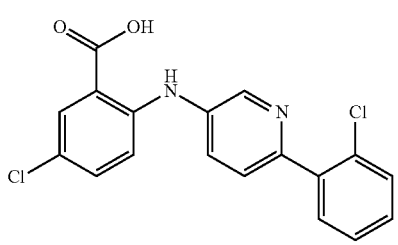 [SMILES: O=C(O)c1cc(Cl)ccc1Nc1ccc(-c2ccccc2Cl)nc1]

5-Chloro-2-(6-(2-chlorophenyl)pyridin-3-ylamino) benzoic acid

Obtained (0.083 g, yield 29%) following the procedure described in Example 83 starting with Intermediate 65 (0.76 mmol, 0.250 g) and 2-chlorophenyl boronic (0.91 mmol, 0.143

$^1$H NMR (400 MHz, DMSO-d$_6$): 7.3 (d, J=9.0 Hz, 1H), 7.5 (m, 3H), 7.6 (m, 2H), 7.7 (d, J=8.2 Hz, 1H), 7.8 (dd, J=8.4, 2.5 Hz, 1H), 7.9 (d, J=2.7 Hz, 1H), 8.6 (d, J=2.3 Hz, 1H), 9.7 (s, 1H), 13.6 (s, 1H).
ESI/MS (m/e, %): 359 [(M+1)$^+$, 100], 361 [(M+1)$^+$, 60], 363 [(M+1)$^+$, 15]

Example 85

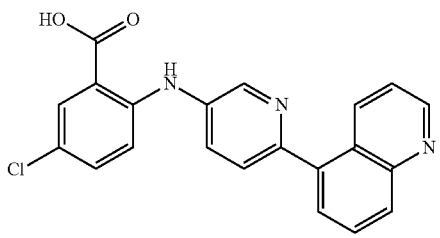 [SMILES: O=C(O)c1cc(Cl)ccc1Nc1ccc(-c2cccc3ncccc23)nc1]

5-Chloro-2-(6-(quinolin-5-yl)pyridin-3-ylamino) benzoic acid

Obtained (0.160 g, yield 53%) following the procedure described in Example 83 starting with Intermediate 65 (0.76 mmol, 0.250 g) and quinolin-5-ylboronic acid (0.91 mmol, 0.158
$^1$H NMR (400 MHz, DMSO-d$_6$): 7.4 (m, 2H), 7.6 (dd, J=8.6, 3.9 Hz, 1H), 7.7 (d, J=8.2 Hz, 1H), 7.8 (d, J=7.0 Hz, 1H), 7.8 (m, 2H), 7.9 (d, J=2.3 Hz, 1H), 8.1 (d, J=8.6 Hz, 1H, 8.6 (d, J=2.3 Hz, 1H), 8.7 (d, J=8.6 Hz, 1H), 8.9 (m, 1H).
ESI/MS (m/e, %): 376 [(M+1)$^+$, 100], 378 [(M+1)$^+$, 35]

Example 86

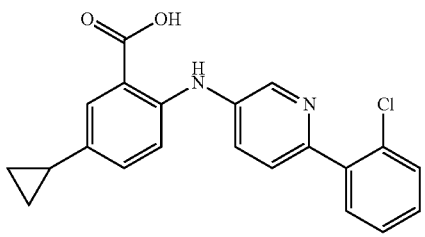 [SMILES: O=C(O)c1cc(C2CC2)ccc1Nc1ccc(-c2ccccc2Cl)nc1]

2-(6-(2-Chlorophenyl)pyridin-3-ylamino)-5-cyclopropylbenzoic acid

A. Ethyl 2-(6-(2-chlorophenyl)pyridin-3-ylamino)-5-cyclopropylbenzoate

Obtained (0.141 g, yield 62%) following the procedure described in Example 57 (step A) starting with Intermediate 9 (0.58 mmol, 0.130 g) and Intermediate 49 (0.58 mmol, 0.118
ESI/MS (m/e, %): 393 [(M+1)$^+$, 100].

B. 2-(6-(2-Chlorophenyl)pyridin-3-ylamino)-5-cyclopropylbenzoic acid

Obtained (0.051 g, yield 39%) following the procedure described in Example 57 (step B) starting with ethyl 2-(6-(2-chlorophenyl)pyridin-3-ylamino)-5-cyclopropylbenzoate (0.141 g, 0.36 mmol).
ESI/MS (m/e, %): 365 [(M+1)$^+$, 100].

Example 87

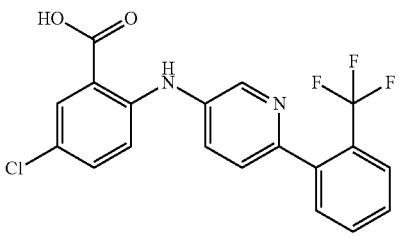 [SMILES: O=C(O)c1cc(Cl)ccc1Nc1ccc(-c2ccccc2C(F)(F)F)nc1]

5-Chloro-2-(6-(2-(trifluoromethyl)phenyl)pyridin-3-ylamino)benzoic acid

Obtained (0.064 g, yield 21%) following the procedure described in Example 83 starting with Intermediate 65 (0.76 mmol, 0.250 g) and 2-(trifluoromethyl)phenylboronic acid (0.83 mmol, 0.158 g). The mixture was diluted with water and extracted with ethyl acetate. The organic phase was evaporated and the solid obtained was washed with diethyl ether and methanol.

$^1$H NMR (400 MHz, DMSO-$d_6$): 7.3 (m, 3H), 7.7 (m, 5H), 8.0 (s, 1H), 8.5 (s, 1H), 12.1 (s, 1H).

ESI/MS (m/e, %): 393 [(M+1)$^+$, 100], 395 [(M+1)$^+$, 35].

Example 88

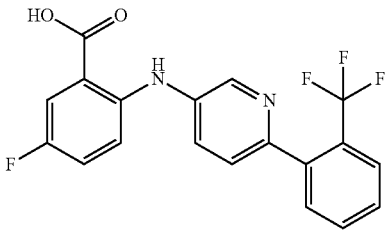 [SMILES: O=C(O)c1cc(F)ccc1Nc1ccc(-c2ccccc2C(F)(F)F)nc1]

5-Fluoro-2-(6-(2-(trifluoromethyl)phenyl)pyridin-3-ylamino)benzoic acid

In a schlenck tube, a mixture of Intermediate 52 (0.91 mmol, 0.200 g), 2-bromo-5-fluorobenzoic acid (0.94 mmol, 0.225 g), Cu (0.16 mmol, 0.010 g), Cu$_2$O (0.06 mmol, 0.009 g), K$_2$CO$_3$ (1.01 mmol, 0.140 g) in diethoxyethane (1.5 ml) was heated at 130° C. for 14 hours, under nitrogen atmosphere. The crude mixture was diluted with water and ethyl acetate and filtered through celite. The organic phase was evaporated and the solid residue was purified by reverse phase using a water/acetonitril/methanol solvent gradient affording 0.092 g (yield 27%) of the expected product.

$^1$H NMR (400 MHz, DMSO-$d_6$): 7.4 (m, 2H), 7.4 (d, J=8.2 Hz, 1H), 7.6 (d, J=7.8 Hz, 1H), 7.7 (m, 2H), 7.8 (m, 2H), 7.9 (d, J=7.4 Hz, 1H), 8.5 (d, J=2.3 Hz, 1H), 9.6 (s, 1H).

ESI/MS (m/e, %): 377 [(M+1)$^+$, 100].

Example 89

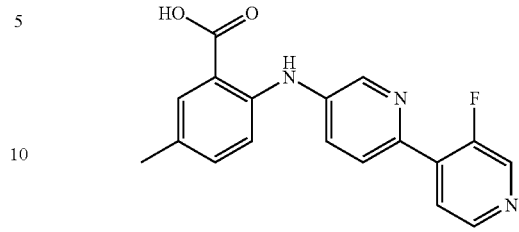

2-(3'-Fluoro-2,4'-bipyridin-5-ylamino)-5-methylbenzoic acid

Obtained (0.082 g, yield 46%) following the procedure described in Example 51 starting with Intermediate 55 (0.56 mmol, 0.100 g) and Intermediate 37 (0.55 mmol, 0.253 g).

δ $^1$H NMR (300 MHz, DMSO-$d_6$): 2.27 (s, 3H), 7.30-7.38 (m, 2H), 7.74-7.77 (m, 2H), 7.86-7.89 (d, 1H), 7.97-8.01 (m, 1H), 8.49-8.51 (d, 1H), 8.63-8.66 (m, 2H), 9.63 (bs, 1H).

ESI/MS (m/e, %): 324 [(M+1)$^+$, 100].

Example 90

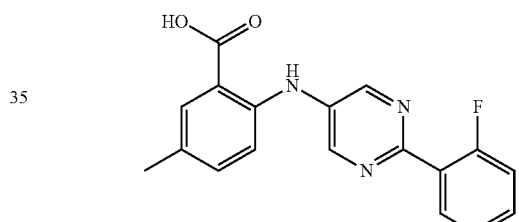

2-(2-(2-Fluorophenyl)pyrimidin-5-ylamino)-5-methylbenzoic acid

A. Tert-butyl 2-(2-(2-fluorophenyl)pyrimidin-5-ylamino)-5-methylbenzoate

Obtained (0.138 g, yield 21%) following the procedure described in Example 57 (step A) starting with Intermediate 11 (1.41 mmol, 0.293 g) and Intermediate 39 (1.42 mmol, 0.466 g).

ESI/MS (m/e, %): 380 [(M+1)$^+$, 100].

B. 2-(2-(2-Fluorophenyl)pyrimidin-5-ylamino)-5-methylbenzoic acid

Obtained (0.060 g, yield 63%) following the procedure described in Example 63 (step B) starting with tert-butyl 2-(2-(2-fluorophenyl)pyrimidin-5-ylamino)-5-methylbenzoate (0.138 g, 0.29 mmol).

$^1$H NMR (400 MHz, DMSO-$d_6$): 7.3 (m, 4H), 7.5 (m, 1H), 7.8 (s, 1H), 8.0 (m, 1H), 8.8 (s, 2H), 9.7 (s, 1H).

ESI/MS (m/e, %): 324 [(M+1)$^+$, 100].

Example 91

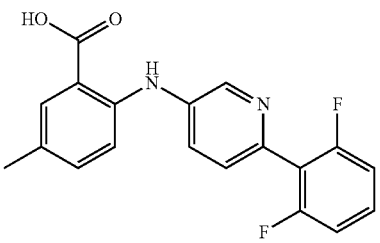 [SMILES: Cc1ccc(Nc2ccc(-c3c(F)cccc3F)nc2)c(C(=O)O)c1]

2-(6-(2,6-Difluorophenyl)pyridin-3-ylamino)-5-methylbenzoic acid

A. Ethyl 2-(6-(2,6-difluorophenyl)pyridin-3-ylamino)-5-methylbenzoate

Obtained (0.133 g, yield 48%) following the procedure described in Example 57 (step A) starting with Intermediate 51 (0.76 mmol, 0.156 g) and Intermediate 10 (0.76 mmol, 0.150 g).

δ $^1$H NMR (300 MHz, CDCl$_3$): 1.41-1.46 (t, 3H), 2.32 (s, 3H), 4.35-4.42 (q, 2H), 6.98-7.03 (m, 2H), 7.21-7.27 (m, 1H), 7.30-7.34 (m, 2H), 7.41-7.44 (d, 1H), 7.63-7.67 (dd, 1H), 7.83 (s, 1H), 8.64-8.66 (d, 1H), 9.50 (s, 1H).

ESI/MS (m/e, %): 369 [(M+1)$^+$, 100].

B. 2-(6-(2,6-Difluorophenyl)pyridin-3-ylamino)-5-methylbenzoic acid

Obtained (0.080 g, yield 65%) following the procedure described in Example 57 (step B) starting with ethyl 2-(6-(2, 6-difluorophenyl)pyridin-3-ylamino)-5-methylbenzoate (0.133 g, 0.36 mmol).

δ $^1$H NMR (300 MHz, DMSO-d$_6$): 2.25 (s, 3H), 7.14-7.32 (m, 4H), 7.44-7.54 (m, 2H), 7.71-7.72 (d, 1H), 7.75-7.77 (m, 1H), 8.54-8.55 (d, 1H).

ESI/MS (m/e, %): 341 [(M+1)$^+$, 100].

Example 92

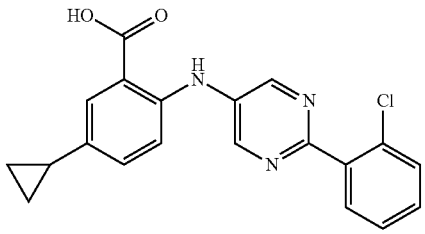

2-(2-(2-Chlorophenyl)pyrimidin-5-ylamino)-5-cyclopropylbenzoic acid

A. Methyl 2-(2-(2-chlorophenyl)pyrimidin-5-ylamino)-5-cyclopropylbenzoate

Obtained (0.210 g, yield 72%) following the procedure described in Example 57 (step A) starting with Intermediate 23 (0.76 mmol, 0.202 g) and Intermediate 57 (0.75 mmol, 0.165 g).

ESI/MS (m/e, %): 380 [(M+1)$^+$, 100], 382 [(M+1)$^+$, 35].

B. 2-(2-(2-Chlorophenyl)pyrimidin-5-ylamino)-5-cyclopropylbenzoic acid

Obtained (0.170 g, yield 81%) following the procedure described in Example 57 (step B) starting with methyl 2-(2-(2-chlorophenyl)pyrimidin-5-ylamino)-5-cyclopropylbenzoate (0.210 g, 0.55 mmol).

δ $^1$H NMR (300 MHz, DMSO-d$_6$): 1.2 (m, 2H), 1.5 (m, 2H), 2.5 (m, 1H), 7.8 (dd, J=8.6, 2.3 Hz, 1H), 7.9 (d, J=8.6 Hz, 1H), 8.0 (m, 2H), 8.1 (m, 1H), 8.2 (d, J=2.3 Hz, 1H), 8.3 (m, 1H), 9.4 (s, 2H), 10.0 (s, 1H), 13.8 (s, 1H).

ESI/MS (m/e, %): 366 [(Mil)$^+$, 100], 368 [(M+1)$^+$, 35].

Example 93

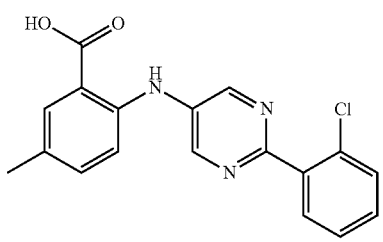 [SMILES: Cc1ccc(Nc2cnc(-c3ccccc3Cl)nc2)c(C(=O)O)c1]

2-(2-(2-Chlorophenyl)pyrimidin-5-ylamino)-5-methylbenzoic acid

A. tert-butyl 2-(2-(2-chlorophenyl)pyrimidin-5-ylamino)-5-methylbenzoate

Obtained (0.203 g, yield 69%) following the procedure described in Example 57 (step A) starting with intermediate 23 (0.74 mmol, 0.200 g) and Intermediate 11 (0.75 mmol, 0.165 g).

ESI/MS (m/e, %): 396 [(M+1)$^+$, 100], 398 [(M+1)$^+$, 35].

B. 2-(2-(2-Chlorophenyl)pyrimidin-5-ylamino)-5-methylbenzoic acid

Obtained (0.170 g, yield 97%) following the procedure described in Example 63 (step B) starting with tert-butyl 2-(2-(2-chlorophenyl)pyrimidin-5-ylamino)-5-methylbenzoate (0.203 g, 0.51 mmol).

δ $^1$H NMR (300 MHz, DMSO-d$_6$): 2.3 (s, 3H), 7.3 (d, J=3.9 Hz, 2H), 7.5 (m, 2H), 7.6 (m, 1H), 7.7 (m, 1H), 7.8 (s, 1H), 8.8 (s, 2H), 9.5 (s, 1H), 13.3 (s, 1H).

ESI/MS (m/e, %): 340 [(M+1)$^+$, 100], 342 [(M+1)$^+$, 35].

Example 94

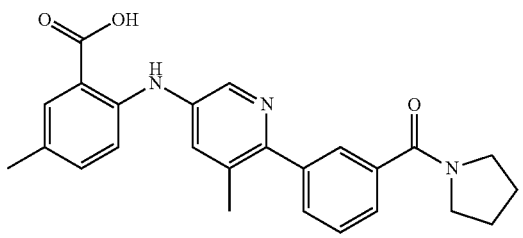 [SMILES: Cc1ccc(Nc2cnc(-c3cccc(C(=O)N4CCCC4)c3)c(C)c2)c(C(=O)O)c1]

5-Methyl-2-(5-methyl-6-(3-(pyrrolidine-1-carbonyl)phenyl)pyridin-3-ylamino)benzoic acid Obtained (0.050 g, yield 39%) following the procedure described in Example 83 starting with Intermediate 67 (0.31 mmol, 0.100 g) and 3-(pyrrolidine-1-carbonyl)phenylboronic acid (0.37 mmol, 0.082 g).

δ ¹H NMR (300 MHz, DMSO-d₆): 0.59 (m, 2H), 0.69 (m, 2H), 2.25 (s, 3H), 2.31 (s, 3H), 2.87 (m, 1H), 7.27 (s, 1H), 7.51 (td, 1H), 7.59 (s, 1H), 7.67 (d, 1H), 7.75 (s, 1H), 7.83 (d, 1H), 7.98 (s, 1H), 8.39 (s, 1H), 8.49 (s, 1H).

ESI/MS (m/e, %): 402 [(M+1)⁺, 100].

Example 95

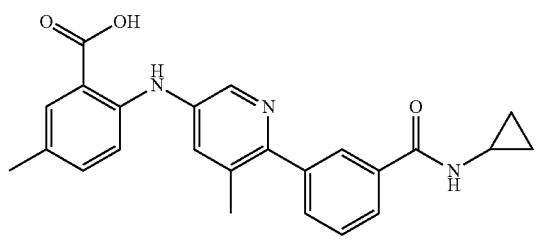 [SMILES: Cc1ccc(Nc2cnc(-c3cccc(C(=O)NC4CC4)c3)c(C)c2)c(C(=O)O)c1]

2-(6-(3-(Cyclopropylcarbamoyl)phenyl)-5-methylpyridin-3-ylamino)-5-methylbenzoic acid Obtained (0.055 g, yield 44%) following the procedure described in Example 83 starting with Intermediate 67 (0.31 mmol, 0.100 g) and 3-(cyclopropylcarbamoyl)phenylboronic acid (0.38 mmol, 0.077 g).

δ ¹H NMR (300 MHz, DMSO-d₆): 1.84 (m, 4H), 2.25 (s, 3H), 2.34 (s, 3H), 3.39-3.48 (m, 4H), 7.27 (s, 2H), 7.51 (m, 2H), 7.58 (s, 1H), 7.64 (m, 2H), 7.75 (s, 1H), 7.83 (d, 1H), 7.98 (s, 1H), 8.39 (s, 1H).

ESI/MS (m/e, %): 416 [(M+1)⁺, 100].

Example 96

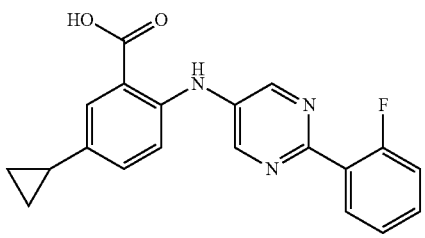

5-Cyclopropyl-2-(2-(2-fluorophenyl)pyrimidin-5-ylamino)benzoic acid

Obtained (0.140 g, yield 39%) following the procedure described in Example 88 starting with Intermediate 39 (1.01 mmol, 0.255 g) and Intermediate 8 (1.47 mmol, 0.261 g).

¹H NMR (400 MHz, DMSO-d₆): 0.6 (d, J=5.1 Hz, 2H), 0.9 (d, J=8.2 Hz, 2H), 1.9 (m, 1H), 7.2 (d, J=8.6 Hz, 1H), 7.3 (m, 3H), 7.5 (m, 1H), 7.7 (s, 1H), 8.0 (t, J=7.8 Hz, 1H), 8.8 (s, 2H), 9.5 (s, 1H) 13.2 (s, 1H).

ESI/MS (m/e, %): 350 [(M+1)⁺, 100].

Example 97

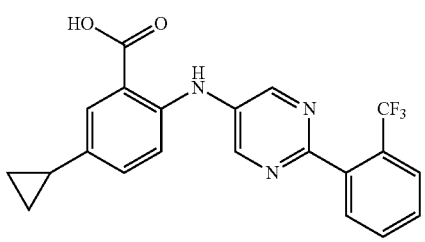

5-cyclopropyl-2-(2-(2-(trifluoromethyl)phenyl)pyrimidin-5-ylamino)benzoic acid

A. Methyl 5-cyclopropyl-2-(2-(2-(trifluoromethyl)phenyl)pyrimidin-5-ylamino)benzoate Obtained (0.290 g, 34% yield) following the procedure described in Example 22 (step A) starting with Intermediate 17 (1.89 mmol, 0.660 g) and 3-(trifluoromethyl)phenylboronic acid (2.89 mmol, 0.550 g).

ESI/MS (m/e, %): 414 [(M+1)⁺, 100]

B. 5-cyclopropyl-2-(2-(2-(trifluoromethyl)phenyl)pyrimidin-5-ylamino)benzoic acid Obtained (0.167 g, yield 63%) following the procedure described in example 22 (step B) starting from methyl 5-cyclopropyl-2-(2-(2-(trifluoromethyl)phenyl)pyrimidin-5-ylamino)benzoate (0.290 g, 0.64 mmol).

₁H NMR (200 MHz, DMSO-d₆) δ ppm 0.6 (m, 2H) 0.9 (m, 2H) 1.9 (m, 1H) 7.3 (m, 2H) 7.8 (m, 5H) 8.8 (s, 2H) 9.5 (s, 1H)

ESI/MS (m/e, %): 400 [(M+1)⁺, 100]

Example 98

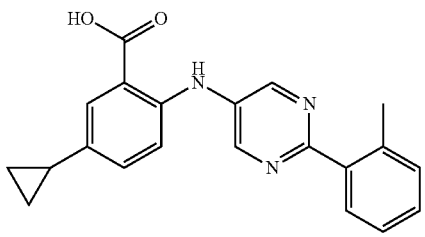 [SMILES: Cc1ccccc1-c1ncc(Nc2ccc(C3CC3)cc2C(=O)O)cn1]

5-Cyclopropyl-2-(2-o-tolylpyrimidin-5-ylamino)benzoic acid

A. Methyl 5-cyclopropyl-2-(2-o-tolylpyrimidin-5-ylamino)benzoate

Obtained (34% yield) following the procedure described in Example 22 (step A) starting with Intermediate 17 and o-tolylboronic acid.

ESI/MS (m/e, %): 360 [(M+1)⁺, 100]

B. 5-Cyclopropyl-2-(2-o-tolylpyrimidin-5-ylamino) benzoic acid

Obtained (77% yield) following the procedure described in example 22 (step B) starting from methyl 5-cyclopropyl-2-(2-o-tolylpyrimidin-5-ylamino)benzoate.

$^1$H NMR (200 MHz, DMSO-$d_6$) δ ppm 0.6 (m, 2H) 0.9 (m, 2H) 1.9 (s, 1H) 2.5 (s, 3H) 7.2 (m, 5H) 7.7 (d, J=2.0 Hz, 1H) 7.8 (m, 1H) 8.8 (s, 2H) 9.5 (s, 1H)

ESI/MS (m/e, %): 346 [(M+1)$^+$, 100]

Example 99

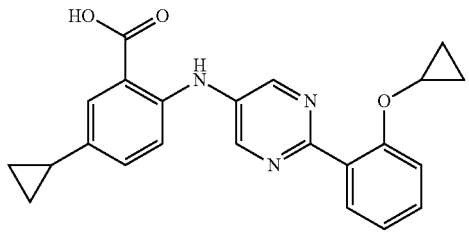 [SMILES: O=C(O)c1cc(C2CC2)ccc1Nc1cnc(-c2ccccc2OC2CC2)nc1]

2-(2-(2-Cyclopropoxyphenyl)pyrimidin-5-ylamino)-5-cyclopropylbenzoic acid

A. Methyl 2-(2-(2-cyclopropoxyphenyl)pyrimidin-5-ylamino)-5-cyclopropylbenzoate Obtained (72% yield) following the procedure described in Example 22 (step A) starting with Intermediate 17 and intermediate 69.

ESI/MS (m/e, %): 402 [(M+1)$^+$, 100]

B. 2-(2-(2-Cyclopropoxyphenyl)pyrimidin-5-ylamino)-5-cyclopropylbenzoic acid Obtained (75% yield) following the procedure described in example 22 (step B) starting from methyl 2-(2-(2-cyclopropoxyphenyl)pyrimidin-5-ylamino)-5-cyclopropylbenzoate.

$^1$H NMR (200 MHz, DMSO-D6) δ ppm 0.9 (m, 8H) 1.9 (m, 1H) 3.9 (s, 1H) 7.1 (m, 1H) 7.3 (m, 2H) 7.4 (m, 2H) 7.6 (d, J=7.4 Hz, 1H) 7.7 (s, 1H) 8.8 (s, 2H) 9.5 (s, 1H)

ESI/MS (m/e, %): 388 [(M+1)$^+$, 100]

Example 100

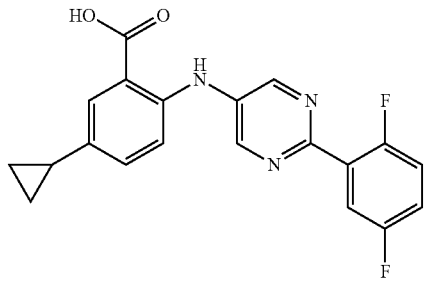 [SMILES: O=C(O)c1cc(C2CC2)ccc1Nc1cnc(-c2cc(F)ccc2F)nc1]

5-Cyclopropyl-2-(2-(2,5-difluorophenyl)pyrimidin-5-ylamino)benzoic acid

A. Methyl 5-cyclopropyl-2-(2-(2,5-difluorophenyl)pyrimidin-5-ylamino)benzoate Obtained (62% yield) following the procedure described in Example 22 (step A) starting with Intermediate 17 and 2,5-difluorophenylboronic acid.

ESI/MS (m/e, %): 382 [(M+1)$^+$, 100]

B. 5-Cyclopropyl-2-(2-(2,5-difluorophenyl)pyrimidin-5-ylamino)benzoic acid

Obtained (88% yield) following the procedure described in example 22 (step B) starting from methyl 5-cyclopropyl-2-(2-(2,5-difluorophenyl)pyrimidin-5-ylamino)benzoate.

$^1$H NMR (400 MHz, DMSO-$d_6$) δ ppm 0.6 (m, 2H) 0.9 (d, J=6.7 Hz, 2H) 1.9 (s, 1H) 7.3 (m, 4H) 7.7 (m, 2H) 8.8 (s, 2H) 9.5 (s, 1H) 13.3 (s, 1H)

ESI/MS (m/e, %): 368 [(M+1)$^+$, 100]

Example 101

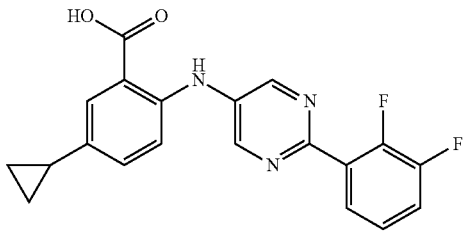 [SMILES: O=C(O)c1cc(C2CC2)ccc1Nc1cnc(-c2cccc(F)c2F)nc1]

5-cyclopropyl-2-(2-(2,3-difluorophenyl)pyrimidin-5-ylamino)benzoic acid

A. Methyl 5-cyclopropyl-2-(2-(2,3-difluorophenyl) pyrimidin-5-ylamino)benzoate Obtained (71% yield) following the procedure described in Example 22 (step A) starting with Intermediate 17 and 2,3-difluorophenylboronic acid.

ESI/MS (m/e, %): 382 [(M+1)$^+$, 100]

B. 5-Cyclopropyl-2-(2-(2,3-difluorophenyl)pyrimidin-5-ylamino)benzoic acid

Obtained (93% yield) following the procedure described in example 22 (step B) starting from methyl 5-cyclopropyl-2-(2-(2,3-difluorophenyl)pyrimidin-5-ylamino)benzoate.

$^1$H NMR (200 MHz, DMSO-$d_5$) δ ppm 0.6 (m, 2H) 0.9 (m, 2H) 1.9 (m, 1H) 7.3 (m, 3H) 7.5 (m, 1H) 7.7 (d, J=2.0 Hz, 1H) 7.8 (m, 1H) 8.8 (s, 2H) 9.5 (s, 1H)

ESI/MS (m/e, %): 368 [(M+1)$^+$, 100]

Example 102

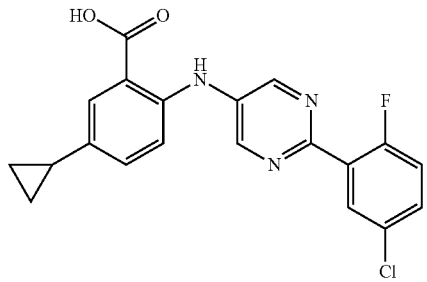 [SMILES: O=C(O)c1cc(C2CC2)ccc1Nc1cnc(-c2cc(Cl)ccc2F)nc1]

2-(2-(5-Chloro-2-fluorophenyl)pyrimidin-5-ylamino)-5-cyclopropylbenzoic acid

A. Methyl 2-(2-(5-chloro-2-fluorophenyl)pyrimidin-5-ylamino)-5-cyclopropylbenzoate Obtained (70% yield) following the procedure described in Example 22 (step A) starting with Intermediate 17 and 5-chloro-2-fluorophenylboronic acid.

ESI/MS (m/e, %): 398 [(M+1)$^+$, 100], 400 [(M+1)$^+$, 35].

B. 2-(2-(5-chloro-2-fluorophenyl)pyrimidin-5-ylamino)-5-cyclopropylbenzoic

Obtained (45% yield) following the procedure described in example 22 (step B) starting from methyl 2-(2-(5-chloro-2-fluorophenyl)pyrimidin-5-ylamino)-5-cyclopropylbenzoate.

$^1$H NMR (400 MHz, DMSO-d$_6$) δ ppm 0.6 (m, 2H) 0.9 (m, 2H) 1.9 (m, 1H) 7.2 (dd, J=8.6, 2.0 Hz, 1H) 7.4 (m, 2H) 7.6 (m, 1H) 7.7 (d, J=2.0 Hz, 1H) 8.0 (dd, J=6.7, 2.7 Hz, 1H) 8.8 (s, 2H) 9.5 (s, 1H) 13.3 (s, 1H).

ESI/MS (m/e, %): 384 [(M+1)$^+$, 100], 386 [(M+1)$^+$, 35].

Example 103

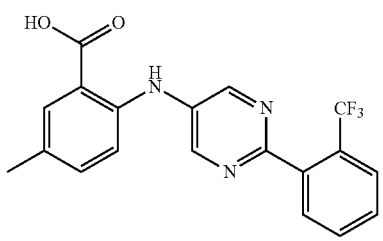

5-Methyl-2-(2-(2-(trifluoromethyl)phenyl)pyrimidin-5-ylamino)benzoic acid

A. tert-Butyl 5-methyl-2-(2-(2-(trifluoromethyl)phenyl)pyrimidin-5-ylamino)benzoate Obtained (86% yield) following the procedure described in example 7 starting with Intermediate 11 and intermediate 74.
ESI/MS (m/e, %): 388 [(M+1)$^+$, 100].

B. 5-Methyl-2-(2-(2-(trifluoromethyl)phenyl)pyrimidin-5-ylamino)benzoic acid Obtained (88% yield) following the procedure described in example 36 (step B) starting from tert-butyl 5-methyl-2-(2-(2-(trifluoromethyl)phenyl)pyrimidin-5-ylamino)benzoate.

$^1$H NMR (300 MHz, DMSO-d$_6$) δ ppm 2.3 (s, 3H) 7.3 (s, 2H) 7.7 (dd, J=7.8, 3.7 Hz, 1H) 7.8 (s, 3H) 7.9 (d, J=8.2 Hz, 1H) 8.8 (s, 2H) 9.6 (s, 1H).

ESI/MS (m/e, %): 374 [(M+1)$^+$, 100].

Example 104

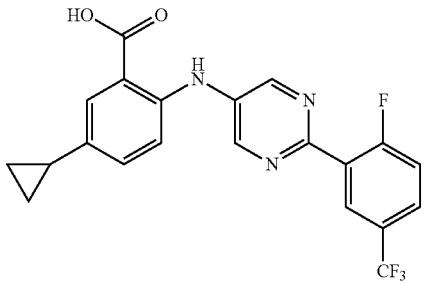 [SMILES: O=C(O)c1cc(C2CC2)ccc1Nc1cnc(-c2cc(C(F)(F)F)ccc2F)nc1]

5-Cyclopropyl-2-(2-(2-fluoro-5-(trifluoromethyl)phenyl)pyrimidin-5-ylamino)benzoic acid

A. Methyl 5-cyclopropyl-2-(2-(2-fluoro-5-(trifluoromethyl)phenyl)pyrimidin-5-ylamino)benzoate Obtained (47% yield) following the procedure described in Example 22 (step A) starting with Intermediate 17 and 2-fluoro-5-(trifluoromethyl)phenylboronic acid.
ESI/MS (m/e, %): 404 [(M+1)$^+$, 100].

B. 5-Cyclopropyl-2-(2-(2-fluoro-5-(trifluoromethyl)phenyl)pyrimidin-5-ylamino)benzoic acid Obtained (44% yield) following the procedure described in example 22 (step B) starting from methyl 5-cyclopropyl-2-(2-(2-fluoro-5-(trifluoromethyl)phenyl)pyrimidin-5-ylamino)benzoate.

$^1$H NMR (400 MHz, DMSO-d$_6$) δ ppm 0.6 (m, 2H) 0.9 (m, 2H) 1.9 (m, 1H) 7.2 (dd, J=8.6, 2.3 Hz, 1H) 7.4 (d, J=8.6 Hz, 1H) 7.6 (m, 1H) 7.7 (d, J=2.0 Hz, 1H) 7.9 (dd, J=5.5, 3.5 Hz, 1H) 8.4 (d. J=5.1 Hz, 1H) 8.9 (s, 2H) 9.5 (s, 1H) 13.3 (s, 1H)

ESI/MS (m/e, %): 418 [(M+1)$^+$, 100].

Example 105

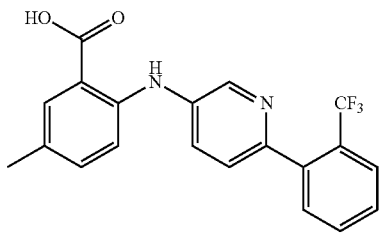

5-Methyl-2-(6-(2-(trifluoromethyl)phenyl)pyridin-3-ylamino)benzoic acid

Obtained (9% yield) following the procedure described in example 1, starting from intermediate 52 and 2-chloro-5-methylbenzoic acid.

$^1$H NMR (300 MHz, DMSO-d$_6$) δ ppm 2.3 (s, 3H) 7.3 (m, 2H) 7.4 (dd, J=8.5, 1.9 Hz, 1H) 7.6 (d, J=7.3 Hz, 1H) 7.6 (t, J=7.3 Hz, 1H) 7.8 (m, 3H) 7.9 (d, J=7.7 Hz, 1H) 8.5 (s, 1H) 9.7 (s, 1H).

ESI/MS (m/e, %): 373 [(M+1)$^+$, 100].

Example 106

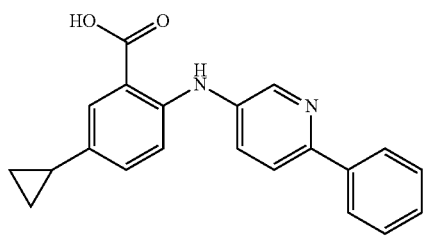 [SMILES: O=C(O)c1cc(C2CC2)ccc1Nc1ccc(-c2ccccc2)nc1]

5-Cyclopropyl-2-(6-(2-fluorophenyl)pyridin-3-ylamino)benzoic acid

Obtained (44% yield) following the procedure described in example 1, starting from intermediate 70 and intermediate 12.

$^1$H NMR (400 MHz, DMSO-d$_6$) δ ppm 0.6 (m, 2H) 0.9 (q, J=6.0 Hz, 2H) 1.9 (m, 1H) 7.2 (m, 2H) 7.4 (t, J=7.0 Hz, 1H) 7.4 (t, J=7.6 Hz, 2H) 7.7 (m, 2H) 7.9 (d, J=8.6 Hz, 1H) 8.0 (d, J=7.8 Hz, 2H) 8.5 (s, 1H) 9.6 (s, 1H)

ESI/MS (m/e, %): 331 [(M+1)$^+$, 100].

Example 107

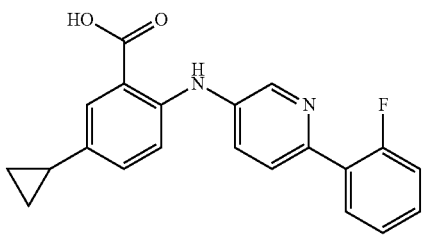 [SMILES: O=C(O)c1cc(C2CC2)ccc1Nc1ccc(-c2ccccc2F)nc1]

5-Cyclopropyl-2-(6-(2-fluorophenyl)pyridin-3-ylamino)benzoic acid

Obtained (14% yield) following the procedure described in example 1, starting from intermediate 50 and intermediate 12.

$^1$H NMR (200 MHz, DMSO-d$_6$) δ ppm 0.6 (m, 2H) 0.9 (m, 2H) 1.9 (m, 1H) 7.3 (m, 5H) 7.7 (m, 3H) 7.9 (m, 1H) 8.6 (s, 1H) 9.6 (s, 1H)

ESI/MS (m/e, %): 349 [(M+1)$^+$, 100].

Example 108

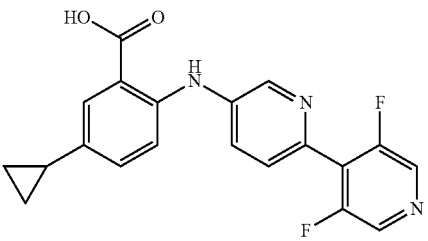 [SMILES: O=C(O)c1cc(C2CC2)ccc1Nc1ccc(-c2c(F)cncc2F)nc1]

2-(3',5'-Difluoro-2,4'-bipyridin-5-ylamino)-5-methylbenzoic acid

A. Ethyl 2-(3',5'-difluoro-2,4'-bipyridin-5-ylamino)-5-methylbenzoate

Obtained (29% yield) following the procedure described in Example 7 (step A) starting with Intermediate 10 and Intermediate 71.

ESI/MS (m/e, %): 370 [(M+1)$^+$, 100].

B. 2-(3',5'-Difluoro-2,4'-bipyridin-5-ylamino)-5-methylbenzoic acid

Obtained (51% yield) following the procedure described in example 21 (step B) starting from ethyl 2-(3',5'-difluoro-2,4'-bipyridin-5-ylamino)-5-methylbenzoate.

$^1$H NMR (300 MHz, DMSO-d$_6$) δ ppm 2.3 (s, 3H) 7.2 (d, J=8.3 Hz, 1H) 7.4 (m, 1H) 7.6 (d, J=8.3 Hz, 1H) 7.8 (m, 2H) 8.6 (d, J=2.5 Hz, 1H) 8.7 (m, 2H)

ESI/MS (m/e, %): 342 [(M+1)$^+$, 100].

Example 109

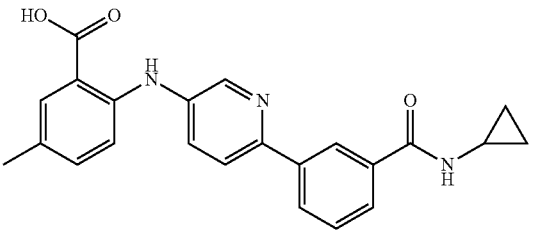 [SMILES: Cc1ccc(Nc2ccc(-c3cccc(C(=O)NC4CC4)c3)nc2)c(C(=O)O)c1]

2-(6-(3-(Cyclopropylcarbamoyl)phenyl)pyridin-3-ylamino)-5-methylbenzoic acid

Obtained (59% yield) following the procedure described in Example 4 starting with Intermediate 13 and 3-(cyclopropylcarbamoyl)phenylboronic acid.

$^1$H NMR (300 MHz, DMSO-d$_6$) δ ppm 0.6 (m, 2H) 0.7 (m, 2H) 2.3 (s, 3H) 2.9 (m, 1H) 7.3 (s, 2H) 7.5 (t, J=7.6 Hz, 1H) 7.8 (m, 3H) 8.0 (d, J=8.8 Hz, 1H) 8.2 (d, J=7.7 Hz, 1H) 8.5 (s, 1H) 8.6 (s, 2H) 9.7 (s, 1H)

ESI/MS (m/e, %): 388 [(M+1)$^+$, 100].

Example 110

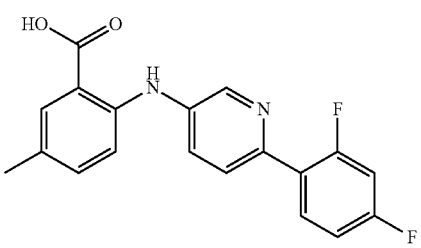 [SMILES: Cc1ccc(Nc2ccc(-c3ccc(F)cc3F)nc2)c(C(=O)O)c1]

2-(6-(2,4-Difluorophenyl)pyridin-3-ylamino)-5-methylbenzoic acid

Obtained (45% yield) following the procedure described in Example 4 starting with Intermediate 13 and 2,4-difluorophenylboronic acid.

$^1$H NMR (300 MHz, DMSO-d$_6$) δ ppm 2.3 (s, 3H) 7.3 (m, 4H) 7.7 (m, 3H) 8.0 (m, 1H) 8.6 (d, J=2.2 Hz, 1H) 9.6 (s, 1H) 13.2 (s, 1H)

ESI/MS (m/e, %): 341 [(M+1)$^+$, 100].

Example 111

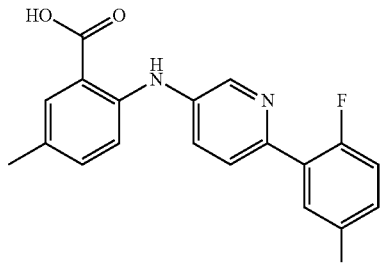

2-(6-(2,5-Difluorophenyl)pyridin-3-ylamino)-5-methylbenzoic acid

Obtained (33% yield) following the procedure described in Example 4 starting with Intermediate 13 and 2,5-difluorophenylboronic acid.

$^1$H NMR (300 MHz, DMSO-d$_6$) δ ppm 2.3 (s, 3H) 7.4 (m, 4H) 7.8 (m, 4H) 8.6 (d, J=1.9 Hz, 1H) 9.6 (s, 1H)

ESI/MS (m/e, %): 341 [(Mil)$^+$, 100].

Example 112

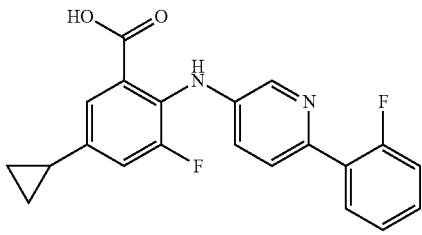 [SMILES: O=C(O)c1cc(C2CC2)cc(F)c1Nc1ccc(-c2ccccc2F)nc1]

5-Cyclopropyl-3-fluoro-2-(6-(2-fluorophenyl)pyridin-3-ylamino)benzoic acid

Obtained (22% yield) following the procedure described in example 1, starting from intermediate 50 and intermediate 72.

$^1$H NMR (200 MHz, DMSO-$d_6$) δ ppm 0.7 (m, 2H) 1.0 (m, 2H) 2.0 (m, 1H) 7.1 (m, 2H) 7.2 (m, 1H) 7.4 (m, 2H) 7.5 (s, 1H) 7.6 (dd, J=8.8, 2.1 Hz, 1H) 7.9 (m, 1H) 8.3 (s, 1H)

ESI/MS (m/e, %): 367 [(M+1)$^+$, 100].

Example 113

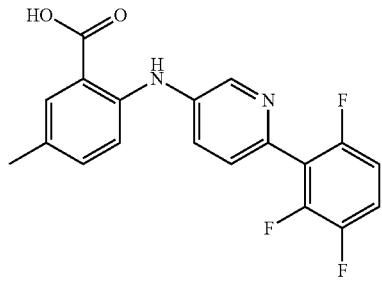 [SMILES: Cc1ccc(Nc2ccc(-c3c(F)ccc(F)c3F)nc2)c(C(=O)O)c1]

5-methyl-2-(6-(2,3,6-trifluorophenyl)pyridin-3-ylamino)benzoic acid

A. tert-Butyl 5-methyl-2-(6-(2,3,6-trifluorophenyl)pyridin-3-ylamino)benzoate

Obtained (93% yield) following the procedure described in intermediate 51, starting from intermediate 15 and 1,2,4-trifluorobenzene.

ESI/MS (m/e, %): 415 [(M+1)$^+$, 100].

B. 5-methyl-2-(6-(2,3,6-trifluorophenyl)pyridin-3-ylamino)benzoic acid

Obtained (66% yield) following the procedure described in example 36 (step B) starting from tert-butyl 5-methyl-2-(6-(2,3,6-trifluorophenyl)pyridin-3-ylamino)benzoate.

$^1$H NMR (300 MHz, DMSO-$d_5$) δ ppm 2.3 (s, 3H) 7.3 (m, 3H) 7.6 (m, 2H) 7.8 (m, 2H) 8.6 (d, J=2.5 Hz, 1H) 9.6 (s, 1H)

ESI/MS (m/e, %): 359 [(M+1)$^+$, 100].

Example 114

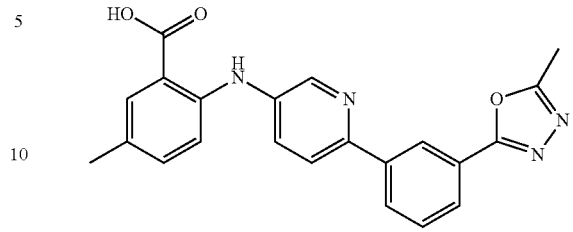

5-methyl-2-(6-(3-(5-methyl-1,3,4-oxadiazol-2-yl)phenyl)pyridin-3-ylamino)benzoic acid A. tert-Butyl 5-methyl-2-(6-(3-(5-methyl-1,3,4-oxadiazol-2-yl)phenyl)pyridin-3-ylamino)benzoate Obtained (74% yield) following the procedure described in Example 4 starting with Intermediate 15 and intermediate 73.

ESI/MS (m/e, %): 443 [(M+1)$^+$, 100].

B. 5-methyl-2-(6-(3-(5-methyl-1,3,4-oxadiazol-2-yl)phenyl)pyridin-3-ylamino)benzoic acid Obtained (74% yield) following the procedure described in example 36 (step B) starting from tert-butyl 5-methyl-2-(6-(3-(5-methyl-1,3,4-oxadiazol-2-yl)phenyl)pyridin-3-ylamino)benzoate.

$^1$H NMR (300 MHz, DMSO-$d_6$) δ ppm 2.3 (s, 3H) 2.6 (s, 3H) 7.3 (s, 2H) 7.7 (t, J=8.0 Hz, 1H) 7.8 (m, 2H) 8.0 (d, J=8.0 Hz, 1H) 8.0 (d, J=8.5 Hz, 1H) 8.3 (d, J=8.2 Hz, 1H) 8.6 (m, 2H) 9.6 (s, 1H)

ESI/MS (m/e, %): 387 [(M+1)$^+$, 100].

Example 115

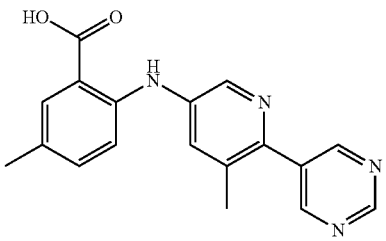 [SMILES: Cc1ccc(Nc2cnc(-c3cncnc3)c(C)c2)c(C(=O)O)c1]

5-methyl-2-(5-methyl-6-(pyrimidin-5-yl)pyridin-3-ylamino)benzoic acid

A. tert-Butyl 5-methyl-2-(5-methyl-6-(pyrimidin-5-yl)pyridin-3-ylamino)benzoate

Obtained (64% yield) following the procedure described in Example 4 starting with Intermediate 16 and pyrimidin-5-ylboronic acid.

ESI/MS (m/e, %): 377 [(M+1)$^+$, 100].

B. 5-methyl-2-(5-methyl-6-(pyrimidin-5-yl)pyridin-3-ylamino)benzoic acid

Obtained (89% yield) following the procedure described in example 36 (step B) starting from tert-butyl 5-methyl-2-(5-methyl-6-(pyrimidin-5-yl)pyridin-3-ylamino)benzoate.

$^1$H NMR (200 MHz, DMSO-d$_6$) δ ppm 2.3 (s, 3H) 2.4 (s, 3H) 7.3 (s, 2H) 7.7 (d, J=2.0 Hz, 1H) 7.7 (s, 1H) 8.5 (d, J=2.0 Hz, 1H) 9.0 (s, 2H) 9.2 (s, 1H) 9.5 (s, 1H)

ESI/MS (m/e, %): 321 [(M+1)$^+$, 100].

Example 116

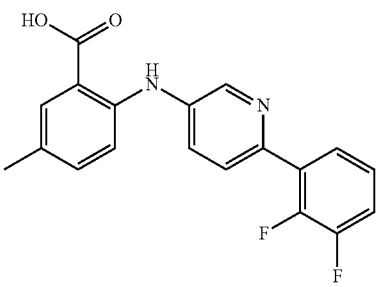 [SMILES: Cc1ccc(Nc2ccc(-c3cccc(F)c3F)nc2)c(C(=O)O)c1]

2-(6-(2,3-difluorophenyl)pyridin-3-ylamino)-5-methylbenzoic acid

A. tert-Butyl 2-(6-(2,3-difluorophenyl)pyridin-3-ylamino)-5-methylbenzoate

Obtained (85% yield) following the procedure described in Example 4 starting with Intermediate 15 and 2,3-difluorophenylboronic acid.

ESI/MS (m/e, %): 397 [(M+1)$^+$, 100].

B. 2-(6-(2,3-difluorophenyl)pyridin-3-ylamino)-5-methylbenzoic acid

Obtained (73% yield) following the procedure described in example 36 (step B) starting from tert-butyl 2-(6-(2,3-difluorophenyl)pyridin-3-ylamino)-5-methylbenzoate.

$^1$H NMR (300 MHz, DMSO-d$_6$) δ ppm 2.3 (s, 3H) 7.3 (m, 3H) 7.5 (m, 1H) 7.7 (m, 4H) 8.6 (s, 1H) 9.7 (s, 1H)

ESI/MS (m/e, %): 341 [(M+1)$^+$, 100].

Example 117

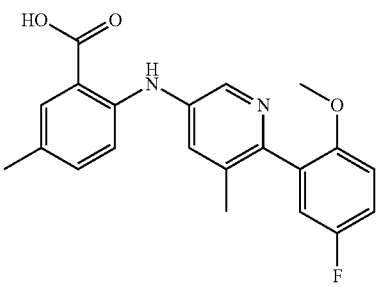 [SMILES: COc1ccc(F)cc1-c1ncc(Nc2ccc(C)cc2C(=O)O)cc1C]

2-(6-(5-fluoro-2-methoxyphenyl)-5-methylpyridin-3-ylamino)-5-methylbenzoic acid

A. tert-Butyl 2-(6-(5-fluoro-2-methoxyphenyl)-5-methylpyridin-3-ylamino)-5-methylbenzoate Obtained (78% yield) following the procedure described in Example 4 starting with Intermediate 16 and 5-fluoro-2-methoxyphenylboronic acid.

ESI/MS (m/e, %): 423 [(M+1)$^+$, 100].

B. 2-(6-(5-fluoro-2-methoxyphenyl)-5-methylpyridin-3-ylamino)-5-methylbenzoic acid Obtained (77% yield) following the procedure described in example 36 (step B) starting from tert-butyl 2-(6-(5-fluoro-2-methoxyphenyl)-5-methylpyridin-3-ylamino)-5-methylbenzoate.

$^1$H NMR (200 MHz, DMSO-d$_6$) δ ppm 2.1 (s, 3H) 2.3 (s, 3H) 3.8 (s, 3H) 7.2 (m, 2H) 7.3 (m, 3H) 7.8 (m, 2H) 8.4 (s, 1H) 9.5 (s, 1H).

ESI/MS (m/e, %): 367 [(M+1)$^+$, 100].

Example 118

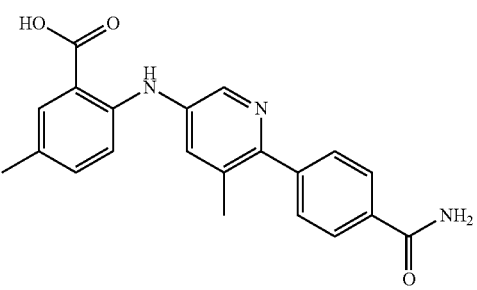 [SMILES: Cc1ccc(Nc2cnc(-c3ccc(C(N)=O)cc3)c(C)c2)c(C(=O)O)c1]

2-(6-(4-carbamoylphenyl)-5-methylpyridin-3-ylamino)-5-methylbenzoic acid

A. 2-(6-(4-carbamoylphenyl)-5-methylpyridin-3-ylamino)-5-methylbenzoic acid Obtained (62% yield) following the procedure described in Example 4 starting with Intermediate 16 and 4-carbamoylphenylboronic acid.

ESI/MS (m/e, %): 418 [(M+1)$^+$, 100].

B. 2-(6-(4-carbamoylphenyl)-5-methylpyridin-3-ylamino)-5-methylbenzoic acid Obtained (78% yield) following the procedure described in example 36 (step B) starting from tert-butyl 2-(6-(4-carbamoylphenyl)-5-methylpyridin-3-ylamino)-5-methylbenzoate.

$^1$H NMR (200 MHz, DMSO-d$_6$) δ ppm 2.3 (s, 3H) 2.3 (s, 3H) 7.3 (s, 2H) 7.5 (s, 1H) 7.7 (d, J=8.2 Hz, 2H) 7.8 (m, 2H) 8.0 (d, J=8.2 Hz, 2H) 8.1 (s, 1H) 8.5 (d, J=2.3 Hz, 2H) 9.5 (s, 1H)

ESI/MS (m/e, %): 362 [(M+1)$^+$, 100].

Pharmacological Activity

Inhibition of Human DHODH Activity Assay

DHODH activity and its inhibition were studied using a chromogen reduction assay with DCIP (2,6-dichlorophenolindophenol). The substrate oxidation (Dihydroorotate, L-DHO), as well as cosubstrate reduction (coenzyme Q, CoQ) is coupled to the chromogen reduction, hence enzymatic activity results in a loss of chromogen absorbance at 600 nm. Enzyme extracts (8 µl, ~1.5 µg of human protein) were incubated in 96-well plates. The assay mixture (200 µl) contained 200 µM CoQD, 100 µM L-DHO, 120 µM DCIP in the assay buffer (100 mM HEPES pH 8.0, 150 mM NaCl, 10% Glicerol, 0.05% Triton X-100) and 2 µl of test compound. The compounds were dissolved in DMSO at a stock concentration of 1 mM, and tested at different concentrations varying from 10 µM to 1 µM to calculate an $IC_{50}$ (concentration of inhibitor required for 50% of inhibition).

The reaction was initiated by adding the enzyme and then incubated for 10 min at room temperature before measuring DCIP reduction by counting a decrease in absorbance at 600 nm using standard instrumentation (Spectramax).

All reactions were carried out in duplicate and graphs, determining $IC_{50}$ values for each compound, were plotted using the ABase software.

Table 1 shows the activities in human DHODH inhibition assay of some compounds of the present invention showing that these compounds are potent DHODH inhibitors.

| Example | hDHODH $IC_{50}$ (nM) |
|---|---|
| 1 | 105 |
| 4 | 98 |
| 6 | 57 |
| 7 | 49 |
| 8 | 18 |
| 14 | 57 |
| 15 | 113 |
| 18 | 62 |
| 19 | 10 |
| 22 | 114 |
| 25 | 28 |
| 30 | 41 |
| 31 | 119 |
| 34 | 109 |
| 41 | 190 |
| 42 | 30 |
| 44 | 78 |
| 50 | 138 |
| 51 | 21 |
| 54 | 19 |
| 56 | 91 |
| 58 | 53 |
| 61 | 28 |
| 62 | 11 |
| 64 | 14 |
| 65 | 190 |
| 66 | 97 |
| 67 | 12 |
| 68 | 33 |
| 71 | 32 |
| 73 | 5 |
| 74 | 6 |
| 75 | 20 |
| 76 | 10 |
| 77 | 5 |
| 79 | 37 |
| 81 | 2 |
| 82 | 7 |
| 84 | 145 |
| 86 | 4 |
| 89 | 90 |
| 91 | 19 |
| 92 | 3 |
| 93 | 57 |
| 94 | 9 |
| 95 | 12 |
| 96 | 10 |
| 97 | 9 |
| 98 | 12 |
| 100 | 38 |
| 104 | 21 |
| 107 | 8 |
| 110 | 146 |
| 113 | 77 |
| 117 | 46 |

Functional Assay: Inhibition of Lymphocyte Proliferation

Peripheral blood mononuclear cells (PBMC) of healthy volunteers were prepared using Ficoll density centrifugation. Cells were seeded at $1\times10^5$ cells per well in 96 well flat bottom plates in RPMI 1640 supplemented with 5% fetal bovine serum, 2 mM L-glutamine and penicillin/streptomycin. Then, PBMC were activated with 1 µg/ml phytohaemagglutinin (PHA, Sigma) and incubated with a dilution series of different concentrations of test compounds for 3 days. After this period, cells were pulsed with 0.5 µCi per well of tritiated thymidine and incubated overnight. Next, the cultures are harvested on filter papers and counted with a B-counter. The $IC_{50}$ value for each compound was calculated from the dose response curves.

The compounds of the invention that have been tested using this Assay had an $IC_{50}$ of less than 10 µM. Preferred compounds of the invention had $IC_{50}$ of less than 4 µM, preferably lower than 2 µM, most preferably lower than 1 µM.

As shown by these results, the compounds of the invention effectively inhibit DHODH thereby inhibiting the proliferation of cells with high turnover, in particular lymphocytes.

The azabiphenylaminobenzoic acid derivatives of the invention are useful in the treatment or prevention of diseases known to be susceptible to improvement by treatment with inhibitor of the dihydroorotate dehydrogenase. Such diseases include but are not limited to rheumatoid arthritis, psoriatic arthritis, ankylosing spondilytis, multiple sclerosis, Wegener's granulomatosis, systemic lupus erythematosus, psoriasis and sarcoidosis.

Accordingly, the azabiphenylaminobenzoic acid derivatives of the invention and pharmaceutical compositions comprising such compound and/or salts thereof may be used in a method of treatment of disorders of the human or animal body which comprises administering to a subject requiring such treatment an effective amount of azabiphenylaminobenzoic acid derivative of the invention or a pharmaceutically acceptable salt thereof.

The azabiphenylaminobenzoic acid derivatives of the invention may also be combined with other active compounds in the treatment of diseases known to be susceptible to improvement by treatment with an inhibitor of the dihydroorotate dehydrogenase.

The combinations of the invention can optionally comprise one or more additional active substances which are known to be useful in the treatment of autoimmune diseases, immune and inflammatory diseases, destructive bone disorders, malignant neoplastic diseases, angiogenic-related disorders, viral diseases, and infectious diseases such as (a) Anti-TNF-alpha monoclonal antibodies such as Infliximab, Certolizumab pegol, Golimumab, Adalimumab and AME-527 from Applied Molecular Evolution, (b) Antimetabolite compounds such as Mizoribine, Cyclophosphamide and Azathiopirine, (c) Calcineurin (PP-2B) Inhibitors/INS Expression Inhibitors such as cyclosporine A, Tacrolimus and ISA-247 from Isotechnika, (d) Cyclooxygenase Inhibitors such as Aceclofenac, Diclofenac, Celecoxib. Rofecoxib; Etoricoxib, Valdecoxib, Lumiracoxib, Cimicoxib and LAS-34475 from Laboratorios Almirall, S.A., (e) TNF-alpha Antagonists such as Etanercept, Lenercept, Onercept and Pegsunercept, (f) NF-kappaB (NFKB) Activation Inhibitors such as Sulfasalazine and Iguratimod, (g) IL-1 Receptor Antagonists such as Anakinra and AMG-719 from Amgen, (h) Dihydrofolate Reductase (DHFR) Inhibitors such as Methrotexate, Aminopterin and CH-1504 from Chelsea, (i) Inhibitors of Inosine 5'-Monophosphate Dehydrogenase (IMPDH) such as Mizoribine, Ribavirin, Tiazofurin, Amitivir, Mycophenolate mofetil, Ribamidine and Merimepodib, (j) Glucocorticoids such as Prednisolone, Methylprednisolone, Dexamethasone, Cortisol, Hydrocortisone, Triamcinolone acetonide, Fluocinolone acetonide, Fluocinonide, Clocortolone pivalate, Hydrocortisone aceponate, Methylprednisolone suleptanate, Betamethasone butyrate propionate, Deltacortisone, Deltadehydrocortisone, Prednisone, Dexamethasone sodium phosphate, Triamcinolone, Betamethasone valerate, Betamethasone, Hydrocortisone sodium succinate, Prednisolone sodium phosphate, Hydrocortisone probutate and Difluprednate, (k) Anti-CD20 monoclonal antibodies such as Rituximab, Ofatumumab, Ocrelizumab, Veltuzumab and TRU-015 from Trubion Pharmaceuticals, (l) B-targeted cell therapies such as BLYSS, BAFF, TACI-Ig and APRIL, (m) p38 Inhibitors such as AMG-548 (from Amgen), ARRY-797 (from Array Biopharma), Chlormethiazole edisylate, Doramapimod, PS-540446, BMS-582949 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06, PH-797804 (all from Pfizer), RWJ-67657 (from R.W. Johnson), RO-3201195, RO-4402257 (all from Roche), AVE-9940 (from Aventis), SCIO-323, SCID-469 (all from Scios), TA-5493 (from Tanabe Seiyaku), and VX-745, VX-702 (all from Vertex) and the compounds claimed or described in Spanish patent applications numbers P200600396 and P200602174, (n) Jak3 Inhibitors such as CP690550 from Pfizer, R-348 (o) Syk inhibitors such as R-112, R-406 and R-788 all from Rigel, (p) MEK inhibitors such as ARRY-142886, ARRY-438162 (all from Array Biopharma), AZD-6244 (from AstraZeneca), PD-098059, PD-0325901 (all from Pfizer), AR-119, AS703026 (q) P2X7 receptor antagonist such as AZD-9056 from AstraZeneca, (r) S1P1 agonists such as Fingolimod, CS-0777 from Sankyo and R-3477 from Actelion, ONO-4641, and KRP-203 from Novartis, (s) Anti-CD49 monoclonal antibodies such as Natalizumab, (t) Integrin Inhibitors such as Cilengitide, Firategrast, Valategrast hydrochloride, SB-273005, SB-683698 (all from Glaxo), HMR-1031 from Sanofi-Aventis, R-1295 from Roche, BMS-587101 from BMS and CDP-323 from UCB Celltech, (u) Anti-CD88 monoclonal antibodies such as Eculizumab and Pexelizumab, (v) IL-6 receptor antagonist such as CBP-1011 from InKine and C-326 from Amgen, (w) Anti IL-6 monoclonal antibodies such as Elsilimomab, CNTO-328 from Centocor and VX-30 from Vaccinex, (x) Anti-CD152 monoclonal antibodies such as Ipilimumab and Ticilimumab, (y) Fusion proteins comprising the extracellular domain of human cytotoxic T-lymphocyte-associated antigen 4 (CTLA-4) linked to portions of human immunoglobulin G1 such as Abatacept, (z) Agents useful in the treatment of bone disorders such as Bisphosphonates such as Tiludronate disodium, Clodronate disodium, Disodium pamidronate, Etidronate disodium, Xydiphone (K, Na salt), Alendronate sodium, Neridronate, Dimethyl-APD, Olpadronic acid sodium salt, Minodronic acid, Apomine, Ibandronate sodium hydrate and Risedronate sodium, (aa) VEGF Try kinase inhibitors such as Pegaptanib octasodium, Vatalanib succinate, Sorafenib, Vandetanib, Sunitinib malate, Cediranib, Pazopanib hydrochloride and AE-941 from AEterna Zentaris, (bb) Other compounds efficacious in autoimmune diseases such as Gold salts, hydroxycloroquinine, Penicilamine, K-832, SMP114 and AD452, (cc) Purine-Nucleoside phosphorylase inhibitors such as Forodesine hydrochloride, R-3421 from Albert Einstein College of Medicine, CI-972 and CI-1000 both from Pfizer, (dd) Anti-RANKL monoclonal antibodies such as Denosumab, (ee) Anti-CD25 monoclonal antibodies such as Inolimomab, Dacliximab, Basiliximab and LMB-2 from the US National Cancer Institute, (ff) Histone Deacetylase (HDAC) Inhibitors such as Divalproex sodium, Acetyldinaline, Depsipeptide, Sodium butyrate, Sodium phenylbutyrate, Vorinostat, MS-27-275 from Mitsui, Valproic acid, Pyroxamide, Tributyrin, PX-105684 from TopoTarget, MG-0103 from MethylGene, G2M-777 from TopoTarget and CG-781 from Celera and (gg) Anti colony-stimulating factor (GM-CSF) monoclonal antibodies such as KB-002 from KaloBios.

When azabiphenylaminobenzoic acid derivatives of the invention are used for the treatment of rheumatoid arthritis, psoriatic arthritis, ankylosing spondilytis, multiple sclerosis, Wegener's granulomatosis, systemic lupus erythematosus, psoriasis and sarcoidosis it may be advantageous to use them in combination with other active compounds known to be useful in the treatment of such diseases such as rheumatoid arthritis, psoriatic arthritis, ankylosing spondilytis, multiple sclerosis, Wegener's granulomatosis, systemic lupus erythematosus, psoriasis and sarcoidosis.

Particularly preferred actives to be combined with the azabiphenylaminobenzoic acid derivatives of the invention for treating or preventing rheumatoid arthritis, psoriatic arthritis, ankylosing spondilytis, multiple sclerosis, Wegener's granulomatosis, systemic lupus erythematosus, psoriasis or sarcoidosis are (a) Anti-TNF-alpha monoclonal antibodies such as Infliximab, Certolizumab pegol, Golimumab, Adalimumab and AME-527 from Applied Molecular Evolution, (b) TNF-alpha Antagonists such as Etanercept, Lenercept, Onercept and Pegsunercept, (c) Calcineurin (PP-2B) Inhibitors/INS Expression Inhibitors such as cyclosporine A, Tacrolimus and ISA-247 from Isotechnika, (d) IL-1 Receptor Antagonists such as Anakinra and AMG-719 from Amgen, (e) Anti-CD$_2$O monoclonal antibodies such as Rituximab, Ofatumumab, Ocrelizumab, Veltuzumab and TRU-015 from Trubion Pharmaceuticals, (f) p38 Inhibitors such as AMG-548 (from Amgen), ARRY-797 (from Array Biopharma), Chlormethiazole edisylate, Doramapimod, PS-540446, BMS-582949 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06, PH-797804 (all from Pfizer), RWJ-67657 (from R.W. Johnson), RO-3201195, RO-4402257 (all from Roche), AVE-9940 (from Aventis), SC10-323, SCID-469 (all from Scios), TA-5493 (from Tanabe Seiyaku), and VX-745, VX-702 (all from Vertex) and the compounds claimed or described in Spanish patent applications numbers P200600396 and P200602174, (g) NF-kappaB (NFKB) Activation Inhibitors such as Sulfasalazine and Iguratimod and (h) Dihydrofolate Reductase (DHFR) Inhibitors such as Methrotexate, Aminopterin and CH-1504 from Chelsea.

The combinations of the invention may be used in the treatment of disorders which are susceptible to amelioration by inhibition of the dihydroorotate dehydrogenase. Thus, the present application encompasses methods of treatment of these disorders, as well as the use of the combinations of the invention in the manufacture of a medicament for the treatment of these disorders.

Preferred examples of such disorders are rheumatoid arthritis, psoriatic arthritis, ankylosing spondilytis, multiple sclerosis, Wegener's granulomatosis, systemic lupus erythematosus, psoriasis and sarcoidosis, more preferably rheumatoid arthritis, psoriatic arthritis and psoriasis and most preferably rheumatoid arthritis.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the inhibitor of the dihydroorotate dehydrogenase of the invention, and the other optional active compounds may be administered together in the same pharmaceutical composition or in different compositions intended for separate, simultaneous, concomitant or sequential administration by the same or a different route.

One execution of the present invention consists of a kit of parts comprising an inhibitor of the dihydroorotate dehydrogenase of the invention together with instructions for simultaneous, concurrent, separate or sequential use in combination with another active compound useful in the treatment of rheumatoid arthritis, psoriatic arthritis, ankylosing spondilytis, multiple sclerosis, Wegener's granulomatosis, systemic lupus erythematosus, psoriasis and sarcoidosis.

Another execution of the present invention consists of a package comprising an inhibitor of the dihydroorotate dehydrogenase of formula (I) and another active compound useful in the treatment of rheumatoid arthritis, psoriatic arthritis, ankylosing spondilytis, multiple sclerosis, Wegener's granulomatosis, systemic lupus erythematosus, psoriasis and sarcoidosis.

The pharmaceutical formulations may conveniently be presented in unit dosage form and may be prepared by any of the methods well known in the art of pharmacy.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, gylcerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 2 µg and 150 µg of each therapeutically active ingredient. Alternatively, the active ingredient (s) may be presented without excipients.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Effective doses are normally in the range of 2-2000 mg of active ingredient per day. Daily dosage may be administered in one or more treatments, preferably from 1 to 4 treatments, per day. Preferably, the active ingredients are administered once or twice a day.

When combinations of actives are used, it is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The following preparations forms are cited as formulation examples:

Composition Example 1

50,000 capsules, each containing 100 mg of 5-cyclopropyl-2-(5-methyl-6-(3-trifluoromethoxy)phenyl)pyridin-3-ylamino)benzoic acid (active ingredient), were prepared according to the following formulation:

| Active ingredient | 5 Kg |
|---|---|
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets, each containing 50 mg of 5-cyclopropyl-2-(5-methyl-6-(3-trifluoromethoxy)phenyl)pyridin-3-ylamino)benzoic acid (active ingredient), were prepared from the following formulation:

| Active ingredient | 2.5 Kg |
|---|---|
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:

1. A method of inhibiting dehydroorotate dehydrogenase (DHODH), wherein the diseases treatable by such inhibition are chosen from rheumatoid arthritis, psoriatic arthritis, ankylosing spondilytis, multiple sclerosis, Wegener's granulomatosis, systemic lupus erythematosus, psoriasis and sarcoidosis, and wherein the method comprises adminstering an effective amount of a compound of formula (I):

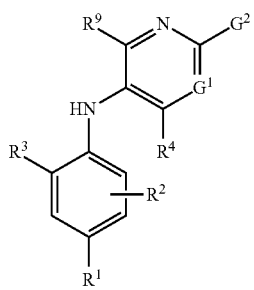

wherein:
R$^1$ is chosen from a hydrogen atom, halogen atoms, C$_{1-4}$ alkyl, C$_{3-4}$ cycloalkyl, —CF$_3$ and —OCF$_3$,
R$^2$ is chosen from a hydrogen atom, halogen atoms and C$_{1-4}$ alkyl groups,
R$^3$ is chosen from —COOR$^5$, —CONHR$^5$, tetrazolyl, —SO$_2$NHR$^5$ and —CONHSO$_2$R$^5$ groups, wherein R$^5$ is chosen from a hydrogen atom and linear or branched C$_{1-4}$ alkyl groups,
R$^4$ is chosen from a hydrogen atom and C$_{1-4}$ alkyl groups,
R$^9$ is chosen from a hydrogen atom and phenyl groups,
G$^1$ represents a group chosen from N and CR$^6$, wherein R$^6$ is chosen from a hydrogen atom, halogen atoms, C$_{1-4}$ alkyl groups, C$_{3-4}$ cycloalkyl groups, C$_{1-4}$ alkoxy groups, —CF$_3$, —OCF$_3$, monocyclic N-containing C$_{5-7}$ heteroaryl groups, monocyclic N-containing C$_{3-7}$ heterocyclyl groups and C$_{6-10}$ aryl groups which are optionally substituted with at least one substituent chosen from halogen atoms and C$_{1-4}$ alkyl groups,
G$^2$ represents a group chosen from:
a hydrogen atom, hydroxy groups, halogen atoms, C$_{3-4}$ cycloalkyl groups, C$_{1-4}$ alkoxy groups and —NR$^a$R$^b$, wherein
R$^a$ is chosen from C$_{1-4}$ alkyl groups, and R$^b$ is chosen from C$_{1-4}$ alkyl groups and C$_{1-4}$ alkoxy-C$_{1-4}$ alkyl groups, or
R$^a$ and R$^b$ together with the nitrogen atom to which they are attached form a saturated 6 to 8 membered heterocyclic ring optionally containing one oxygen atom as an additional heteroatom,
a monocyclic or bicyclic 5 to 10 membered heteroaromatic ring containing one or more nitrogen atoms, which is optionally substituted by at least one substituent chosen from halogen atoms, C$_{1-4}$ alkyl groups, C$_{1-4}$ alkoxy groups, C$_{3-4}$ cycloalkyl groups, C$_{3-4}$ cycloalkoxy groups, —CF$_3$, —OCF$_3$, and —CONR$^7$R$^8$, wherein R$^7$ and R$^8$ are independently chosen from a hydrogen atom, linear or branched C$_{1-4}$ alkyl groups, C$_{3-7}$ cycloalkyl groups, or R$^7$ and R$^8$ together with the nitrogen atom to which they are attached form a group of formula

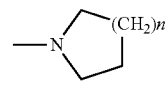

wherein n is an integer from 0 to 3,
and
a phenyl group, which is optionally substituted by at least one substituent chosen from halogen atoms, C$_{1-4}$ alkyl groups, hydroxyl, C$_{1-4}$ alkoxy groups, C$_{3-4}$cycloalkyl groups, C$_{3-4}$ cycloalkoxy groups, cyano groups, —CF$_3$, —OCF$_3$, —CONR$^7$R$^8$, oxadiazolyl groups, triazolyl groups, pyrazolyl groups and imidazolyl groups, wherein the oxadiazolyl, triazolyl, pyrazolyl and imidazolyl groups are optionally substituted by C$_{1-4}$ alkyl groups or C$_{3-7}$ cycloalkyl groups and wherein R$^7$ and R$^8$ are independently chosen from a hydrogen atom, linear or branched C$_{1-4}$ alkyl groups, and C$_{3-7}$ cycloalkyl groups, or R$^7$ and R$^8$ together with the nitrogen atom to which they are attached form a group of formula

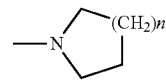

wherein n is an integer from 0 to 3
or, G$^2$ together with R$^6$ forms a non-aromatic C$_{5-10}$ carbocyclic group or a C$_{5-10}$ aryl group,
or a pharmaceutically acceptable salt or N-oxide thereof.

2. The method according to claim 1, wherein R$^1$ is chosen from a hydrogen atom, a fluorine atom, a chlorine atom, a bromine atom, C$_{1-4}$ alkyl groups, C$_{3-4}$ cycloalkyl groups, and —CF$_3$.

3. The method according to claim 1, wherein R$^2$ is chosen from a hydrogen atom, halogen atoms, and methyl groups.

4. The method according to claim 1, wherein G$^1$ is chosen from a nitrogen atom, CCl, CF, CH, C(CH$_3$), C(cyclopropyl), C(phenyl) and C(CF$_3$) groups.

5. The method according to claim 1, wherein G$^2$ is chosen from:
a hydrogen atom, halogen atoms, C$_{3-4}$ cycloalkyl groups, C$_{1-2}$ alkoxy groups and —NR$^a$R$^b$, wherein
R$^a$ represents a C$_{1-2}$ alkyl group and R$^b$ is chosen from C$_{1-2}$ alkyl groups and C$_{1-2}$ alkoxy-C$_{1-2}$ alkyl groups, or
R$^a$ and R$^b$ together with the nitrogen atom to which they are attached form a saturated 6 or 7 membered heterocyclic ring optionally containing one oxygen atom as an additional heteroatom,
a monocyclic or bicyclic 5 to 10 membered heteroaromatic ring containing one or two nitrogen atoms which is optionally substituted by at least one substituent chosen from halogen atoms and C$_{1-4}$ alkyl groups,
and
phenyl groups which are optionally substituted by one, two or three substituents chosen from halogen atoms, C$_{1-4}$ alkyl groups, hydroxyl, C$_{1-4}$ alkoxy groups, C$_{3-4}$cycloalkyl groups, C$_{3-4}$ cycloalkoxy groups, cyano groups, —CF$_3$, —OCF$_3$, —CONR$^7$R$^8$ and oxadiazolyl groups, wherein the oxadiazolyl group is optionally substituted by at least one group chosen from C$_{1-4}$ alkyl groups and C$_{3-7}$ cycloalkyl groups, and wherein $R^7$ and $R^8$ are each independently chosen from a hydrogen atom, linear or branched $C_{1-4}$ alkyl groups, $C_{3-4}$ cycloalkyl groups, or $R^7$ and $R^8$ together with the nitrogen atom to which they are attached form a group of formula

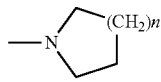

wherein n is 1 or 2, or, $G^2$ together with $R^6$ forms a non-aromatic $C_6$ carbocyclic group or a phenyl group.

6. The method according to claim 1, wherein $G^2$ represents a group chosen from:

a hydrogen atom, a fluorine atom, cyclopropyl groups, methoxy groups, —NMeEt, —NEt$_2$, —N(Me)-(CH$_2$)$_2$—O—CH$_3$, 6-morpholinyl, azepan-1-yl and piperidin-1-yl, pyridinyl, pyridiminyl, quinolinyl and pyrazinyl rings optionally substituted with at least one substituent chosen from Me and F
and
phenyl groups which are optionally substituted by one, two or three substituents chosen from fluorine, chlorine, methyl, hydroxy, methoxy, ethoxy, isopropyloxy, cyclopropyl, cyclopropyloxy, cyano, —CF$_3$, —OCF$_3$, oxadiazolyl and —CONR$^7$R$^8$ groups, wherein the oxadiazolyl group is optionally substituted by a methyl group and wherein $R^7$ and $R^8$ are each independently chosen from a hydrogen atom, methyl groups, isopropyl groups, cyclopropyl groups, or $R^7$ and $R^8$ together with the nitrogen atom to which they are attached form a group of formula

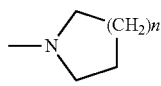

wherein n is 1, or, $G^2$ together with $R^6$ forms a non-aromatic $C_6$ carbocyclic group or a phenyl group.

7. The method according to claim 1, wherein $G^2$ represents a group chosen from methoxy groups, cyclopropyl groups and optionally substituted phenyl, pyridyl, quinolynyl, pyrimidinyl and pyrazinyl groups.

8. The method according to claim 1, wherein:

$R^1$ is chosen from a hydrogen atom, halogen atoms, $C_{1-4}$ alkyl groups, $C_{3-4}$ cycloalkyl groups, —CF$_3$ and —OCF$_3$, $R^2$ is chosen from a hydrogen atom, halogen atoms and $C_{1-4}$ alkyl groups, $R^3$ is chosen from —COOR$^5$, —CONHR$^5$, tetrazolyl, —SO$_2$NHR$^5$ and —CONHSO$_2$R$^5$ groups, wherein $R^5$ is chosen from a hydrogen atom and linear or branched $C_{1-4}$ alkyl groups, $R^4$ is chosen from hydrogen atom and $C_{1-4}$ alkyl groups, $R^9$ represents a hydrogen atom, $G^1$ represents a group chosen from N and CR$^6$ wherein $R^6$ is chosen from a hydrogen atom, halogen atoms, $C_{1-4}$ alkyl groups, $C_{3-4}$ cycloalkyl groups, $C_{1-4}$ alkoxy groups, —CF$_3$, —OCF$_3$, monocyclic N-containing $C_{5-7}$ heteroaryl groups, monocyclic N-containing $C_{3-7}$ heterocyclyl groups and $C_{6-10}$ aryl groups which are optionally substituted with at least one substituent chosen from halogen atoms and $C_{1-4}$ alkyl groups, $G^2$ represents a group chosen from:

monocyclic or bicyclic 5 to 10 membered heteroaromatic rings containing a nitrogen atom which is optionally substituted by at least one substituent chosen from halogen atoms, $C_{1-4}$ alkyl groups, $C_{1-4}$ alkoxy groups, $C_{3-4}$ cycloalkyl groups, $C_{3-4}$ cycloalkoxy groups, —CF$_3$, —OCF$_3$, and —CONR$^7$R$^8$, wherein $R^7$ and $R^8$ are independently chosen from a hydrogen atom, linear or branched $C_{1-4}$ alkyl groups, $C_{3-7}$ cycloalkyl groups, or $R^7$ and $R^8$ together with the nitrogen atom to which they are attached form a group of formula

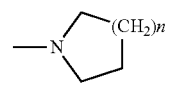

wherein n is an integer from 0 to 3,
and
phenyl group which is optionally substituted by at least one substituent chosen from halogen atoms, $C_{1-4}$ alkyl groups, $C_{1-4}$ alkoxy groups, $C_{3-4}$cycloalkyl groups, $C_{3-4}$ cycloalkoxy groups, —CF$_3$, —OCF$_3$, —CONR$^7$R$^8$, oxadiazolyl, triazolyl, pyrazolyl and imidazolyl groups, wherein the oxadiazolyl, triazolyl, pyrazolyl and imidazolyl groups are optionally substituted by a group chosen from $C_{1-4}$ alkyl groups and $C_{3-7}$ cycloalkyl groups, and wherein $R^7$ and $R^8$ are independently chosen from a hydrogen atom, linear or branched $C_{1-4}$ alkyl groups, $C_{3-7}$ cycloalkyl groups, or $R^7$ and $R^8$ together with the nitrogen atom to which they are attached form a group of formula

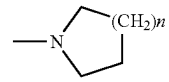

wherein n is an integer from 0 to 3.

9. The method according to claim 1, wherein $R^1$ is chosen from $C_{1-4}$ alkyl groups, $C_{3-4}$ cycloalkyl groups and —CF$_3$ groups.

10. The method according to claim 1, wherein $R^1$ is chosen from methyl and cyclopropyl groups.

11. The method according to claim 10, wherein $R^1$ is a cyclopropyl group.

12. The method according to claim 1, wherein $R^2$ is chosen from a hydrogen atom and halogens.

13. The method according to claim 12, wherein $R^2$ is a hydrogen atom.

14. The method according to claim 1, wherein $R^3$ is chosen from COOR$^5$, —CONHR$^5$ and tetrazolyl groups.

15. The method according to claim 1, wherein $R^3$ is a COOH group.

16. The method according to claim 1, wherein $R^4$ is chosen from a hydrogen atom and a methyl group.

17. The method according to claim 1, wherein $R^9$ represents a hydrogen atom.

18. The method according to claim 1, wherein $G^1$ is chosen from a nitrogen atom, and CH, C(CH$_3$), C(cyclopropyl), C(phenyl) and C(CF$_3$) groups.

19. The method according to claim 1, wherein $G^2$ represents a group chosen from optionally substituted phenyl, pyridyl, quinolynyl, pyrimidinyl and pyrazinyl groups.

20. The method according to claim 19, wherein $G^2$ represents a group chosen from optionally substituted phenyl, 4-pyridyl, 5-quinolynyl and 2-pyrazinyl groups.

21. The method according to claim 1, wherein $R^1$ is chosen from methyl and cyclopropyl groups, $R^2$ represents a hydrogen atom, $R^3$ is a COOH group, $R^4$ represents a hydrogen atom or a methyl group, $G^1$ is chosen from a nitrogen atom and CH, $C(CH_3)$, C(cyclopropyl), C(phenyl) and $C(CF_3)$ groups and $G^2$ represents a group chosen from optionally substituted phenyl, 4-pyridyl, 5-quinolynyl and 2-pyrazinyl groups.

22. The method according to claim 21, wherein $R^9$ represents a hydrogen atom.

23. The method according to claim 1, wherein $R^1$ is chosen from methyl and cyclopropyl groups, $R^2$ represents a hydrogen atom, $R^3$ is a COOH group, $R^4$ represents a hydrogen atom, $G^1$ is chosen from a nitrogen atom and CH, $C(CH_3)$ and $C(CF_3)$ groups and $G^2$ represents a phenyl group optionally substituted with at least one substituent chosen from chloro, fluoro, methoxy, ethoxy, isopropoxy, trifluoromethoxy and $-CONR^7R^8$, wherein $R^7$ is hydrogen and $R^8$ is cyclopropyl or $R^7$ and $R^8$ together with the nitrogen atom to which they are attached form a group of formula

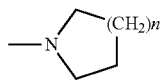

wherein n is 1.

24. A method of inhibiting dehydroorotate dehydrogenase (DHODH), wherein the diseases treatable by such inhibition are chosen from rheumatoid arthritis, psoriatic arthritis, ankylosing spondilytis, multiple sclerosis, Wegener's granulomatosis, systemic lupus erythematosus, psoriasis and sarcoidosis, and wherein the method comprises adminstering an effective amount of a compound of formula (I):

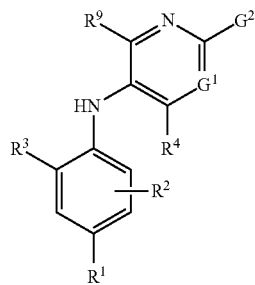

wherein:
$R^1$ is chosen from a hydrogen atom, halogen atoms, $C_{1-4}$ alkyl, $C_{3-4}$ cycloalkyl, $-CF_3$ and $-OCF_3$,
$R^2$ is chosen from a hydrogen atom, halogen atoms and $C_{1-4}$ alkyl groups,
$R^3$ is chosen from $-COOR^5$, $-CONHR^5$, tetrazolyl, $-SO_2NHR^5$ and $-CONHSO_2R^5$ groups, wherein $R^5$ is chosen from a hydrogen atom and linear or branched $C_{1-4}$ alkyl groups,
$R^4$ is chosen from a hydrogen atom and $C_{1-4}$ alkyl groups,
$R^9$ is chosen from a hydrogen atom and phenyl groups, $G^1$ represents a group chosen from N and $CR^6$, wherein $R^6$ is chosen from a hydrogen atom, halogen atoms, $C_{1-4}$ alkyl groups, $C_{3-4}$ cycloalkyl groups, $C_{1-4}$ alkoxy groups, $-CF_3$, $-OCF_3$, monocyclic N-containing $C_{5-7}$ heteroaryl groups, monocyclic N-containing $C_{3-7}$ heterocycyl groups and $C_{6-10}$ aryl groups which are optionally substituted with at least one substituent chosen from halogen atoms and $C_{1-4}$ alkyl groups, $G^2$ represents a group chosen from:
a hydrogen atom, hydroxy groups, halogen atoms, $C_{3-4}$ cycloalkyl groups, $C_{1-4}$ alkoxy groups and $-NR^aR^b$, wherein
$R^a$ is chosen from $C_{1-4}$ alkyl groups, and $R^b$ is chosen from $C_{1-4}$ alkyl groups and $C_{1-4}$ alkoxy-$C_{1-4}$ alkyl groups, or
$R^a$ and $R^b$ together with the nitrogen atom to which they are attached form a saturated 6 to 8 membered heterocyclic ring optionally containing one oxygen atom as an additional heteroatom,
a monocyclic 5 to 10 membered heteroaromatic ring containing one or more nitrogen atoms, which is optionally substituted by at least one substituent chosen from halogen atoms, $C_{1-4}$ alkyl groups, $C_{1-4}$ alkoxy groups, $C_{3-4}$ cycloalkyl groups, $C_{3-4}$ cycloalkoxy groups, $-CF_3$, $-OCF_3$, and $-CONR^7R^8$, wherein $R^7$ and $R^8$ are independently chosen from a hydrogen atom, linear or branched $C_{1-4}$ alkyl groups, $C_{3-4}$ cycloalkyl groups, or $R^7$ and $R^8$ together with the nitrogen atom to which they are attached form a group of formula

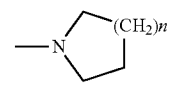

wherein n is an integer from 0 to 3,
and
a phenyl group, which is optionally substituted by at least one substituent chosen from halogen atoms, $C_{1-4}$ alkyl groups, hydroxyl, $C_{1-4}$ alkoxy groups, $C_{3-4}$ cycloalkyl groups, $C_{3-4}$ cycloalkoxy groups, cyano groups, $-CF_3$, $-OCF_3$, $-CONR^7R^8$, oxadiazolyl groups, triazolyl groups, pyrazolyl groups and imidazolyl groups, wherein the oxadiazolyl, triazolyl, pyrazolyl groups and imidazolyl groups are optionally substituted by $C_{1-4}$ alkyl groups or $C_{3-7}$ cycloalkyl groups and wherein $R^7$ and $R^8$ are independently chosen from a hydrogen atom, linear or branched $C_{1-4}$ alkyl groups, and $C_{3-7}$ cycloalkyl groups, or $R^7$ and $R^8$ together with the nitrogen atom to which the are attached form a group of formula

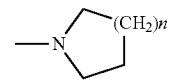

wherein n is an integer from 0 to 3
or, $G^2$ together with $R^6$ forms a non-aromatic $C_{5-10}$ carbocyclic group or a $C_{6-10}$ aryl group,
or a pharmaceutically acceptable salt or N-oxide thereof,
with the proviso that when $G^2$ is a hydrogen or chlorine atom, a methoxy or butoxy group or together with $R^6$ forms a phenyl group, then $R^1$ is not a hydrogen atom or a chlorine atom, to a human or animal body.

* * * * *

UNITED STATES PATENT AND TRADEMARK OFFICE
CERTIFICATE OF CORRECTION

| | | |
|---|---|---|
| PATENT NO. | : 8,536,165 B2 | Page 1 of 1 |
| APPLICATION NO. | : 12/672725 | |
| DATED | : September 17, 2013 | |
| INVENTOR(S) | : Castro Palomino Laria et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 463 days.

Signed and Sealed this
Twenty-eighth Day of January, 2014

Michelle K. Lee
*Deputy Director of the United States Patent and Trademark Office*